(12) United States Patent
Tayeb et al.

(10) Patent No.: US 12,186,184 B2
(45) Date of Patent: *Jan. 7, 2025

(54) DOCKING STATIONS FOR TRANSCATHETER VALVES

(71) Applicant: Edwards Lifesciences Corporation, Irvine, CA (US)

(72) Inventors: Liron Tayeb, Peduel (IL); Eran Goldberg, Nesher (IL); David Maimon, Atlit (IL); Adi Carmi, Ganei Tikva (IL); Arie Tylis, Kiryat Motzkin (IL); Ralph Schneider, Trabuco Canyon, CA (US); Mohammad Jafari, Foothill Ranch, CA (US); Hengchu Cao, Irvine, CA (US); Eitan Atias, Tel Aviv (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/657,732

(22) Filed: Apr. 1, 2022

(65) Prior Publication Data

US 2022/0226110 A1 Jul. 21, 2022

Related U.S. Application Data

(63) Continuation of application No. 16/034,794, filed on Jul. 13, 2018, now Pat. No. 11,291,540, which is a
(Continued)

(51) Int. Cl.
*A61F 2/24* (2006.01)
*A61F 2/88* (2006.01)
*A61F 2/90* (2013.01)

(52) U.S. Cl.
CPC .......... *A61F 2/2418* (2013.01); *A61F 2/2433* (2013.01); *A61F 2/2436* (2013.01); *A61F 2/88* (2013.01);
(Continued)

(58) Field of Classification Search
CPC .... A61F 2/2418; A61F 2/2433; A61F 2/2436; A61F 2/90; A61F 2220/0016; A61F 2220/005; A61F 2220/0075
See application file for complete search history.

(56) References Cited

U.S. PATENT DOCUMENTS 519,297 A    5/1894   Bauer
4,035,849 A  7/1977   Angell et al.
(Continued)

FOREIGN PATENT DOCUMENTS

CA    2 827 556 A1    7/2012
DE    19532846 A1     3/1997
(Continued)

OTHER PUBLICATIONS

Walther, et al., "Trans-catheter valve-in-valve implantation: in vitro hydrodynamic performance of the SAPIEN + cloth trans-catheter heart valve in the Carpentier-Edwards Perimount valves," European Journal of Cardio-thoracic Surgery, 40 (2011) 1120-1126, Sep. 23, 2010.

*Primary Examiner* — Paul B Prebilic
(74) *Attorney, Agent, or Firm* — David J. Grover; Calfee, Halter & Griswold LLP

(57) ABSTRACT

An expandable docking station includes an annular valve seat having an end, an annular outer wall comprising struts disposed around the valve seat, and links that connect the end of the annular valve seat to the annular outer wall. Each of the links extends from the struts of the annular outer wall directly toward a longitudinal axis that runs longitudinally (Continued)

through a center of the docking station, and to a corresponding one of a plurality of circumferentially spaced axially extending legs at least partially defining the annular valve seat. The outer wall is configured to conform to an interior shape of a blood vessel, when expanded inside the blood vessel, such that the outer wall can expand in multiple locations to conform to multiple bulges of the blood vessel and can contract in multiple locations to conform to multiple narrowed regions of the blood vessel.

17 Claims, 94 Drawing Sheets

Related U.S. Application Data continuation of application No. PCT/US2018/040425, filed on Jun. 29, 2018.

(60) Provisional application No. 62/529,902, filed on Jul. 7, 2017, provisional application No. 62/529,996, filed on Jul. 7, 2017, provisional application No. 62/527,577, filed on Jun. 30, 2017.

(52) U.S. Cl.
CPC .......... *A61F 2/90* (2013.01); *A61F 2220/0016* (2013.01); *A61F 2220/005* (2013.01); *A61F 2220/0075* (2013.01); *A61F 2230/005* (2013.01); *A61F 2230/0054* (2013.01); *A61F 2250/0039* (2013.01); *A61F 2250/0063* (2013.01)

(56) References Cited

U.S. PATENT DOCUMENTS

| | | |
|---|---|---|
| 4,592,340 A | 6/1986 | Boyles |
| 4,790,843 A | 12/1988 | Carpentier et al. |
| 4,955,895 A | 9/1990 | Sugiyama et al. |
| 4,994,077 A | 2/1991 | Dobben |
| 5,059,177 A | 10/1991 | Towne et al. |
| 5,176,698 A | 1/1993 | Burns et al. |
| 5,192,297 A | 3/1993 | Hull |
| 5,266,073 A | 11/1993 | Wall |
| 5,325,845 A | 7/1994 | Adair |
| 5,358,496 A | 10/1994 | Ortiz et al. |
| 5,411,552 A | 5/1995 | Andersen et al. |
| 5,554,185 A | 9/1996 | Block et al. |
| 5,591,195 A | 1/1997 | Taheri et al. |
| 5,599,305 A | 2/1997 | Hermann et al. |
| 5,632,760 A | 5/1997 | Sheiban et al. |
| 5,639,274 A | 6/1997 | Fischell et al. |
| 5,728,068 A | 3/1998 | Leone et al. |
| 5,749,890 A | 5/1998 | Shaknovich |
| 5,782,809 A | 7/1998 | Umeno et al. |
| 5,824,044 A | 10/1998 | Quiachon et al. |
| 5,840,081 A | 11/1998 | Andersen et al. |
| 5,908,405 A | 6/1999 | Imran et al. |
| 5,916,147 A | 6/1999 | Boury |
| 5,961,536 A | 10/1999 | Mickley et al. |
| 5,968,068 A | 10/1999 | Dehdashtian et al. |
| 6,019,777 A | 2/2000 | Mackenzie |
| 6,027,510 A | 2/2000 | Alt |
| 6,033,381 A | 3/2000 | Kontos |
| 6,143,016 A | 11/2000 | Bleam et al. |
| 6,162,208 A | 12/2000 | Hipps |
| 6,168,614 B1 | 1/2001 | Andersen et al. |
| 6,174,327 B1 | 1/2001 | Mertens et al. |
| 6,217,585 B1 | 4/2001 | Houser et al. |
| 6,235,050 B1 | 5/2001 | Quiachon et al. |
| 6,251,092 B1 | 6/2001 | Qin et al. |
| 6,273,909 B1 | 8/2001 | Kugler et al. |
| 6,379,372 B1 | 4/2002 | Dehdashtian et al. |
| 6,383,171 B1 | 5/2002 | Gifford et al. |
| 6,419,696 B1 | 7/2002 | Ortiz et al. |
| 6,425,916 B1 | 7/2002 | Garrison et al. |
| 6,432,134 B1 | 8/2002 | Anson et al. |
| 6,454,799 B1 | 9/2002 | Schreck |
| 6,458,153 B1 | 10/2002 | Bailey et al. |
| 6,461,382 B1 | 10/2002 | Cao |
| 6,471,672 B1 | 10/2002 | Brown et al. |
| 6,500,147 B2 | 12/2002 | Omaleki et al. |
| 6,514,228 B1 | 2/2003 | Hamilton et al. |
| 6,527,979 B2 | 3/2003 | Constantz et al. |
| 6,579,305 B1 | 6/2003 | Lashinski |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,730,121 B2 | 5/2004 | Ortiz et al. |
| 6,733,525 B2 | 5/2004 | Yang et al. |
| 6,764,504 B2 | 7/2004 | Wang et al. |
| 6,767,362 B2 | 7/2004 | Schreck |
| 6,776,791 B1 | 8/2004 | Stallings et al. |
| 6,797,002 B2 | 9/2004 | Spence et al. |
| 6,830,584 B1 | 12/2004 | Seguin |
| 6,887,268 B2 | 5/2005 | Butaric et al. |
| 6,893,460 B2 | 5/2005 | Spenser et al. |
| 6,908,481 B2 | 6/2005 | Cribier |
| 7,011,094 B2 | 3/2006 | Rapacki et al. |
| 7,018,406 B2 | 3/2006 | Seguin et al. |
| 7,018,408 B2 | 3/2006 | Bailey et al. |
| 7,037,334 B1 | 5/2006 | Hlavka et al. |
| 7,077,861 B2 | 7/2006 | Spence |
| 7,101,395 B2 | 9/2006 | Tremulis et al. |
| 7,125,421 B2 | 10/2006 | Tremulis et al. |
| 7,137,993 B2 | 11/2006 | Acosta et al. |
| 7,276,084 B2 | 10/2007 | Yang et al. |
| 7,318,278 B2 | 1/2008 | Zhang et al. |
| 7,320,702 B2 | 1/2008 | Hammersmark et al. |
| 7,320,704 B2 | 1/2008 | Lashinski et al. |
| 7,374,571 B2 | 5/2008 | Pease et al. |
| 7,393,360 B2 | 7/2008 | Spenser et al. |
| 7,435,257 B2 | 10/2008 | Lashinski et al. |
| 7,445,632 B2 | 11/2008 | McGuckin, Jr. et al. |
| 7,510,575 B2 | 3/2009 | Spenser et al. |
| 7,585,321 B2 | 9/2009 | Cribier |
| 7,594,926 B2 | 9/2009 | Linder et al. |
| 7,597,709 B2 | 10/2009 | Goodin |
| 7,618,446 B2 | 11/2009 | Andersen et al. |
| 7,637,946 B2 | 12/2009 | Solem et al. |
| 7,708,775 B2 | 5/2010 | Rowe et al. |
| 7,737,060 B2 | 6/2010 | Strickler et al. |
| 7,780,723 B2 | 8/2010 | Taylor |
| 7,785,366 B2 | 8/2010 | Maurer et al. |
| 7,951,195 B2 | 5/2011 | Antonsson et al. |
| 7,959,661 B2 | 6/2011 | Hijlkema et al. |
| 8,029,556 B2 | 10/2011 | Rowe |
| 8,128,691 B2 | 3/2012 | Keranen |
| 8,142,492 B2 | 3/2012 | Forster et al. |
| 8,167,932 B2 | 5/2012 | Bourang et al. |
| 8,236,049 B2 | 8/2012 | Rowe et al. |
| RE43,882 E | 12/2012 | Hopkins et al. |
| 8,323,335 B2 | 12/2012 | Rowe et al. |
| 8,377,115 B2 | 2/2013 | Thompson |
| 8,398,708 B2 | 3/2013 | Meiri et al. |
| 8,449,599 B2 | 5/2013 | Chau et al. |
| 8,449,605 B2 | 5/2013 | Lichtenstein et al. |
| 8,449,606 B2 | 5/2013 | Eliasen et al. |
| 8,475,523 B2 | 7/2013 | Duffy |
| 8,568,472 B2 | 10/2013 | Marchand et al. |
| 8,657,872 B2 | 2/2014 | Seguin |
| 8,663,322 B2 | 3/2014 | Keranen |
| 8,672,998 B2 | 3/2014 | Lichtenstein et al. |
| 8,685,086 B2 | 4/2014 | Navia et al. |
| 8,734,507 B2 | 5/2014 | Keranen |
| 8,801,776 B2 | 8/2014 | House et al. |
| 8,840,664 B2 | 9/2014 | Karapetian et al. |
| 9,061,119 B2 | 6/2015 | Le et al. |
| 9,078,747 B2 | 7/2015 | Conklin |
| 9,095,434 B2 | 8/2015 | Rowe |
| 9,119,716 B2 | 9/2015 | Lee et al. |
| 9,119,718 B2 | 9/2015 | Keranen |

(56) References Cited

U.S. PATENT DOCUMENTS

| | | |
|---|---|---|
| 9,192,471 B2 | 11/2015 | Bolling |
| 9,237,886 B2 | 1/2016 | Seguin et al. |
| 9,314,335 B2 | 4/2016 | Konno |
| 9,326,853 B2 | 5/2016 | Olson et al. |
| 9,364,326 B2 | 6/2016 | Yaron |
| 9,463,268 B2 | 10/2016 | Spence |
| 9,474,599 B2 | 10/2016 | Keranen |
| 9,526,572 B2 | 12/2016 | Kunis |
| 9,597,205 B2 | 3/2017 | Tuval |
| 9,622,863 B2 | 4/2017 | Karapetian et al. |
| 9,795,477 B2 | 10/2017 | Tran et al. |
| 9,867,702 B2 | 1/2018 | Keränen et al. |
| 10,016,272 B2 | 7/2018 | Spence et al. |
| 10,016,276 B2 | 7/2018 | Brunnett et al. |
| 10,034,749 B2 | 7/2018 | Spence et al. |
| 10,039,637 B2 | 8/2018 | Maimon et al. |
| 10,052,198 B2 | 8/2018 | Chau et al. |
| 10,195,028 B2 | 2/2019 | Hosmer et al. |
| 10,195,033 B2 | 2/2019 | Tuval et al. |
| 10,226,339 B2 | 3/2019 | Spence et al. |
| 10,357,361 B2 | 7/2019 | Rafi et al. |
| 10,463,479 B2 | 11/2019 | Manash et al. |
| 10,702,378 B2* | 7/2020 | Miyashiro ............... A61F 2/243 |
| 10,828,150 B2 | 11/2020 | Tamir |
| 11,020,225 B2 | 6/2021 | Keränen et al. |
| 11,039,924 B2 | 6/2021 | Yaron |
| 11,065,111 B2 | 7/2021 | Manash et al. |
| 11,141,273 B2 | 10/2021 | Dakin et al. |
| 11,185,406 B2 | 11/2021 | Haivatov et al. |
| 11,364,114 B2 | 6/2022 | Gorman, III et al. |
| 11,382,748 B2 | 7/2022 | Keränen et al. |
| 11,471,282 B2 | 10/2022 | Argento et al. |
| 11,547,563 B2 | 1/2023 | Keränen et al. |
| 11,654,025 B2 | 5/2023 | O'Carroll et al. |
| 11,666,441 B2 | 6/2023 | McDaniel et al. |
| 2001/0002445 A1 | 5/2001 | Vesely |
| 2001/0007082 A1 | 7/2001 | Dusbabek et al. |
| 2002/0032481 A1 | 3/2002 | Gabbay |
| 2002/0058995 A1 | 5/2002 | Stevens |
| 2002/0107535 A1 | 8/2002 | Wei et al. |
| 2002/0107536 A1 | 8/2002 | Hussein |
| 2002/0151970 A1 | 10/2002 | Garrison et al. |
| 2002/0165461 A1 | 11/2002 | Hayzelden et al. |
| 2003/0040792 A1 | 2/2003 | Gabbay |
| 2003/0050694 A1 | 3/2003 | Yang et al. |
| 2003/0093087 A1 | 5/2003 | Jones et al. |
| 2003/0120341 A1 | 6/2003 | Shennib et al. |
| 2003/0130611 A1 | 7/2003 | Martin |
| 2003/0225420 A1 | 12/2003 | Wardle |
| 2004/0093061 A1 | 5/2004 | Acosta et al. |
| 2004/0111006 A1 | 6/2004 | Alferness et al. |
| 2004/0133263 A1 | 7/2004 | Dusbabek et al. |
| 2004/0143197 A1 | 7/2004 | Soukup et al. |
| 2004/0148008 A1 | 7/2004 | Goodson et al. |
| 2004/0186563 A1 | 9/2004 | Lobbi |
| 2004/0186565 A1 | 9/2004 | Schreck |
| 2004/0204749 A1 | 10/2004 | Gunderson |
| 2004/0210306 A1 | 10/2004 | Quijano et al. |
| 2004/0260389 A1 | 12/2004 | Case et al. |
| 2005/0043790 A1 | 2/2005 | Seguin |
| 2005/0080474 A1 | 4/2005 | Andreas et al. |
| 2005/0096736 A1 | 5/2005 | Osse et al. |
| 2005/0119682 A1 | 6/2005 | Nguyen et al. |
| 2005/0119735 A1 | 6/2005 | Spence et al. |
| 2005/0137689 A1 | 6/2005 | Salahieh et al. |
| 2005/0137691 A1 | 6/2005 | Salahieh et al. |
| 2005/0149160 A1 | 7/2005 | McFerran |
| 2005/0182483 A1 | 8/2005 | Osborne et al. |
| 2005/0182486 A1 | 8/2005 | Gabbay |
| 2005/0203614 A1 | 9/2005 | Forster et al. |
| 2005/0203617 A1 | 9/2005 | Forster et al. |
| 2005/0245894 A1 | 11/2005 | Zadno-Azizi |
| 2005/0283231 A1 | 12/2005 | Haug et al. |
| 2006/0025857 A1 | 2/2006 | Bergheim et al. |
| 2006/0173524 A1 | 8/2006 | Salahieh et al. |
| 2006/0195134 A1 | 8/2006 | Crittenden |
| 2006/0271172 A1 | 11/2006 | Tehrani |
| 2006/0282150 A1 | 12/2006 | Olson et al. |
| 2007/0005131 A1 | 1/2007 | Taylor |
| 2007/0073389 A1 | 3/2007 | Bolduc et al. |
| 2007/0088431 A1 | 4/2007 | Bourang et al. |
| 2007/0112422 A1 | 5/2007 | Dehdashtian |
| 2007/0186933 A1 | 8/2007 | Domingo et al. |
| 2007/0203575 A1 | 8/2007 | Forster et al. |
| 2007/0219612 A1 | 9/2007 | Andreas et al. |
| 2007/0239254 A1 | 10/2007 | Chia et al. |
| 2007/0244546 A1 | 10/2007 | Francis |
| 2007/0265700 A1 | 11/2007 | Eliasen et al. |
| 2007/0293808 A1 | 12/2007 | Williams et al. |
| 2008/0002696 A1 | 1/2008 | Claessens et al. |
| 2008/0004696 A1 | 1/2008 | Vesely |
| 2008/0033542 A1 | 2/2008 | Antonsson et al. |
| 2008/0065011 A1 | 3/2008 | Marchand et al. |
| 2008/0077235 A1 | 3/2008 | Kirson |
| 2008/0125853 A1 | 5/2008 | Bailey et al. |
| 2008/0140190 A1 | 6/2008 | Macoviak et al. |
| 2008/0188923 A1 | 8/2008 | Chu |
| 2008/0208327 A1 | 8/2008 | Rowe |
| 2008/0208330 A1 | 8/2008 | Keranen |
| 2008/0294230 A1 | 11/2008 | Parker |
| 2009/0024428 A1 | 1/2009 | Hudock, Jr. |
| 2009/0069889 A1 | 3/2009 | Suri et al. |
| 2009/0138079 A1 | 5/2009 | Tuval et al. |
| 2009/0157175 A1 | 6/2009 | Benichou |
| 2009/0192585 A1 | 7/2009 | Bloom et al. |
| 2009/0192601 A1 | 7/2009 | Rafiee et al. |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2010/0030318 A1 | 2/2010 | Berra |
| 2010/0036472 A1 | 2/2010 | Papp |
| 2010/0036473 A1 | 2/2010 | Roth |
| 2010/0036484 A1 | 2/2010 | Hariton et al. |
| 2010/0049313 A1 | 2/2010 | Alon et al. |
| 2010/0063573 A1 | 3/2010 | Hijlkema et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0145440 A1 | 6/2010 | Keranen |
| 2010/0161036 A1 | 6/2010 | Pintor et al. |
| 2010/0174363 A1 | 7/2010 | Castro |
| 2010/0198347 A1 | 8/2010 | Zakay et al. |
| 2010/0274344 A1 | 10/2010 | Dusbabek et al. |
| 2010/0298927 A1 | 11/2010 | Greenberg |
| 2010/0312333 A1 | 12/2010 | Navia et al. |
| 2010/0318184 A1 | 12/2010 | Spence |
| 2011/0015729 A1 | 1/2011 | Jimenez et al. |
| 2011/0022149 A1 | 1/2011 | Cox et al. |
| 2011/0054596 A1 | 3/2011 | Taylor |
| 2011/0137331 A1 | 6/2011 | Walsh et al. |
| 2011/0160846 A1 | 6/2011 | Bishop et al. |
| 2012/0059458 A1 | 3/2012 | Buchbinder et al. |
| 2012/0078347 A1* | 3/2012 | Braido ............... A61F 2/915<br>623/1.26 |
| 2012/0078353 A1* | 3/2012 | Quadri ............... A61F 2/2436<br>623/2.14 |
| 2012/0123529 A1 | 5/2012 | Levi et al. |
| 2012/0150287 A1 | 6/2012 | Forster et al. |
| 2012/0239142 A1 | 9/2012 | Liu et al. |
| 2012/0283820 A1 | 11/2012 | Tseng et al. |
| 2013/0030519 A1 | 1/2013 | Tran et al. |
| 2013/0035636 A1 | 2/2013 | Beasley et al. |
| 2013/0190865 A1 | 7/2013 | Anderson |
| 2013/0204311 A1 | 8/2013 | Kunis |
| 2013/0274855 A1 | 10/2013 | Stante et al. |
| 2013/0310918 A1 | 11/2013 | Taylor et al. |
| 2013/0317598 A1 | 11/2013 | Rowe et al. |
| 2014/0012373 A1 | 1/2014 | Chau et al. |
| 2014/0074299 A1 | 3/2014 | Endou et al. |

(56) References Cited

U.S. PATENT DOCUMENTS

| | | |
|---|---|---|
| 2014/0081394 A1 | 3/2014 | Keranen et al. |
| 2014/0155996 A1 | 6/2014 | Wilson et al. |
| 2014/0163669 A1 | 6/2014 | Ben-Zvi et al. |
| 2014/0172070 A1 | 6/2014 | Seguin |
| 2014/0222142 A1 | 8/2014 | Kovalsky et al. |
| 2014/0257452 A1 | 9/2014 | Slazas et al. |
| 2014/0296962 A1 | 10/2014 | Cartledge et al. |
| 2014/0316513 A1 | 10/2014 | Tang |
| 2014/0358222 A1 | 12/2014 | Gorman, III et al. |
| 2014/0379074 A1 | 12/2014 | Spence et al. |
| 2015/0025623 A1 | 1/2015 | Granada et al. |
| 2015/0100114 A1 | 4/2015 | Shahriari |
| 2015/0173897 A1 | 6/2015 | Raanani et al. |
| 2015/0190227 A1 | 7/2015 | Johnson et al. |
| 2015/0230921 A1 | 8/2015 | Chau et al. |
| 2015/0245910 A1 | 9/2015 | Righini et al. |
| 2015/0282931 A1 | 10/2015 | Brunnett et al. |
| 2015/0335428 A1 | 11/2015 | Keranen |
| 2015/0335429 A1* | 11/2015 | Morriss .............. A61F 2/2409 623/2.4 |
| 2015/0335430 A1 | 11/2015 | Loulmet et al. |
| 2015/0374493 A1 | 12/2015 | Yaron et al. |
| 2016/0015514 A1 | 1/2016 | Lashinski et al. |
| 2016/0074165 A1 | 3/2016 | Spence et al. |
| 2016/0095705 A1 | 4/2016 | Keranen et al. |
| 2016/0143732 A1 | 5/2016 | Glimsdale |
| 2016/0184095 A1 | 6/2016 | Spence et al. |
| 2016/0199177 A1 | 7/2016 | Spence et al. |
| 2016/0256276 A1 | 9/2016 | Yaron |
| 2016/0346080 A1 | 12/2016 | Righini et al. |
| 2017/0007399 A1 | 1/2017 | Keranen |
| 2017/0007402 A1 | 1/2017 | Zerkowski et al. |
| 2017/0065415 A1 | 3/2017 | Rupp et al. |
| 2017/0217385 A1 | 8/2017 | Rinkleff et al. |
| 2017/0231756 A1 | 8/2017 | Armer et al. |
| 2017/0266005 A1 | 9/2017 | McGuckin, Jr. |
| 2017/0273788 A1 | 9/2017 | O'Carroll et al. |
| 2017/0273789 A1 | 9/2017 | Yaron et al. |
| 2017/0281337 A1 | 10/2017 | Campbell |
| 2017/0360426 A1 | 12/2017 | Hacohen et al. |
| 2018/0000580 A1 | 1/2018 | Wallace et al. |
| 2018/0085217 A1 | 3/2018 | Lashinski et al. |
| 2018/0153689 A1 | 6/2018 | Maimon et al. |
| 2018/0206074 A1 | 7/2018 | Tanasa et al. |
| 2018/0289481 A1 | 10/2018 | Dolan |
| 2018/0303606 A1 | 10/2018 | Rothstein et al. |
| 2018/0318073 A1 | 11/2018 | Tseng et al. |
| 2018/0318080 A1 | 11/2018 | Quill et al. |
| 2018/0344456 A1 | 12/2018 | Barash et al. |
| 2020/0054453 A1 | 2/2020 | Zerkowski et al. |
| 2020/0360143 A1 | 11/2020 | O'Carroll et al. |
| 2021/0212826 A1 | 7/2021 | Zerkowski et al. |
| 2021/0361426 A1 | 11/2021 | Hacohen |
| 2023/0086853 A1 | 3/2023 | Zerkowski et al. |
| 2023/0201015 A1* | 6/2023 | Gurovich .............. A61F 2/2409 623/2.11 |

FOREIGN PATENT DOCUMENTS

| | | |
|---|---|---|
| DE | 19907646 A1 | 8/2000 |
| EP | 0592410 B1 | 10/1995 |
| EP | 0850607 A1 | 7/1998 |
| EP | 1432369 | 6/2004 |
| EP | 1521550 | 4/2005 |
| EP | 1296618 B1 | 1/2008 |
| EP | 1827314 B1 | 12/2010 |
| EP | 2620125 A1 | 7/2013 |
| EP | 2726018 | 5/2014 |
| EP | 2747708 A1 | 7/2014 |
| EP | 2806829 | 12/2014 |
| EP | 3395296 A1 | 10/2018 |
| FR | 2815844 A1 | 5/2002 |
| JP | 2004000464 A | 1/2004 |
| JP | 2007509698 A | 4/2007 |
| JP | 2008541886 A | 11/2008 |
| JP | 2009508641 A | 3/2009 |
| JP | 2013540481 A | 11/2013 |
| JP | 2014171894 A | 9/2014 |
| JP | 2015504698 A | 2/2015 |
| JP | 2018505740 A | 3/2018 |
| WO | 9117720 A1 | 11/1991 |
| WO | 9829057 A1 | 7/1998 |
| WO | 9912483 A1 | 3/1999 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 02060352 | 8/2002 |
| WO | 03028558 A2 | 4/2003 |
| WO | 03030776 A2 | 4/2003 |
| WO | 03047468 A1 | 6/2003 |
| WO | 2004019825 A1 | 3/2004 |
| WO | 2005084595 A1 | 9/2005 |
| WO | 2006011127 A2 | 2/2006 |
| WO | 2006032051 A2 | 3/2006 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2009155561 A2 | 12/2009 |
| WO | 2010121076 A2 | 10/2010 |
| WO | 2012009006 A1 | 1/2012 |
| WO | 2012063228 A1 | 5/2012 |
| WO | 2013028387 A2 | 2/2013 |
| WO | 2013059747 A1 | 4/2013 |
| WO | 2013110722 A2 | 8/2013 |
| WO | 2013114214 A2 | 8/2013 |
| WO | 2015023579 A1 | 2/2015 |
| WO | 2015023862 A2 | 2/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016128983 A1 | 8/2016 |
| WO | 2016130820 A1 | 8/2016 |
| WO | 2017103833 A1 | 6/2017 |
| WO | 2019006387 A1 | 1/2019 |

* cited by examiner

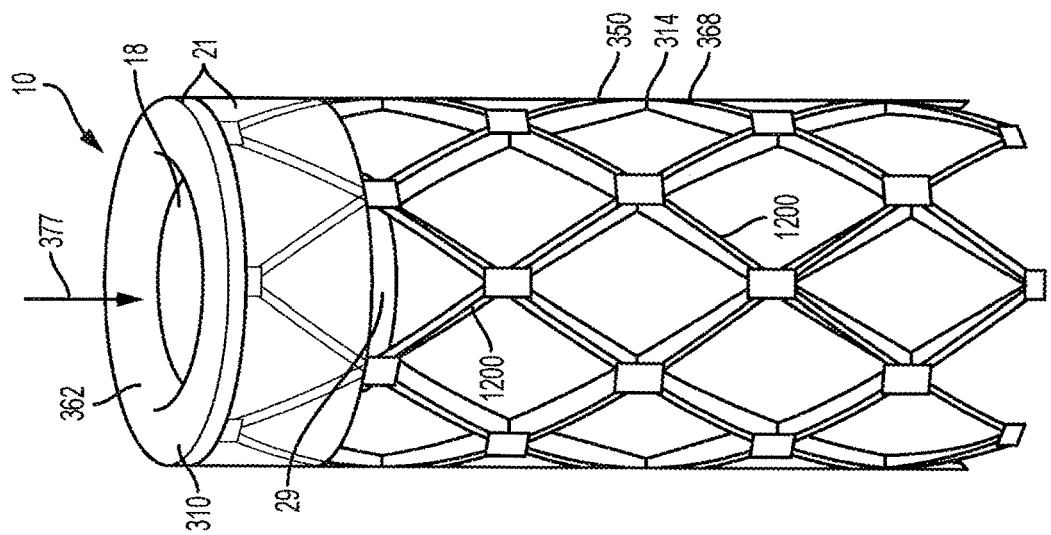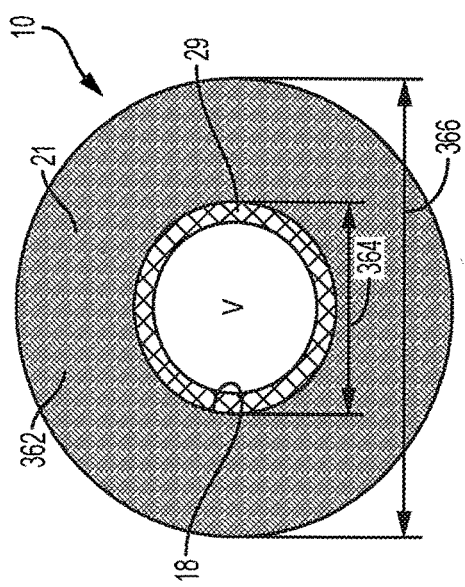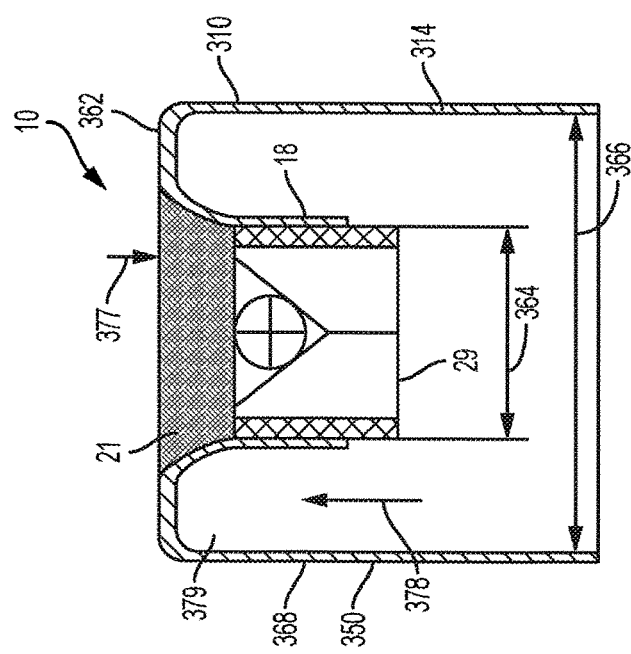

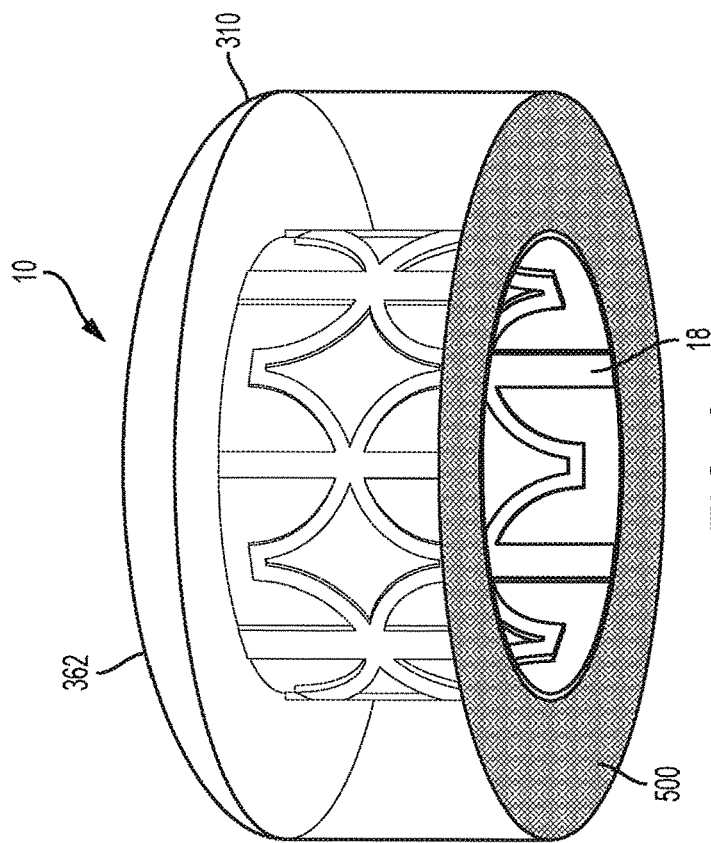
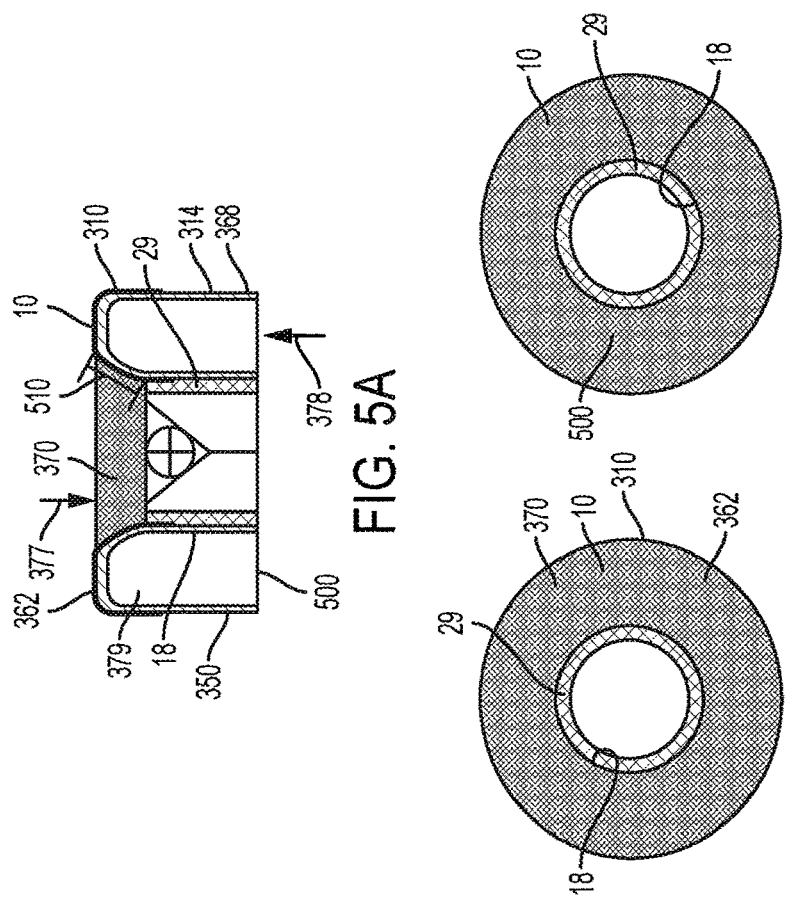

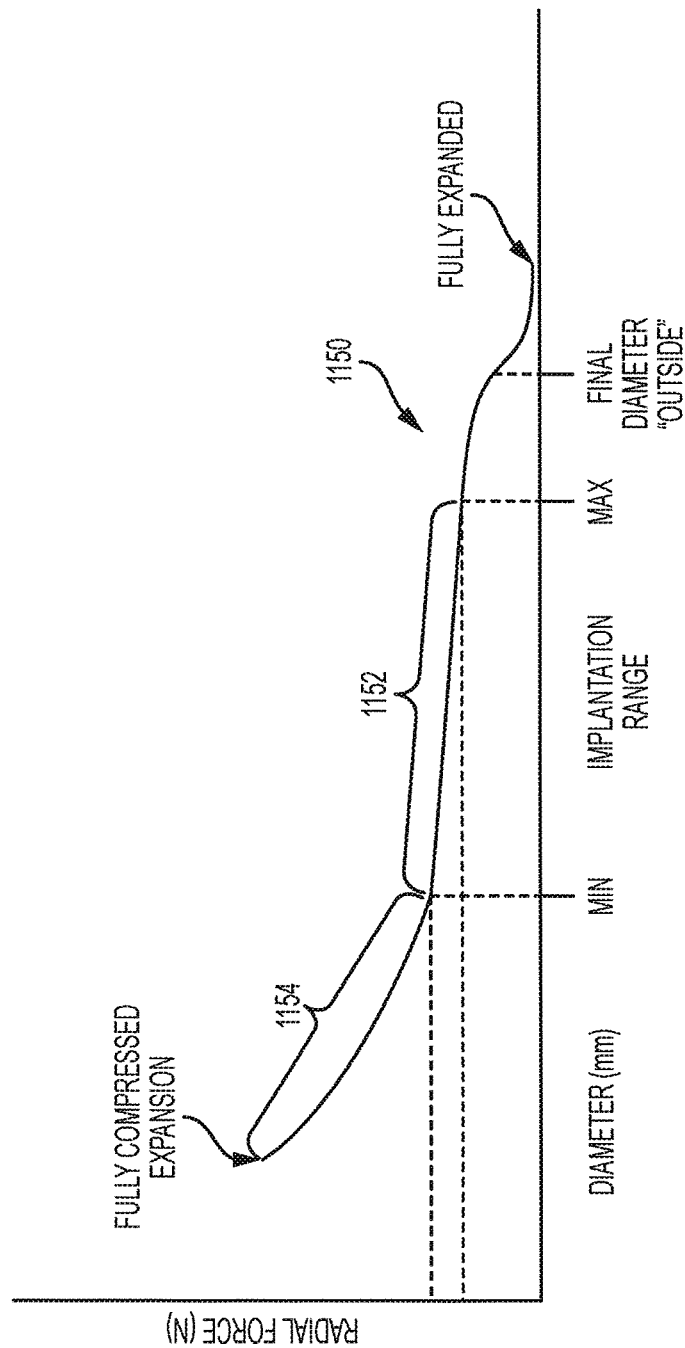

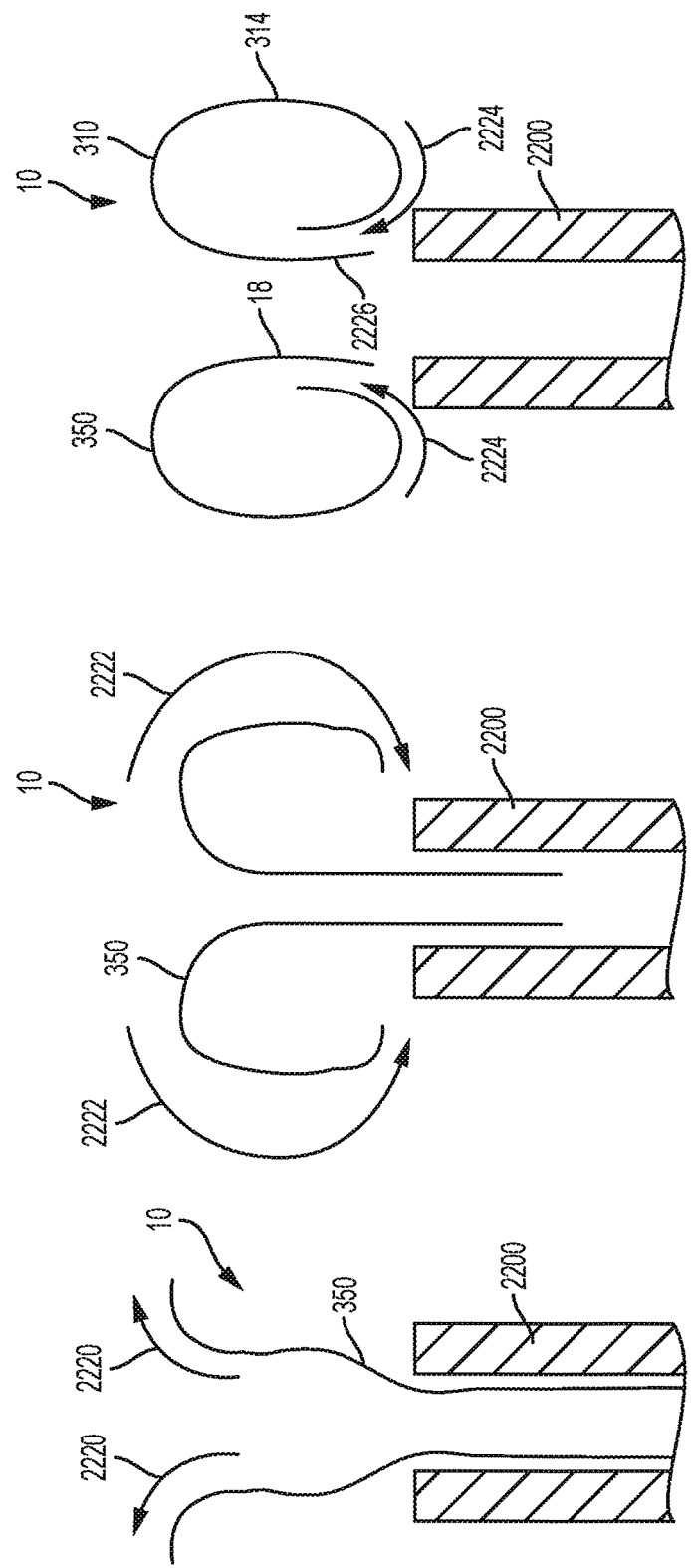

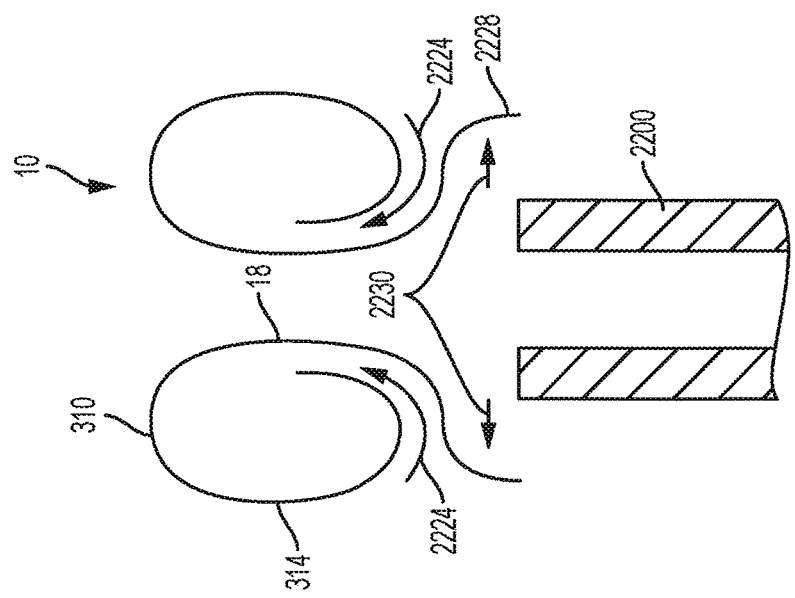
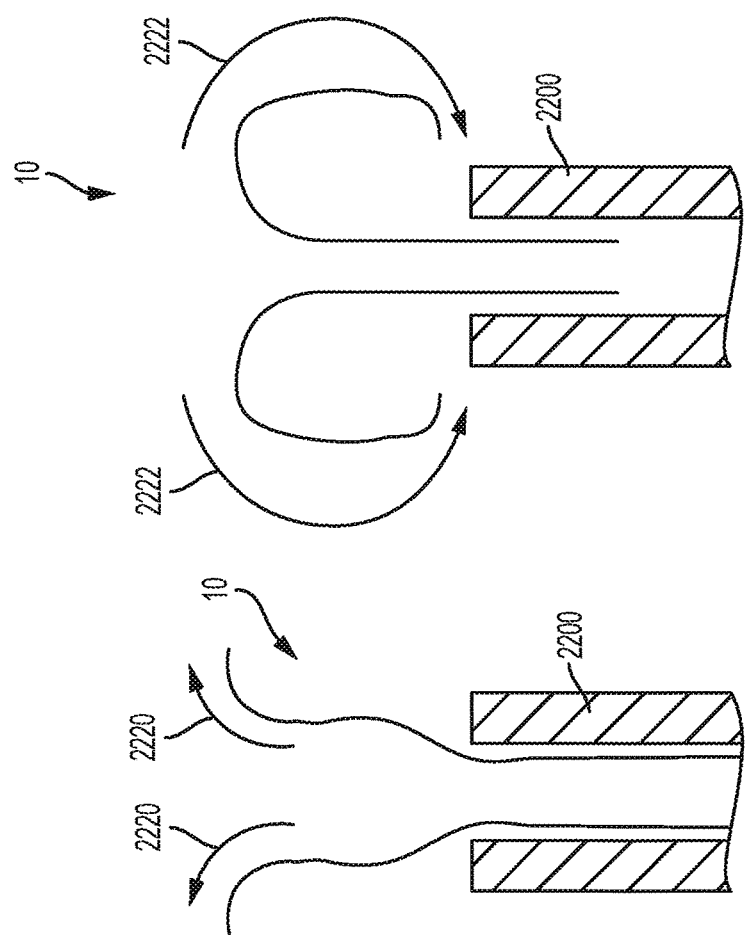
FIG. 23C
FIG. 23B
FIG. 23A

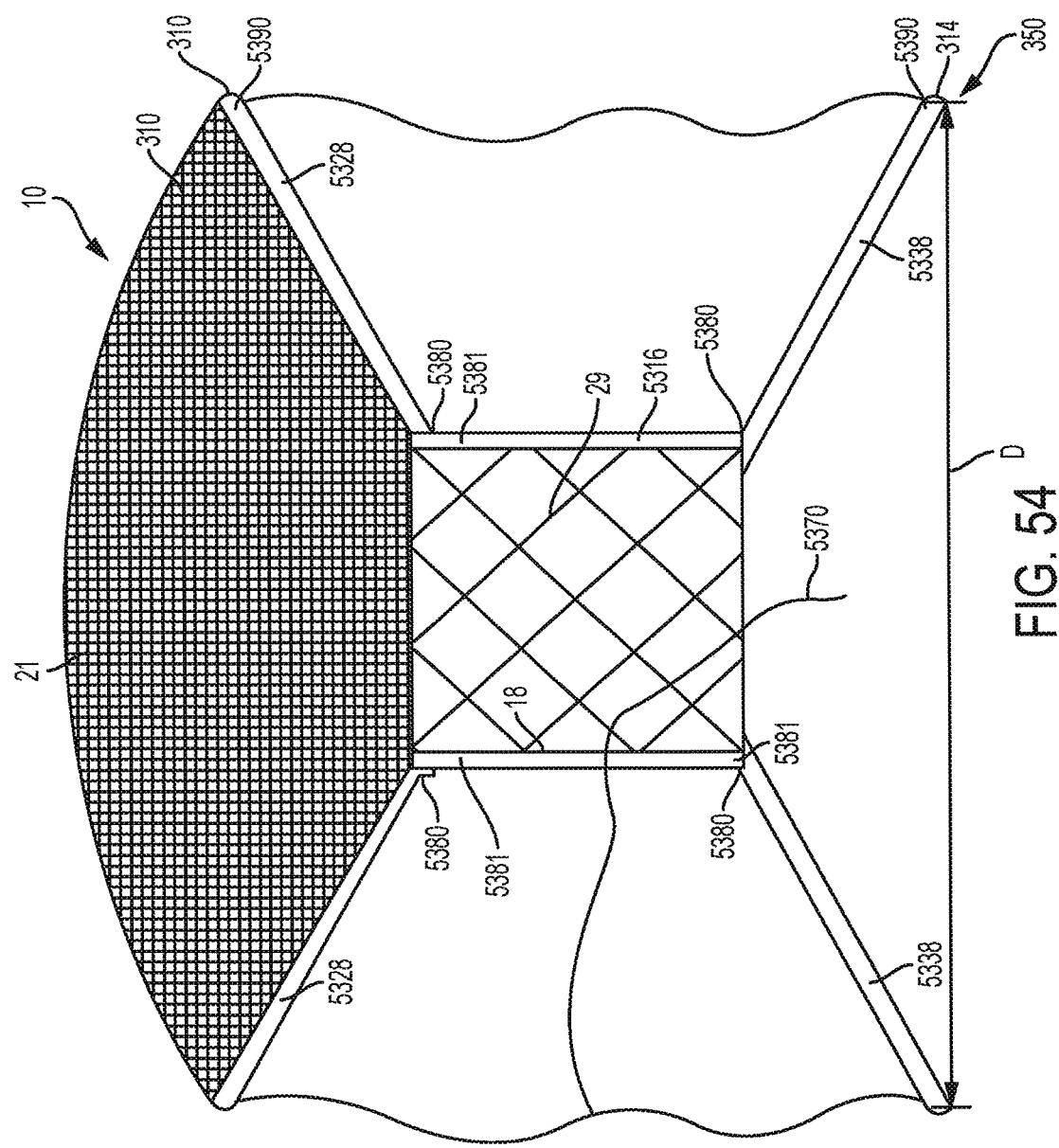

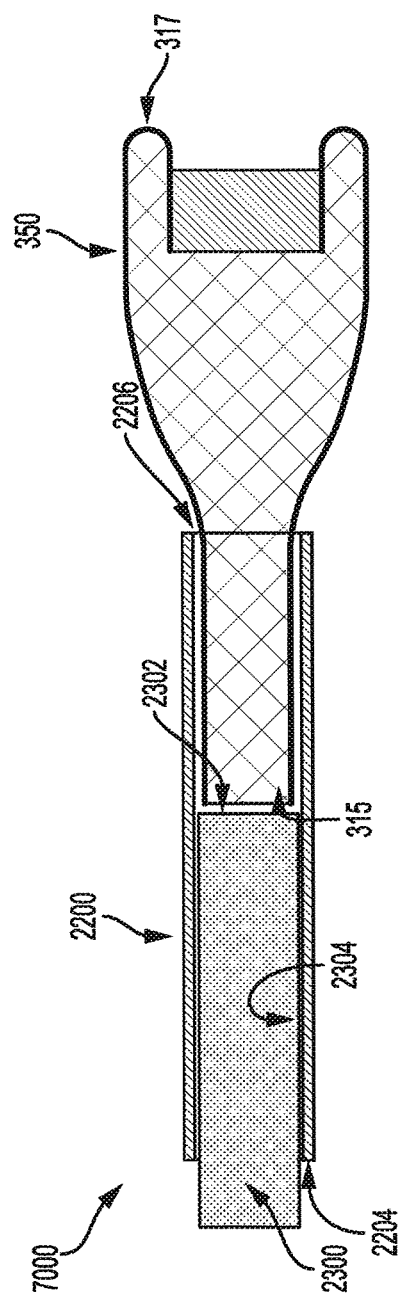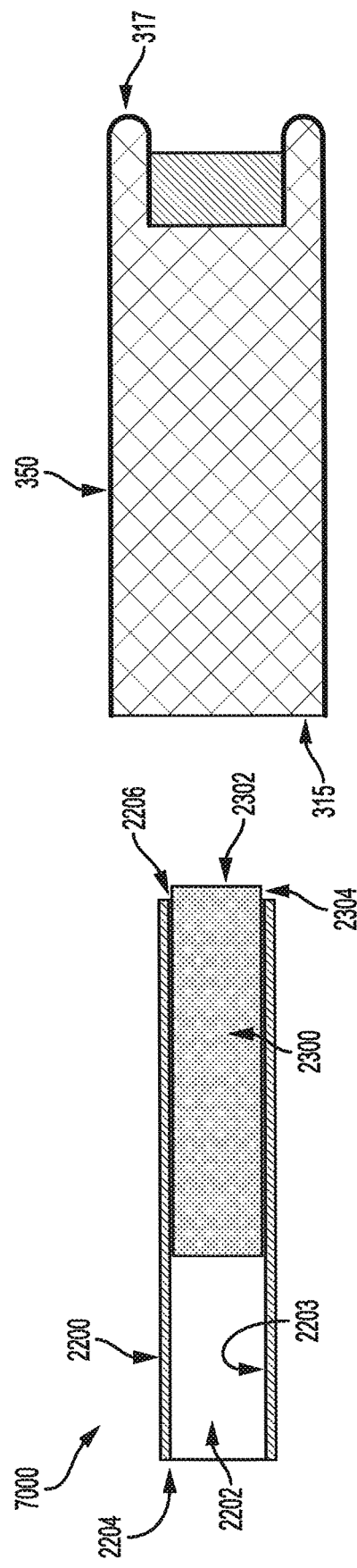
FIG. 66A
FIG. 66B

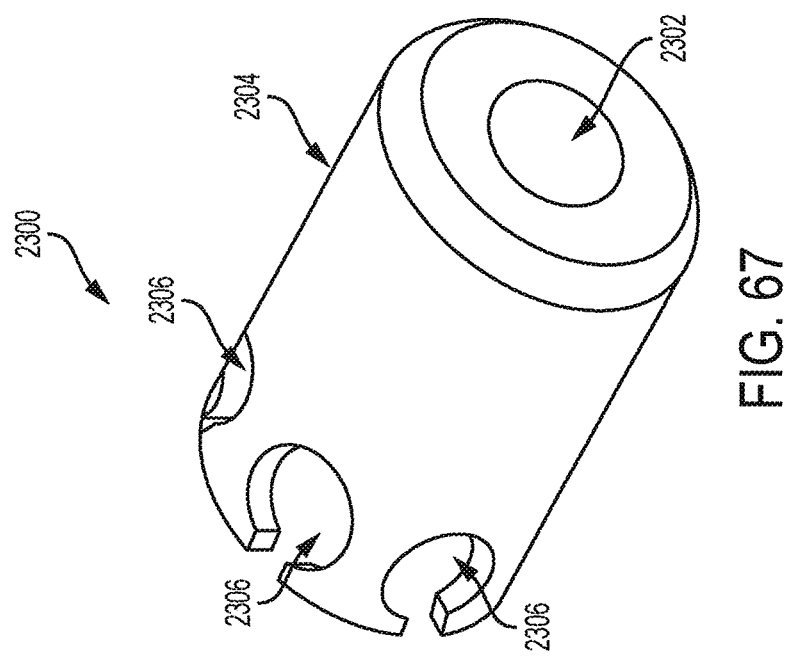

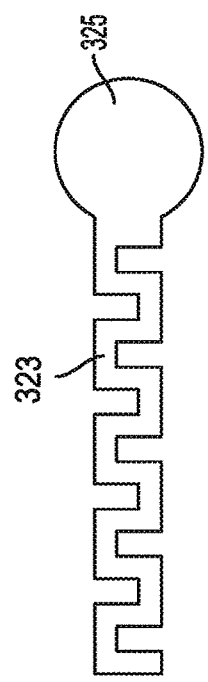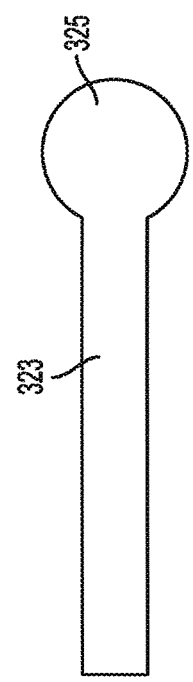

DOCKING STATIONS FOR TRANSCATHETER VALVES

CROSS-REFERENCE

The present application is a continuation of U.S. Ser. No. 16/034,794, filed on Jul. 13, 2018, issued as U.S. Pat. No. 11,291,540, which is a continuation of International Application No. PCT/US2018/040425 filed Jun. 29, 2018, which claims priority to U.S. Provisional Patent Application No. 62/527,577, filed Jun. 30, 2017, U.S. Provisional Patent Application No. 62/529,996, filed Jul. 7, 2017, and U.S. Provisional Patent Application No. 62/529,902, filed Jul. 7, 2017. The entire disclosures of the foregoing are incorporated herein by reference in their entirety.

BACKGROUND OF THE INVENTION

Prosthetic heart valves can be used to treat cardiac valvular disorders. The native heart valves (the aortic, pulmonary, tricuspid, and mitral valves) function to prevent backward flow or regurgitation, while allowing forward flow. These heart valves can be rendered less effective by congenital, inflammatory, infectious conditions, etc. Such conditions can eventually lead to serious cardiovascular compromise or death. For many years, the doctors attempted to treat such disorders with surgical repair or replacement of the valve during open heart surgery.

A transcatheter technique for introducing and implanting a prosthetic heart valve using a catheter in a manner that is less invasive than open heart surgery can reduce complications associated with open heart surgery. In this technique, a prosthetic valve can be mounted in a crimped state on the end portion of a catheter and advanced through a blood vessel of the patient until the valve reaches the implantation site. The valve at the catheter tip can then be expanded to its functional size at the site of the defective native valve, such as by inflating a balloon on which the valve is mounted or, for example, the valve can have a resilient, self-expanding stent or frame that expands the valve to its functional size when it is advanced from a delivery sheath at the distal end of the catheter. Optionally, the valve can have a balloon-expandable, self-expanding, mechanically-expandable frame, and/or a frame expandable in multiple or a combination of ways.

Transcatheter heart valves (THVs) may be appropriately sized to be placed inside many native aortic valves. However, with larger native valves, blood vessels (e.g., an enlarged aorta), grafts, etc., aortic transcatheter valves might be too small to secure into the larger implantation or deployment site. In this case, the transcatheter valve may not be large enough to sufficiently expand inside the native valve or other implantation or deployment site or the implantation/deployment site may not provide a good seat for the THV to be secured in place. As one example, aortic insufficiency can be associated with difficulty securely implanting a THV in the aorta and/or aortic valve.

SUMMARY OF THE DISCLOSURE

This summary is meant to provide examples and is not intended to limit the scope of the invention in any way. For example, any feature included in an example of this summary is not required by the claims, unless the claims explicitly recite the feature. The description discloses exemplary embodiments of trans-catheter implantable device frames, and docking stations or docking devices for trans-catheter implantable devices. The trans-catheter implantable device frames and docking stations/devices can be constructed in a variety of ways. A trans-catheter device frame can include a device such as a valve. A docking station or docking device provides a landing zone for a transcatheter device, such as a transcatheter valve.

Docking stations/devices for use in the body or a circulatory system of the body (e.g., a heart, native heart valve, blood vessel, vasculature, artery, vein, aorta, inferior vena cava (IVC), superior vena cava (SVC), pulmonary artery, aortic valve, pulmonary valve, mitral valve, tricuspid valve, etc.) can include at least one sealing portion, frame, and valve seat. The docking station and its frame can be configured or shaped to conform to a shape of a portion of the body in which it is to be implanted, such as to a shape of an aorta, IVC, SVC, etc. For example, the docking stations and frames herein can be configured to conform to an interior shape of circulatory system (e.g., a blood vessel, aorta, IVC, SVC, pulmonary artery, etc.) when expanded inside the circulatory system such that the expandable frame can expand in multiple locations (e.g., 2, 3, 4, 5, 6, 7, 8, or more) to conform to multiple bulges of the circulatory system and/or can contracts (e.g., is less expanded, has a smaller diameter, etc.) in multiple locations (e.g., 2, 3, 4, 5, 6, 7, 8, or more) to conform to multiple narrowed regions of the circulatory system. Further, whether the anatomy is varied or more uniform, the docking stations and frames herein can be configured such that, when expanded inside the circulatory system, the majority (e.g., more than 50%), more than 60%, more than 70%, more than 80%, or more of the docking station contacts an interior surface of the circulatory system and distributes the pressure and force exerted by the docking station over the portion or length of the docking station in contact with the interior surface. This can be helpful, for example, in treating aortic insufficiency caused by an enlarging of the aortic valve and/or aorta.

The sealing portion(s) of the various docking stations/devices herein can be formed and configured in any of the ways described in this disclosure, for example, the sealing portion(s) can be integrally formed with the frame, include a covering/material attached to the frame, or include a combination of integral and attached elements/components. The sealing portion can be configured to contact an interior surface of the circulatory system (e.g., of a blood vessel, vasculature, aorta, IVC, SVC, heart, native heart valve, aortic valve, pulmonary valve, mitral valve, tricuspid valve, etc.).

The frame(s) of the various docking stations herein can be made and configured in any of the ways described in this disclosure, for example, the frame(s) can be made from nitinol, elgiloy, stainless steel, and combinations thereof. The frame can be an expandable frame, e.g., self-expandable, manually-expandable (e.g., balloon-expandable), mechanically expandable, or a combination of these). The frame can be configured to conform to an interior shape of a portion of a circulatory system (e.g., of a blood vessel, vasculature, heart, native heart valve, etc.) when expanded inside the circulatory system.

Optionally, the frame can comprise a plurality of spring segments connected to a plurality of stent segments. The spring elements can comprise spring wire and can be compression springs, torsion springs, or tension springs. The stent segments can be integrally formed with the spring elements or attached to the spring elements.

Similarly, the valve seat(s) of the various docking stations herein can also be formed and configured in any of the ways described in this disclosure, for example, the valve seat(s) be integrally formed with the frame, be separately attached, or include a combination of integral and attached elements/components. The valve seat can be connected to the expandable frame. The valve seat can be configured to support a prosthetic valve (e.g., an expandable transcatheter valve, transcatheter heart valve, transcatheter aortic valve, expandable valve, etc.).

The docking stations/devices described above and elsewhere herein can be used to form a docking assembly or system, e.g., including a graft or other elements. For example, a docking assembly/system (e.g., a docking device assembly, docking station assembly, docking device system, etc.) can include a graft and a docking station/device. The graft can be shaped to conform to a portion of an interior shape of a first portion of a blood vessel (e.g., vein, artery, aorta, etc.). The docking station/device and the graft can be coupled to each other. A portion of the docking station/device can engage an interior of the graft.

Various docking stations/devices described herein can be used in the assembly and can include an expandable frame, at least one sealing portion, and a valve seat as discussed above, and each of these can include features of these types of components described elsewhere herein. The expandable frame can be configured to conform to an interior shape of a second portion of the blood vessel when expanded inside the blood vessel. The sealing portion can be configured to contact an interior surface of the circulatory system or blood vessel. The sealing portion can include a covering/material or fabric attached to the frame. The valve seat can be part of and/or connected to the expandable frame and can be configured to support a prosthetic valve (e.g., an expandable transcatheter valve, transcatheter heart valve, aortic valve, expandable valve, etc.).

The docking assembly/system can optionally be integrally formed with a valve, e.g., such that the docking station/device and valve combination is a prosthetic valve or transcatheter prosthetic valve that can be implanted in the same step.

In one embodiment, a docking station comprises an expandable frame configured to conform to an interior shape of a blood vessel (and/or other part of the circulatory system) when expanded inside the blood vessel. The docking station can comprise at least one sealing portion configured to contact an interior surface of the blood vessel. The docking station comprises a valve seat, wherein the valve seat is configured to support a prosthetic valve or expandable transcatheter valve. The valve seat can be located in radially inside the outer wall of the frame, e.g., overlapping in a radial direction, or can be axially spaced from the outer wall so there is no overlap in the radial direction. The valve seat can be coaxial with the outer wall of the frame.

The valve seat may comprise a first portion of the expandable frame (which can be annular), and links can connect the first portion of the expandable frame to a second portion of the expandable frame, the second portion comprising an outer wall (which can be annular). The links can be curved, e.g., such as in a semi-circular shape, an undulating shape, etc. The entire frame and/or an outer wall of the frame can comprise a plurality of struts. A thickness of the links may be the same as or less than a thickness of the struts. The links and the struts can be integrally formed, and a transition portion may transition from the thickness of the links to the thickness of the struts.

An apex of the links can be bent such that portions of the links on opposite sides of the apex extend away from each other at an acute angle. The apex of the links can include an upwardly extending circular portion and/or a downwardly extending circular portion. The links can extend from the first portion of the expandable frame to the second portion at an angle with respect to a radial direction. The links can be twisted as they extend from the valve seat to the annular wall.

A tubular graft can be coupled to the expandable frame, and the graft can be configured to extend axially beyond an end of the expandable frame. The frame can comprise a plurality of stent segments connected to a plurality of spring elements. The spring elements consist of spring wires, compression springs, torsion springs, tension springs, and combinations thereof. The struts of the expandable frame can be integrally formed with the spring elements. The sealing portion and/or valve seat can be integrally formed with the frame. The expandable frame can include no legs, only one leg, or multiple legs that extend proximally beyond the remainder of the frame. The frame can include an elongated second leg that extends proximally further than an end of the first leg.

In one embodiment, an expandable docking station frame comprises an annular valve seat having an end, an annular outer wall comprising struts disposed around the valve seat, and links that connect the end of the annular valve seat to the annular outer wall. A thickness of the links can be the same as or less than a thickness of the struts. The links and the struts can be integrally formed, and can have a transition portion that transitions from the thickness of the links to the thickness of the struts. The links are curved, e.g., in a semi-circular shape. An apex of the links can be bent such that portions of the links on opposite sides of the apex extend away from each other at an acute angle. The apex of the links can include an upwardly extending circular portion and/or a downwardly extending circular portion. The links can extend from the first portion of the expandable frame to the second portion at an angle with respect to a radial direction. The links can be twisted as they extend from the valve seat to the annular wall. The expandable frame can include no legs, only one leg, or multiple legs that extend proximally beyond the remainder of the frame. The frame can include an elongated second leg that extends proximally further than an end of the first leg.

In one embodiment, an expandable docking station frame comprises an annular valve seat having an end, an annular outer wall comprising struts disposed around the valve seat, and links that connect the end of the annular valve seat to the annular outer wall. The links can be twisted and/or angled as the links extend between the annular outer wall and the annular valve seat. A thickness of the links can be the same as or less than a thickness of the struts. The frame and its components (e.g., struts, links, etc.) can have the same or similar features to those discussed above and elsewhere herein.

In one embodiment, an expandable docking station frame comprises an annular valve seat having an end, an annular outer wall comprising struts disposed around the valve seat, and links that connect the end of the annular valve seat to the annular outer wall, wherein the links extend from the valve seat to the annular wall at an angle with respect to a radial direction. The links can be twisted and/or angled as the links extend between the annular outer wall and the annular valve seat. A thickness of the links can be the same as or less than a thickness of the struts. The frame and its components (e.g., struts, links, etc.) can have the same or similar features to those discussed above and elsewhere herein.

In one embodiment, a docking station assembly comprises a graft configured to conform to an interior shape of a first portion of a blood vessel when expanded inside the blood vessel, and a docking station coupled to the graft. The docking station can comprise an expandable frame configured to conform to an interior shape of a second portion of the blood vessel when expanded inside the blood vessel. The docking station can comprise at least one sealing portion configured to contact an interior surface of the blood vessel when expanded inside the blood vessel. The docking station can comprise a valve seat, wherein the valve seat is configured to support an expandable transcatheter valve. The graft, frame, sealing portion, and valve seat can have the same or similar features to those discussed above and elsewhere herein.

In one embodiment, a docking station comprises a frame configured to transition from a first configuration to a second configuration, wherein, when in the second configuration, at least a first portion of the frame is curled, and wherein the frame is configured such that as the frame transitions from the first configuration to the second configuration, the frame curls back on itself. The docking station is configured to capture native leaflets of a native valve as the frame curls back on itself. The docking station can be configured such that the native leaflets can be clamped between the valve seat and another portion of the docking station. In one embodiment, when in the second configuration, the first portion of the frame can be curled at least 360 degrees. In the second configuration, the second end can overlap at least a portion of the first end. The first configuration of the frame can be a straightened configuration or a configuration in which no portion of the frame is curled. The frame can be configured to be held in the straightened configuration inside a delivery catheter and prevented from transitioning to the second configuration until exiting the catheter.

The docking station can also comprise a valve seat configured to support an expandable transcatheter valve. The valve seat can be formed by inner struts that extend from a first end of the frame to a junction. The inner struts can form diamond shaped openings. Top and outer struts can extend from the junction to a second end and form continuous openings. The docking station can also comprise at least one sealing portion configured to contact an interior surface of anatomy.

The frame can comprise one or more legs that extend to an end of the frame. The one or more legs can extend from inner struts of the valve seat. The one or more legs can comprise an elongated leg that extends axially further than a shorter leg of the one or more legs.

In one embodiment, a docking station comprises a frame comprising a retaining portion circumscribing an inflow area and a valve seat configured to support an expandable transcatheter valve, wherein the retaining portion has a first diameter larger than a second diameter of the valve seat, and wherein a tapered region transitions between the first diameter and the second diameter. The docking station can comprise at least one sealing portion configured to contact an interior surface of a circulatory system. The tapered region can be configured to transition between the first diameter of the retaining portion and the second diameter of the valve seat in a direction from the inflow area to an outflow area. The frame can comprise a plurality of metal struts that form cells.

The docking station can comprise a band that extends about the valve seat to cause the valve seat to be unexpandable or substantially unexpandable. The valve seat may be configured such that it does not radially overlap any of the retaining portion. The valve seat can be positioned entirely to one axial side of the retaining portion.

The docking station can further comprise an atraumatic outer segment that extends radially outwardly from the valve seat. The outer segment can be round and/or toroidal. The outer segment can comprise a plurality of struts that form cells and/or can comprise a foam material. The docking station can comprise a first sealing portion configured to inhibit blood flow between an atrium-vein junction in the body and the docking station when implanted, and can comprise a second sealing portion configured to inhibit blood flow between the valve seat and a transcatheter valve implanted at the valve seat.

The frame can be configured to conform to an interior shape of blood vessel, when expanded inside the blood vessel, such that the frame can expand in multiple locations to conform to multiple bulges of the blood vessel and multiple narrowed regions of the blood vessel to distribute the pressure on the blood vessel from the docking station over most of the length of the docking station. This can be helpful, for example, in treating aortic insufficiency caused by an enlarging of the aortic valve and/or aorta, e.g., where excessive outward pressure on the aortic valve and/or aorta is desired to be avoided. The docking station can comprise a leg that extends axially at an end of the retaining portion, and can further comprise an elongated leg that extends axially further from the remainder of the retaining portion than the leg.

A system can comprise a first docking station having a first valve seat, a second docking station having a second valve seat, wherein each of the first valve seat and the second valve seat is configured to support an expandable valve (e.g., an expandable transcatheter valve); and a connecting portion connecting the first docking station and the second docking station together to form a dual docking station. The system can comprise at least one sealing portion or multiple sealing portions configured to contact one or more interior surfaces of a circulatory system. The connecting portion can be configured to allow blood to freely flow through the connecting portion when the system is implanted in a body. The connecting portion can be integrally formed with the first docking station and the second docking station.

The dual docking station can be configured such that the first docking station can be implanted in an inferior vena cava of a body and the second docking station can be deployed in a superior vena cava of the body, with a first valve expanded within the first valve seat and a second valve expanded within the second valve seat. The dual docking station can be configured such that the first docking station can be implanted in an inferior vena cava of a body and the second docking station can be deployed in a superior vena cava of the body, with only one of the first docking station and the second docking station receiving an expandable valve therein.

The system can comprise a first valve expandable within the first valve seat such that the first valve is securely held in the first valve seat. The system can comprise a second valve expandable within the second valve seat such that the second valve is securely held in the second valve seat.

The system and/or dual docking station can be configured to be adjustable in overall length inside a circulatory system at an implantation site, for example, such that the dual docking station can be sized during delivery to fit different anatomy (e.g., various distances between the IVC and SVC of different patients). Other features and components of dual docking stations described elsewhere herein can also be incorporated.

A docking deployment system/assembly (e.g., a docking station deployment system, docking device deployment system, etc.) can comprise a catheter defining a delivery passage and having a distal opening. The deployment system can also include a self-expandable docking station capable of being radially compressed and expanded, e.g., between a first configuration and a second configuration or between a compressed configuration and an expanded configuration. The docking station can be configured to be held in a compressed configuration inside the delivery passage of the catheter, e.g., until delivery at an implantation site. The deployment system includes a retention device releasably connectable to the docking station. The retention device can be configured to inhibit the docking station from jumping distally out of the catheter. The retention device can be configured to inhibit the docking station from moving axially relative to the retention device and/or a proximal handle of the system. The retention device can be configured to maintain the axial position of the docking station until the docking station is fully expanded at an implantation site. In one embodiment, the retention device is a pusher having a distal end connectable to a proximal end of the docking station. Features and components of other docking deployment systems/assemblies described herein can be included as well.

The docking station can include at least one leg that extends proximally at a proximal end of the docking station and is releasably connectable to the retention device. The docking station can include multiple legs that extends proximally at a proximal end of the docking station, and the multiple legs can be spaced evenly radially around the proximal end of the docking station. The docking station includes only one leg that extends proximally at a proximal end of the docking station and is releasably connectable to the retention device, such that the docking station can fully expand while the one leg is connected to the retention device and then be released.

The docking station can include a first leg and a second leg that each extend proximally at a proximal end of the docking station and are releasably connectable to the retention device, wherein the first leg is longer than the second leg. The retention device, the first leg, and the second leg can be configured such that during delivery the retention device first releases the second leg to allow docking station to fully expand while the first leg is still connected to the retention device.

The retention device can comprise a lock and release connector having a body and a door, wherein the door is moveable from a first position to a second position. The lock and release connector can have a second door moveable from a third position to a fourth position, and wherein the lock and release connector is configured such that it can hold a first leg of the docking station between the door and the body in the first position and can hold a second leg of the docking station between the second door and the body in the third position. The retention device can comprise a lock and release connector having a body and a door, wherein the door is moveable from a first position to a second position, and wherein the retention device is connected to the docking station when the leg is between the door and the body and the door is in the first position. The retention device can be configured to release the leg when the door is moved to the second position.

The retention device can comprise a retaining line usable to maintain the position of the docking station as the docking station is deployed from the catheter and fully radially expanded.

The retention device comprises a pin (or narrowed portion of a pusher, inner shaft, etc.) that extends inside of at least a proximal end of the docking station and can inhibit the docking station from jumping out of a distal end of the catheter. The pin can be configured to inhibit the docking station from jumping out of the distal end of the catheter by inhibiting the proximal end of the docking station from angling out of parallel (e.g., with respect to the inner surface of the catheter and/or the outer surface of the pin/pusher/shaft).

Various features as described elsewhere in this disclosure can be included in the examples summarized here and various methods and steps for using the examples and features can be used, including as described elsewhere herein.

Further understanding of the nature and advantages of the disclosed inventions can be obtained from the following description and claims, particularly when considered in conjunction with the accompanying drawings in which like parts bear like reference numerals.

BRIEF DESCRIPTION OF THE DRAWINGS

Further understanding of the nature and advantages of the disclosed inventions can be obtained from the following description and claims, particularly when considered in conjunction with the accompanying drawings in which like parts bear like reference numerals.

To further clarify various aspects of embodiments of the present disclosure, a more particular description of the certain embodiments will be made by reference to various aspects of the appended drawings. These drawings depict only exemplary embodiments of the present disclosure and are therefore not to be considered limiting of the scope of the disclosure. Moreover, while the figures may be drawn to scale for some embodiments, the figures are not necessarily drawn to scale for all embodiments. Embodiments of the present disclosure will be described and explained with additional specificity and detail through the use of the accompanying drawings.

FIG. 3A is a sectional view of an exemplary embodiment of a docking station with an exemplary transcatheter valve disposed inside the docking station;

FIG. 3B is a top view of the docking station and valve illustrated by FIG. 3A;

FIG. 3C is a perspective view of an exemplary embodiment of a docking station that illustrates an example of a frame portion that can be used in the docking station of FIGS. 3A-3B;

FIG. 5A is a sectional view of an exemplary embodiment of a docking station with an exemplary transcatheter valve disposed inside the docking station;

FIG. 5B is a top view of the docking station and valve illustrated by FIG. 5A;

FIG. 5C is a bottom view of the docking station and valve illustrated by FIG. 5A;

FIG. 6 is a perspective view of an exemplary embodiment of a docking station;

FIG. 11 is a graph illustrating a relationship between radially outward force and the expanded diameter of a docking station frame;

FIGS. 22A-22C illustrate an exemplary deployment of an exemplary docking station;

FIGS. 23A-23C illustrate an exemplary deployment of an exemplary docking station;

FIG. 54 is a schematic illustration of an exemplary embodiment of a docking station;

FIGS. 66A and 66B schematically illustrate outward radial expansion of a docking station as the docking station is deployed;

FIG. 67 is a perspective view of an exemplary distal end of an exemplary pusher or retention device;

FIG. 69A is a side view of an exemplary embodiment of an extension of a frame, e.g., the frame of FIG. 68A, 68B, or 68C;

FIG. 69B is a side view of an exemplary embodiment of an extension of a frame, e.g., the frame of FIG. 68A, 68B, or 68C;

DETAILED DESCRIPTION

The following description refers to the accompanying drawings, which illustrate specific embodiments of the invention. Other embodiments having different structures and operation do not depart from the scope of the present invention. Exemplary embodiments of the present disclosure are directed to devices and methods for providing a docking station/device or landing zone for a prosthetic valve (e.g., a transcatheter valve, such as a transcatheter heart valve), e.g., valve 29. In some exemplary embodiments, docking stations/devices for prosthetic valves or THVs are illustrated as being used within the superior vena cava (SVC), inferior vena cava (IVC), or both the SVC and the IVC, although the docking stations/devices (e.g., docking station/device 10, other docking stations/devices herein, modified versions of the docking stations, etc.) can be used in other areas of the anatomy, heart, or vasculature, such as the tricuspid valve, the pulmonary valve, the pulmonary artery, the aortic valve, the aorta, the mitral valve, or other locations. The docking stations/devices described herein can be configured to compensate for the deployed transcatheter valve or THV being smaller and/or having a different geometrical shape than the space (e.g., anatomy/heart/vasculature/etc.) in which it is to be placed. For example, the native anatomy (e.g., the IVC) can be oval, egg shaped, or another shape, while the prosthetic valve or THV can be cylindrical.

Various embodiments of docking stations/devices and examples of prosthetic valves or transcatheter valves are disclosed herein, and any combination of these options can be made unless specifically excluded. For example, any of the docking stations/devices disclosed, can be used with any type of valve, and/or any delivery system, even if a specific combination is not explicitly described. Likewise, the different constructions and features of docking stations/devices and valves can be mixed and matched, such as by combining any docking station type/feature, valve type/feature, tissue cover, etc., even if not explicitly disclosed. In short, individual components of the disclosed systems can be combined unless mutually exclusive or physically impossible.

For the sake of uniformity, in these Figures and others in the application the docking stations are typically depicted such that the right atrium end is up, while the ventricular end or IVC end is down unless otherwise indicated.

Figure 1A:
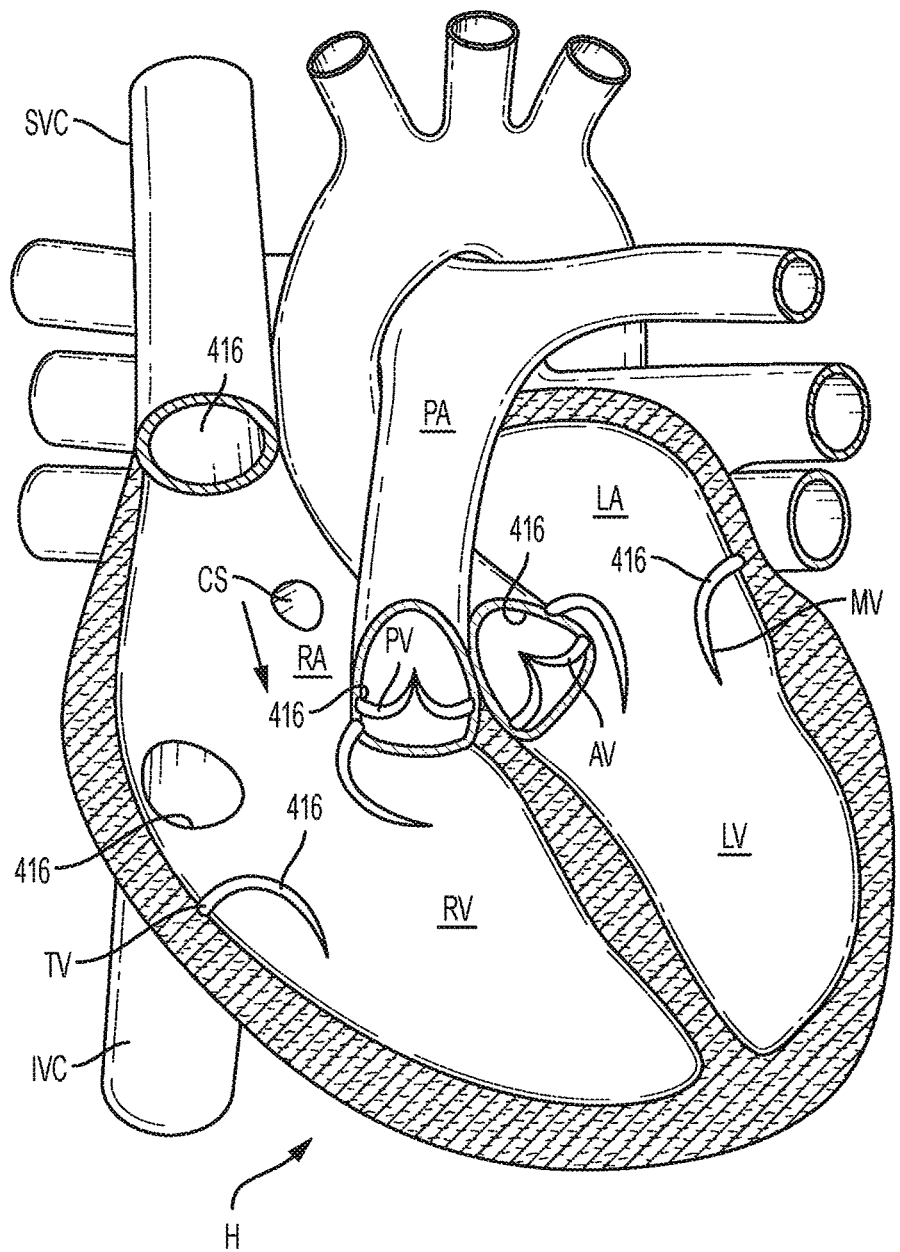
FIG. 1A is a cutaway view of the human heart in a diastolic phase.
Figure 1B:
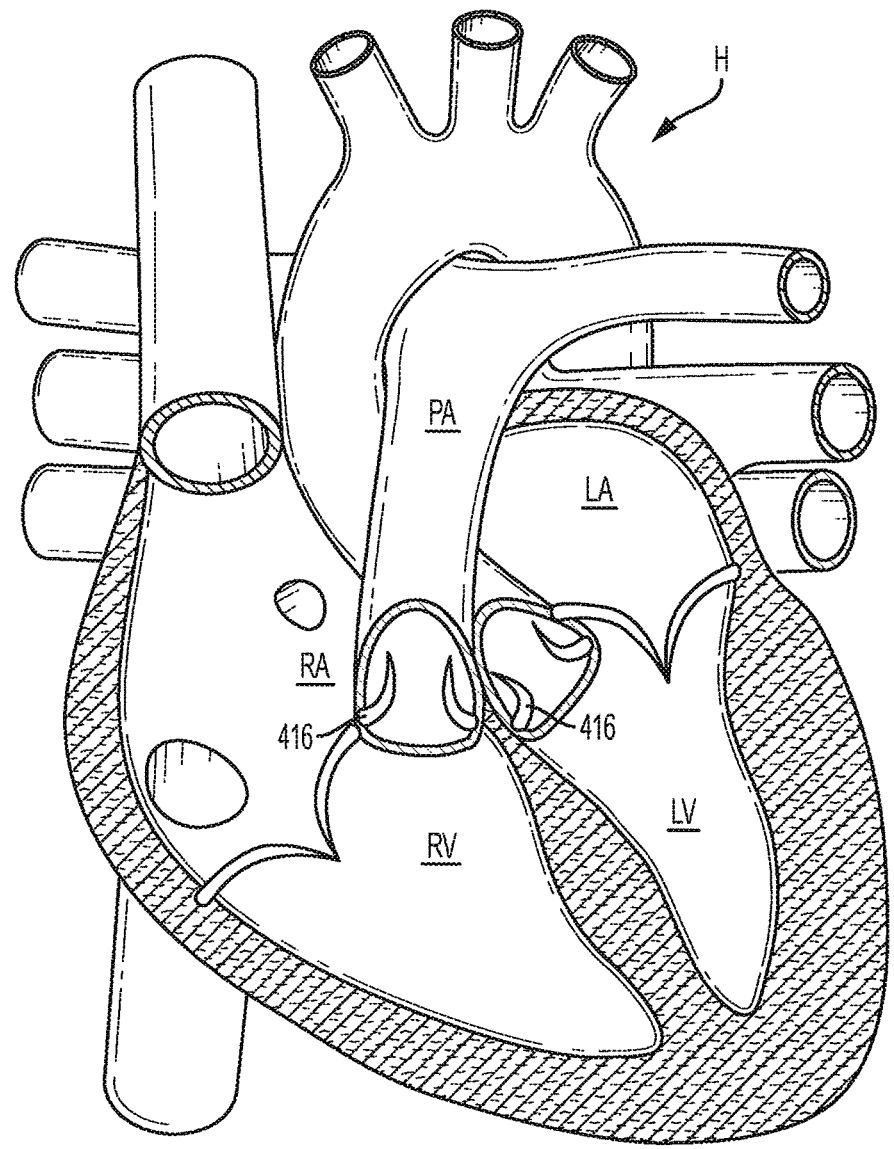
FIG. 1B is a cutaway view of the human heart in a systolic phase.

FIGS. 1A and 1B are cutaway views of the human heart H in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta (not identified) and the pulmonary valve PV separates the right ventricle from the pulmonary artery PA. Each of these valves has flexible leaflets extending inward across the respective orifices that come together or "coapt" in the flowstream to form the one-way, fluid-occluding surfaces. The docking stations and valves of the present application are described, for illustration, primarily with respect to the inferior vena cava IVC, superior vena cava SVC, and aorta/aortic valve. A defective aortic valve, for example, can be a stenotic aortic valve and/or suffer from insufficiency and/or regurgitation. The blood vessels, such as the aorta, IVC, SVC, pulmonary artery, may be healthy or may be dilated, distorted, enlarged, have an aneurysm, or be otherwise impaired. Anatomical structures of the right atrium RA, right ventricle RV, left atrium LA, and left ventricle LV will be explained in greater detail. The devices described herein can be used in various areas whether explicitly described herein or not, e.g., in the IVC and/or SVC, in the aorta (e.g., an enlarged aorta) as treatment for a defective aortic valve, in other areas of the heart or vasculature, in grafts, etc.

The right atrium RA receives deoxygenated blood from the venous system through the superior vena cava SVC and the inferior vena cava IVC, the former entering the right atrium from above, and the latter from below. The coronary sinus CS is a collection of veins joined together to form a large vessel that collects deoxygenated blood from the heart muscle (myocardium), and delivers it to the right atrium RA. During the diastolic phase, or diastole, seen in FIG. 1A, the deoxygenated blood from the IVC, SVC, and CS that has collected in the right atrium RA passes through the tricuspid valve TV and into the RV as the right ventricle RV expands. In the systolic phase, or systole, seen in FIG. 1B, the right ventricle RV contracts to force the deoxygenated blood collected in the RV through the pulmonary valve PV and pulmonary artery into the lungs.

The devices described by the present application can be used to supplement the function of a defective tricuspid valve and/or to prevent too much pressure from building up in the RA. During systole, the leaflets of a normally functioning tricuspid valve TV close to prevent the venous blood from regurgitating back into the right atrium RA. When the tricuspid valve does not operate normally, blood can backflow or regurgitate into the right atrium RA, the inferior vena cava IVC, the superior vena cava SVC, and/or other vessels in the systolic phase. Blood regurgitating backward into the right atrium increases the volume of blood in the atrium and the blood vessels that direct blood to the heart. This can cause the right atrium to enlarge and cause blood pressure to increase in the right atrium and blood vessels, which can cause damage to and/or swelling of the liver, kidneys, legs, other organs, etc. A transcatheter valve or THV implanted in the inferior vena cava IVC and/or the superior vena cava SVC can prevent or inhibit blood from backflowing into the inferior vena cave IVC and/or the superior vena cava SVC during the systolic phase.

The length L, diameter D, and curvature or contour may vary greatly between the superior vena cava SVC and inferior vena cava IVC of different patients. The relative orientation and location of the IVC and/or SVC can also vary between patients Further, the size or diameter D can vary significantly along the length L of an individual IVC and/or SVC. Also, the anatomy of the IVC and/or SVC is soft, flexible, and dynamic as compared to other cardiac vessels, such as the aorta. This softer, more flexible, and/or more dynamic (moving and/or shape changing) characteristic of the IVC and SVC make it more difficult for a transcatheter valve frame or a docking station that supports a transcatheter valve to anchor in the IVC and/or the SVC than in the aorta. Further, other regions or other vasculature in other areas of the body and across patients where docking stations could be used can also vary significantly in shape and size.

The left atrium LA receives oxygenated blood from the left and right pulmonary veins, which then travels through the mitral valve to the left ventricle. During the diastolic phase, or diastole, seen in FIG. 1A, the oxygen rich blood that collects in the left atrium LA passes through the mitral valve MV by and into the left ventricle LV as the left ventricle LV expands. In the systolic phase, or systole, seen in FIG. 1B, the left ventricle LV contracts to force the oxygen rich blood through the aortic valve AV and aorta into the body through the circulatory system. In one exemplary embodiment, the devices described by the present application are used to supplement or replace the function of a defective aortic valve. For example, the devices herein are particularly effective for treating aortic insufficiency. During diastole, the leaflets of a normally functioning aortic valve AV close to prevent the oxygen rich blood from regurgitating back into the left ventricle LV. When the aortic valve does not operate normally, blood backflows or regurgitates into the left ventricle LV. A THV implanted in the aortic valve helps prevent or inhibit blood from back-flowing into the left ventricle LV during the diastole phase. The length L, diameter, D, and curvature or contour of the aortic root may vary greatly between different patients, especially if the aorta is a dilated, distorted, or enlarged. Further, the size or diameter D may vary significantly along the length L of an individual aorta.

Referring to FIGS. 2, 3A, 3B, and 3C, in one exemplary embodiment an expandable docking station/device 10 includes one or more sealing portions 310, a valve seat 18, and one or more retaining portions 314. The sealing portion(s) 310 provide a seal between the docking station 10 and an interior surface 416 (See FIG. 2) of the circulatory system. The valve seat 18 provides a supporting surface for implanting or deploying a valve 29 in the docking station 10 after the docking station 10 is implanted in the circulatory system. Optionally, the docking station 10 and the valve 29 can be integrally formed, for example, in one embodiment, the valve seat 18 can be omitted. When integrally formed, the docking station 10 and the valve 29 can be deployed as a single device, rather than first deploying the docking station 10 and then deploying the valve 29 into the docking station. Any of the docking stations and/or valve seats 18 described herein can be provided or formed with an integrated valve 29.

The retaining portion 314 helps retain the docking station 10 and the valve 29 at the implantation position or deployment site in the circulatory system. The retaining portion 314 can take a wide variety of different forms. In one exemplary embodiment, the retaining portion 314 includes friction enhancing features that reduce or eliminate migration of the docking station 10. The friction enhancing features can take a wide variety of different forms. For example, the friction enhancing features can comprise barbs, spikes, texturing, adhesive, and/or a cloth or polymer cover with high friction properties on the retaining portions 314. Such friction enhancing features can also be used on any of the various docking stations or retaining portions described herein.

Expandable docking station 10 and valve 29 as described in the various embodiments herein are also representative of a variety of docking stations and/or valves described herein or that might be known or developed, e.g., a variety of different types of valves could be substituted for and/or used as valve 29 in the various docking stations.

Figure 2:
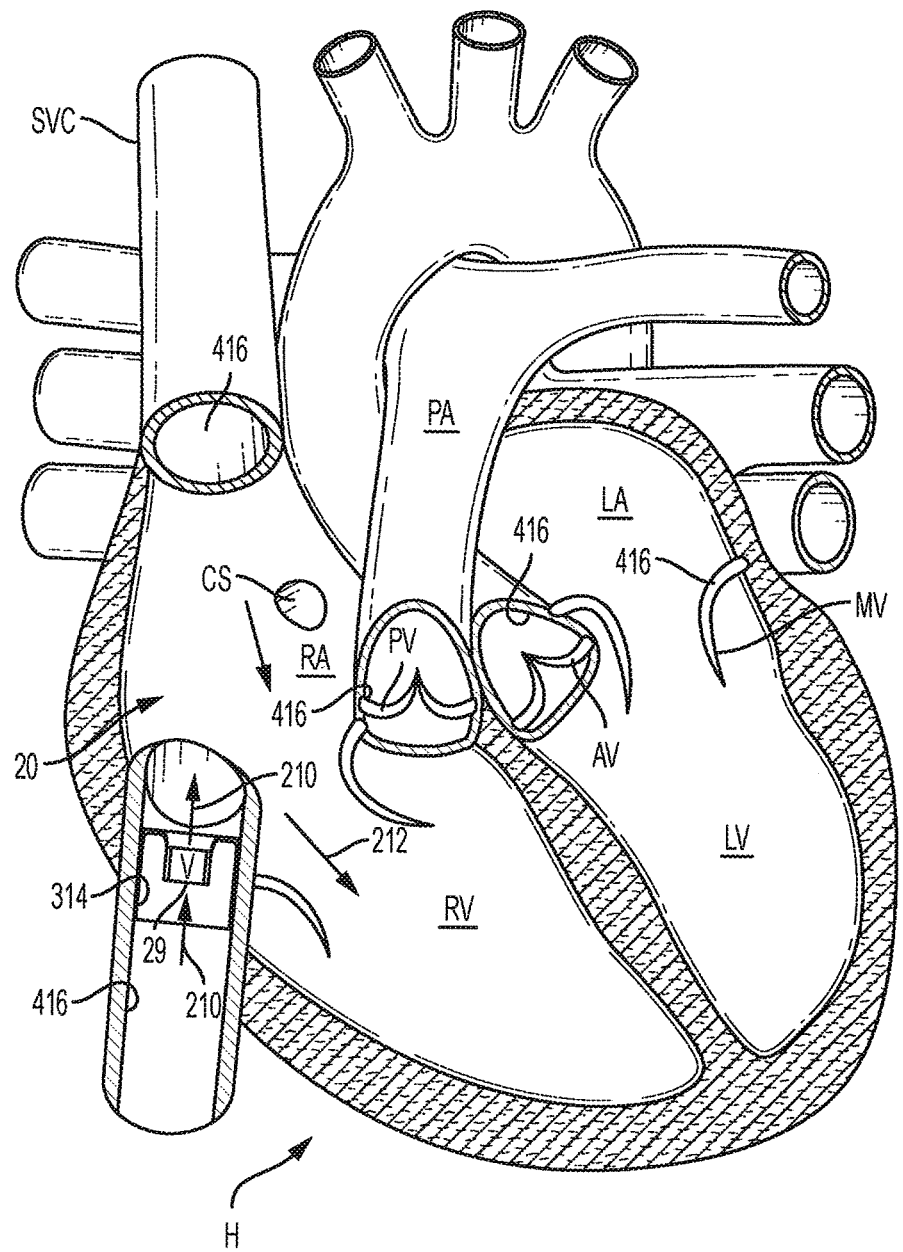
FIG. 2 is a cutaway view of the human heart with an exemplary embodiment of an exemplary docking station positioned in a blood vessel, the inferior vena cava IVC.
Figure 2A:
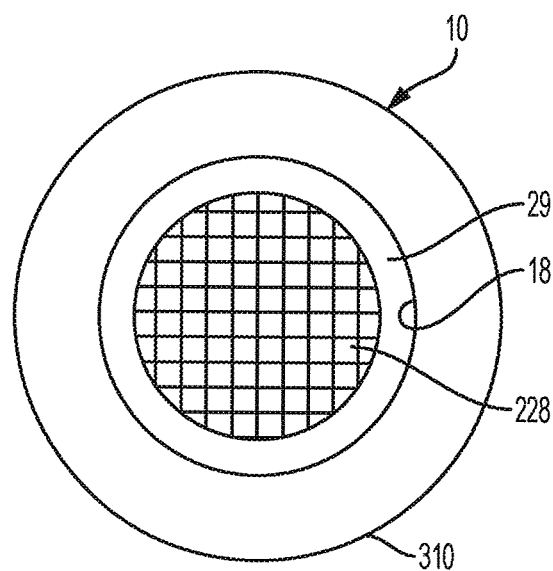
FIG. 2A is an end view of an exemplary docking station and valve showing the valve in an open configuration such that blood can flow through the valve, e.g., when the heart is in a diastolic phase.
Figure 2B:
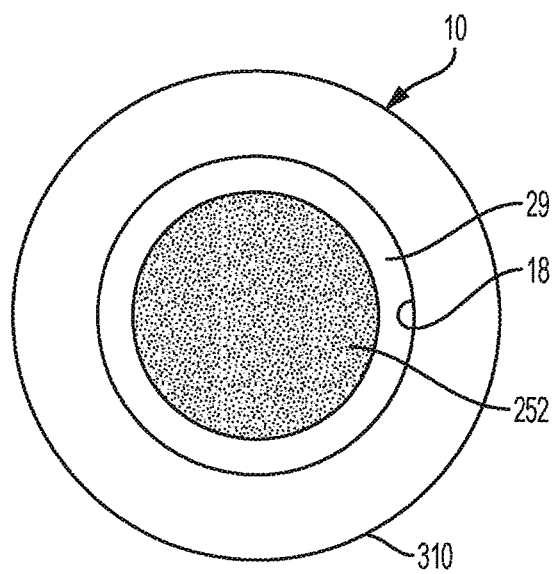
FIG. 2B is an end view of the docking station and valve of FIG. 2 showing the valve in a closed configuration, e.g., when the heart is in a systolic phase.

FIGS. 2, 2A, and 2B illustrate a representative example of the operation of the docking stations 10 and valves 29 disclosed herein. In the example of FIGS. 2, 2A, and 2B, the docking station 10 and valve 29 are deployed in the inferior vena cava IVC. However, the docking station 10 and valve 29 can be deployed in any interior surface within the heart or a lumen of the body. For example, the various docking stations and valves described herein can be deployed in the superior vena cava SVC, the tricuspid valve TV, the pulmonary valve PV, pulmonary artery, the mitral valve MV, the aortic valve AV, aorta, or other vasculature/lumens in the body.

FIGS. 2 and 2A illustrate the valve 29, docking station 10 and heart H, when implanted in the IVC and the heart H is in the diastolic phase. When the heart is in the diastolic phase, the valve 29 opens. Blood flows from the inferior vena cava IVC and the superior vena cava SVC, into the right atrium RA. The blood that flows from the inferior vena cava IVC flows through the docking station 10 and valve 29 as indicated by arrows 210. Also, while in the diastolic phase, blood in the right atrium flows through the tricuspid valve TV, and into the right ventricle RV and valve as indicated by arrows 212. FIG. 2A illustrates space 228 that represents the valve 29 being open when the heart is in the diastolic phase. A variety of types of valves can be used that may open and close in a variety of ways (e.g., including valves with leaflets of tissue that open then coapt to close), so the drawings are meant to be representative of a variety of valves that can operate in different ways. FIG. 2A does not show the interface between the docking station 10 and the inferior vena cava to simplify the drawing. The cross-hatching in FIG. 2A represents blood flow through the valve 29. In an exemplary embodiment, blood is prevented or inhibited from flowing between the inferior vena cava IVC and the docking station 10 by the seal 310 and blood is prevented or inhibited from flowing between the docking station 10 and the valve by implanting or seating the valve in the seat 18 of the docking station 10. In this example, blood only substantially flows or is only able to flow through the valve 29 when the valve is open (e.g., in one embodiment, only when the heart is in the diastolic phase).

FIG. 2B illustrates the valve 29 and docking station 10, when the valve 29 is closed (e.g., when implanted in the IVC and the heart H is in the systolic phase). When implanted in the IVC and the heart is in the systolic phase, the valve 29 closes. Blood is prevented from flowing from the right atrium RA into the inferior vena cava IVC by the valve 29 being closed. As such, the closed valve 29 prevents any blood that regurgitates through the through the tricuspid valve TV during the systolic phase from being forced into the inferior vena cava IVC. The solid area 252 in FIG. 2B represents the valve 29 being closed valve is open (e.g., in one embodiment, when the heart is in the systolic phase). FIG. 2B is meant to be representative of a variety of valves, even though those valves may close in different ways.

In one exemplary embodiment, the docking station 10 acts as an isolator that prevents or substantially prevents radial outward forces of the valve 29 from being transferred to the inner surface 416 of the circulatory system. In one embodiment, the docking station 10 includes a valve seat 18 that resists expansion, e.g., is not expanded radially outwardly (e.g., the diameter of the valve seat does not increase) or is not substantially expanded radially outward (e.g., the diameter of the valve seat increases by less than 4 mm) by the radially outward force of the transcatheter valve or valve 29. The valve seat can be configured such that expansion of a THV/valve 29 increases the diameter of the valve seat only to a diameter less than an outer diameter of the docking station 10 when the docking station is implanted. Retaining portions 314 and sealing portions 310 can be configured to impart only relatively small radially outward forces on the inner surface 416 of the circulatory system (as compared to the radially outward force applied to the valve seat 18 by the valve 29). Having a valve seat 18 that is stiffer or less radially expansive than the outer portions of the docking station (e.g., retaining portions 314 and sealing portions 310), as in the various docking stations described herein, provides many benefits, including allowing a THV/valve 29 to be implanted in vasculature or tissue of varying strengths, sizes, and shapes. The outer portions of the docking station can better conform to the anatomy (e.g., vasculature, tissue, heart, etc.) without putting too much pressure on the anatomy, while the THV/valve 29 can be firmly and securely implanted in the valve seat 18 with forces that will prevent or mitigate the risk of migration or slipping.

The docking station 10 can include any combination of one or more than one different types of valve seats 18, retaining portions 314, and/or sealing portions 310. For example, the valve seat 18 can be a separate component that is attached to the frame 350 of the docking station 10, while the sealing portion is integrally formed with the frame 350 of the docking station. Also, the valve seat 18 can be a separate component that is attached to the frame 350 of the docking station 10, while the sealing portion 310 is a separate component that is also attached to the frame 350 of the docking station. Optionally, the valve seat 18 can be integrally formed with the frame 350 of the docking station 10, while the sealing portion is integrally formed with the frame 350 of the docking station. Further, the valve seat 18 can be integrally formed with the frame 350 of the docking station 10, while the sealing portion is a separate component that is attached to the frame 350 of the docking station 10.

The sealing portion 310, the valve seat 18, and one or more retaining portions 314 of the various docking stations herein can take a variety of different forms and characteristics. In FIGS. 3A-3C, an expandable frame 350 provides the shape of the sealing portion 310, the valve seat 18, and the retaining portion 314. The expandable frame 350 can take a wide variety of different forms. The illustrated expandable frame 350 in FIGS. 3A-3C has an end 362 having an inside diameter 364 and an outside diameter 366. An annular or cylindrical outer portion or wall 368 extends downward from the outside diameter 366 of the end 362. An annular or cylindrical valve seat or wall 18 extends downward from the inside diameter 364 of the end 362. In the illustrated example, the expandable frame 350 is an expandable lattice. The expandable lattice can be made in a variety of ways, e.g., with individual wires connected to form the lattice, braiding, cut from a sheet and then rolled or otherwise formed into the shape of the expandable frame, molded, cut from a cylindrical tube (e.g., cut from a nitinol), other ways, or a combination of these.

The frame 350 can be made from a highly flexible metal, metal alloy, or polymer. Examples of metals and metal alloys that can be used include, but are not limited to, nitinol and other shape memory alloys, elgiloy, and stainless steel, but other metals and highly resilient or compliant non-metal materials can be used to make the frame 350. These materials can allow the frame to be compressed to a small size, and then when the compression force is released, the frame will self-expand back to its pre-compressed diameter and/or the frame can be expanded by inflation of a device positioned inside the frame. The frame 350 can also be made of other materials and be expandable and collapsible in different ways, e.g., mechanically-expandable, balloon-expandable, self-expandable, or a combination of these.

The sealing portions can take a wide variety of different forms. In the example of FIGS. 3A-3C, a covering/material 21 is attached to a portion of the frame 350 to form the sealing portion 310. However, the sealing portion 310 can be formed in a wide variety of other ways. The covering/material 21 can be a fabric material, polymer material, or other material. The sealing portion 310 can take any form that prevents or inhibits the flow of blood from flowing around the outside surface of the valve 29 and through the docking station. In the example of FIGS. 3A, 3B, and 3C, the sealing portion 310 comprises a covering/material 21 (e.g., a fabric or other covering material that can be the same as or similar to other coverings/materials described herein) that extends up to the valve seat 18. The covering/material 21 can be shaped and positioned in a variety of ways, e.g., the covering/material can be configured to partially cover the valve seat 18, entirely cover the valve seat 18, or not cover the valve seat 18 when the frame 350 is expanded. The covering/material 21 (e.g., fabric or other covering material) that forms the sealing portion 310 can also extend radially outward, covering the end 362 of the frame 350, and can optionally extend (e.g., longitudinally, downward, etc.) to cover at least a portion of the annular outer portion or wall 368. The sealing portion 310 provides a seal between the docking station 10 and an interior surface 416 (See FIG. 2) of the circulatory system. That is, the sealing portion 310 and the closed valve 29 prevent or inhibit blood from flowing in the direction indicated by arrow 377. In the example of FIGS. 3A and 3B, blood is not inhibited from flowing in the direction indicated by arrow 378 into the area 379 between the valve seat 18 and the annular outer portion or wall 368.

Figure 3D:
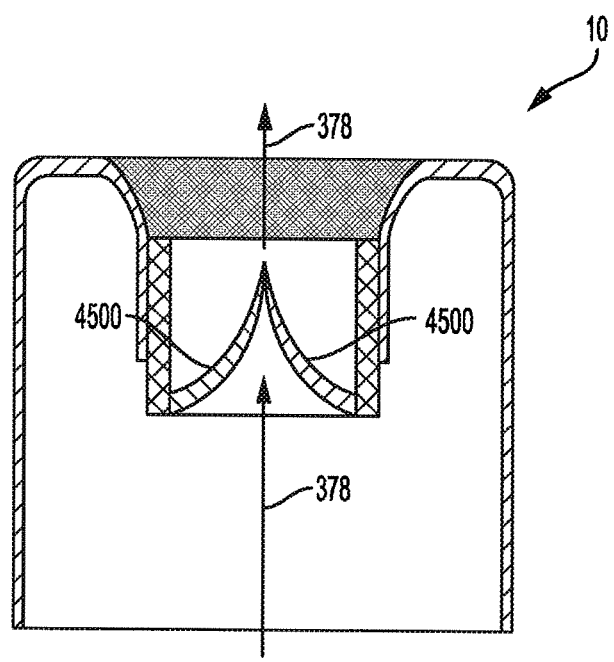
FIG. 3D is a sectional view of the docking station illustrated by FIG. 3A where the transcatheter valve shown is representative of a leaflet type transcatheter valve.

The valve seat can take a wide variety of different forms. The valve seat 18 is a portion of the frame 350 in the example of FIGS. 3A-3C. However, the valve seat 18 can be formed separately from the frame 350. The valve seat 18 can take any form that provides a supporting surface for implanting or deploying a valve 29 in the docking station 10 after the docking station 10 is implanted in the circulatory system. The valve seat can optionally be reinforced with a reinforcing material (e.g., a suture, wire, band, collar, etc. that can circumscribe the valve seat or a portion of the valve seat). The valve 29 is schematically illustrated in FIG. 3A to indicate that the valve 29 can take a wide variety of different forms. FIG. 3D illustrates the more specific example where the valve 29 is a leaflet type THV, such as the Sapien 3 valve available from Edwards Lifesciences. In one exemplary embodiment, a valve 29 is integrated with or replaces the valve seat 18, such that docking station 10 is configured as a transcatheter valve that is delivered as a single unit in the same step (as opposed to first implanting a docking stations and subsequently implanting a separate valve/THV in the docking station). Optionally, any of the docking stations described herein can be formed as a valve or THV, e.g., with valve tissue or other valve material integrated into the docking station.

The retaining portions 314 can take a wide variety of different forms. For example, the retaining portion(s) 314 can be any structure that sets the position of the docking station 10 in the circulatory system. For example, the retaining portion(s) 314 can press against or into the inside surface 416 or contour/extend around anatomical structures of the circulatory system to set and maintain the position of the docking station 10. The retaining portion(s) 314 can be part of or define a portion of the body and/or sealing portion of the docking station 10 or the retaining portion(s) 314 can be a separate component that is attached to the body of the docking station. The docking station 10 can include a single retaining portion 314 or two, or more than two retaining portions. The retaining portion(s) 314 can include friction enhancing features as discussed above.

In the example of FIGS. 3A-3C, the retaining portion 314 comprises the annular outer portion or wall 368 of the frame 350. A shape set (e.g., a programmed shape of a shape memory material) of annular outer portion or wall 368 can bias the annular outer portion or wall 368 radially outward and into contact with/against the interior surface 416 of the circulatory system to retain the docking station 10 and the valve 29 at the implantation position. In the illustrated embodiment, the retaining portion 314 is elongated to allow a relatively small force to be applied to a large area of the interior surface 416, while the valve 29 can apply a relatively large force to the valve seat 18. For example, the length of the retaining portion 314 can be twice, three times, four times, five times, or greater than five times the outside diameter of the transcatheter valve. Applying a small radially outward force over a larger area can be sufficient to securely hold the docking station in place, and this design/configuration can allow the docking station to conform to the unique shape/size of the anatomy and avoid/reduce the likelihood of damaging relatively weaker native tissue. Thereby the valve 29 can be securely held in a variety of locations and anatomies (e.g., the docking station of FIGS. 3A-D is usable in the IVC, SVC, aorta, etc.).

Figure 77:
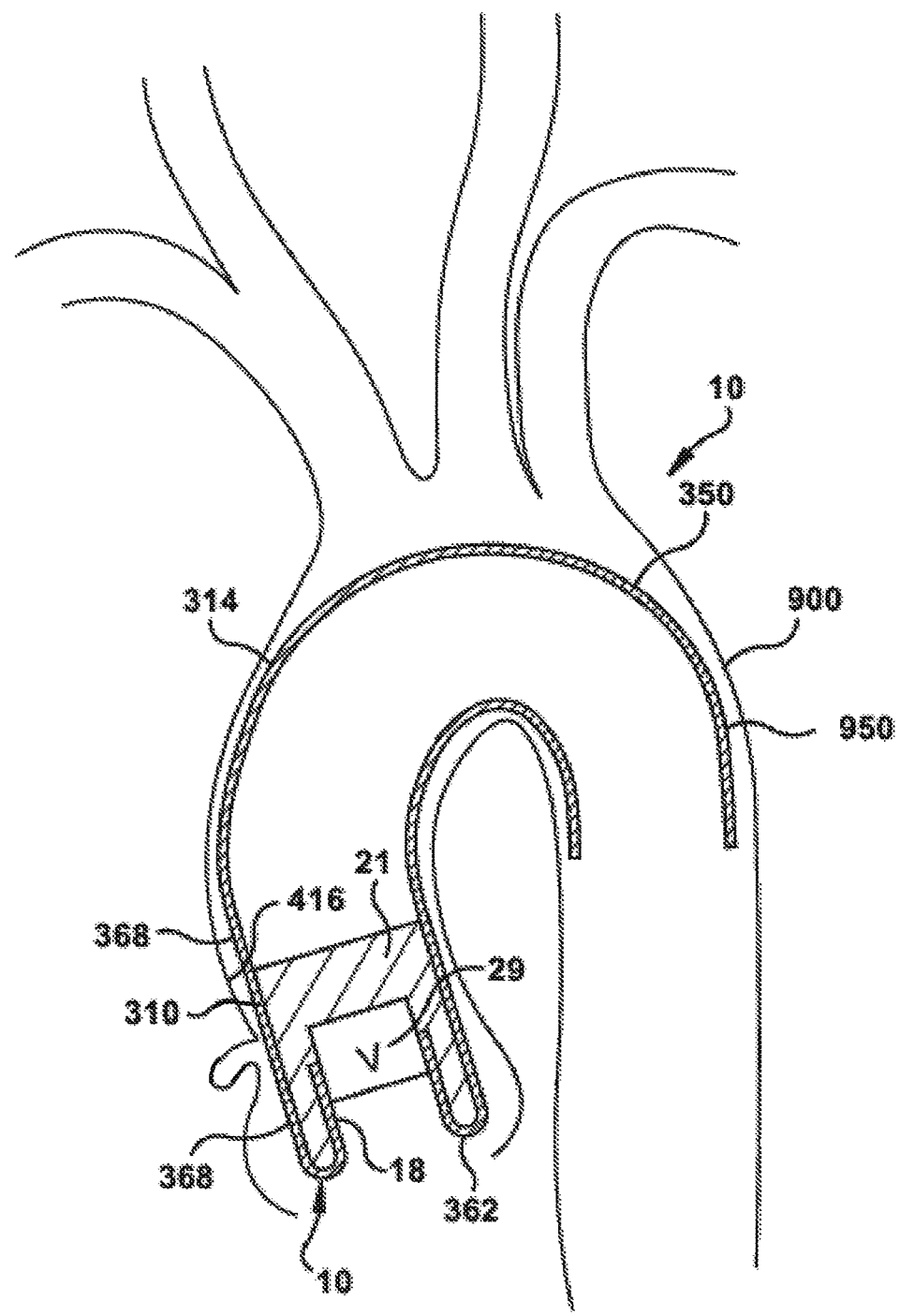
FIG. 77 is a cutaway view of the human heart with an exemplary embodiment of a docking station positioned in an aorta of a human heart.
Figure 78:
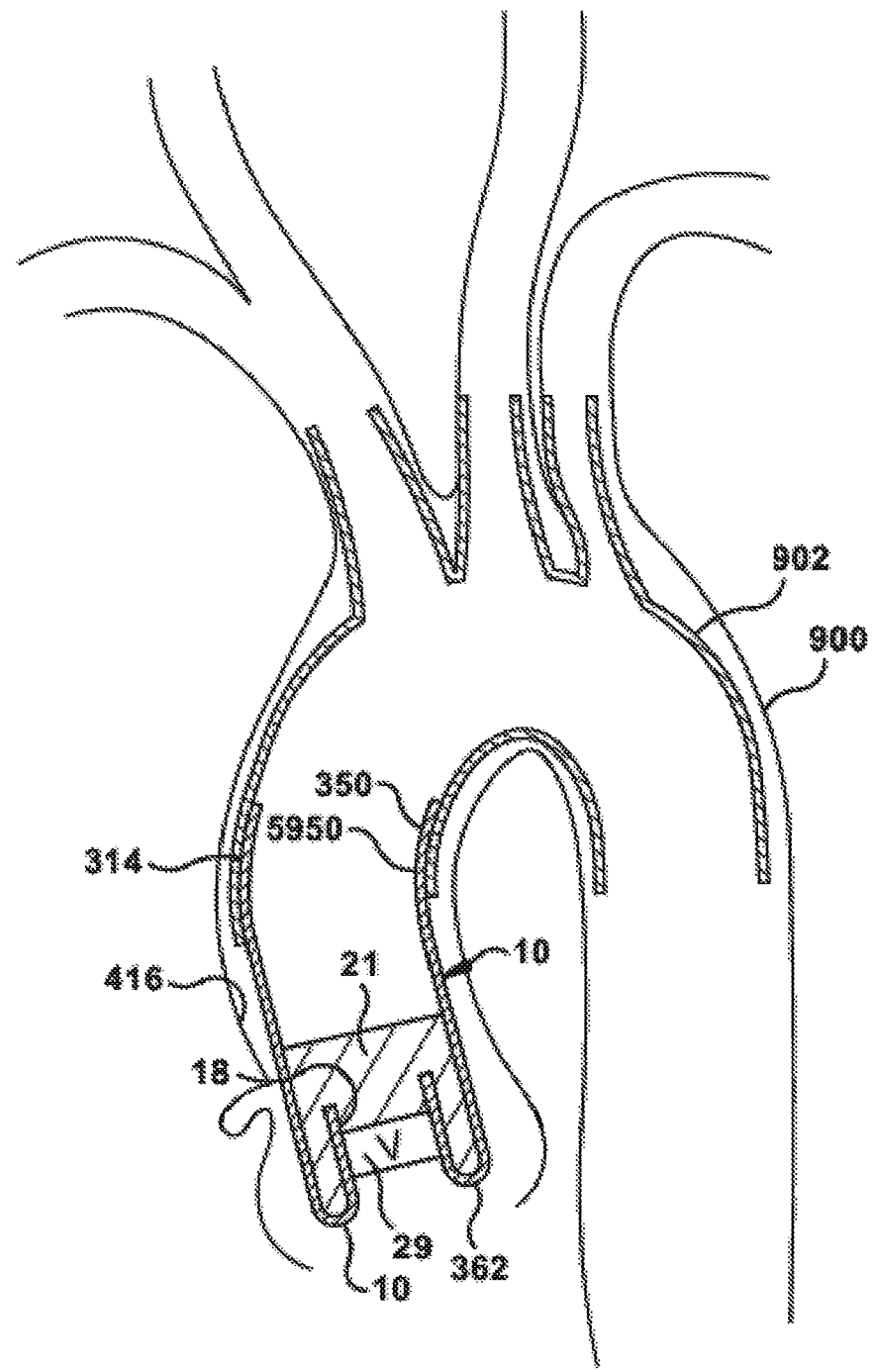
FIG. 78 is a cutaway view of the human heart with an exemplary embodiment of a docking station and a reinforcement device positioned in an aorta of a human heart.

In the examples of FIGS. 77 and 78, the retaining portion 314 can comprise the annular outer portion or wall 368 of the frame 350. A shape set (e.g., a programmed shape of a shape memory material) of annular outer portion or wall 368 biases the annular outer portion or wall 368 radially outward and into contact with/against the interior surface 416 of the aorta to retain the docking station 10 and the valve 29 at the implantation position. In the examples of FIGS. 77 and 78, the shape set can also be selected to substantially match the shape of a portion of the aorta. The retaining portion 314 can be elongated to allow a relatively small force to be applied to a large area of the interior surface 416, while the valve 29 can apply a relatively large force to the valve seat 18, as discussed above.

Figure 4A:
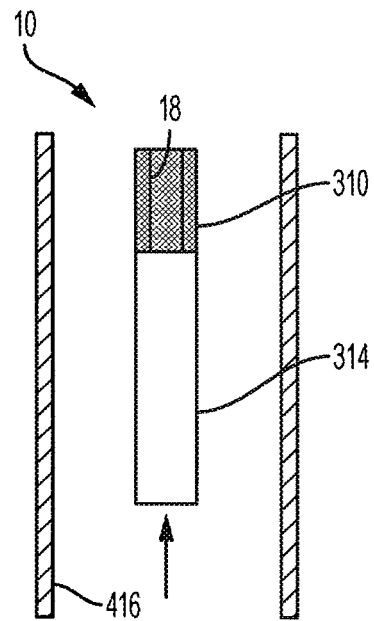
FIGS. 4A and 4B schematically illustrate deployment of a docking station.
Figure 4B:
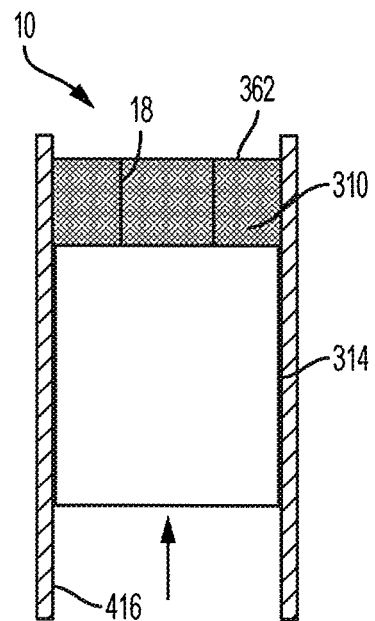
Figure 4C:
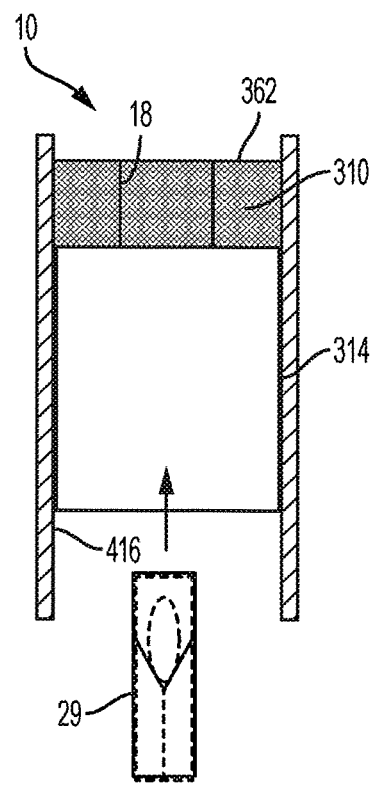
FIGS. 4C and 4D schematically illustrate deployment of a valve in the docking station.
Figure 4D:
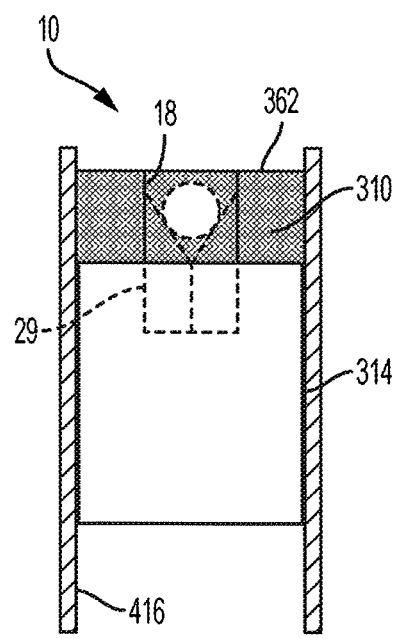

FIGS. 4A-4D schematically illustrate an exemplary deployment of the docking station 10 and valve 29 in the circulatory system. Referring to FIG. 4A, the docking station 10 is in a compressed form/configuration and is introduced to a deployment site in the circulatory system. For example, the docking station 10, can be positioned at a deployment site in a SVC, IVC, aorta, or other location. Referring to FIG. 4B, the docking station 10 is expanded in the circulatory system such that the sealing portion(s) 310 and the retaining portion(s) 314 engage the inside surface 416 of a portion of the circulatory system. Referring to FIG. 4C, after the docking station 10 is deployed, the valve 29 is in a compressed form and is introduced into the valve seat 18 of the docking station 10. Referring to FIG. 4D, the valve 29 is expanded in the docking station, such that the valve 29 engages the valve seat 18 and the seat 18 of the docking station supports the valve. The docking station 10 allows the valve 29 to operate within the expansion diameter range for which it is designed. In the examples depicted herein, the docking station 10 is longer than the valve. However, in some embodiments the docking station 10 can be the same length or shorter than the length of the valve 29. Similarly, the valve seat 18 can be longer, shorter, or the same length as the length of the valve 29.

Figure 4E:
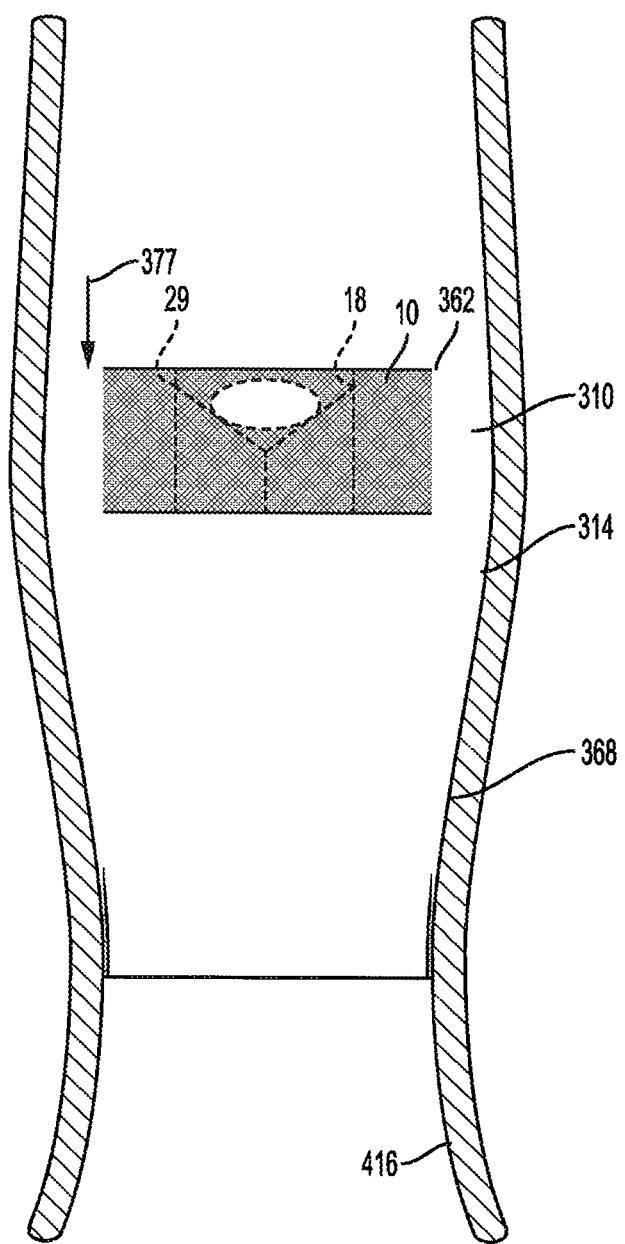
FIG. 4E schematically illustrates conformance of a docking station to an inner surface having a varying size.

FIG. 4E illustrates that the inner surface 416 of the circulatory system, such as the inner surface of a blood vessel or anatomy of the heart can vary in cross-section size and/or shape along its length. In an exemplary embodiment, the docking station 10 is configured such that it can expand radially outwardly to varying degrees along its length L to conform to shape of the inner surface 416. In one exemplary embodiment, the docking station 10 is configured such that the sealing portion(s) 310 and/or the retaining portion(s) 314 engage the inner surface 416, even though the shape of the blood vessel or anatomy of the heart vary significantly along the length L of the docking station. The docking station can be made from a very resilient or compliant material to accommodate large variations in the anatomy.

Figure 7A:
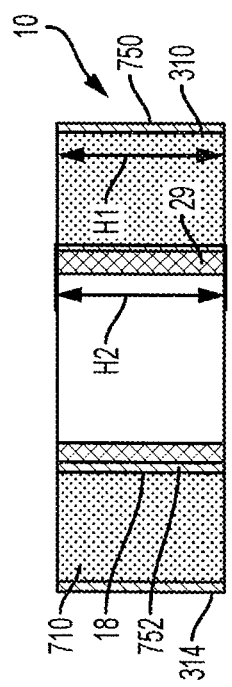
FIG. 7A is a sectional view of an exemplary embodiment of a docking station with an exemplary transcatheter valve disposed inside the docking station.
Figure 7B:
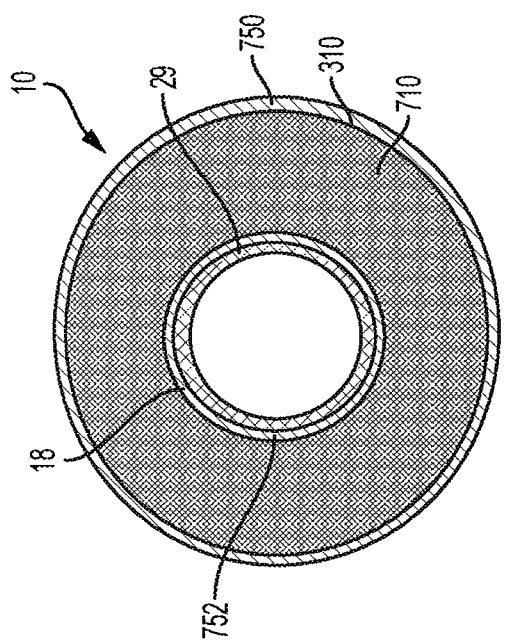
FIG. 7B is a top view of the docking station and valve illustrated by FIG. 7A.

FIGS. 5A-5C and 6 illustrate an exemplary embodiment of an expandable docking station that is similar to the embodiment of FIGS. 3A and 3B, except blood is inhibited from flowing in the direction indicated by arrow 378 into the area 379 between the valve seat 18 and the annular outer portion or wall 368. Blood can be prevented or inhibited from flowing into the area 379 in a wide variety of different ways. In the example of FIGS. 5A-5C, a covering material 500 forms a closed toroid over the frame 350. That is, the covering material 500 covers the end surface 362 and a span 510 between the end surface 362 and the annular valve seat or wall 18. As such, the covering material 500 prevents entry or slows entry of blood into the area 379. In the example of FIGS. 5A-5C and 6, the end surface 362 and the valve seat or wall 18 are offset and the span 510 is a conical or inclined ring with a hole in the center. In one exemplary embodiment, an end 362 of the annular outer portion or wall 368 and the valve seat or wall 18 are coplanar or substantially coplanar and the end surface 362 is a ring or a disc with a hole in the center FIGS. 7A, 7B, 8A and 8B illustrate additional embodiments where blood is inhibited from flowing between the valve seat 18 and the annular outer wall 368. In the example of FIGS. 7A and 7B, the expandable docking station includes an outer frame ring 750 and a separate inner frame ring 752, instead of unitary frame 350. A toroid-shaped foam piece 710 fills the space 712 between the outer frame ring 750 and the inner frame ring 752. The toroid-shaped foam piece 710 is illustrated as filling an entire volume defined by the rings 750, 752, and having the same height as rings 750 and 752. However, in other exemplary embodiments a height H1 of the foam piece 710 can be less than or greater than the height H2 of the rings 750, 752. Similarly, while the expandable frame rings are illustrated as being the same heights, the heights of each of the frame rings can be different, e.g., the outer frame ring 750 can have a large height to spread the retaining force across a large area of internal surface 416. The inner frame ring 752 can have a small height to focus the radial outward force of the valve on a small area of the inner frame ring 752.

In the example of FIGS. 7A and 7B, the sealing portion 310 comprises the foam piece 710 and the outer ring 750. The outer ring 750 also acts as the retaining portion 314 against the inner surface 416. The inner ring 752 acts as the valve seat 18.

The inner and outer expandable frames 750, 752 can take a wide variety of different forms. The expandable frames 750, 752 can be an expandable lattice. The expandable lattice can be made from individual wires, cut from a sheet and then rolled or otherwise formed into the shape of the expandable frame, cut from a cylinder/tube/cylindrical sheet, molded, etc. The frames 750, 752 can be made from a highly flexible metal, metal alloy, or polymer. Examples of metals and metal alloys that can be used include, but are not limited to, nitinol and other shape memory alloys, elgiloy, and stainless steel, but other metals and highly resilient or compliant non-metal materials can be used to make the frame 750, 752. These materials can allow the frame to be compressed to a small size, and then when the compression force is released, the frame will self-expand back to its pre-compressed diameter and/or the frames can be expanded by inflation of a device/balloon.

An example of an open cell foam that can be used to form foam piece 710 (or any other foam parts mentioned in this application) of the docking station is a bio-compatible foam, such as a polyurethane foam (e.g., as may be obtained from Biomerix, Rockville, MD). The docking stations with the foam piece 710 can be self-expanding and/or expandable with an inflatable device to cause the docking station to engage an inner surface 416 having a variable shape.

Figure 8A:
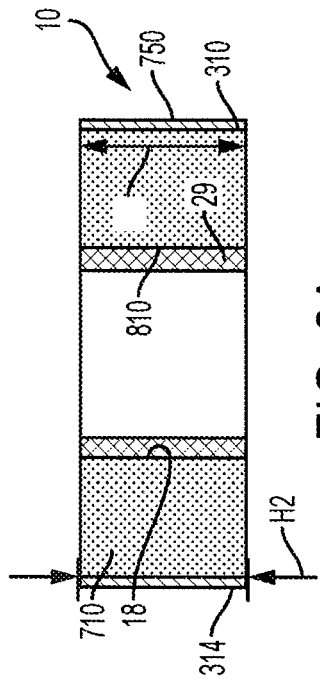
FIG. 8A is a sectional view of an exemplary embodiment of a docking station with an exemplary transcatheter valve disposed inside the docking station.
Figure 8B:
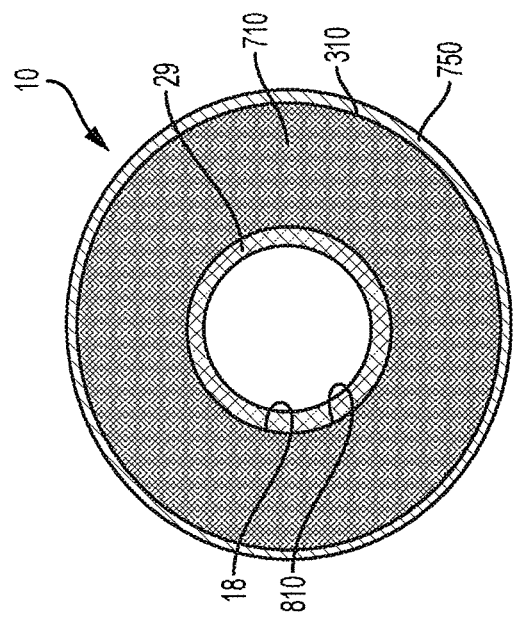
FIG. 8B is a top view of the docking station and valve illustrated by FIG. 8A.

FIGS. 8A and 8B illustrate an exemplary embodiment of a docking station 10 that is substantially the same as the docking station of FIGS. 7A and 7B, except the inner frame ring 752 is omitted. In the example of FIGS. 8A and 8B, the inner surface 810 of the foam piece 710 acts as the valve seat 18. The inner surface 810 of the foam piece 710 can form a valve seat in a wide variety of different ways. For example, the inner surface 810 can be made to be substantially inelastic or unexpandable from a predetermined deployed size. For example, the inner surface can be provided with an inelastic or substantially inelastic skin, which can be made from the same polymer as the foam (or another polymer), or the inner surface 810 can include a band, ring, or strand. The valve seat 18 can be any material capable of supporting the radially outward force of the transcatheter valve 29.

Figure 9A:
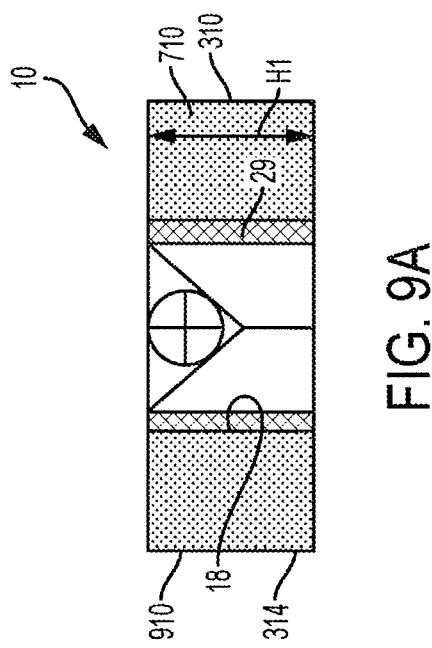
FIG. 9A is a sectional view an exemplary embodiment of a docking station with an exemplary transcatheter valve disposed inside the docking station.
Figure 9B:
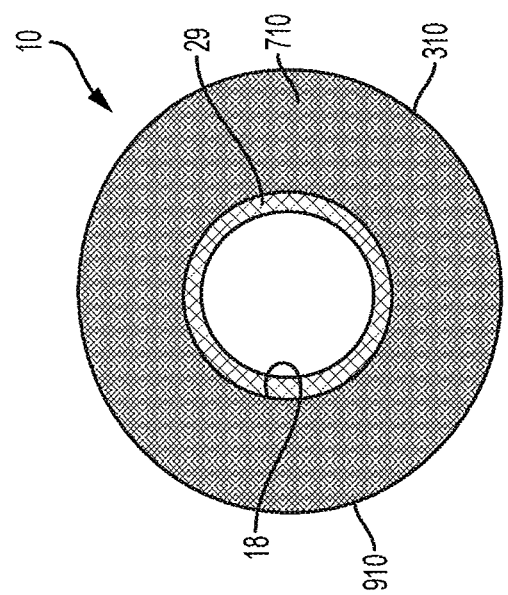
FIG. 9B is a top view of the docking station and valve illustrated by FIG. 9A.

FIGS. 9A and 9B illustrate an exemplary embodiment of a docking station 10 that is substantially the same as the docking station of FIGS. 8A and 8B, except the outer frame ring 750 is omitted. In the example of FIGS. 9A and 9B, the outer surface 910 of the foam piece 710 acts as the sealing and retaining portions 310, 314.

Figure 10:
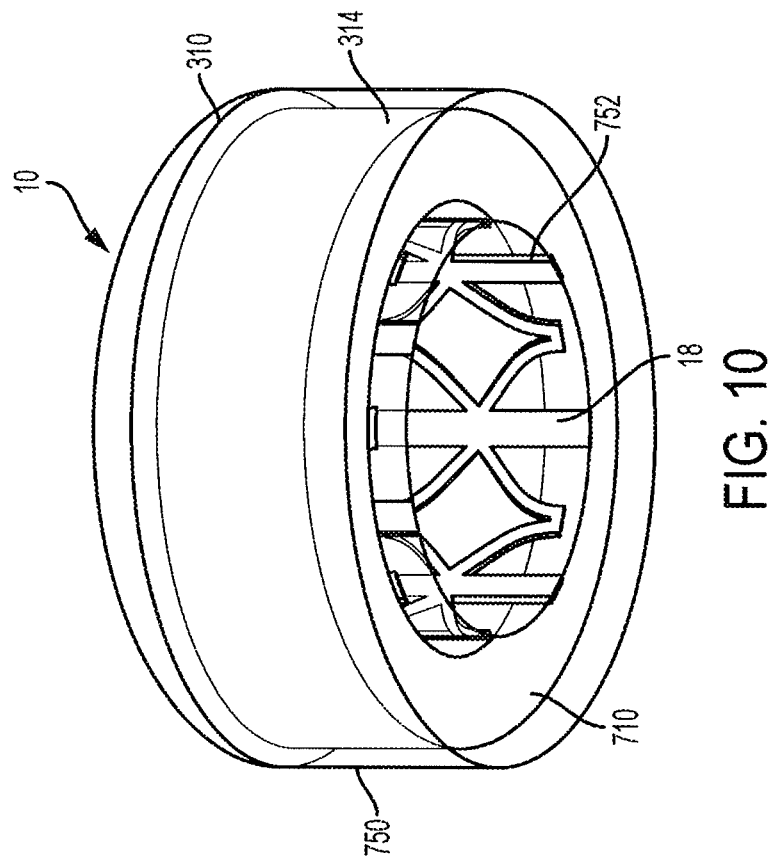
FIG. 10 is a perspective view of an exemplary embodiment of a docking station.

FIG. 10 is a perspective view of a docking station 10 that includes a foam piece 710. The docking station of FIG. 10 can include both the inner frame ring 7520 and the outer frame ring 750, the outer frame ring 750 only, the inner frame ring 752 only, or no frame ring.

FIGS. 6-10 can be separate docking stations or form a portion of another docking station, e.g., part of one of the docking stations described/shown elsewhere herein. For example, the embodiments shown in FIGS. 6-10 can be used as or can form an end portion (e.g., region including and around the valve seat) of any of the docking stations shown in FIGS. 3A-3D, 12-18, 32-36, 42-45, (can be used at either end or both ends), and 60A-60J, etc., and can be integral or attached.

Optionally, the docking station frame 350 in the various embodiments herein can be made from an elastic or superelastic material or metal. One such metal is nitinol. When the frame 350 of the docking station 10 is made from a lattice of metal struts, the body can have the characteristics of a spring. Referring to FIG. 11, like a spring, when the frame 350 of the docking station 10 is unconstrained and allowed to relax to its largest diameter the frame of the docking station applies little or no radially outward force. As the frame 350 of the docking station 10 is compressed, like a spring, the radially outward force applied by the docking station increases.

As is illustrated by FIG. 11, in one exemplary embodiment the relationship of the radially outward force of the docking station frame 350 to the diameter of the docking station is non-linear, though it can also be linear. In the example of FIG. 11, the curve 1150 illustrates the relationship between the radially outward force exerted by the docking station 10 and the compressed diameter of the docking station. In the region 1152, the curve 1150 has a low slope. In this region 1152, the radially outward force is low and changes only a small amount. In one exemplary embodiment, the region 1152 corresponds to a diameter between 25 mm and 40 mm, such as between 27 mm and 38 mm. The radially outward force is small in the region 1152, but is not zero. In the region 1154, the curve 1150 has a higher slope. In this region 1154 the radially outward force increases significantly as the docking station is compressed. In one exemplary embodiment, the body of the stent is constructed to be in the low slope region 1152 for both a largest vessel accommodated by the docking station 10 and a smallest vessel. This allows the sealing and retaining portions 310, 314 to apply only a small radially outward force to the inner surface 416 of the circulatory system over a wide range of implantation diameters.

Figures 12, 12A, 12B:
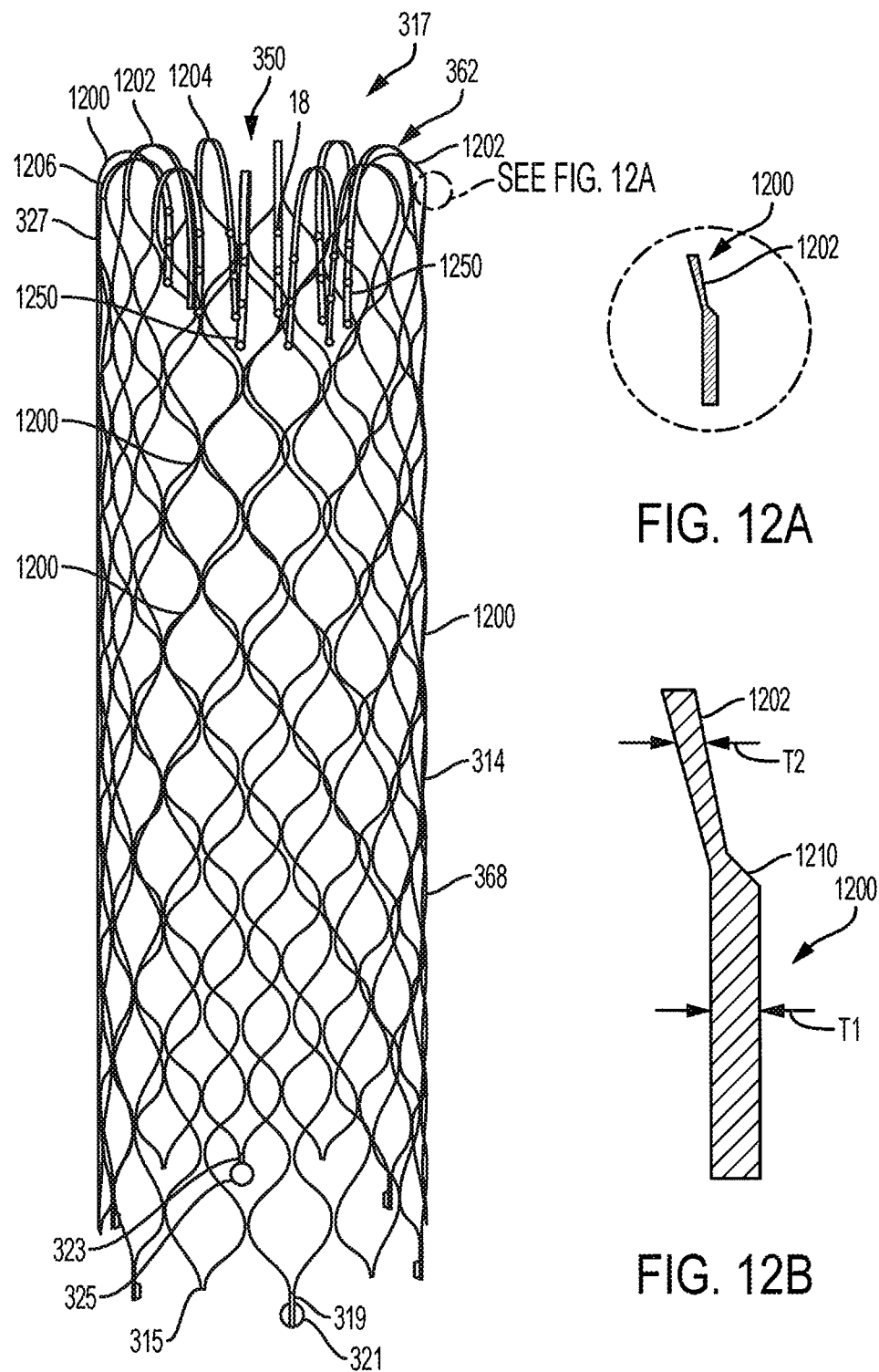
FIG. 12 is a perspective view of an exemplary embodiment of a docking station frame.
FIGS. 12A and 12B illustrate enlarged portions of FIG. 12.
Figure 13:
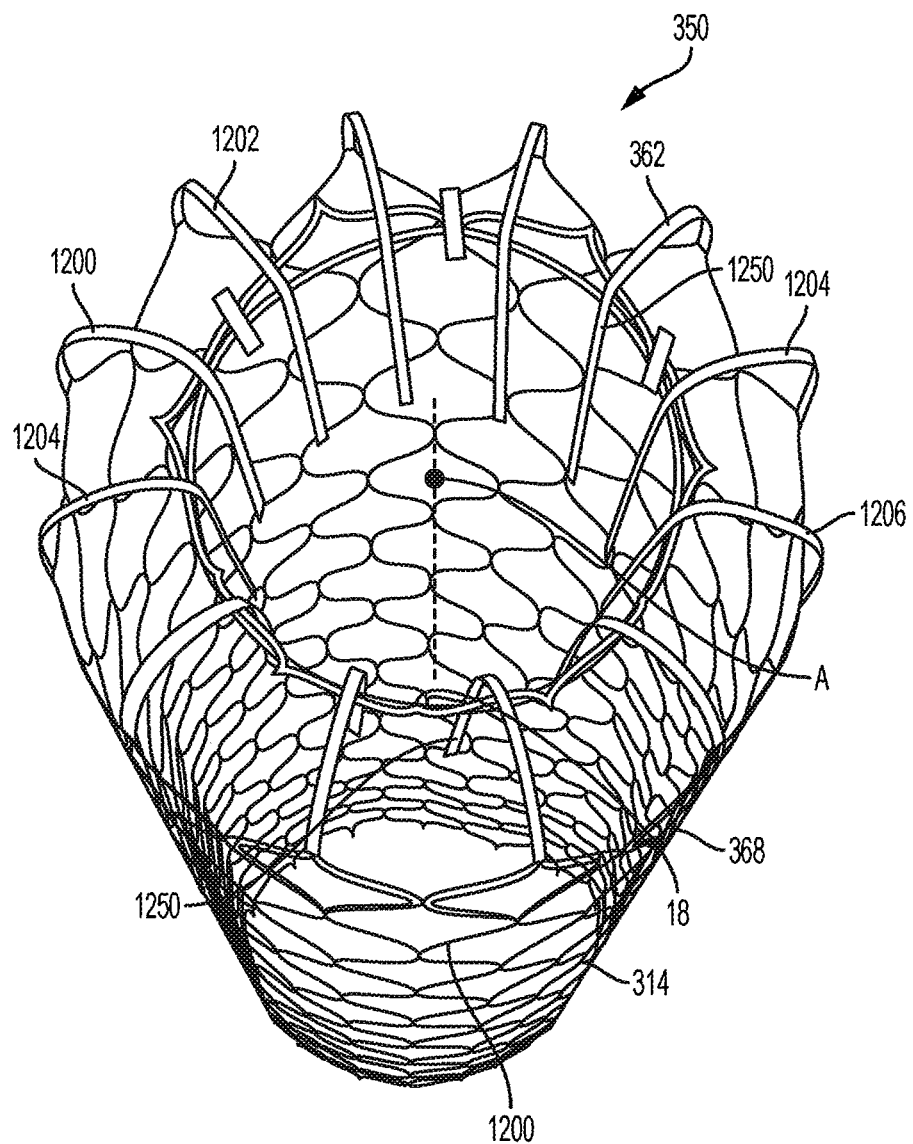
FIG. 13 is a perspective view of the docking station frame illustrated by FIG. 12.
Figure 14:
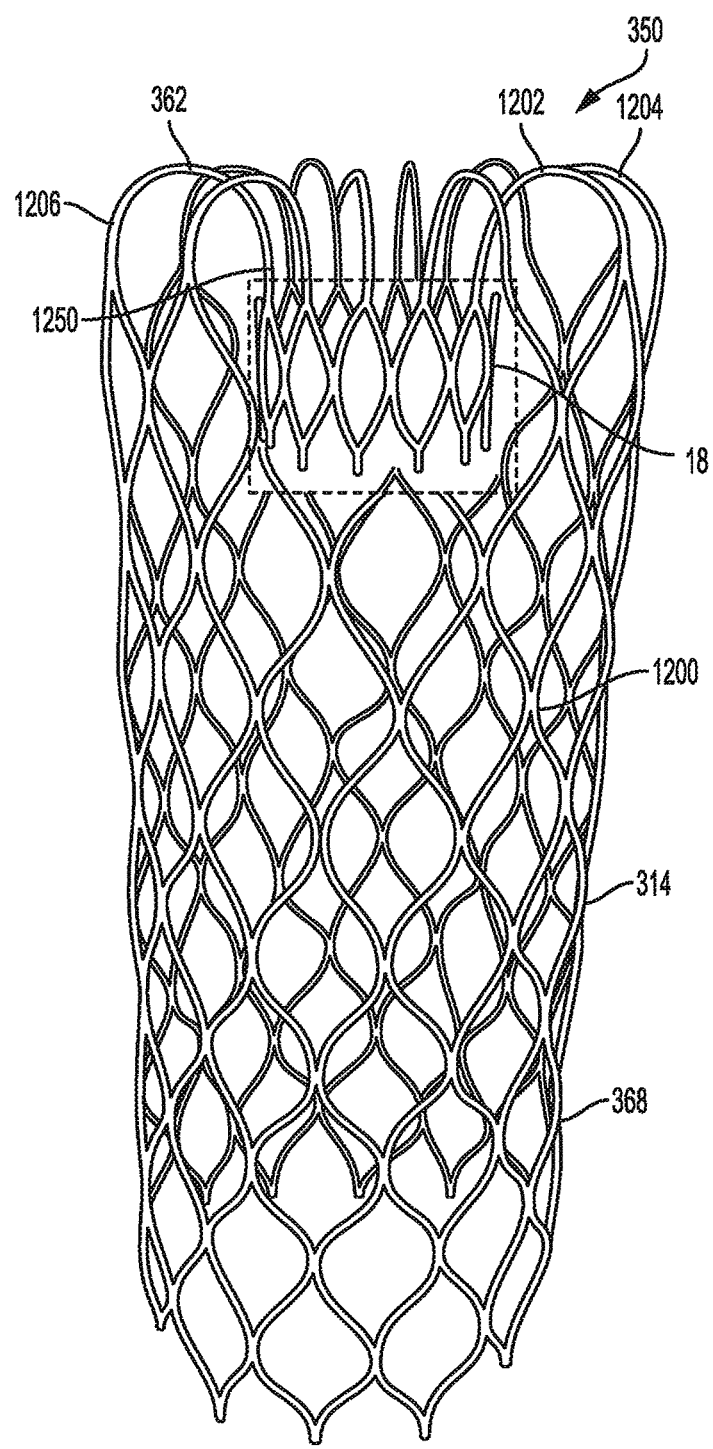
FIG. 14 is a perspective view of an exemplary embodiment of a docking station frame.

The docking station frame 350 can take a wide variety of different forms. FIGS. 12, 13 and 14 illustrate exemplary embodiments of docking station frames. In FIG. 12, a portion of the valve seat 18 is omitted, but the frame includes legs 1250 for supporting a valve seat 18 or forming a portion of a valve seat. In FIGS. 13 and 14 two examples of valve seats 18 are shown connected to the legs 1250. In FIG. 13, the valve seat 18 comprises a separate valve seat component attached to the legs 1250. In FIG. 14, the valve seat 18 is integrally formed with the legs 1250. In other embodiments, the valve seat 18 is replaced/integrated with a valve/THV 29 and the docking station 10 and valve/THV are configured and deployed as a single unit. In FIG. 14, a portion of the annular outer wall 368 is removed to show the integrally formed valve seat 18.

In one exemplary embodiment, a thickness of struts 1200 of the frame varies. A wide variety of different portions of the struts 1200 can vary and the struts can vary in different ways. Referring to FIGS. 12A and 12B, in one exemplary embodiment a strut 1200 has a first thickness T1 and a second thickness T2. In the illustrated example, the struts 1200 of the annular wall portion 314 have the first thickness T1 and strut portions or links 1202 of the struts 1200 that form the end 362 have the second thickness T2. In this example, the thickness T2 is less than the thickness T1. This reduced thickness allows the end 362 to bend or flex more easily and connect the annular outer portion or wall 368 to the valve seat 18. In the illustrated example, the thicknesses T1, T2 are measured in the radial outward direction (i.e. measured from an inside surface of the frame 350 to the outside surface). In one exemplary embodiment, the width of the struts 1200 is also reduced with the thickness reduction or, optionally, the width of the strut portions can be reduced instead of the thickness reduction. The thickness T2 can be 90% or less of the thickness T1, the thickness T2 can be 80% or less of the thickness T1, thickness T2 can be 70% or less of the thickness T1, thickness T2 can be 60% or less of the thickness T1, thickness T2 can be half or less of the thickness T1, thickness T2 can be 40% or less of the thickness T1, thickness T2 can be 30% or less of the thickness T1, thickness T2 can be ¼ or less of the thickness T1, or the thickness T2 can be 20% or less of the thickness T1.

In the illustrated example, the entirety of the strut portions or links 1202 of the struts 1200 that form the end 362 have the second thickness T2. However, in other embodiments, only part of the portions/links 1202 that form the end 362 have the reduced thickness. For example, the thickness of the portions/links 1202 can have the thickness T2 at the top or apex 1204 of the illustrated bend 1206 while another part(s) can have the thickness T1. In one embodiment, a taper 1210 transitions the struts 1200 or strut portions/links 1202 from the thickness T1 to the thickness T2. In one embodiment, the taper is more gradual (e.g., occurs over a longer distance or length) and extends into the bend of the links 1206. The thickness can also increase (e.g., taper) in the area from the top or apex 1204 to the valve seat 18 or area where the valve seat will be attached.

The length of the retaining portion 314 in FIGS. 12-13 is shows as being many times both the length/height of the valve seat and diameter of the valve seat. As discussed previously, this configuration applies a relatively small radially outward force over a larger area to the interior surface of the circulatory system and is sufficient to secure the docking station in place against the interior surface. Further, this design/configuration allows the docking station to conform to the unique shape/size of the anatomy expanding more or less in many different locations to adjust to the contours (e.g., bulges, narrowed regions, contractions, etc.) of the interior surface of the circulatory system (e.g., blood vessel) and contact more of the interior surface. In one embodiment, the docking station and frame are configures such that, when implanted, all or most of the outer surface of the docking station or frame contacts the interior surface of the circulatory system (even when irregular or varied in shape). This also helps avoid/reduce the likelihood of damaging relatively weaker native tissue (e.g., by having too much localized force and/or pressure in one, two, or more particular locations). Thereby the valve 29 can be securely held in a variety of locations and anatomies.

For example, the frame shown in FIGS. 12, 13, and 14 is configured such that a docking station incorporating this frame can conform to an interior shape of circulatory system when expanded inside the blood vessel such that the expandable frame can expand in multiple locations (e.g., 2, 3, 4, 5, 6, 7, 8, or more) to conform to multiple bulges of the circulatory system and/or can contracts (e.g., is less expanded, has a smaller diameter, etc.) in multiple locations (e.g., 2, 3, 4, 5, 6, 7, 8, or more) to conform to multiple narrowed regions of the circulatory system. Further, whether the native anatomy is varied or more uniform, the frame is configured such that, when a docking station incorporating the frame is expanded in the circulatory system, the majority (e.g., more than 50%), more than 60%, more than 70%, more than 80%, 50-90%, or more of an outer surface of the docking station contacts an interior surface of the circulatory system and distributes the pressure and force exerted on the interior surface by the docking station over the portion or length of the outer surface of the docking station in contact with the interior surface.

Figure 15:
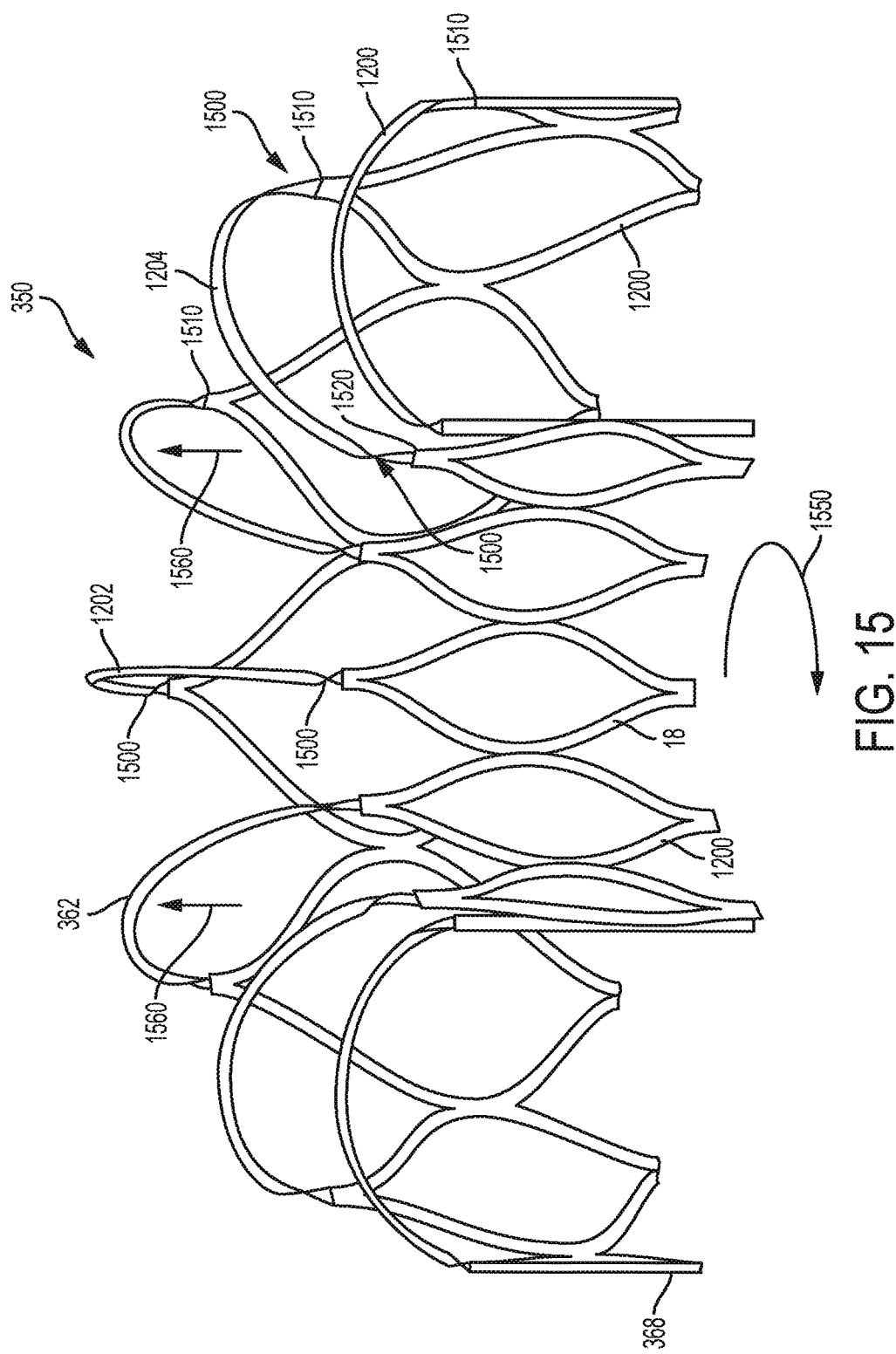
FIG. 15 is a perspective view of a portion of an exemplary embodiment of a docking station frame.
Figure 16:
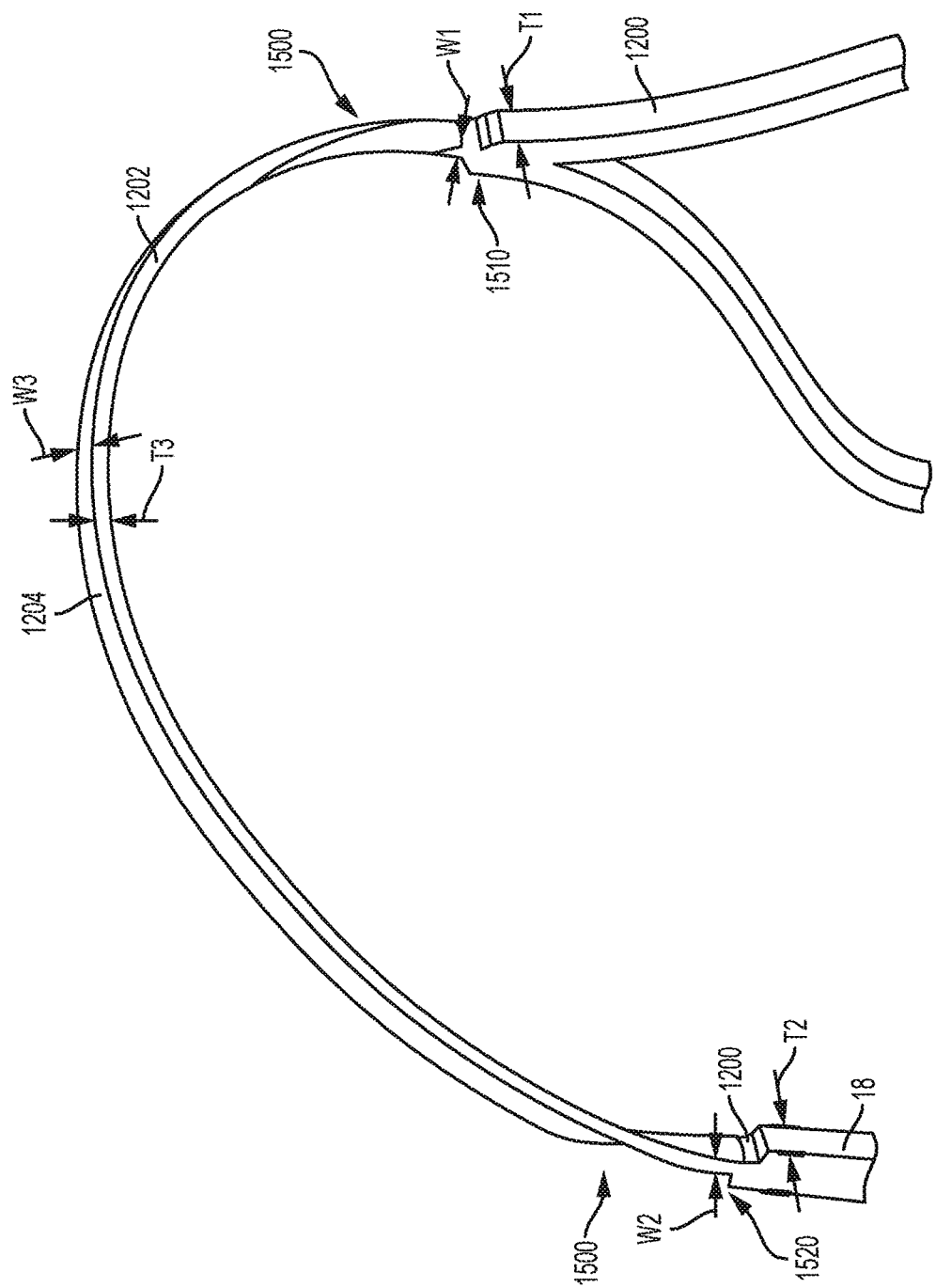
FIG. 16 is a perspective view of an exemplary embodiment of a link between an inner portion (e.g., valve seat) and an outer portion of the docking station frame of FIG. 15.

Referring to FIGS. 15 and 16, in one exemplary embodiment the strut portions or links 1202 that form the end 362 of the frame 350 are twisted or otherwise angled. The portions/links 1202 can be twisted in a wide variety of different ways and can be twisted along their full length or just a portion of their length. The twists 1500 aid in crimping or compressing of the frame 350. In the illustrated example, a twist 1500 is included at or near (e.g., adjacent) the junction 1510 of the portion/link 1202 and the annular outer portion or wall 368 and at or near (e.g., adjacent) the junction 1520 of the portion/link 1202 and the valve seat 18. However, in other embodiments a twist 1500 can be provided at only one of the junction 1510 and the junction 1520. In the illustrated example, the twists 1500 are ninety degree twists, forming one-hundred-eighty total degrees of twist. At the junction 1510 the thickness T1 is greater than the width W1 of the portion/link 1202. At the junction 1520 the thickness T2 is greater than the width W2 of the portion/link 1202. Due to the two twists 1500, at the apex 1204, the thickness T3 can be less than the width W3, even though the portion/link 1202 is uniform at the apex 1204. That is, due to the twists 1500, the widths W1, W2 at the junctions 1510, 1520 can become the thickness T3 at the apex 1204 and the thicknesses T1, T2 at the junctions 1510, 1520 can become the width W3. The thickness T3 can be 90% or less of the width W3, the thickness T3 can be 80% or less of the width W3, thickness T3 can be 70% or less of the width W3, thickness T3 can be 60% or less of the width W3, thickness T3 can be half or less of the width W3, thickness T3 can be 40% or less of the width W3, thickness T3 can be 30% or less of the width W3, thickness T3 can be ¼ or less of the width W3, or the thickness T3 can be 20% or less of the width W3. Optionally, twists 1500 and a strut portion/link 1202 could be used that have a uniform or equal thickness with other struts 1200 of the frame.

The twists 1500 make the frame 350 easier to crimp or compress. For example, a thinner thickness T3 at the apex 1204 makes the portions/links 1202 easier to bend at the apex 1204 and along their length. In addition, the angles and/or twists 1500 facilitate offsetting/rotation 1550 of the valve seat 18 relative to the annular outer portion or wall 368. This offsetting/rotation 1550 reduces the amount of bending and axial outward movement 1560 needed when compressing or crimping the frame 350. As a result, a radius of curvature of the apex 1204 of the compressed or crimped frame is greater than would be the case if the twists 1500 were not included. Since the radius of curvature is increased, the stress on the apex 1204 is reduced when the frame is compressed or crimped.

Figure 17:
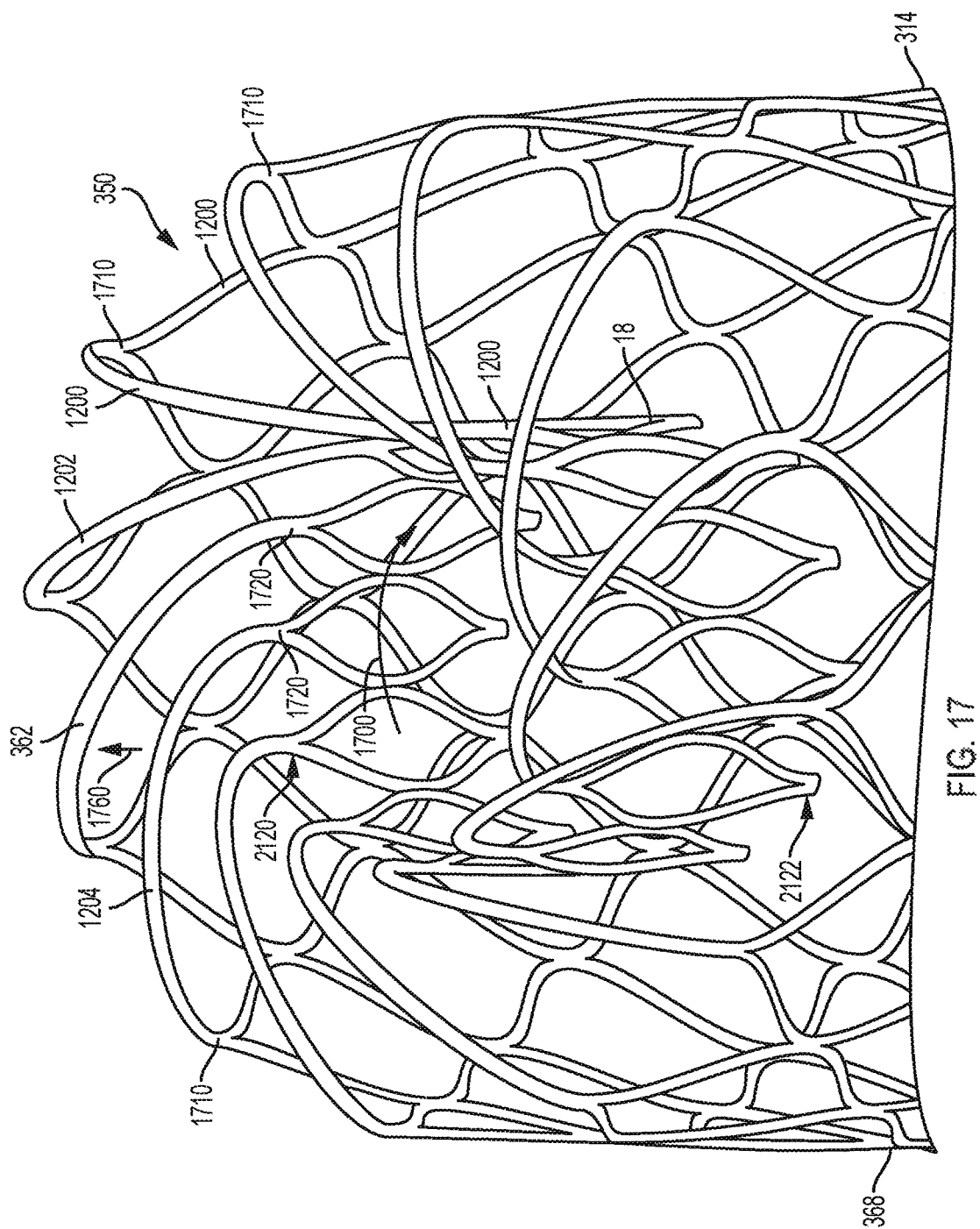
FIG. 17 is a perspective view of a portion of an exemplary embodiment of a docking station frame.
Figure 18:
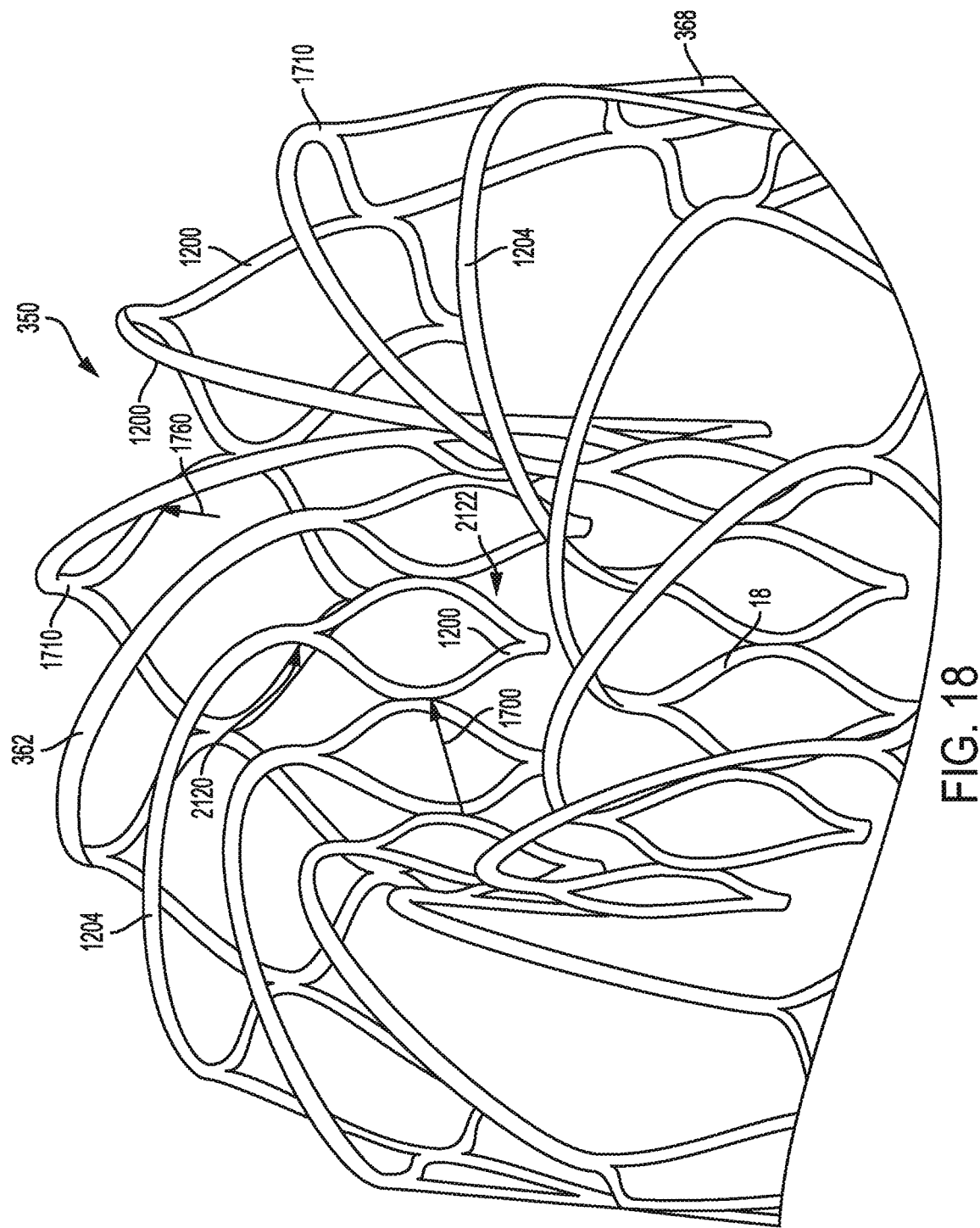
FIG. 18 is another perspective view of a portion of the docking station frame of FIG. 17.
Figure 19:
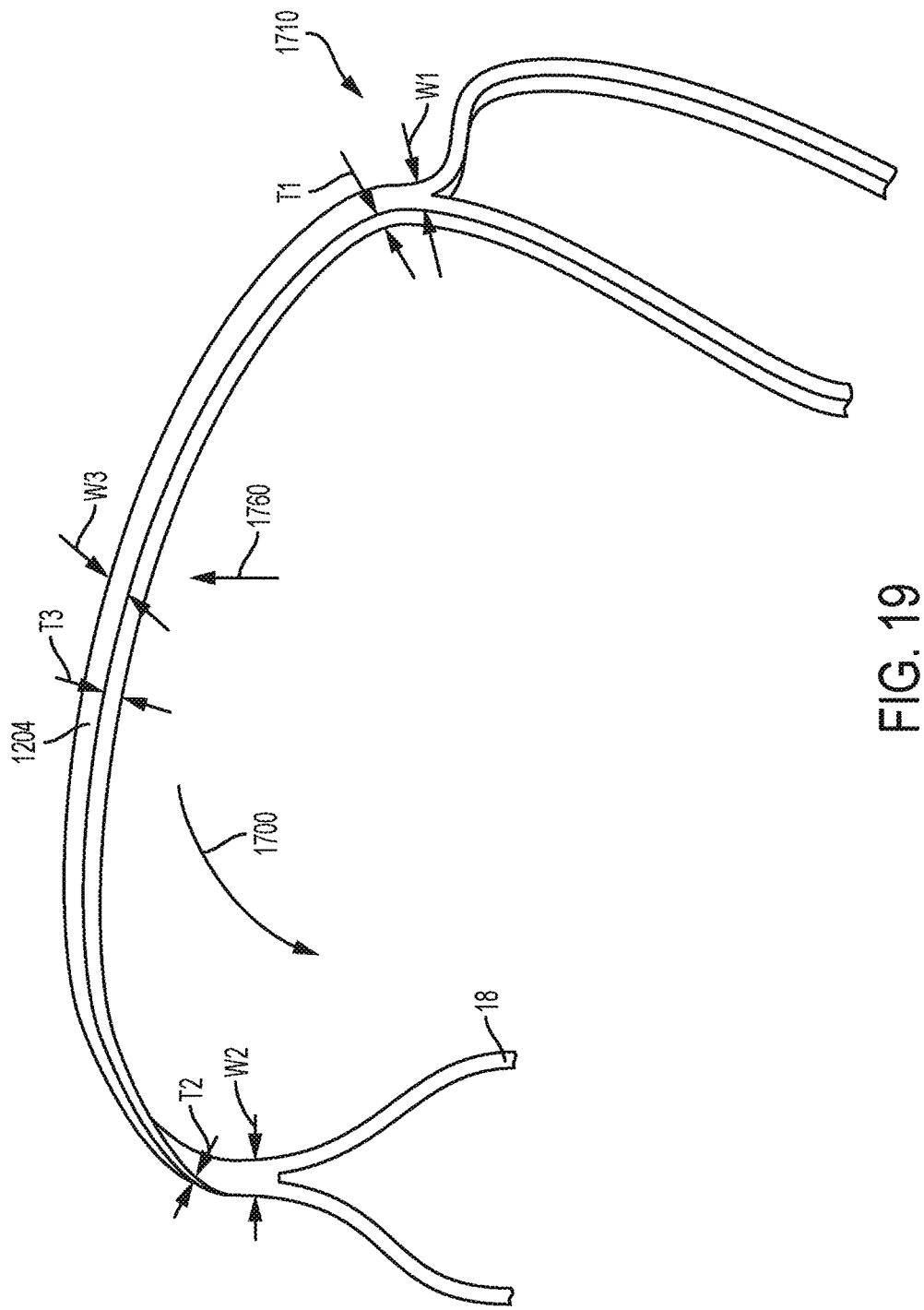
FIG. 19 is a perspective view of an exemplary embodiment of a link between an inner portion (e.g., valve seat) and an outer portion of the docking station frame of FIGS. 17 and 18.

Referring to FIGS. 17-19, in one exemplary embodiment the frame 350 includes a valve seat 18 that is offset or rotated 1700 relative to the annular outer portion or wall 368. This offset or rotation 1700 angles and/or twists the portions/links 1202. The offset/rotation 1700 aids in crimping or compressing of the frame 350. Any degree of offset or rotation can be implemented. For example, compared to a strut portion/link 1202 of FIG. 13 that extends from the annular outer portion or wall 368 directly toward a longitudinal or center axis A that runs longitudinally through the center of the docking station (e.g., the axis parallel to the outer wall 368 and in the center thereof), the offset/rotation 1700 can, optionally, cause each of the strut portions/links to be angled 80 degrees or less, 70 degrees or less, 60 degrees or less, 50 degrees or less, 40 degrees or less, 30 degrees or less, 20 degrees or less or 10 degrees or less relative to a radial line between the longitudinal or center axis A and the junction of the strut portion to the outer wall (e.g., relative to links or strut portions shown in FIG. 13, which are parallel to such a radial line).

In FIGS. 17-19, at the junction 1710 the thickness T1 is less than the width W1 of the strut 1200. At the junction 1720 the thickness T2 is less than the width W2 of the strut 1200. At the apex 1204 the thickness T3 is also less than the width W3. In one exemplary embodiment, the widths W1, W2, W3 are all the same. In one exemplary embodiment, the thicknesses T1, T2, T3 are all the same. The thickness T3 can be 90% or less of the width W3, the thickness T3 can be 80% or less of the width W3, thickness T3 can be 70% or less of the width W3, thickness T3 can be 60% or less of the width W3, thickness T3 can be half or less of the width W3, thickness T3 can be 40% or less of the width W3, thickness T3 can be 30% or less of the width W3, thickness T3 can be ¼ or less of the width W3, or the thickness T3 can be 20% or less of the width W3.

The offset/rotation 1700 makes the frame 350 easier to crimp or compress. For example, the offset/rotation 1700 reduces the amount of bending and axial outward movement 1760 needed when compressing or crimping the frame 350. As a result, a radius of curvature of the apex 1204 of the compressed or crimped frame is greater than would be the case if the offset/rotation 1700 were not included. Since the radius of curvature is increased, the stress on the apex 1204 is reduced when the frame is compressed or crimped.

Figure 20A:
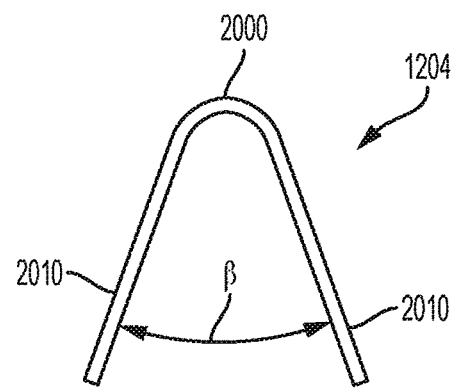
FIGS. 20A-20C show exemplary embodiments of shapes of links or portions of links that can be used between an inner portion/valve seat and an outer portion of a docking device frame.
Figure 20B:
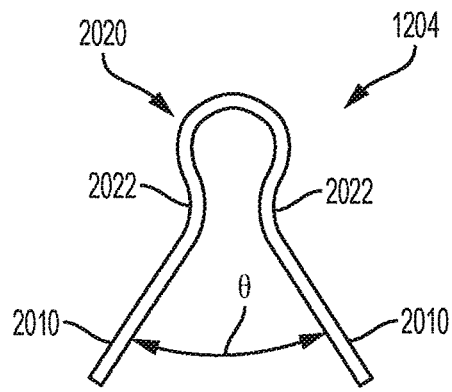
Figure 20C:
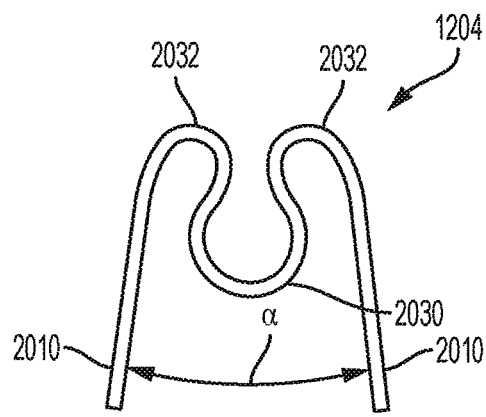

Referring to FIGS. 20A-20C, in some exemplary embodiments the apex 1204 of the strut portion or link 1202 (See FIG. 12) is shaped to make the frame 350 easier to compress or crimp. The apex 1204 can have a wide variety of different shapes. In the example of FIG. 20A, the apex includes a sharp bend 2000. Leg portions 2010 form an acute angle (3, such as less than 60 degrees, less than 45 degrees, or less than 30 degrees. In the example of FIG. 20B, the apex 1204 includes an upwardly extending rounded end or tip 2020 that transitions to two leg portions 2010 at two bends 2022. The rounded end or tip 2020 is substantially circular. For example, the rounded end or tip can be formed by a 180 degree to 300 degree (or any sub-range) arc. Leg portions 2010 form an acute angle θ, such as less than 60 degrees, less than 45 degrees, less than 30 degrees, less than 20 degrees, or less than 10 degrees. In the example of FIG. 20C, the apex 1204 includes a downwardly extending rounded end 2030, two upwardly extending rounded portions 2032, and two leg portions 2010. The downwardly extending end 2030 is substantially circular. For example, the end 2030 can be formed by a 180 degree to 300 degree (or any sub-range) arc. The upwardly extending rounded portions 2032 are also substantially circular. For example, the upwardly extending rounded portions can be formed by a 180 degree to 300 degree (or any sub-range) arc. Leg portions 2010 form an acute angle α, such as less than 60 degrees, less than 45 degrees, less than 30 degrees, less than 20 degrees, or less than 10 degrees.

Figure 21A:
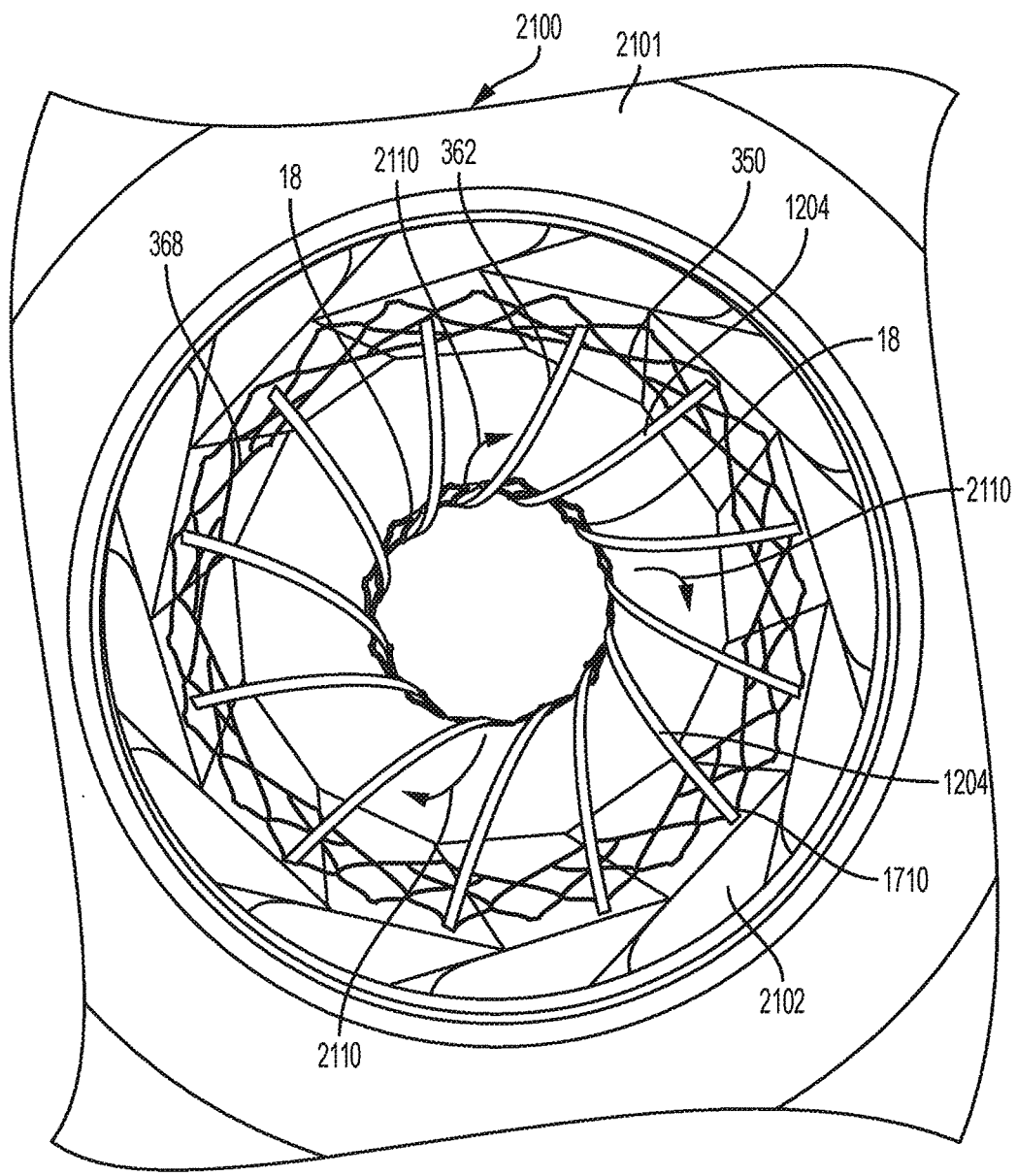
FIGS. 21A-21H illustrate an exemplary embodiment of crimping of an exemplary docking station frame.

FIGS. 21A-21H illustrate crimping of a docking station frame 350, such as the docking station frame illustrated by FIGS. 17-19 for installation into a delivery catheter (See for example delivery catheter 2200 in FIG. 22A). Depending on the implantation site, the catheter can be flexible or rigid. A rigid or substantially rigid catheter can be used to access the inferior vena cava IVC or the superior vena cava SVC. A percutaneous path to the inferior vena cava IVC that is relatively straight can be used. In the example, a crimping apparatus 2100 includes a housing 2101 and wedge shaped drive members 2102. In FIG. 21A, the docking station frame 350 is in a fully expanded or substantially fully expanded condition inside the wedge shaped driving members 2102. In this position, both annular outer portion or wall 368 and the valve seat 18 are fully expanded. The strut portions/links 1202 are shown angled in a generally clockwise direction 2110 as they extend from the valve seat 18 to the annular outer portion or wall 368. Optionally, the portions/links 1202 can be angled in a generally counter-clockwise direction (i.e., opposite clockwise direction 2110) as they extend from the valve seat 18 to the annular outer portion or wall 368 (crimping would be similar but opposite to that shown in FIGS. 21A-21H).

Figure 21B:
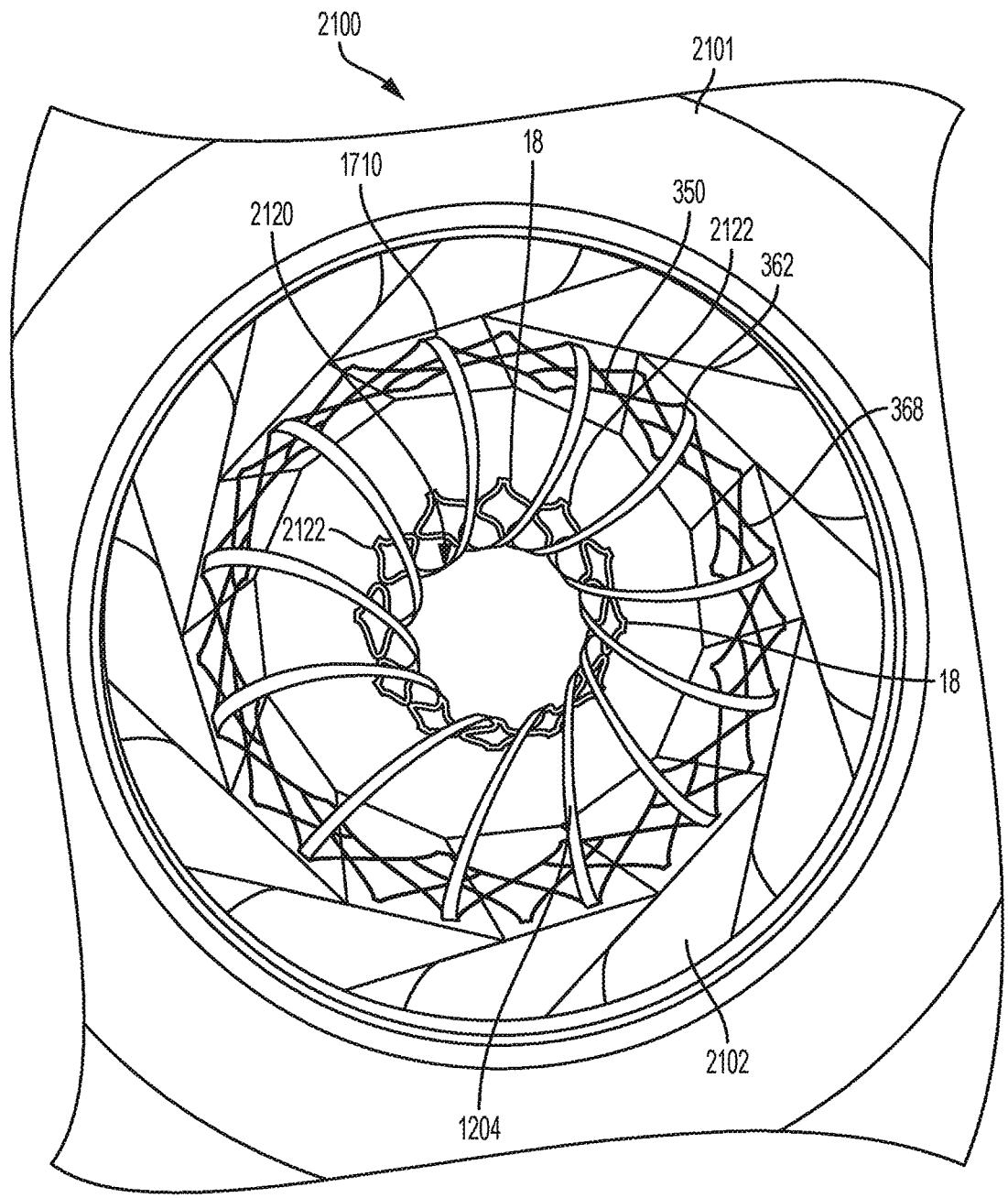

In FIG. 21B, the wedge shaped driving members 2102 begin to move the annular outer portion 368 or wall radially inward. As the annular outer portion 368 moves radially inward, the junctions 1710 (See FIG. 17) moves radially inward and the strut portions/links 1202 force a top end 2120 of the valve seat 18 radially inward, while a bottom/proximal end 2122 of the valve seat remains substantially expanded.

Figure 21C:
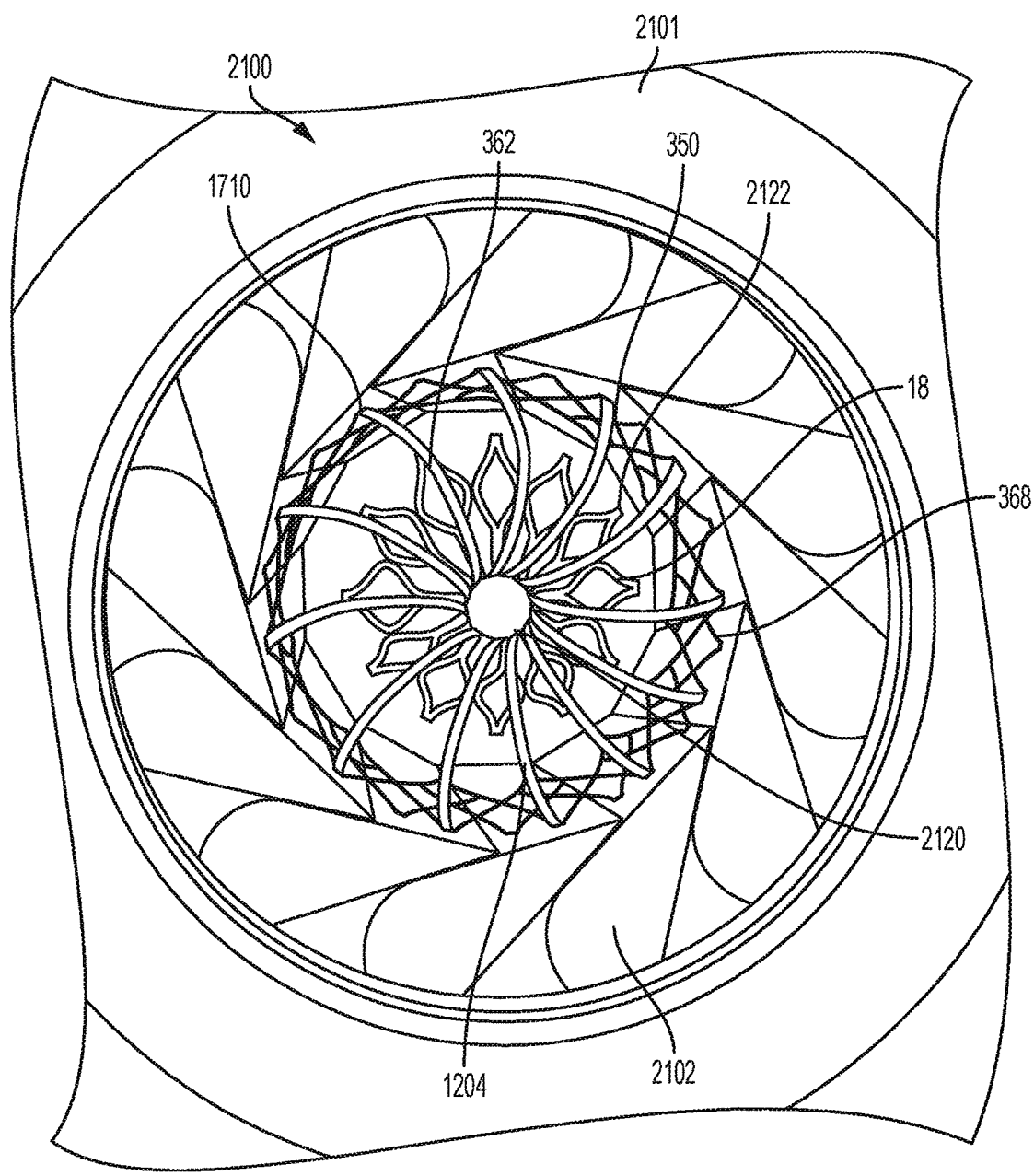

In FIG. 21C, the wedge shaped driving members 2102 continue to move the annular outer portion 368 or wall radially inward. As the annular outer portion 368 moves radially inward, the junction 1710 (See FIG. 17) continues to move radially inward. The strut portions/links 1202 continue to force the top end 2120 of the valve seat 18 radially inward, while a bottom end 2122 of the valve seat remains substantially expanded. As can be seen by comparing FIGS. 21A-21C, the orientation of the portions/links 1202 has changed such that the angle in the clockwise direction 2110 has been diminished, eliminated, or the portions/links 1202 extend in the counterclockwise direction. As frame 350 is compressed or crimped, the radii of curvature of the apexes 1204 becomes smaller.

Figure 21D:
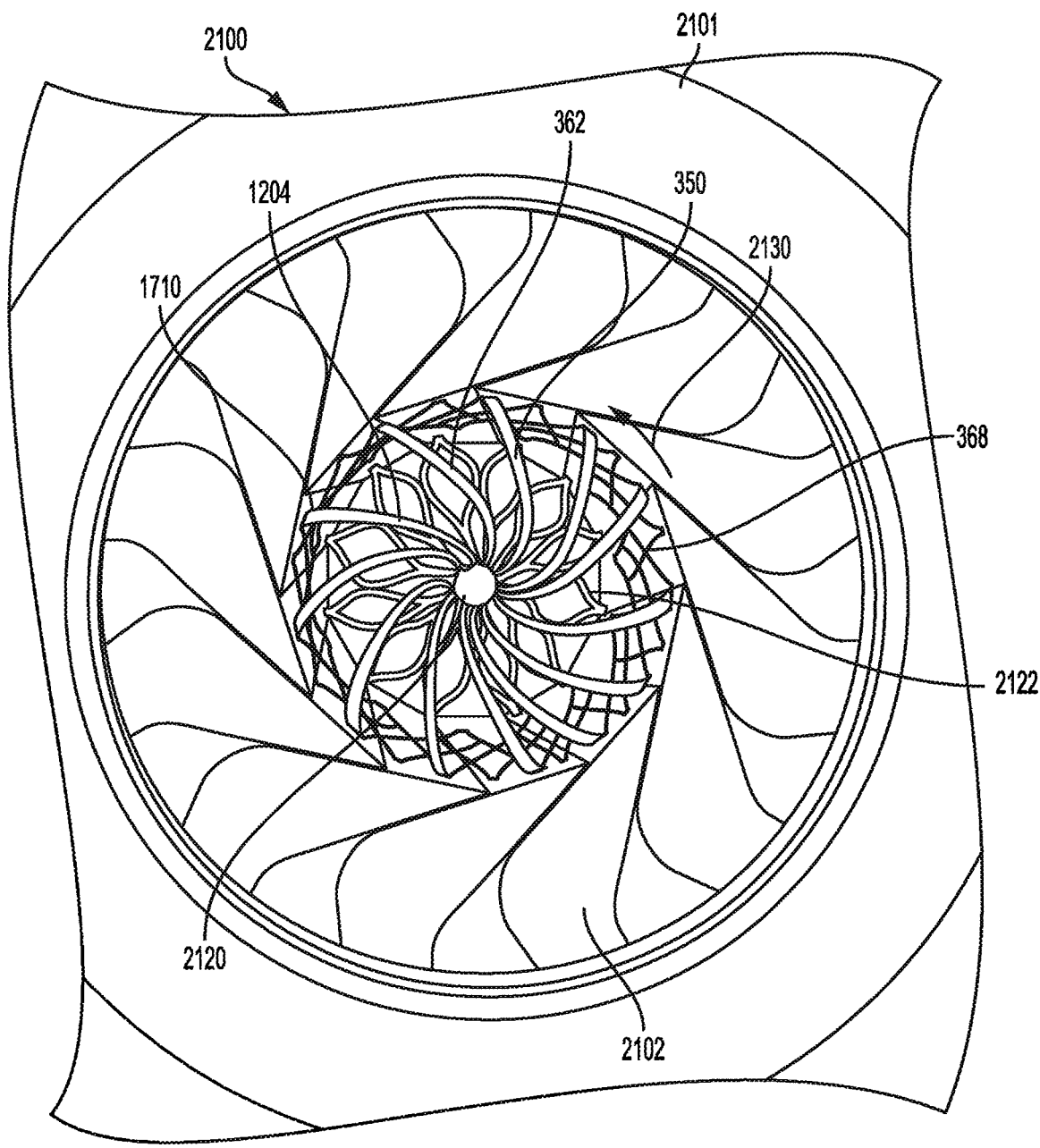

In FIG. 21D, the wedge shaped driving members 2102 continue to move the annular outer portion 368 or wall radially inward. As the annular outer portion 368 moves radially inward, the junction 1710 (See FIG. 17) continues to move radially inward. The portions/links 1202 force the top end 2120 of the valve seat 18 substantially closed, while a bottom end 2122 of the valve seat remains open. In FIG. 21D, the bottom end 2122 of the valve seat is in contact with the annular outer portion 368. The orientation of the strut portions/links 1202 has now clearly changed from the clockwise direction 2110 to the counterclockwise direction 2130 as they extend from the valve seat 18 to the annular outer portion or wall 368. The radii of curvature of the apexes 1204 continues to become smaller. However, the angled orientation of the portion/links 1202 helps keep the distance between the junctions 1710, 1720 larger to increase the radii of curvature of the apexes 1204 relative to non-angled portions 2102 that are crimped.

Figure 21E:
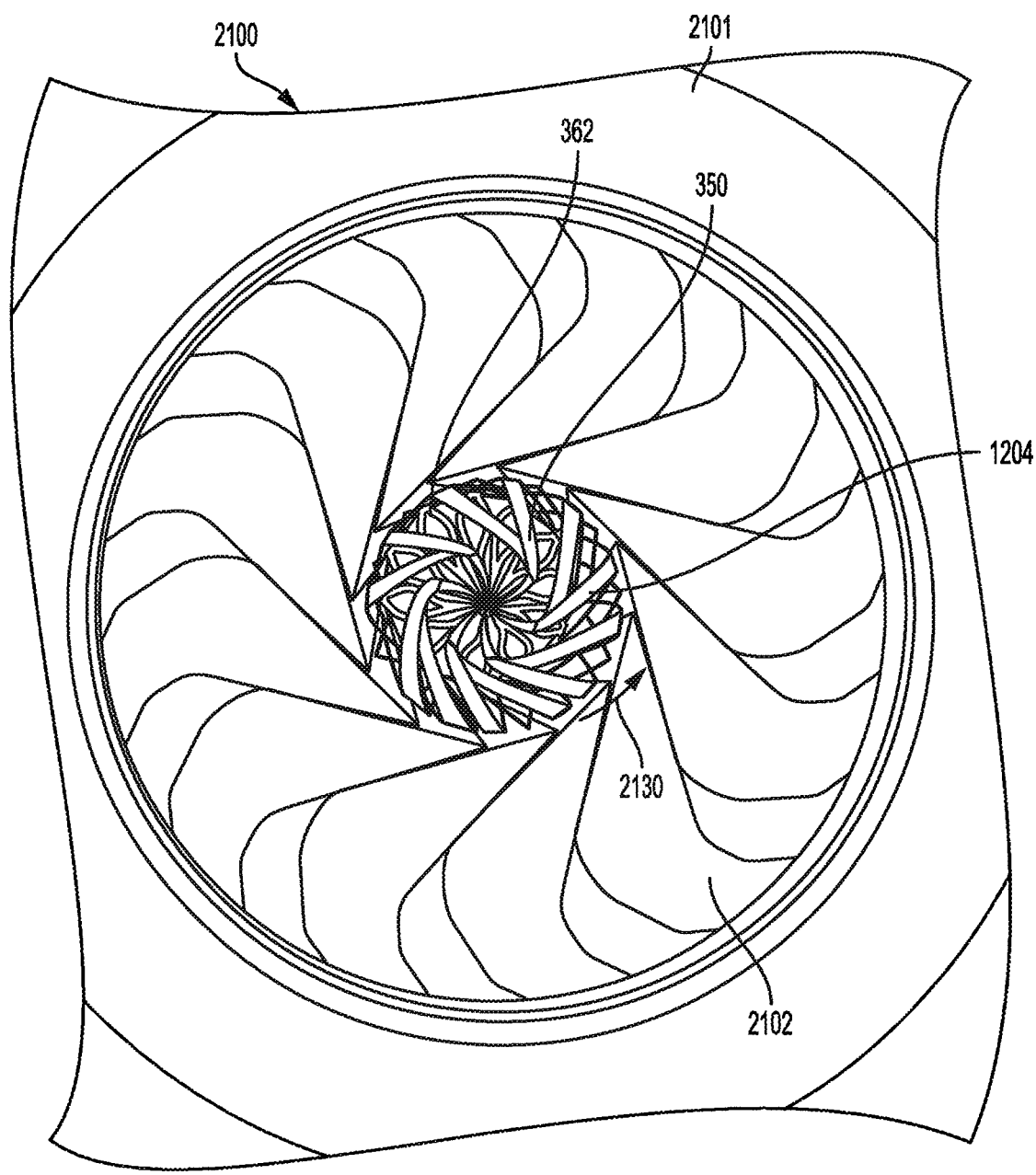

In FIG. 21E, the wedge shaped driving members 2102 drive the annular outer portion 368 and the bottom end 2122 of the valve seat 18 radially inward. The orientation of the portions/links 1202 is in the counterclockwise direction 2130. The radii of curvature of the apexes 1204 continue to become smaller.

Figure 21F:
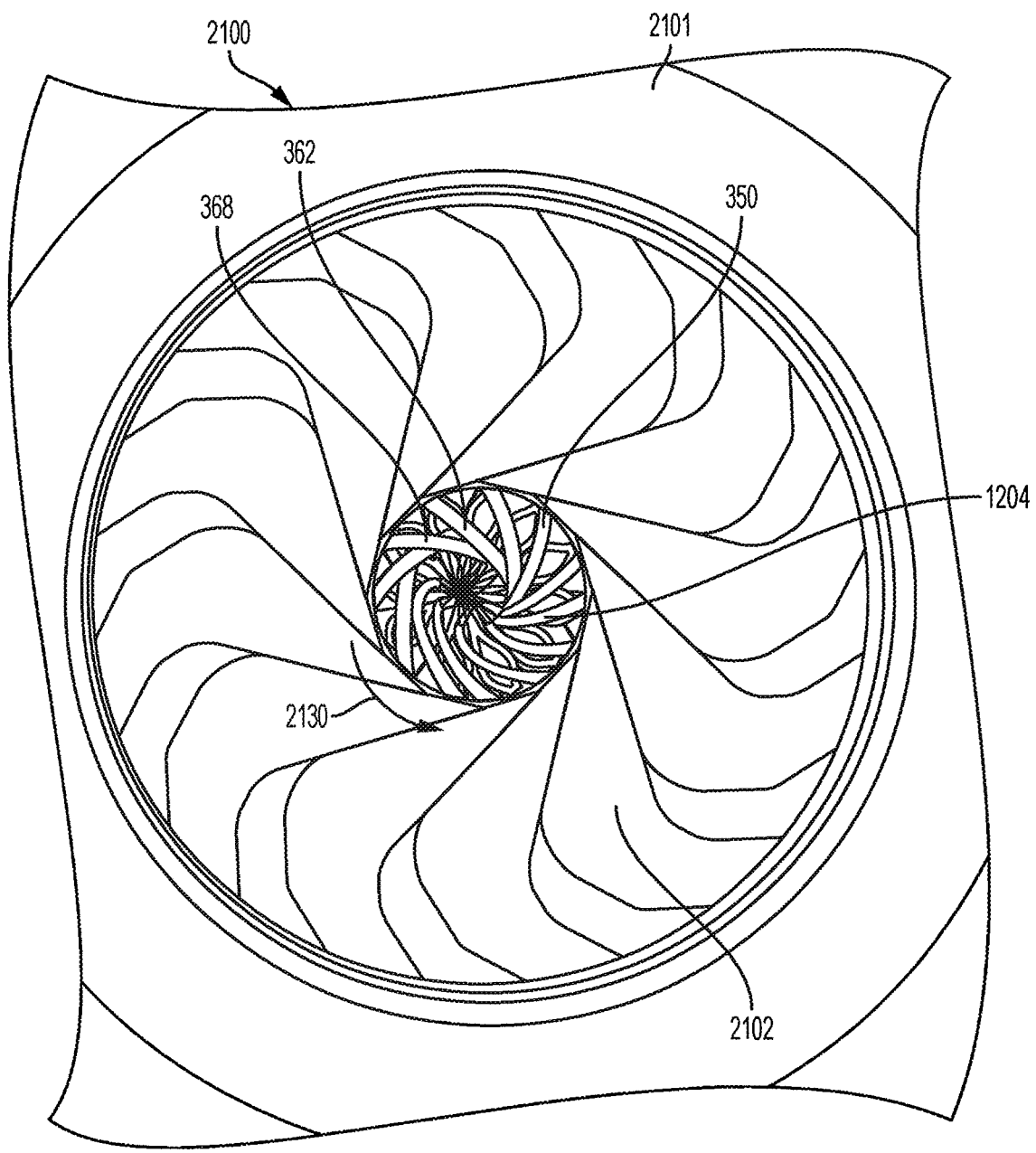

In FIG. 21F, the wedge shaped driving members 2102 continue to drive the annular outer portion 368 and the bottom end 2122 of the valve seat 18 radially inward. The orientation of the portions/links 1202 is in the counterclockwise direction 2130. The radii of curvature of the apexes 1204 continue to become smaller.

Figure 21G:
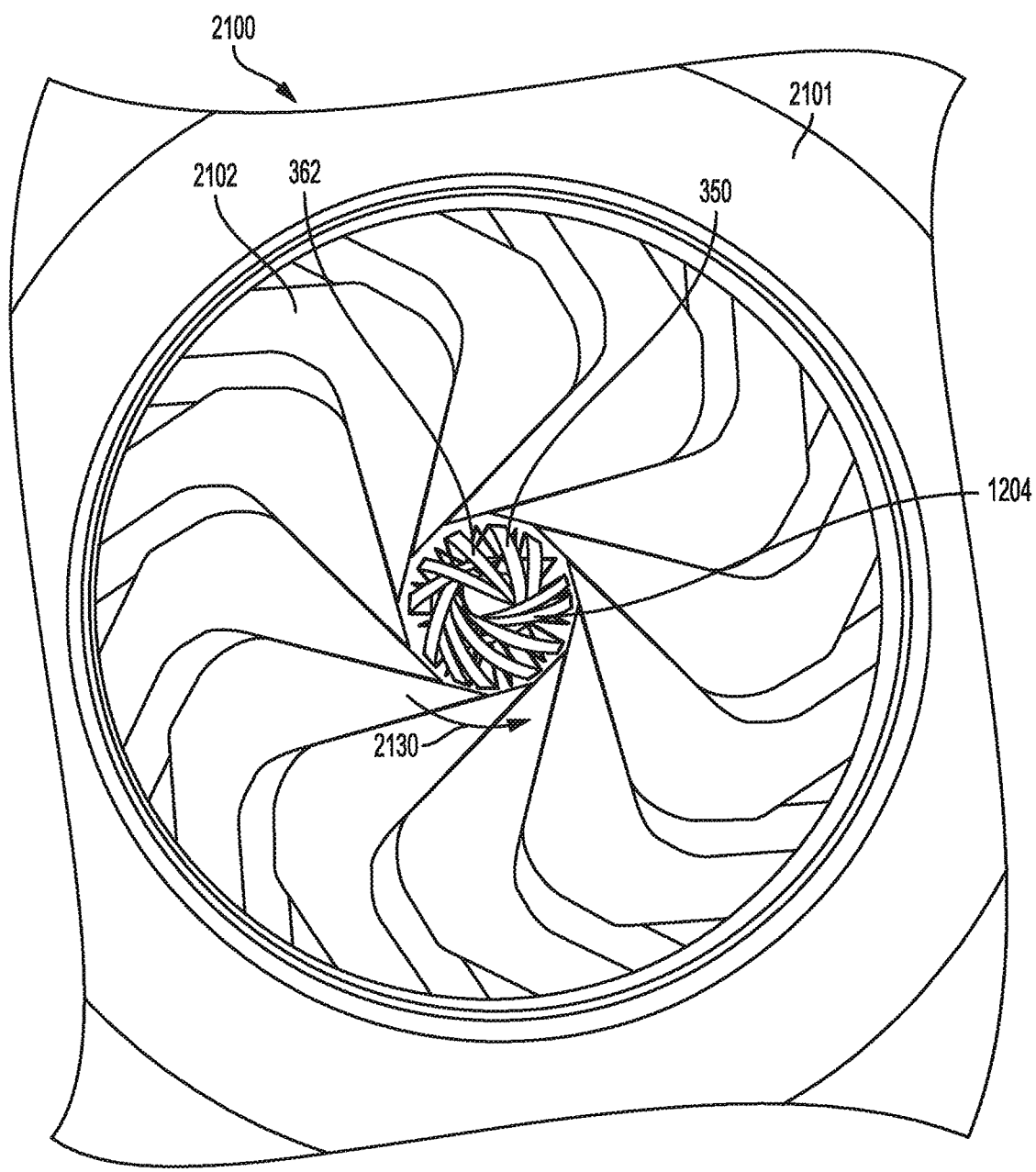
Figure 21H:
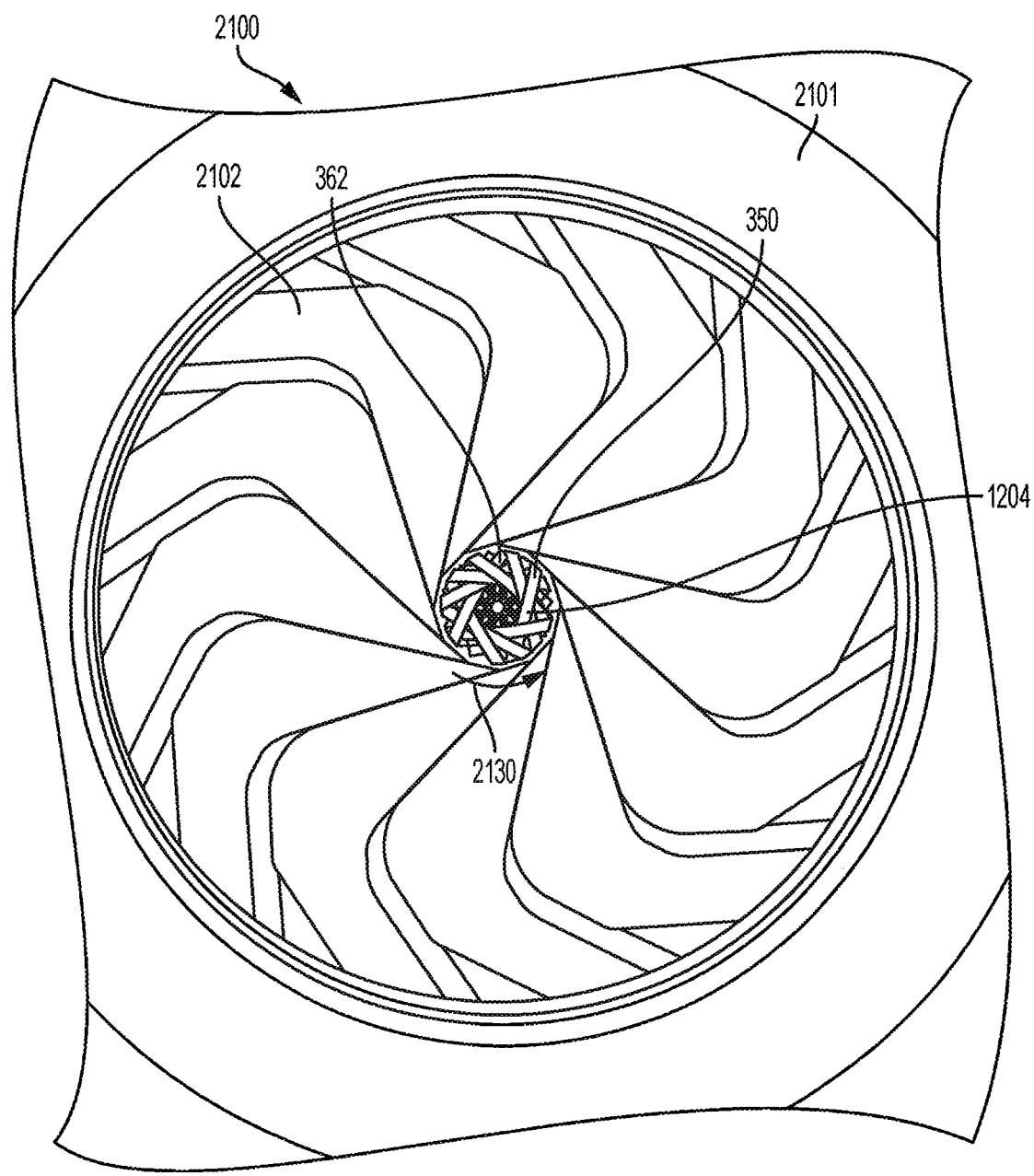

In FIG. 21G, the wedge shaped driving members 2102 continue to drive the annular outer portion 368 and the bottom end 2122 of the valve seat 18 radially inward. The orientation of the portions/links 1202 is in the counterclockwise direction 2130. The radii of curvature of the apexes 1204 continue to become smaller.

The wedge shaped driving members 2102 continue to drive the annular outer portion 368 and the bottom end 2122 of the valve seat 18 radially inward. The radii of curvature of the apexes 1204 continue to become smaller. The frame 350 is in the fully compressed or crimped state in FIG. 21H. The compressed or crimped frame 350 can be loaded into a catheter or a sleeve/sheath for deployment into a patient.

Figure 24A:
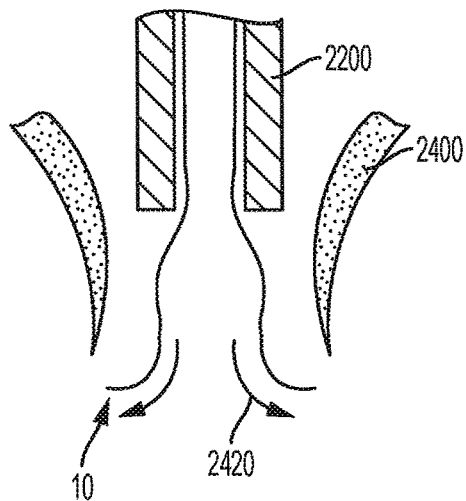
FIGS. 24A-24C illustrate an exemplary deployment of an exemplary docking station.
Figure 24B:
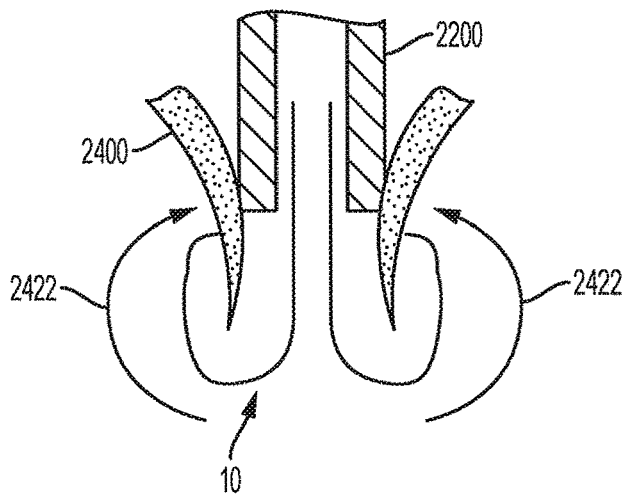
Figure 24C:
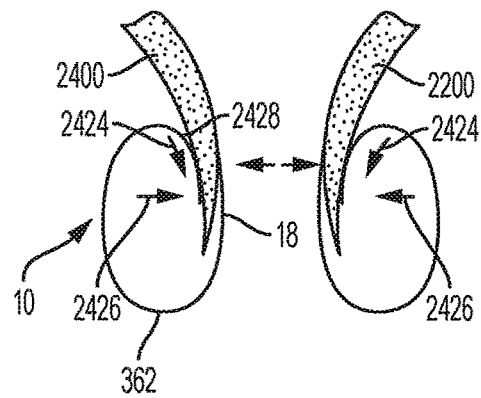

Referring to FIGS. 22A-22C, 23A-23C, and 24A-24C, in some exemplary embodiments the docking station 10 can be configured to curl back on itself as it is deployed from a catheter 2200. The docking stations 10 illustrated by FIGS. 22A-22C and 23A-23C can be deployed in any of the interior surfaces 416 or implantation locations mentioned herein. The docking station 10 illustrated by FIGS. 24A-24C is configured for deployment in a native valve. FIGS. 22A-22C, 23A-23C, and 24A-24C schematically illustrate a cross-section of a docking station 10 being deployed from the catheter 2200. The docking station 10 can be made from any combination of the materials disclosed herein. For example, the docking station 10 can be made from a shape memory alloy frame, foam, fabric coverings, etc. The illustrated docking station 10 defines a valve seat 18, a sealing portion 310, and a retaining portion 314. Embodiments shown only in cross-section in this application can be assumed to have an annular or cylindrical shape.

Referring to FIG. 22A, during deployment, the docking station 10 first extends radially outward 2220 from the deployment catheter 2200. Referring to FIG. 22B, the docking station 10 then extends or curls back 2222 toward the deployment catheter. Referring to FIG. 22C, the docking station 10 then extends back up 2224 to overlap the last portion 2226 of the docking station to be deployed from the catheter 2200.

FIGS. 23A-23C illustrate another exemplary embodiment of a docking station 10 that is configured to curl back on itself as it is deployed from a catheter 2200. The docking station 10 illustrated by FIGS. 23A-23C can be deployed in any of the interior surfaces 416 mentioned herein. Referring to FIG. 23A, during deployment, the docking station 10 first extends radially outward 2220 from the deployment catheter 2200. Referring to FIG. 23B, the docking station 10 then extends or curls back 2222 toward the deployment catheter. Referring to FIG. 23C, the docking station 10 then extends back up 2224 to overlap a valve seat 18 of the docking station and a last portion 2228 of the docking station to be deployed extends radially outward 2230 below the curled toroidal portion 2230.

FIGS. 24A-24C illustrate another exemplary embodiment of a docking station 10 that is configured to curl back on itself as it is deployed from a catheter 2200. In the example of FIGS. 24A-24C, the docking station 10 is configured to curl back on itself and capture one or more leaflets 2400 of a native valve. For example, the docking station 10 can be configured to capture the leaflets of a mitral valve MV, aortic valve AV, tricuspid valve TV, or the pulmonary valve PV. Referring to FIG. 24A, from inside the leaflets 2400 of the native valve, the docking station 10 deploys and extends radially outward 2420 from the deployment catheter 2200 outward of the leaflets 2400. Referring to FIG. 24B, the docking station 10 then extends or curls back 2422 toward and behind the leaflets 2400. Referring to FIG. 24C, the docking station 10 then extends back 2424 and the leaflets are sandwiched or clamped 2426 between the valve seat 18 and the portion 2428 of the docking station. The clamping secures the docking station 10 to the valve leaflets and thereby the native valve.

Figure 25:
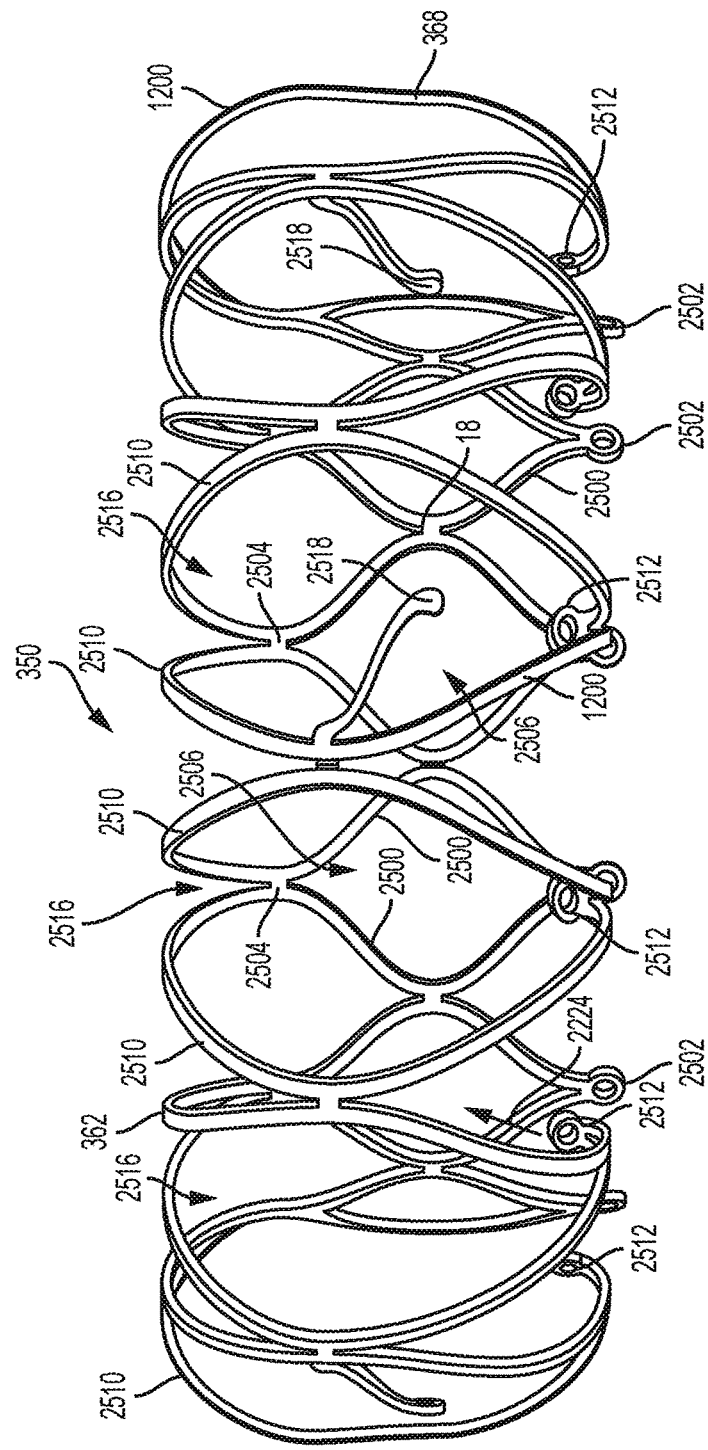
FIG. 25 is a side elevational view of an exemplary docking station frame.

FIG. 25 illustrates an example of a strut configuration that can be employed to make or be incorporated in the curling docking station 10 of FIGS. 22A-22C and 24A-24C. In FIG. 25, the valve seat 18 is formed by inner struts 2500. The inner struts 2500 extend from an end 2502 to a junction 2504 and form generally diamond shaped openings 2506. Top and outer struts 2510 extend from the junction 2504 to a second end 2512. The top and outer struts 2510 form continuous openings 2516. Optionally, the end 2512 can extend back up 2224 to overlap the end 2502.

Figure 26:
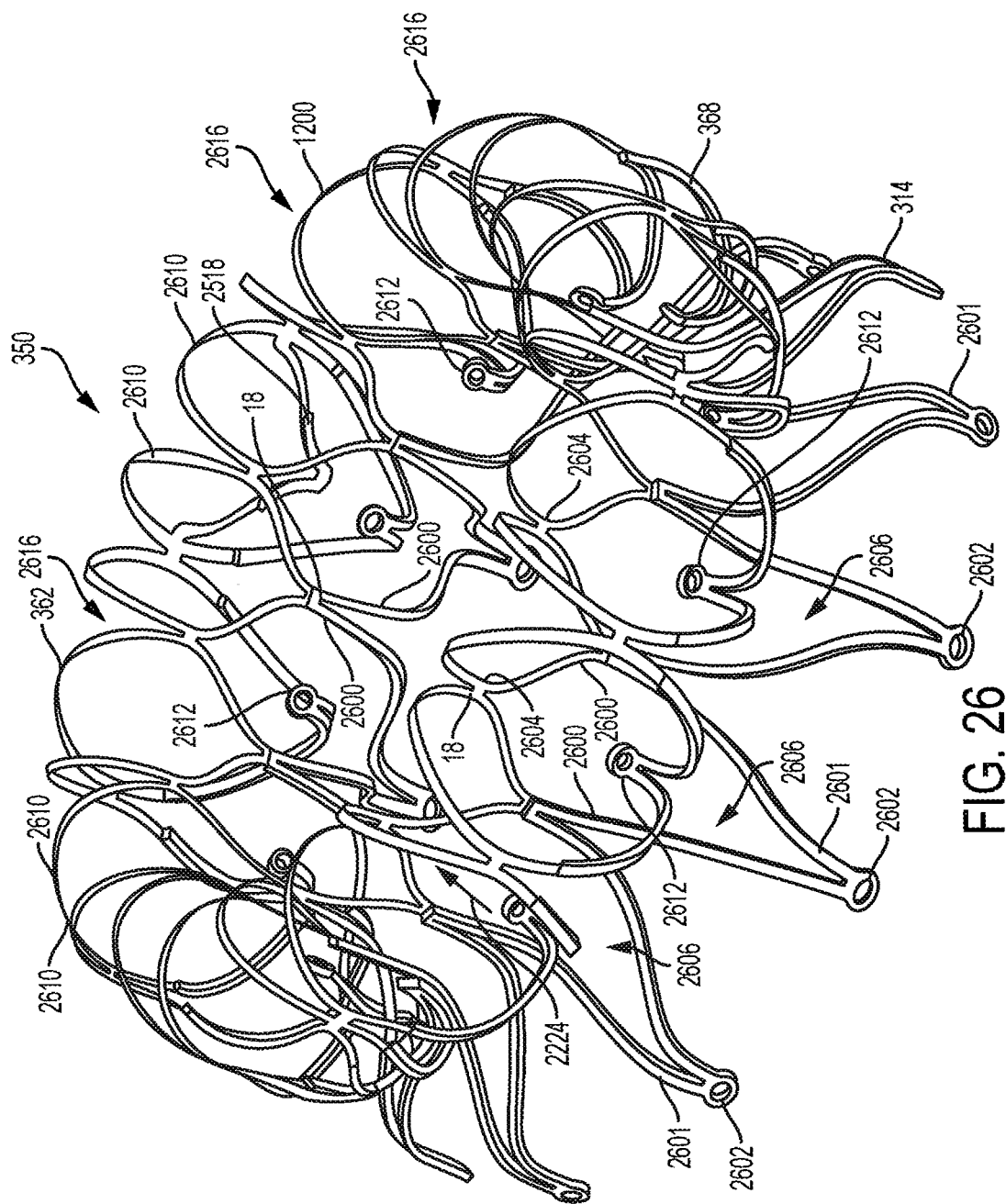
FIG. 26 is a perspective view of an exemplary embodiment of a docking station frame.
Figure 27:
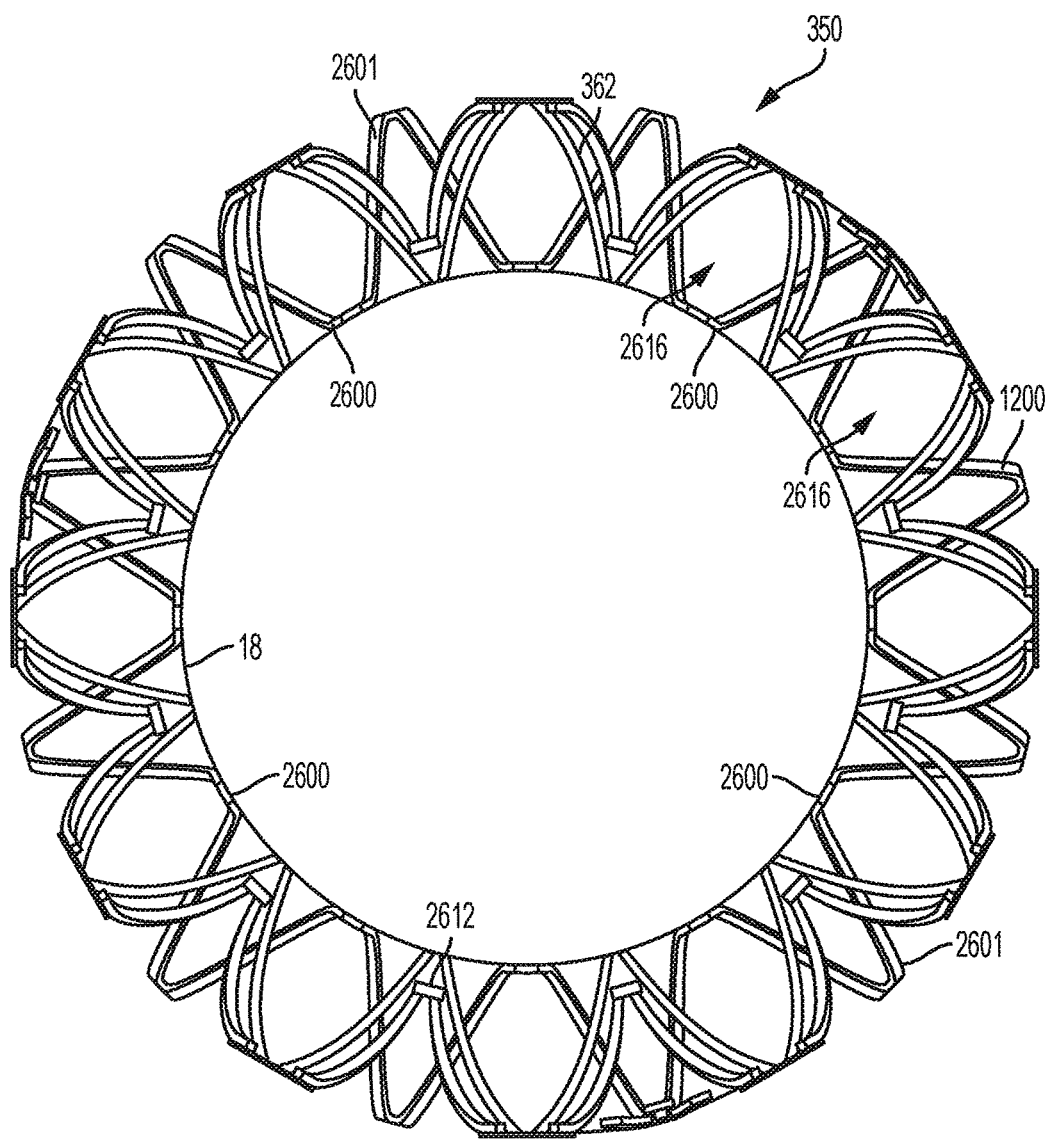
FIG. 27 is a top view of the docking station frame illustrated by FIG. 26.
Figure 28:
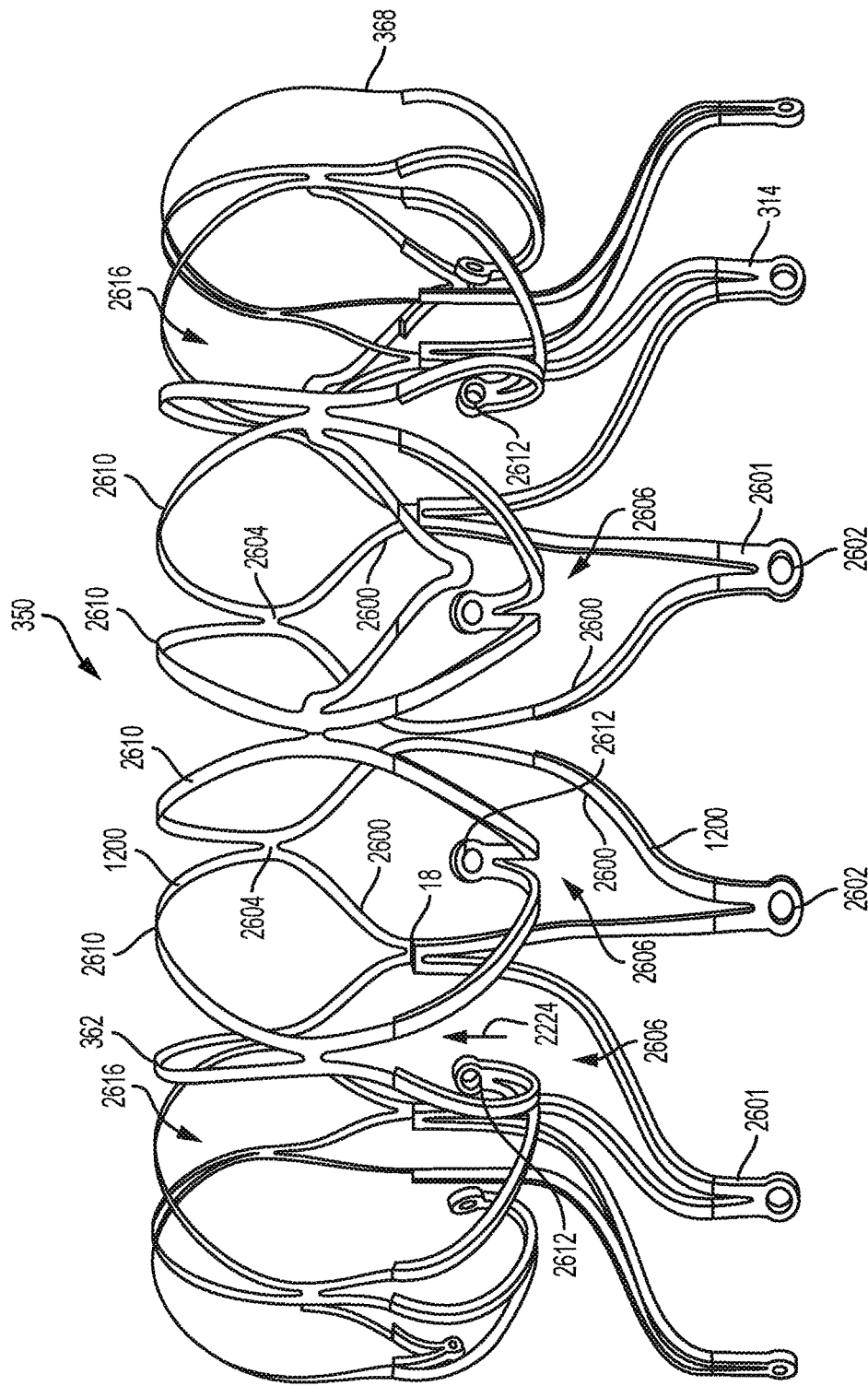
FIG. 28 is a side view of the docking station frame illustrated by FIG. 26.

FIGS. 26-28 illustrate an example of a strut configuration that can be employed to make or be incorporated in the curling docking station 10 of FIGS. 23A-23C. In FIG. 25, the valve seat 18 is formed by inner struts 2600. The inner struts 2600 are elongated and extend (e.g., longitudinally and radially outward) to form legs 2601 that extend to an end 2602. The inner struts also extend upward to a junction 2604 and form openings 2606. Top and outer struts 2610 extend from the junction 2604 to a second end 2612. The top and outer struts 2610 form continuous openings 2616. In one embodiment, end 2612 extends back up 2224 and overlaps the legs 2601.

Figure 29:
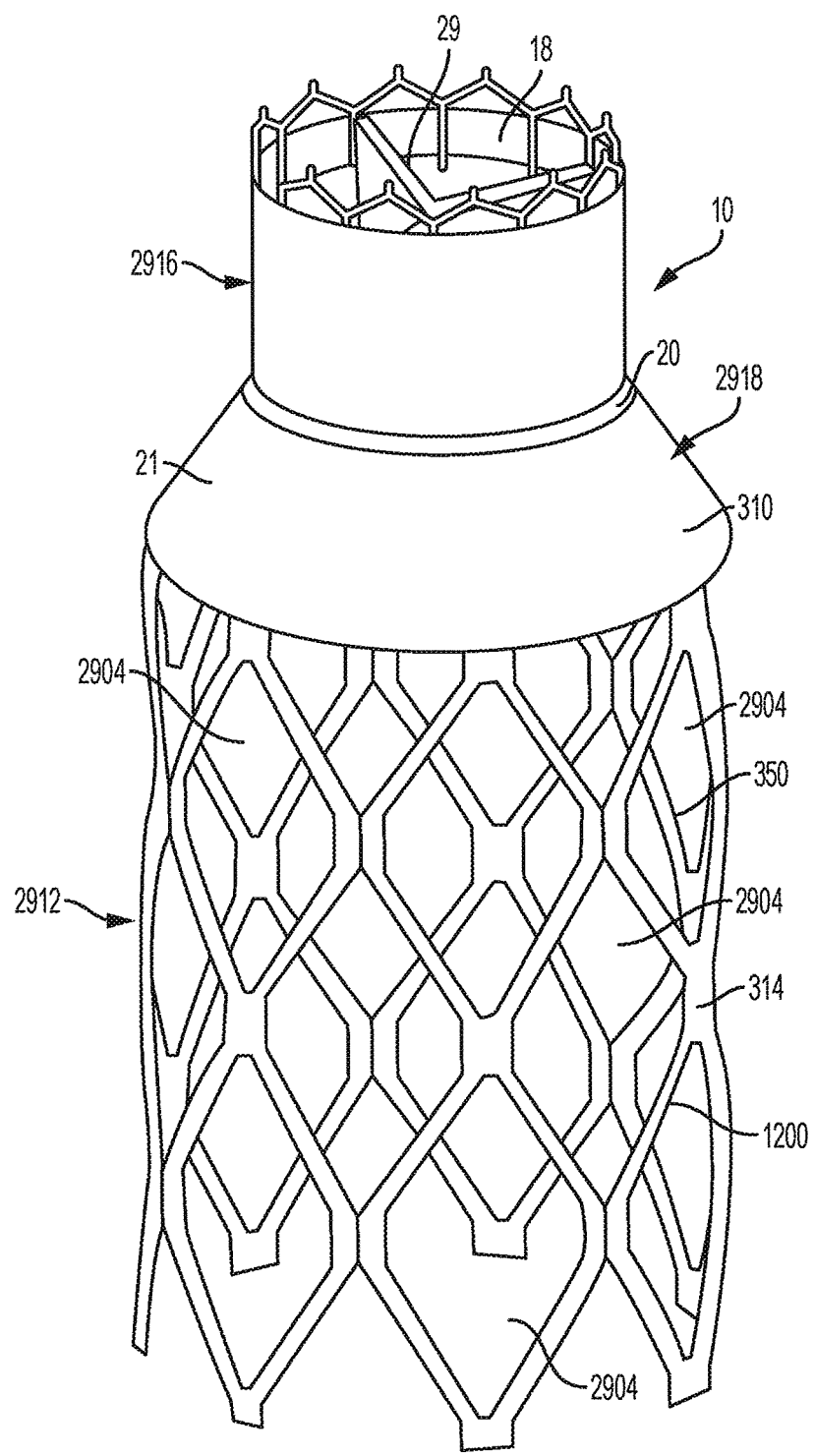
FIG. 29 is a perspective view of an exemplary embodiment of a docking station including an exemplary transcatheter valve therein.

FIG. 29 illustrates an exemplary embodiment of a docking station 10. The frame 350 or body can take a wide variety of different forms and FIG. 29 illustrates just one of the many possible configurations. In the example of FIG. 29, the retaining portion 314 forms a relatively wider inflow portion 2912. A relatively narrower portion 2916 forms the seat 18. A tapered portion 2918 joins the wider portion 2912 and the seat 18.

Figure 30:
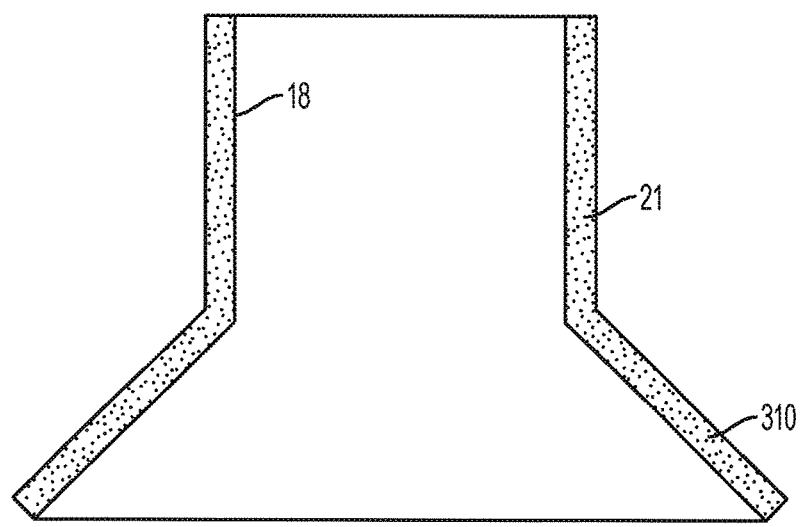
FIG. 30 is a sectional view of an exemplary embodiment of a covering material that can be used with the docking station illustrated in FIG. 29.

In the example of FIG. 29, the frame 350 comprises a plurality of metal struts 1200 that form cells 2904. In the example of FIG. 29, cells of the retaining portion 314 are uncovered. A covering/material 21 (e.g., an impermeable material, a semi-permeable material, a material like those discussed above, etc.), such as a cloth or fabric (FIG. 29) or a protective foam (FIG. 30) is provided over the narrow portion 2916, the tapered portion 2918, and the round or outer segment 3216 to form the sealing portion 310 of the docking station 10. The valve 29 expands in the narrow portion 2916, which forms the valve seat 18.

The docking station can be made from a very resilient or compliant material to accommodate large variations in the anatomy. For example, the docking station can be made from a highly flexible metal, metal alloy, polymer, or an open cell foam. An example of a highly resilient metal is nitinol, but other metals and highly resilient or compliant non-metal materials can be used. The docking station 10 can be self-expandable, manually expandable (e.g., expandable via balloon), mechanically expandable, or a combination of these. A self-expandable docking station 10 can be made of a shape memory material such as, for example, nitinol.

Referring to FIG. 29, in one exemplary embodiment, a band 20 extends about the waist or narrow portion 2916, or is integral to the waist to form an unexpandable or substantially unexpandable valve seat 18. The band 20 stiffens the waist and, once the docking station is deployed and expanded, makes the waist/valve seat relatively unexpandable in its deployed configuration. Optionally the band 20 can extend over some or all of the narrow portion 2916. In the example of FIG. 29, the valve 29 is secured by expansion of its collapsible frame into the valve seat 18, of the docking station 10. The unexpandable or substantially unexpandable valve seat 18 prevents the radially outward force of the valve 29 from being transferred to the inside surface 416 of the circulatory system. However in one exemplary embodiment, the waist/valve seat of the deployed docking station can optionally expand slightly in an elastic fashion when the valve 29 is deployed against it. This optional elastic expansion of the waist 18 can put pressure on the valve 29 to help hold the valve 29 in place within the docking station.

The band 20 can take a wide variety of different forms and can be made from a wide variety of different materials. For example, the band 20 can be made of PET, PTFE, ePTFE, one or more sutures, fabric, metal, polymer, a biocompatible tape, or other relatively unexpandable materials known in the art that are sufficient to maintain the shape of the valve seat 18 and hold the valve 29 in place. The band can extend about the exterior of the stent, or can be an integral part of it, such as when fabric or another material is interwoven into or through cells of the stent. The band 20 can be narrow, such as the suture band in FIG. 29, or can be wider. The band can be a variety of widths, lengths, and thicknesses. In one non-limiting example, the valve seat 18 is between 15-35 mm wide, 18-31 mm wide, 20-29 mm wide, etc., although the diameter of the valve seat should be within the operating range of the particular valve 29 that will be secured within the valve seat 18, and can be different than the foregoing example. The valve 29, when docked within the docking station, can optionally expand around either side of the valve seat slightly. This aspect, sometimes referred to as a "dog-bone" (e.g., because of the shape it forms around the valve seat or band), can also help hold the valve in place.

Figure 31:
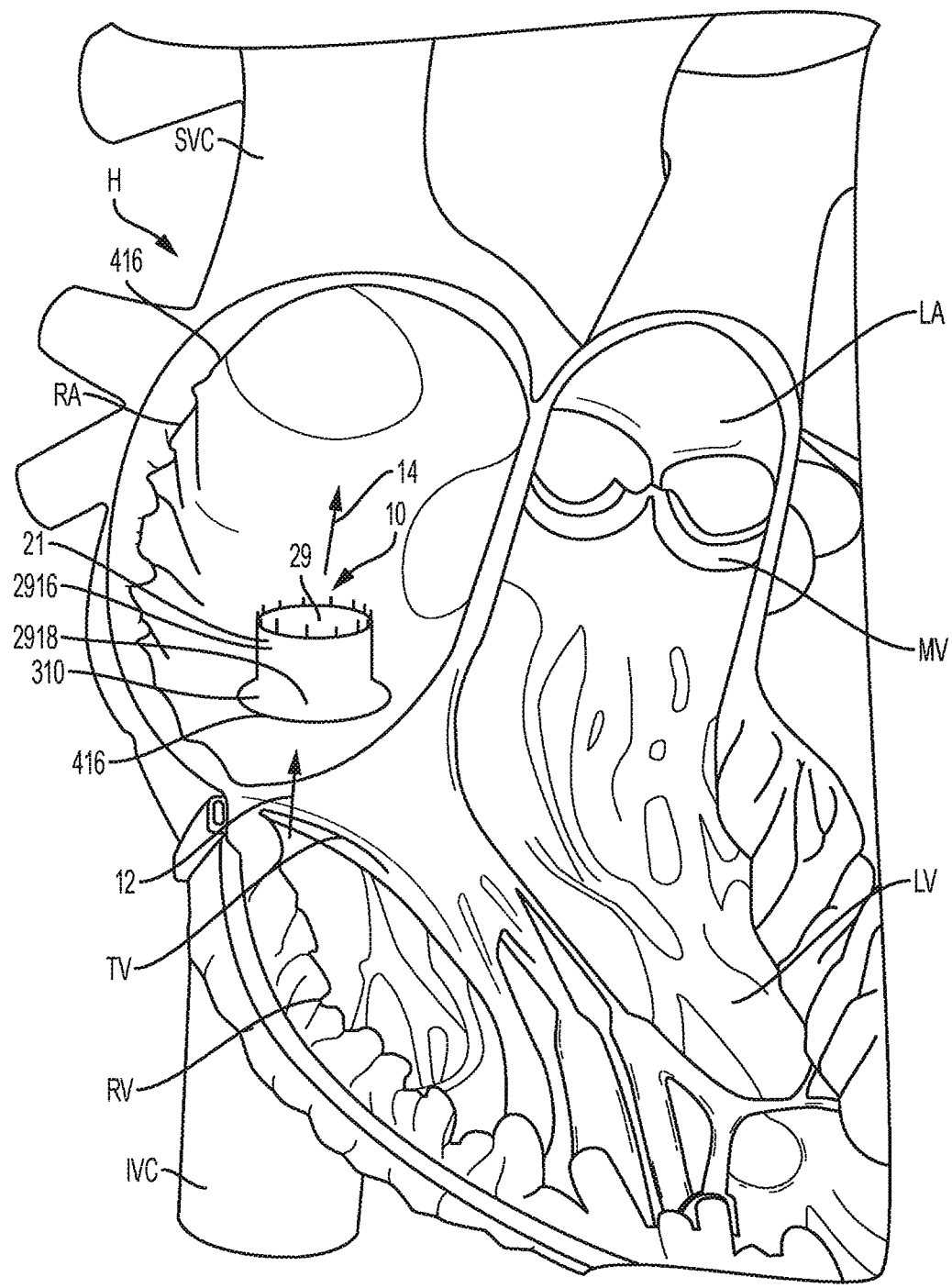
FIG. 31 is a cutaway view of a human heart showing a portion of a right atrium and IVC of the human heart with the docking station illustrated by FIG. 29 positioned in the IVC.

FIG. 31 illustrates the docking station 10 of FIG. 29 implanted in the circulatory system, such as in the inferior vena cava IVC. In the example of FIG. 31, the narrow portion 2916 and/or the tapered portion 2918 extend into the right atrium RA and the retaining portion 314 (hidden in FIG. 31) is held in place in the inferior vena cava IVC. The reduced size of the narrow portion 2916 can prevent the docking station 10 from contacting an interior surface of the circulatory system or native tissue (e.g., of the right atrium RA). The covering 21 illustrated by FIG. 30 can be used to cushion any contact between the narrow portion 2916 and the circulator system or native tissue (e.g., right atrium) that might occur. The sealing portion 310 provides a seal between the docking station 10 and an interior surface 416 of the circulatory system, such as at the junction between the inferior vena cava IVC and the right atrium.

In the example of FIG. 31, the sealing portion 310 is formed by providing the covering/material 21 over the frame 350 or a portion thereof. In particular, the sealing portion 310 can comprise the narrow portion 2916, the tapered portion 2918 and/or the retaining portion 314. In an exemplary embodiment, the covering/material 21 (e.g., an impermeable material, semi-permeable material, cloth, polymer, foam, wax, etc.) covers the narrow portion 2916, the tapered portion 2918, and optionally a portion of the retaining portion 314. In one embodiment, the covering/material can be configured to encourage or enhance tissue ingrowth (e.g., covering/material 21 can have a large surface area and/or be hydrophilic to enhance tissue ingrowth). This provides a seal and makes the docking station impermeable or substantially impermeable from the sealing portion 310 to the seal between the valve 29 and the docking station 10 at the valve seat 18. As such, blood flowing in the inflow direction 12 toward the outflow direction 14 is directed to the valve seat 18 and valve 29, once installed/deployed in the valve seat.

As one non-limiting example, when the docking station 10 is placed in the inferior vena cava, which is a large vessel, the significant volume of blood flowing through the vein is funneled into the valve 29 by the covering 21. The covering 21 can be fluid impermeable or become fluid impermeable (e.g., via tissue ingrowth) so that blood cannot pass through. A variety of other covering materials (including any materials described elsewhere herein), can be used such as, for example, foam (FIG. 30) or a fabric that is treated with a coating that is impermeable to blood, polyester, or a processed biological material, such as pericardium. More of the docking station frame 350 can be provided with the material 21, forming a relatively large impermeable portion.

Figure 32:
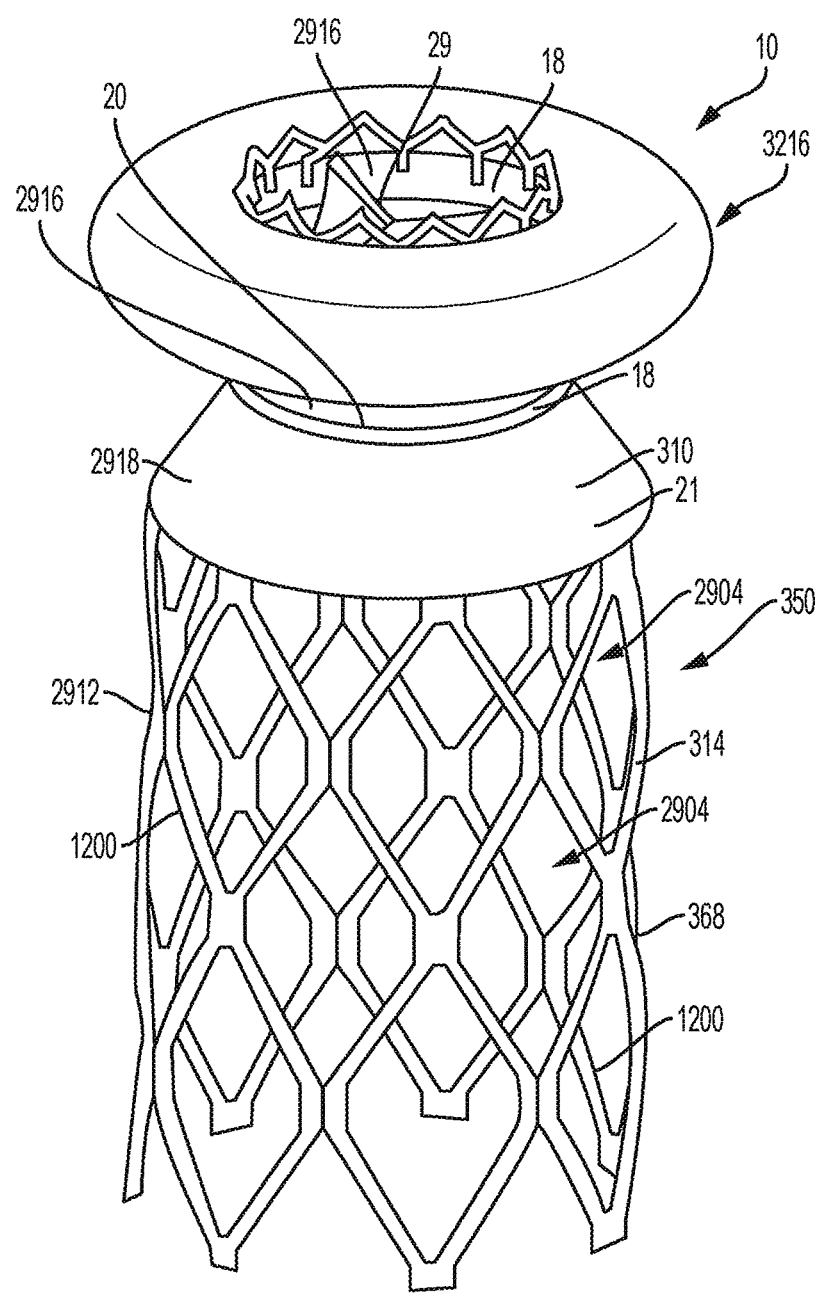
FIG. 32 is a perspective view of an exemplary embodiment of a docking station.

FIG. 32 illustrates an exemplary embodiment of a docking station 10. The docking station illustrated by FIG. 32 is similar to the docking station illustrated by FIG. 29, except an outer segment 3216 extends from the narrow portion 2916. The outer segment 3216 is shaped to be atraumatic to the interior surface 416 or native anatomy. For example, the outer segment 3216 can be round or toroidal. The round or outer segment 3216 can take a wide variety of different forms. For example, the round or outer segment 3216 can comprise a plurality of metal struts that form cells and form part of the frame 350 or be attached to the frame 350. The round or outer segment 3216 can be made of a foam material. FIG. 32 illustrates one of many possible configurations.

In the example of FIG. 32, the retaining portion 314 forms a relatively wider inflow portion 2912. A relatively narrower portion 2916 forms the seat 18. A tapered portion 2918 joins the wider portion 2912 and the seat 18. The round or outer segment 3216 extends radially outward from the relatively narrower portion 2916.

In the example of FIG. 32, the frame 350 comprises a plurality of metal struts 1200 that form cells 2904. In the example of FIG. 32, cells of the retaining portion 314 are uncovered. A covering/material 21 (e.g., an impermeable material, semi-permeable material, material like those discussed above, etc.), such as a cloth or fabric or a protective foam can be provided over the narrow portion 2916, the tapered portion 2918, and the round or outer segment 3216. The covering/material 21 that extends to the frame 350 forms the sealing portion 310 of the docking station 10. The valve 29 expands in the narrow portion 2916 that forms the valve seat 18.

The docking station can be made from a very resilient or compliant material to accommodate large variations in the anatomy. For example, the docking station can be made from a highly flexible metal, metal alloy, polymer, or an open cell foam. An example of a highly resilient metal is nitinol, but other metals and highly resilient or compliant non-metal materials can be used. The docking station 10 can be self-expandable, manually expandable (e.g., expandable via balloon), mechanically expandable, or a combination of these. A self-expandable docking station 10 can be made of a shape memory material such as, for example, nitinol.

Referring to FIG. 32, in one exemplary embodiment a band 20 extends about the waist or narrow portion 2916, or is integral to the waist to form an unexpandable or substantially unexpandable valve seat 18. The band 20 can also extend over other portions of the docking station as well. The band 20 stiffens the waist and, once the docking station is deployed and expanded, makes the waist/valve seat relatively unexpandable in its deployed configuration. In the example of FIG. 32, the valve 29 is secured by expansion of its collapsible frame into the valve seat 18, of the docking station 10. The unexpandable or substantially unexpandable valve seat 18 prevents the radially outward force of the valve 29 from being transferred to the inside surface 416 of the circulatory system. However in one exemplary embodiment, the waist/valve seat of the deployed docking station can optionally expand slightly in an elastic fashion when the valve 29 is deployed against it. This optional elastic expansion of the waist 18 can put pressure on the valve 29 to help hold the valve 29 in place within the docking station.

The band 20 can take a wide variety of different forms and can be made from a wide variety of different materials. The band 20 can be made of PET, one or more sutures, fabric, metal, polymer, a biocompatible tape, or other relatively unexpandable materials known in the art that are sufficient to maintain the shape of the valve seat 18 and hold the valve 29 in place. The band can extend about the exterior of the stent, or can be an integral part of it, such as when fabric or another material is interwoven into or through cells of the stent. The band 20 can be narrow, such as the suture band in FIG. 32, or can be wider. The band can be a variety of widths, lengths, and thicknesses. In one non-limiting example, the valve seat 18 is between 27-28 mm wide, although the diameter of the valve seat should be within the operating range of the particular valve 29 that will be secured within the valve seat 18, and can be different than the foregoing example. The valve 29, when docked within the docking station, can optionally expand around either side of the valve seat slightly, e.g., in an hourglass-like shape.

Figure 33:
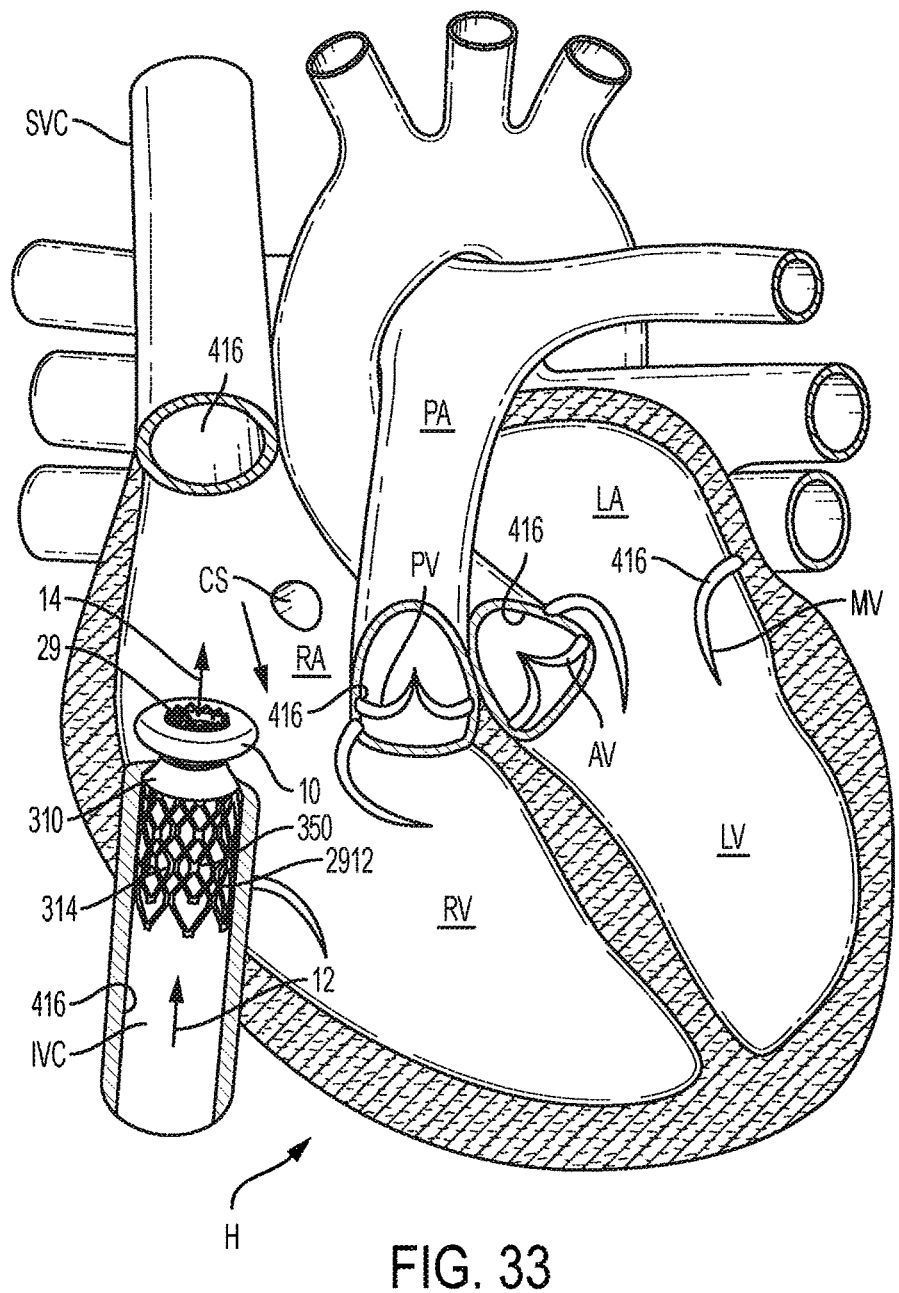
FIG. 33 is a cutaway view of a human heart with the docking station illustrated by FIG. 32 positioned in the inferior vena cava.

FIG. 33 illustrates the docking station 10 of FIG. 32 implanted in the circulatory system, such as in the inferior vena cava IVC. In FIG. 33, outer segment 3216, the narrow portion 2916 and/or the tapered portion 2918 extend into the right atrium RA and the retaining portion 314 is held in place in the inferior vena cava IVC. Any contact between the interior surface of the right atrium RA and the docking station 10 is with the outer segment 3216. The shape and atraumatic configuration of the outer segment 3216 protects the interior surface of the right atrium RA.

The sealing portion 310 provides a seal between the docking station 10 and an interior surface 416 of the circulatory system, such as at the junction between the inferior vena cava IVC and the right atrium. In the example of FIG. 33, the sealing portion 310 is formed by providing the covering/material 21 (which can be the same as or similar to other coverings/materials described elsewhere herein) over the frame 350 or a portion thereof. In particular, the sealing portion 310 can comprise the narrow portion 2916, the outer segment 3216, the tapered portion 2918 and/or a covered portion of the retaining portion 314. In an exemplary embodiment, the covering/material 21 covers the outer segment 3216, the narrow portion 2916, the tapered portion 2918, and optionally a portion of the retaining portion 314. In one embodiment, the covering/material can be configured to encourage or enhance tissue ingrowth (e.g., covering/material 21 can have a large surface area and/or be hydrophilic to enhance tissue ingrowth). This provides a seal and makes the docking station impermeable or substantially impermeable from the sealing portion 310 to the seal between the valve 29 and the docking station 10 at the valve seat 18. As such, blood flowing in the inflow direction 12 toward the outflow direction 14 is directed to the valve seat 18 (and valve 29 once installed in the valve seat).

As one example, when the docking station 10 is placed in the inferior vena cava IVC, which is a large vessel, the significant volume of blood flowing through the vein is funneled into the valve 29 by the covering 21. The covering 21 can be fluid impermeable or become fluid impermeable (e.g., via tissue ingrowth) so that blood cannot pass through.

A variety of biocompatible covering materials can be used such as any materials described elsewhere herein, including foam or a fabric that is treated with a coating that is impermeable to blood, polyester, or a processed biological material, such as pericardium. More of the docking station frame 350 can be provided with the covering/material 21, forming a relatively large impermeable portion.

Figure 34:
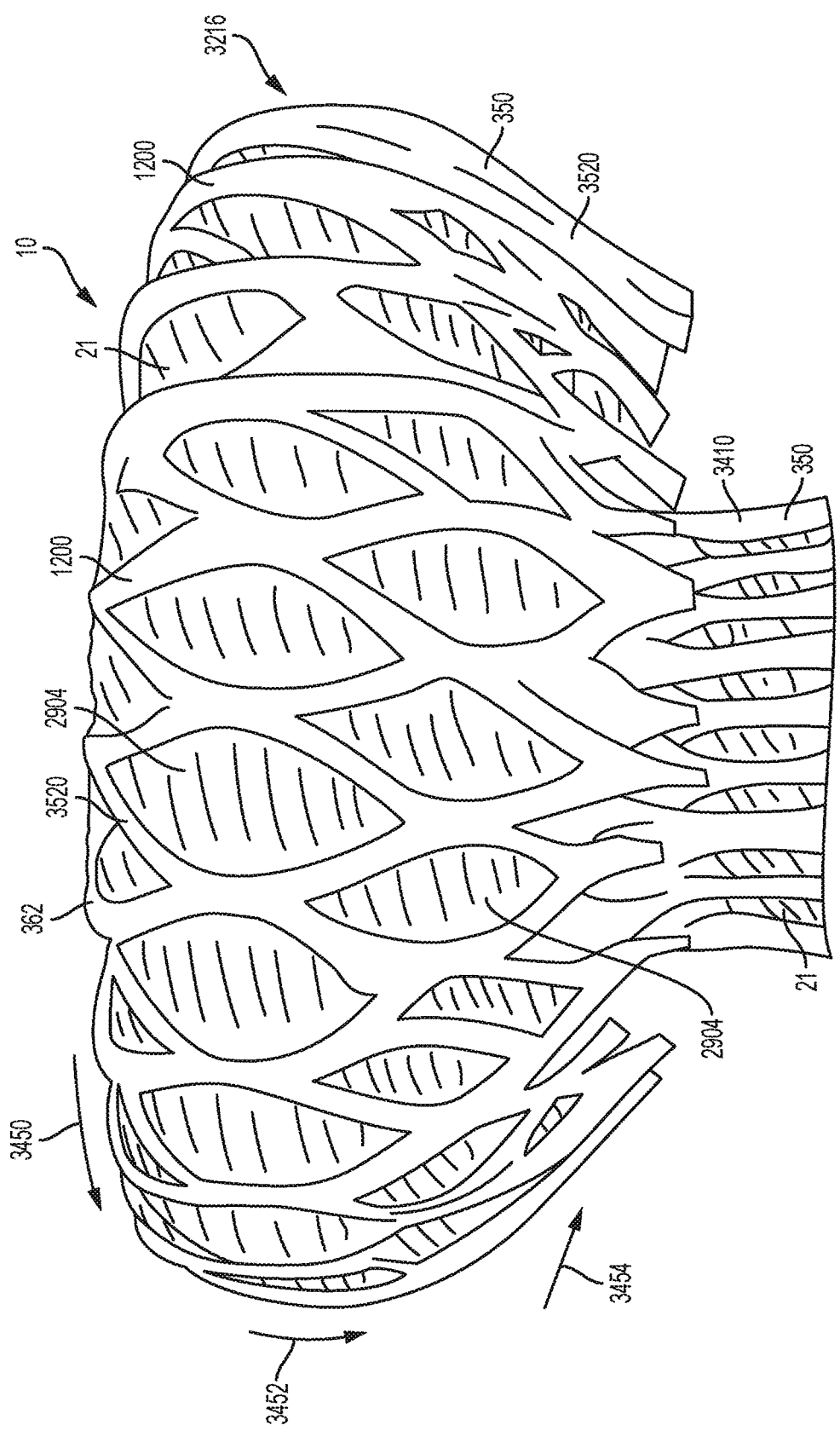
FIG. 34 is a side view of a portion of an exemplary embodiment of a docking station.
Figure 35:
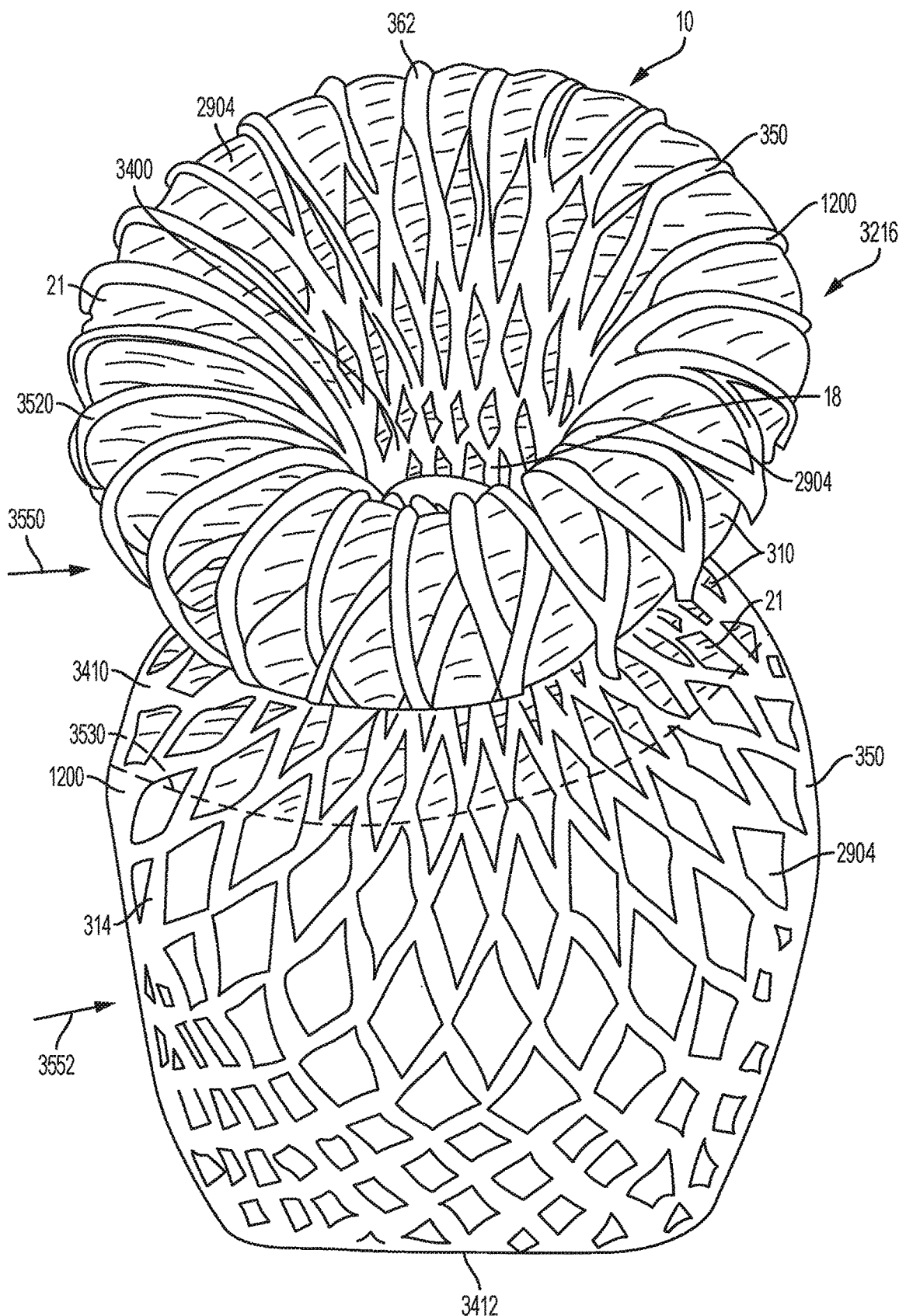
FIG. 35 is a perspective view of the docking station illustrated in FIG. 34.

FIGS. 34 and 35 illustrate an exemplary embodiment where the outer segment 3216 of the docking station 10 illustrated by FIG. 32 is formed as a portion of the frame 350. In the example of FIGS. 34 and 35, the valve seat 18 is formed by inner struts 3400. The retaining portion 314 is formed by lower struts 3410. The lower struts 3410 extend longitudinally and radially outward from the inner struts 3400. The lower struts 3410 terminate at a lower end 3412 of the docking station 10. The outer segment 3216 is formed by top and outer struts 3520 that extend radially outward 3450, and then downward 3452 and inward 3454.

In FIG. 35, the entire frame 350 is comprises a plurality of metal struts 1200 that form cells 2904. In FIG. 32, cells of the retaining portion 314 are uncovered. A covering/material 21 (which can be the same as or similar to coverings/materials 21 discussed previously), such as a cloth or fabric or a protective foam can be provided at the valve seat 18 (i.e. inside or outside the struts 1200), the round or outer segment 3216 and part of the retaining portion 314. For example, referring to FIG. 35 all of the portion 3550 above the line 3530 can be covered and the portion 3552 below the line 3530 can be uncovered. The line 3530 can be adjusted to ensure that the material 21 extends to the area of contact with the inside surface 416 (e.g., to an area expected to be in contact with the inside surface 416 at the junction between the IVC and the right atrium).

The docking station illustrated by FIGS. 34 and 35 can be made from a very resilient or compliant material to accommodate large variations in the anatomy. For example, the docking station 10 can be made from a highly flexible metal, metal alloy, polymer, or an open cell foam. An example of a highly resilient metal is nitinol, but other metals and highly resilient or compliant non-metal materials can be used. The docking station 10 can be self-expandable, manually expandable (e.g., expandable via balloon), mechanically expandable, or a combination of these. A self-expandable docking station 10 can be made of a shape memory material such as nitinol.

Figure 36:
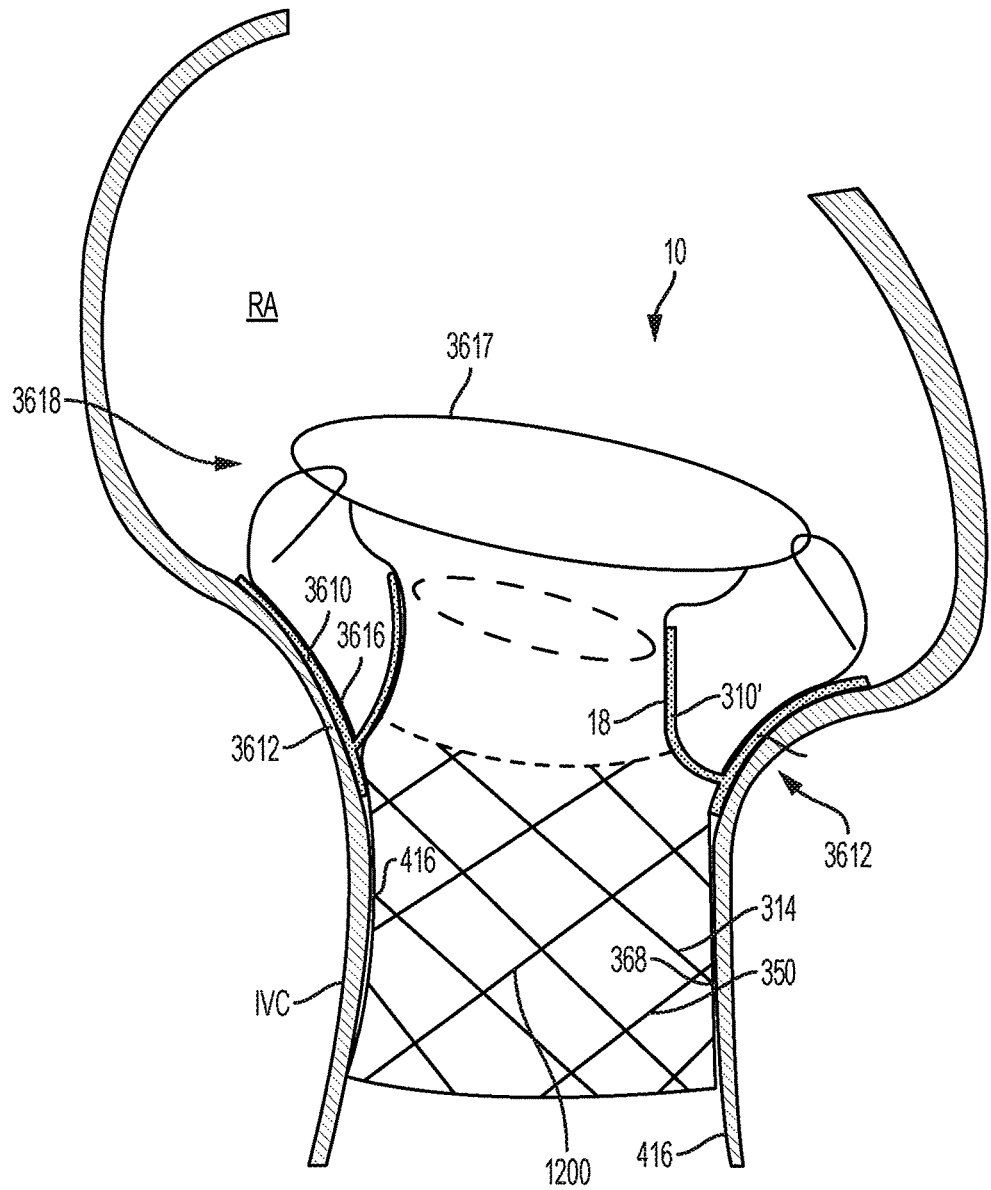
FIG. 36 is a schematic cutaway view of a portion the human heart with an exemplary docking station positioned in the inferior vena cava and the right atrium.

FIG. 36 illustrates an exemplary embodiment of an expandable docking station 10 with a retaining portion 314 that is disposed in the inferior vena cava IVC and a valve seat 18 that is disposed in the right atrium RA. The expandable docking station 10 includes one or more sealing portions 310, a valve seat 18, and one or more retaining portions 314. In FIG. 36, the docking station 10 is configured to provide a seal 3610 at the atrium-vein junction 3612. The seal 3610 at the atrium-vein junction 3612 can be provided in a variety of different ways. In FIG. 36, the frame 350 transitions 3616 radially outward from the retaining portion 314 toward the end 3617 of the docking station 10 to form an enlarged portion or skirt 3618. The enlarged portion or skirt 3618 is flexible such that the portion of the docking station that makes contact with a surface of the atrium is soft. The enlarged portion or skirt can also be covered with a foam or other material to further soften the potential areas of contact between the atrium and the docking station 10.

A sealing portion 310 is configured to prevent or inhibit blood flow where the atrium-vein junction 3612 meets the enlarged portion or skirt 3618 when implanted. An additional sealing portion 310' is provided to prevent or inhibit blood from flowing between the valve 29 and docking station. In the example of FIG. 36, the additional sealing element 310' is disposed on the portion of the frame 350 that forms the valve seat 18 and extends to the sealing element 310. As such, the two sealing elements 310, 310' prevent or inhibit blood from flowing around the outside of the transcatheter valve 29. In another exemplary embodiment, the sealing element 310 can cover the entire enlarged portion 3618 or skirt and extend into the area of the valve seat 18 to eliminate the need for the second sealing element 310'.

The sealing portions can take a wide variety of different forms. In the example of FIG. 36, a fabric, polymer, or other covering is attached to a portion of the frame 350 to form the sealing portion 310. However, the sealing portion 310 can be formed in a wide variety of other ways. The sealing portion 310 can take any form that prevents or inhibits the blood from flowing around the outside surface of the valve 29 through the docking station frame.

The retaining portions 314 of the FIG. 36 embodiment can take a wide variety of different forms. For example, the retaining portion(s) 314 can be any structure that sets the position of the docking station 10 in the circulatory system and can be the same as or similar to retaining portion(s) 314 discussed elsewhere in this disclosure. For example, the retaining portion(s) 314 can press against or into the inside surface 416 or extend around an anatomical structure of the circulatory system to set the position of the docking station 10. The retaining portion(s) 314 can be part of or define a portion of the body and/or sealing portion of the docking station 10 or the retaining portion(s) 314 can be a separate component that is attached to the body of the docking station. The docking station 10 can include a single retaining portion 314, two of these, or more than two.

In FIG. 36, the retaining portion 314 comprises the annular outer portion or wall 368 of the frame 350. A shape set of annular outer portion or wall 368 biases the annular outer portion or wall 368 radially outward and into contact with the interior surface 416 of the circulatory system to retain the docking station 10 and the valve 29 at the implantation position. The retaining portion 314 can be elongated to allow a small force to be applied to a large area of the interior surface 416. For example, the length of the retaining portion 314 can be twice, three times, four times, five times, or greater than five times the outside diameter of the transcatheter valve.

Figure 37:
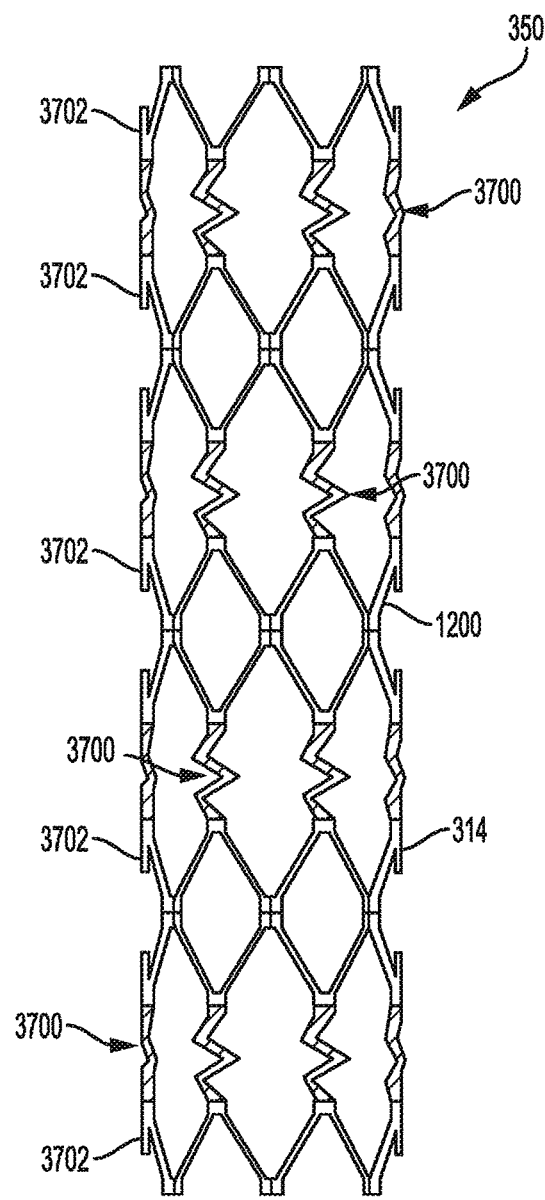
FIG. 37 is a side view of an exemplary embodiment of a docking station frame or portion.

Referring to FIGS. 37-41, in one exemplary embodiment the frames 350 used in the docking stations 10 include springs or spring/flexible segments 3700 to allow the frames 350 to bend. The spring/flexible segments 3700 allow the stent segments to anchor on the walls of the blood vessel while enabling the docking station to curve if needed. In the example of FIG. 37, frame or stent segments 3702 are attached to each other by multiple springs or spring/flexible segments 3700. Any of the frames shown and described herein can optionally have any combination of spring/flexible segments 3700 and frame or stent segments 3702. The spring/flexible segments 3700 can take a wide variety of different forms. Examples of spring/flexible segments 3700 include, without limit, spring wires, springs constructed by selective removal of material (see FIG. 40) compression springs, torsion springs, and/or tension springs.

Figure 38:
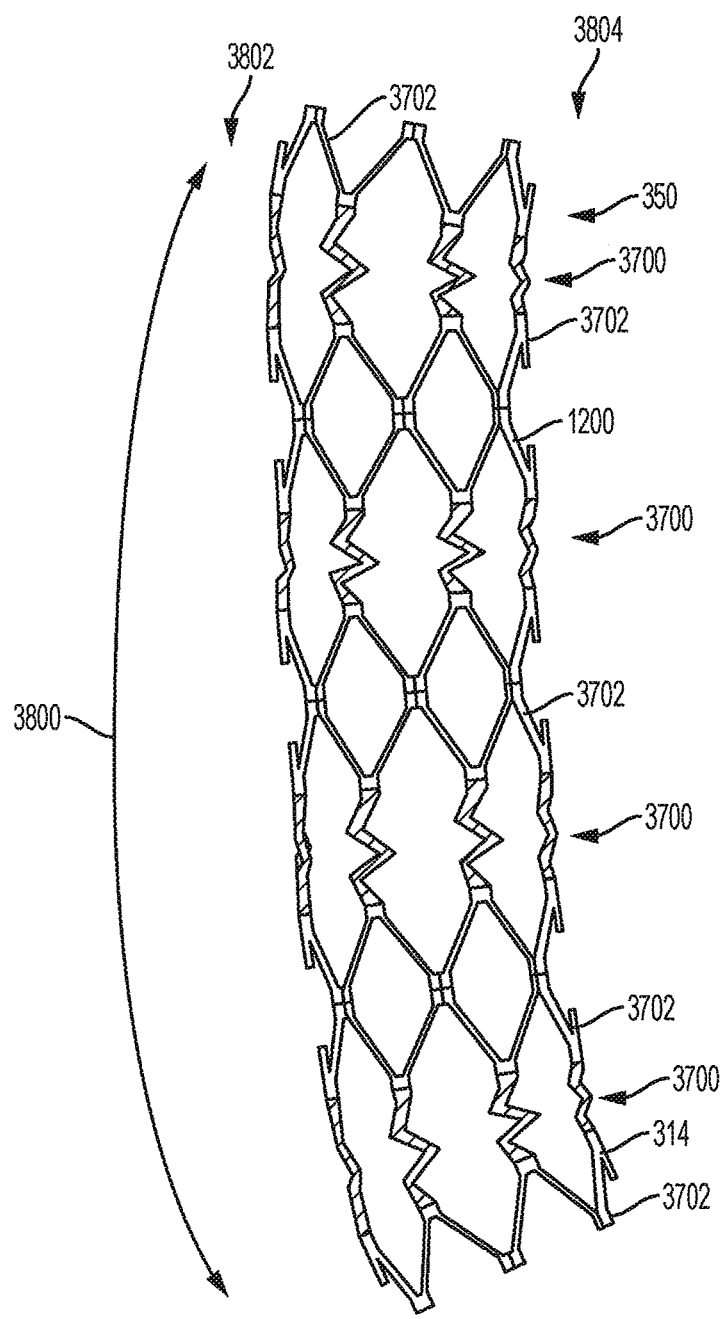
FIG. 38 illustrates bending of the docking station frame/frame portion of FIG. 37.

In FIG. 38, the spring/flexible segments 3700 allow the frame 350 to more easily bend 3800. The frame 350 can bend in a wide variety of different ways. In the example of FIG. 38, springs on one side 3802 stretch and springs on another side 3804 compress to bend 3800 in the indicated direction. Since multiple spring/flexible segments 3700 are provided in the frame 350, the frame can easily bend in different directions along the length of the frame 350.

Figure 39:
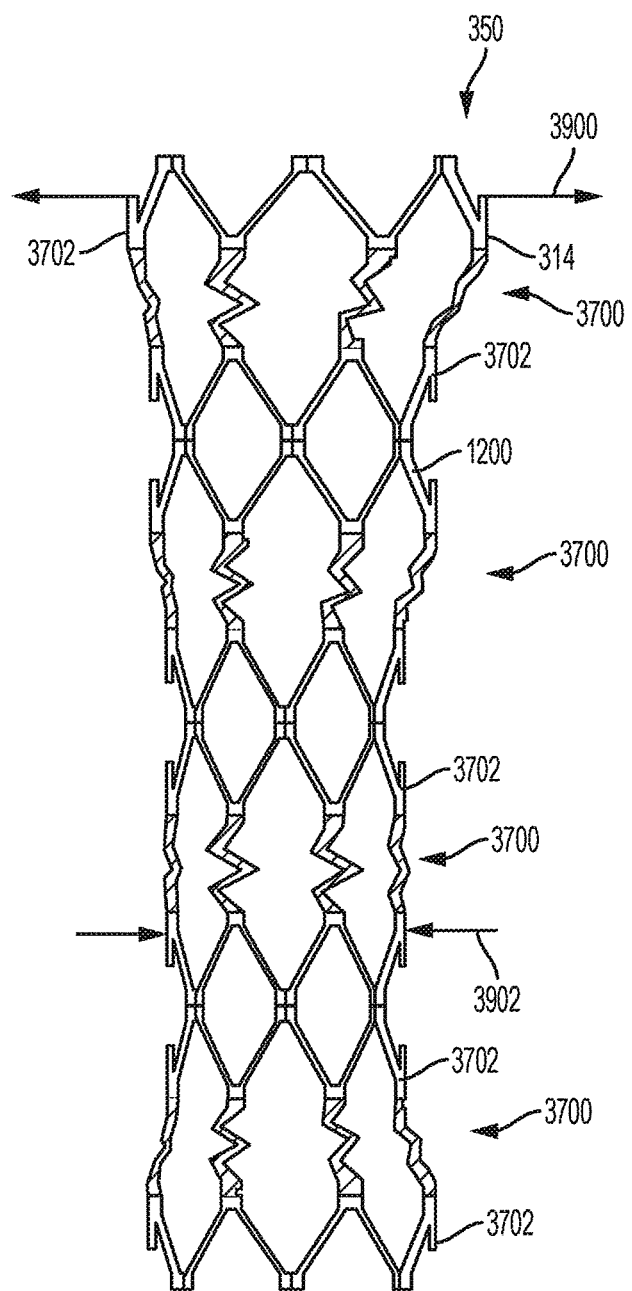
FIG. 39 illustrates expansion and contraction of portions of the docking station frame/frame portion illustrated by FIG. 37.

FIG. 39 illustrates that the frame or stent segments 3702 are expandable 3900 and compressible 3902. By having separate frame or stent segments 3702 connected by spring/flexible segments 3700, the frame can more easily conform to blood vessels that have varying sizes. The combination of the frame or stent segments 3702 and spring segments allows the frame to conform to blood vessels that vary in cross-sectional size of the vessel, cross-sectional shape of the vessel, and the flow shape or path of the vessel.

Figure 40:
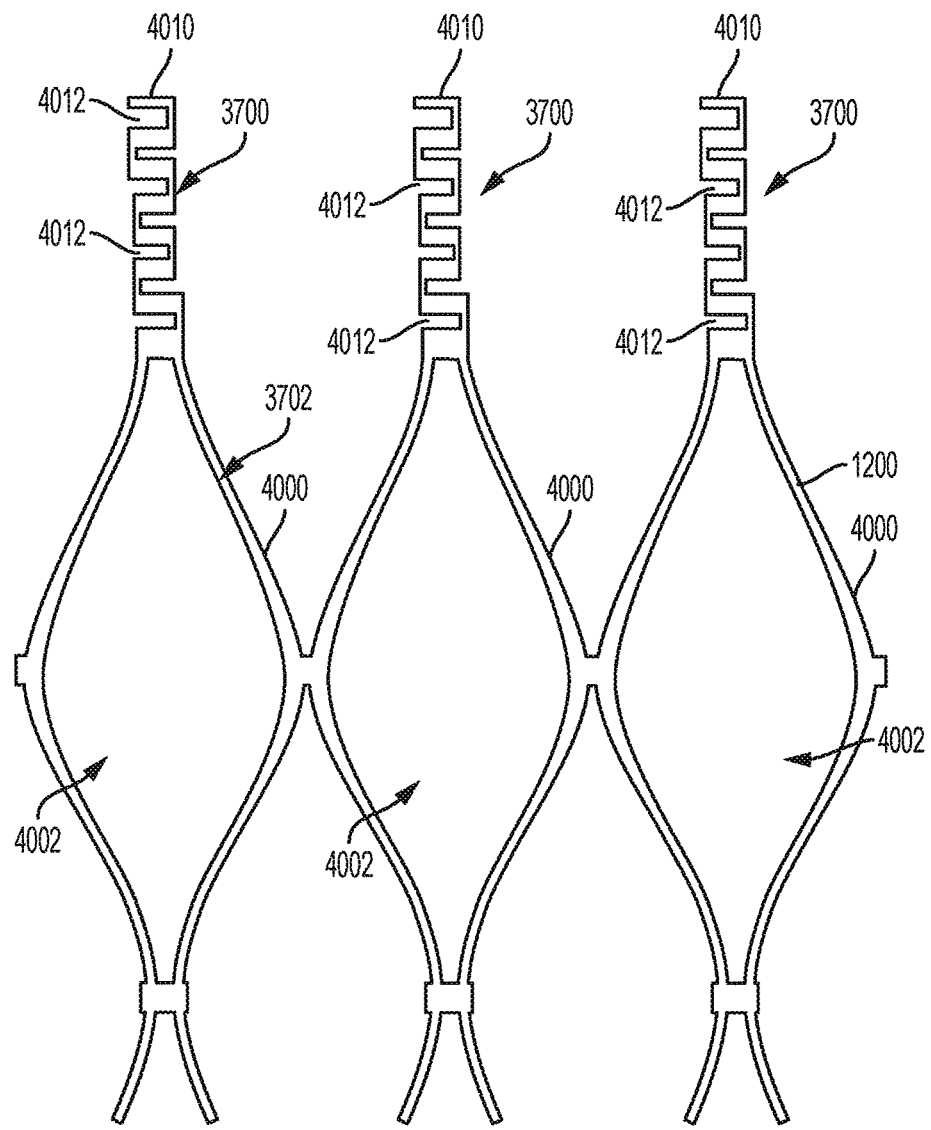
FIG. 40 illustrates an exemplary embodiment of frame portions and spring/flexible portions of a docking station.

FIG. 40 illustrates an exemplary embodiment where the frame or stent segments 3702 are integrally formed with the spring/flexible segments 3700. For example, the frame or stent segments 3702 and the spring/flexible segments 3700 can be cut from a single piece of material, such as a shape memory alloy, such as nitinol. In the illustrated example, the stent segment 3702 comprises a matrix of interconnected struts 1200 that are joined to form cells 4000 with openings 4002. However, the stent segments 3702 can be formed by a wide variety of different cutting patterns. The illustrated spring segments 3700 are formed by cutting a strap/strut 4010 with notches 4012. But the spring/flexible segments 3700 can be formed with many different cutting patterns.

Figure 41:
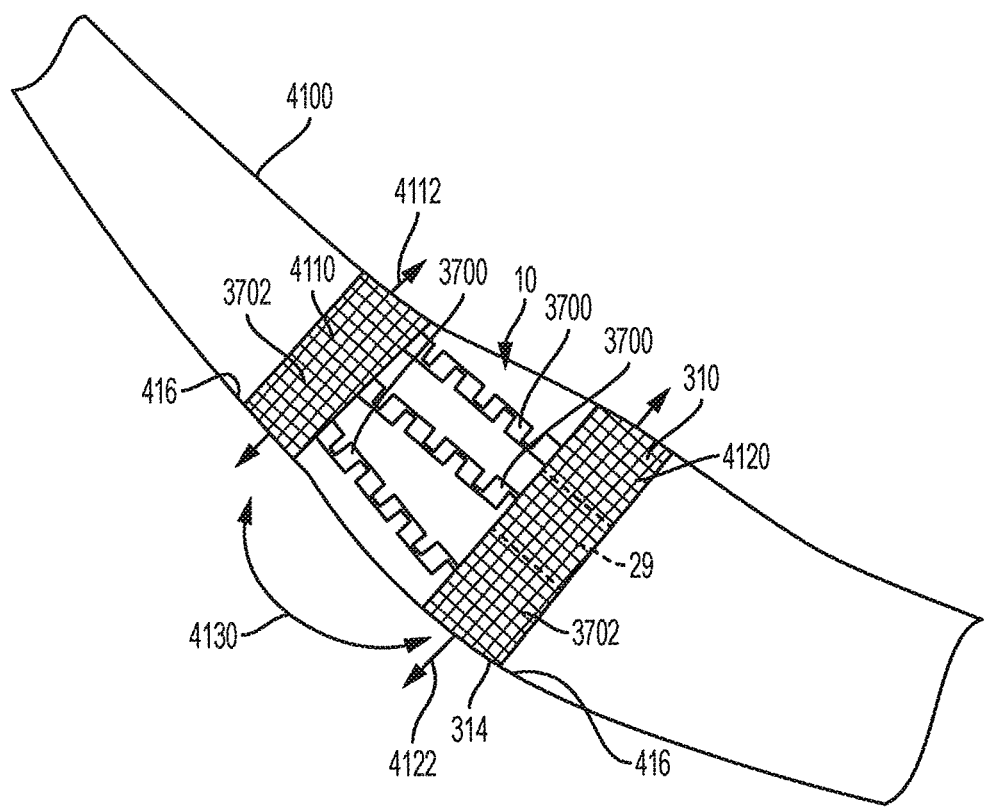
FIG. 41 illustrates an exemplary embodiment of a docking station deployed in a vessel.

FIG. 41 illustrates an exemplary embodiment of a docking station 10 that includes two frame or stent segments 3702 connected by spring/flexible segments 3700. In the example of FIG. 41, the docking station 10 is deployed in a blood vessel 4100 that is curved and has a varying cross-sectional size. A first frame or stent segment 4110 expands 4112 to a first size to conform to the size of the vessel 4100 at the location where the first frame or stent segment is deployed. A second frame or stent segment 4120 expands 4122 to a second, larger size to conform to the size of the vessel 4100 at the location where the second frame or stent segment is deployed. The vessel 4100 is curved from the location of the first stent or frame segment 4110 to the location of the second stent or frame segment 4120. The spring/flexible segments 3700 allow the frame 350 to bend 4130 and conform to the curvature of the vessel 4100.

FIGS. 42-45 illustrate exemplary embodiments where two docking stations 10 are connected together by a connecting portion 4250 to form a dual docking station 4200. In the examples of FIGS. 42-45, the dual docking station 4200 is configured such that a first docking station 4210 can be deployed in the inferior vena cava IVC and a second docking station 4212 can be deployed in the superior vena cava SVC. The docking stations 4210 and 4212 can be connected together in a wide variety of different ways.

The docking stations 4210, 4212 can take a wide variety of different forms. For example, the docking stations 4210, 4212 can be any of the docking stations 10 disclosed herein. In the examples of FIGS. 42-45, one of the docking stations 10 illustrated by FIGS. 12-19 and 20A-20C can be incorporated. The dockings stations 4210, 4212 can be the same or the docking stations 4210, 4212 can be a different size and/or type.

In one exemplary embodiment, one of the ends is not provided with a docking station. For example, a docking station 4210 can be positioned in the inferior vena cava IVC and the connecting portion 4250 and/or and an expandable frame 4110 (See FIG. 41) extends into the superior vena cava SVC to stabilize the docking station 4210, without acting as a docking station. Similarly, a docking station 4212 can be positioned in the superior vena cava SVC and the connecting portion 4250 and/or and an expandable frame 4110 (See FIG. 41) extends into the inferior vena cava IVC to stabilize the docking station 4212, without acting as a docking station.

Figure 42:
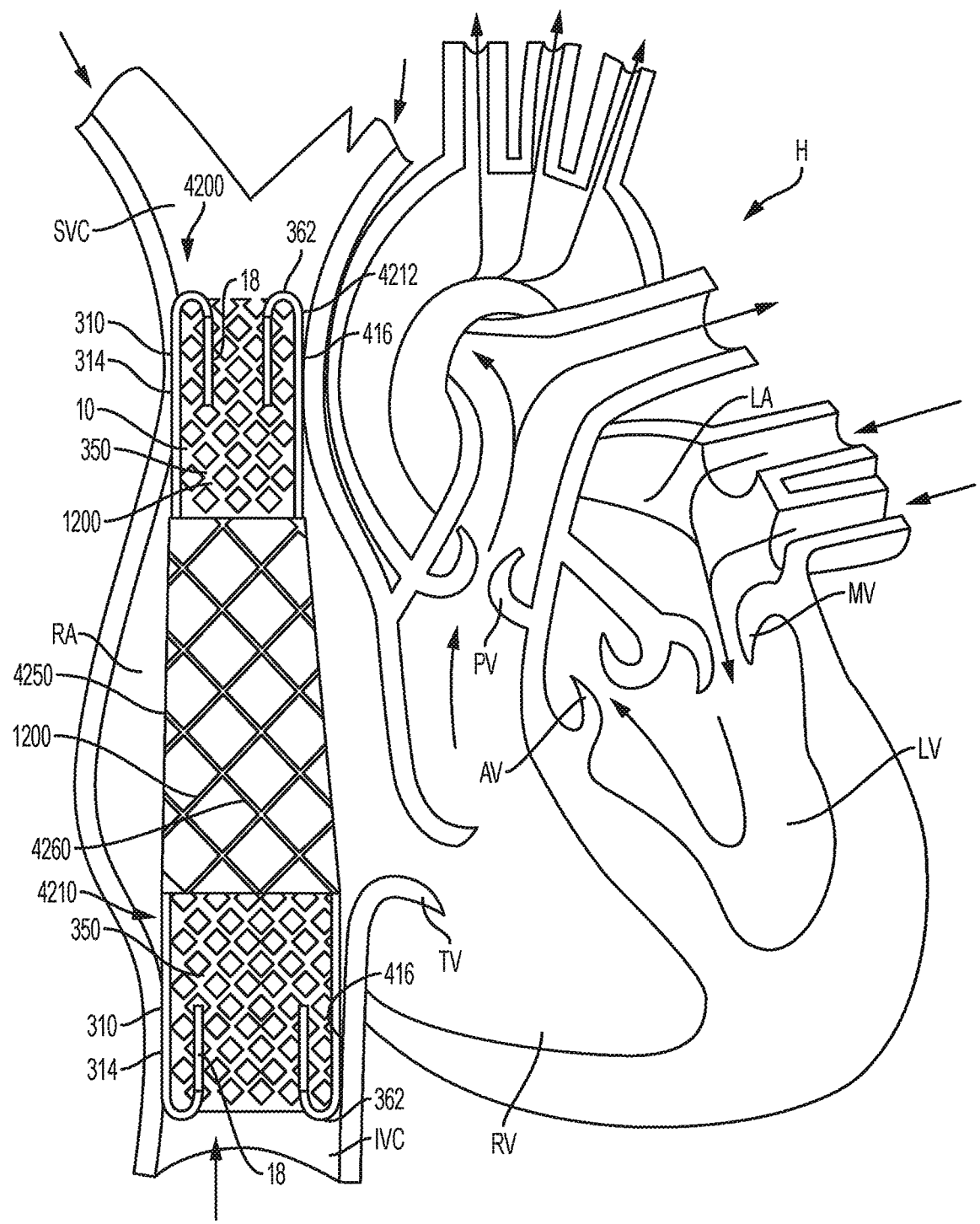
FIG. 42 is a cutaway view of the human heart with an exemplary embodiment of a docking station that extends from the superior vena cava to the inferior vena cava.
Figure 43:
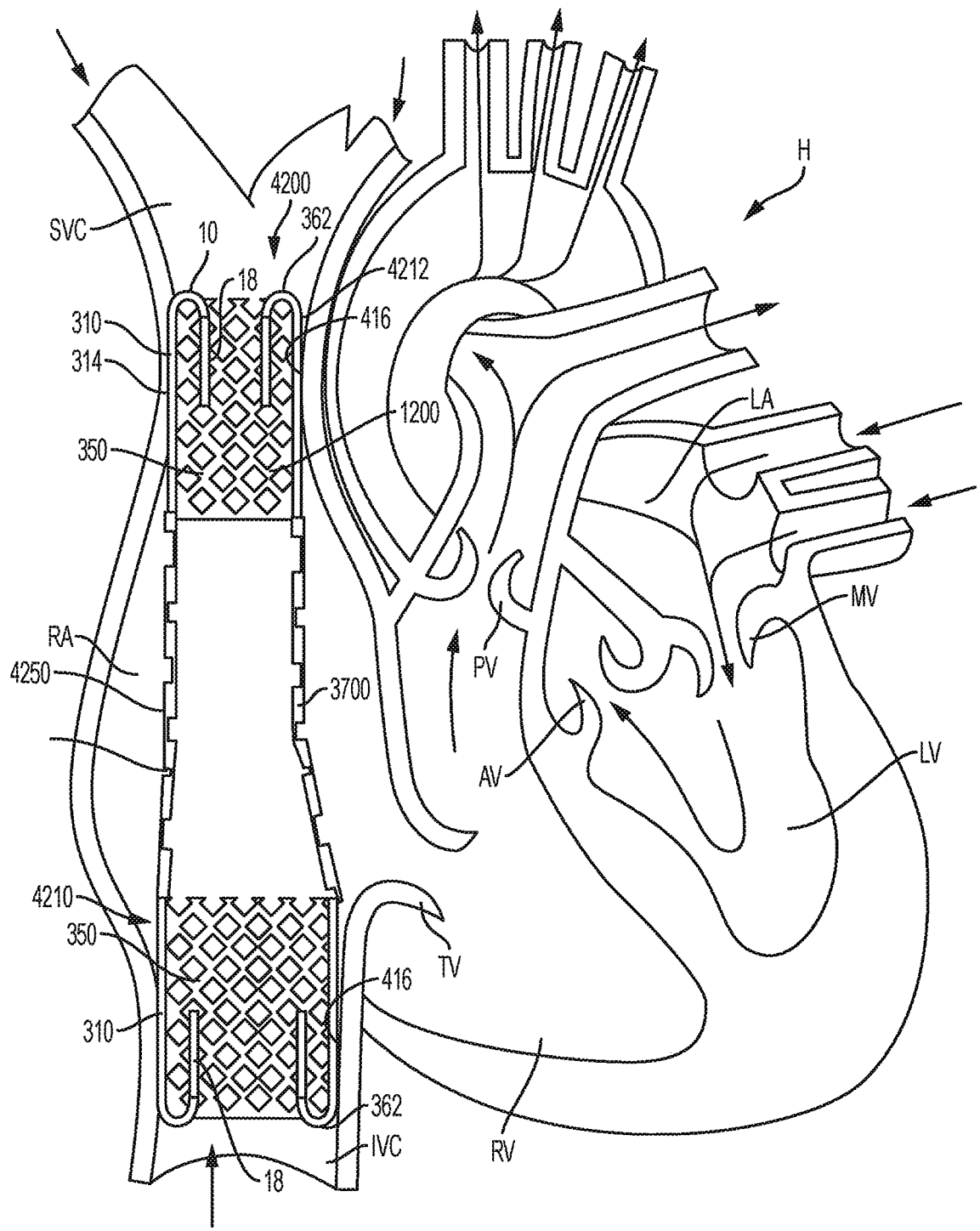
FIG. 43 is a cutaway view of the human heart with an exemplary embodiment of a docking station that extends from the superior vena cava to the inferior vena cava.
Figure 44:
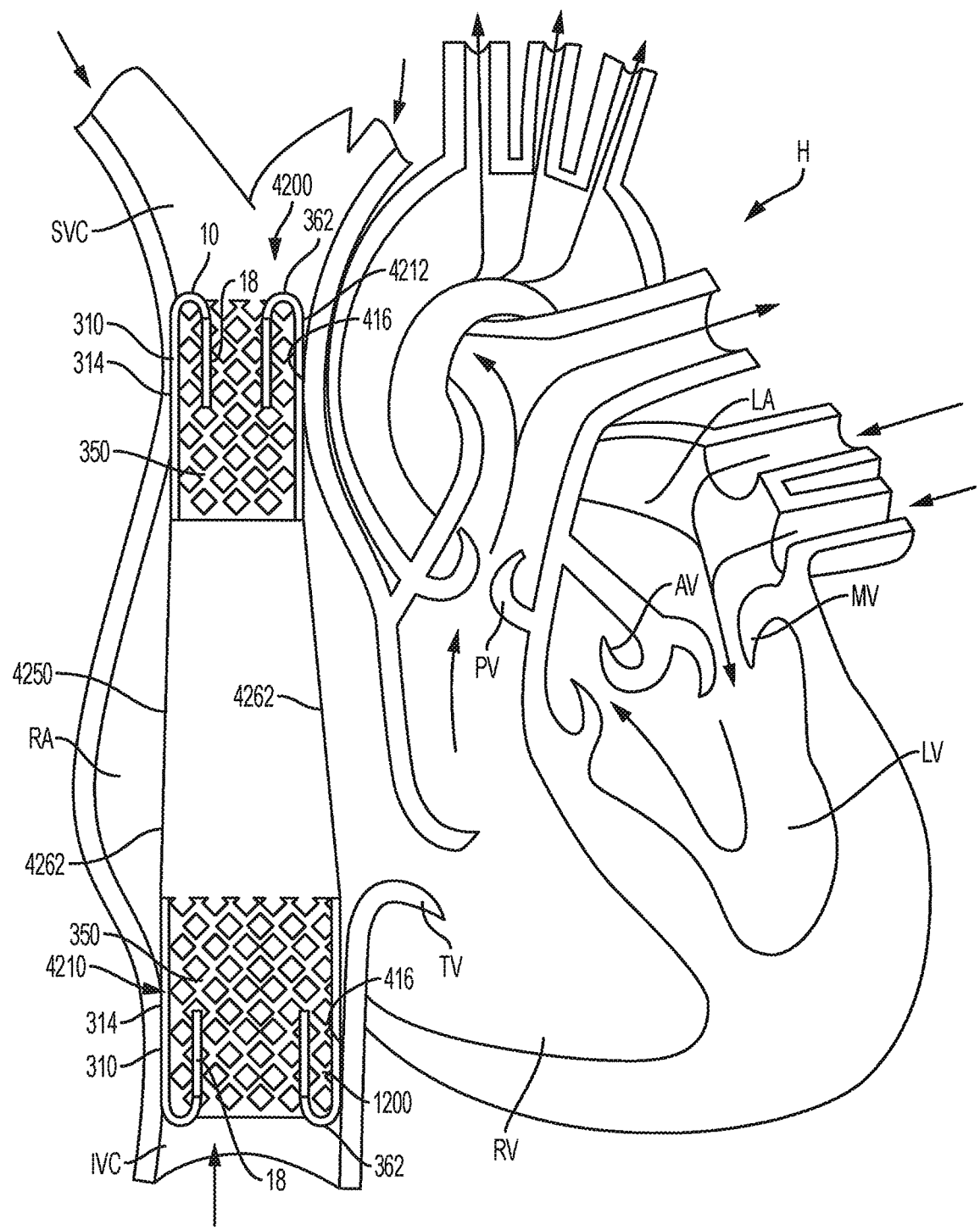
FIG. 44 is a cutaway view of the human heart with an exemplary embodiment of a docking station that extends from the superior vena cava to the inferior vena cava.
Figure 45:
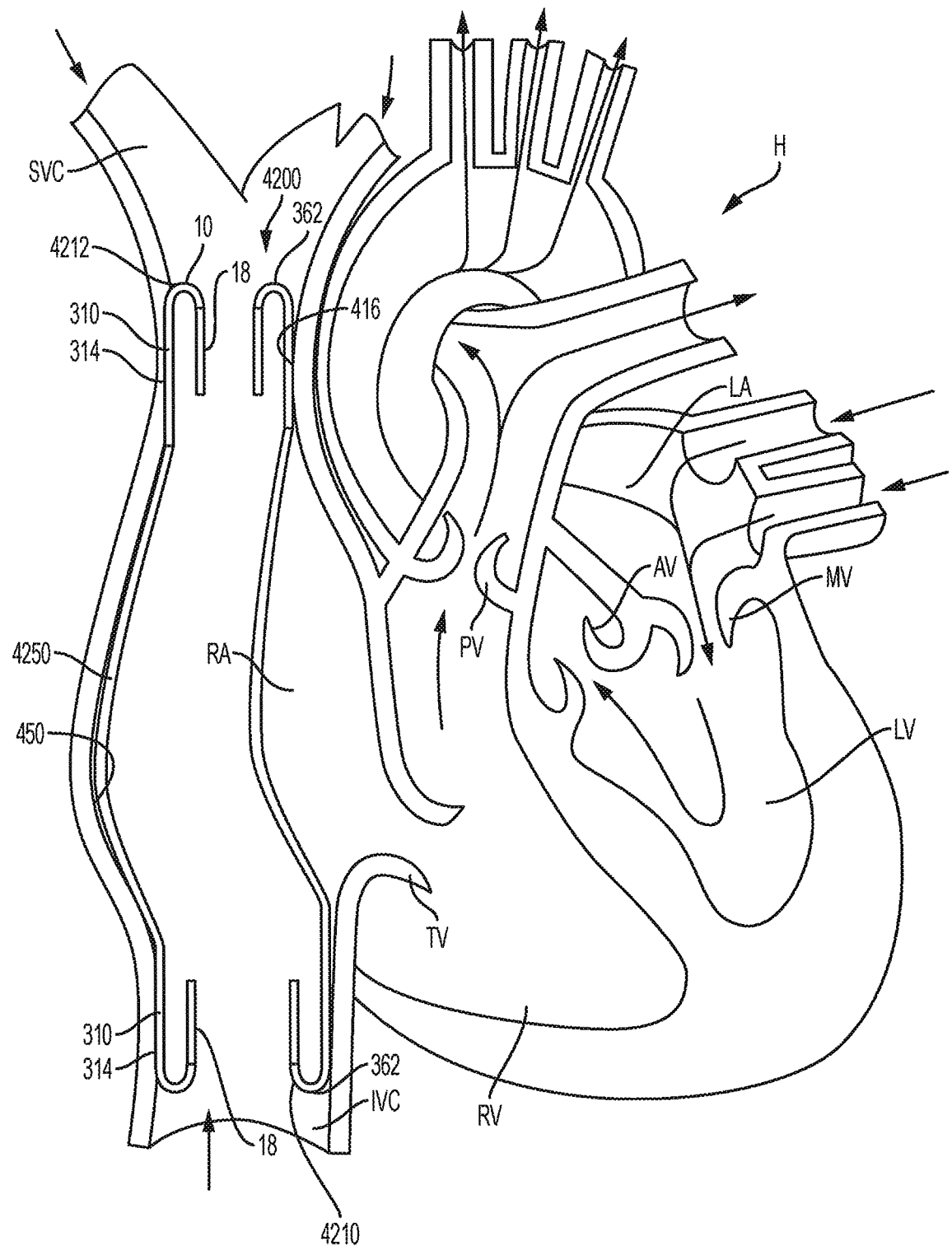
FIG. 45 is a cutaway view of the human heart with an exemplary embodiment of a docking station that extends from the superior vena cava to the inferior vena cava.

The connecting portion 4250 can take a wide variety of different forms. In one exemplary embodiment, the connecting portion 4250 is constructed to allow blood to freely flow through the connecting portion. For example, the connecting portion 4250 can be an open cell frame 4260 as illustrated by FIG. 42. The connecting portion 4250 can comprise spring portions 3700 as illustrated by FIG. 43. The connecting portion 4250 can comprise wires 4262 as illustrated by FIG. 44. In one embodiment, the connecting portion 4250 comprises an open cell frame 4260, spring portions 3700, and/or wires 4262. Referring to FIG. 45, in one embodiment the connecting portion 4250 is configured to bend as it extends from the superior vena cava SVC to the inferior vena cava IVC. In the example of FIG. 45, the connecting portion 4250 is configured to rest against an interior wall 450 of the right atrium RA. The connecting portion 4250 can be integrally formed with the docking stations 4210, 4212 or the connecting portion can be made separately from one or both of the docking stations 4210, 4212 and attached to the docking station(s).

Figure 46:
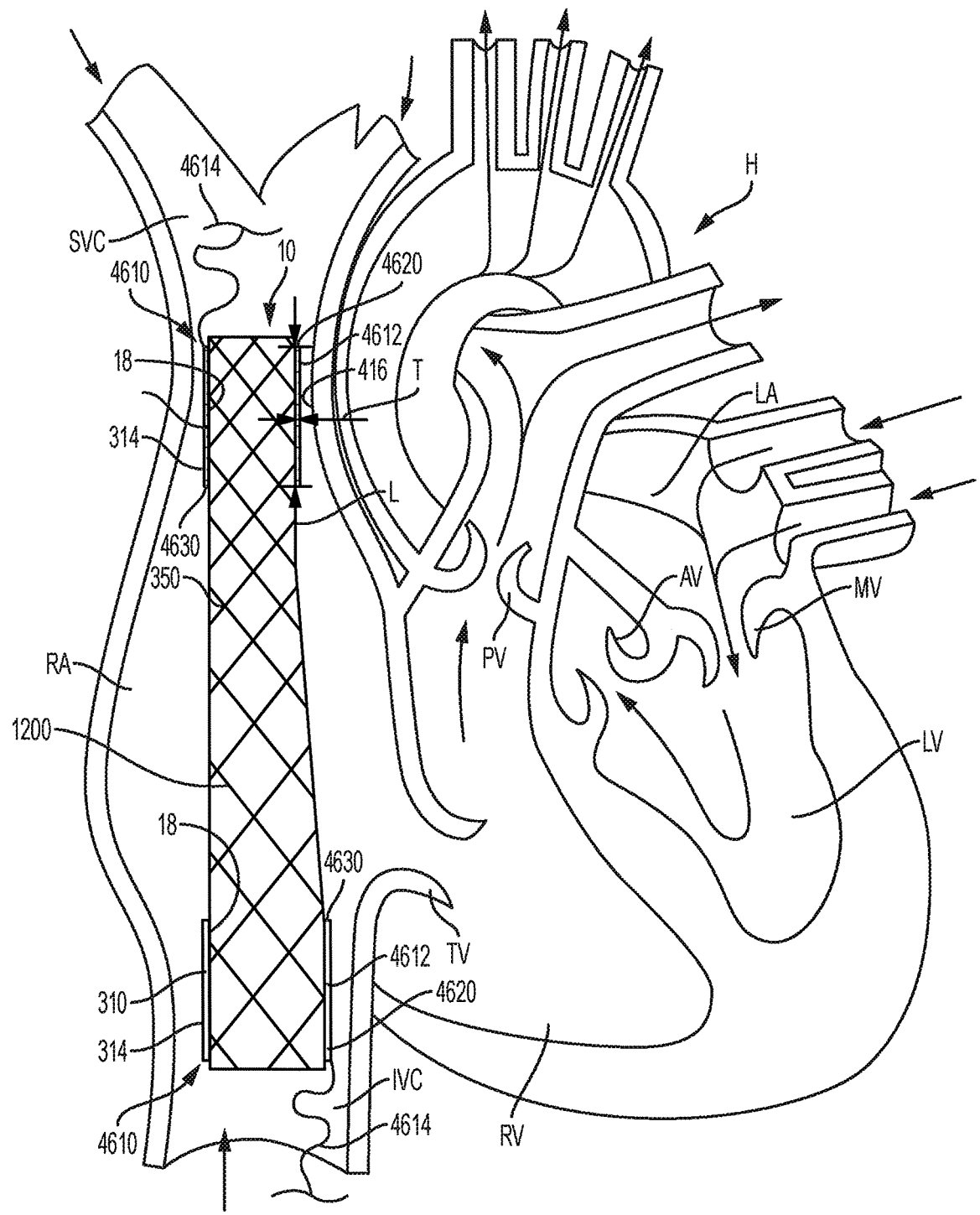
FIG. 46 is a cutaway view of the human heart with an exemplary embodiment of a docking station that extends from the superior vena cava to the inferior vena cava.
Figure 47:
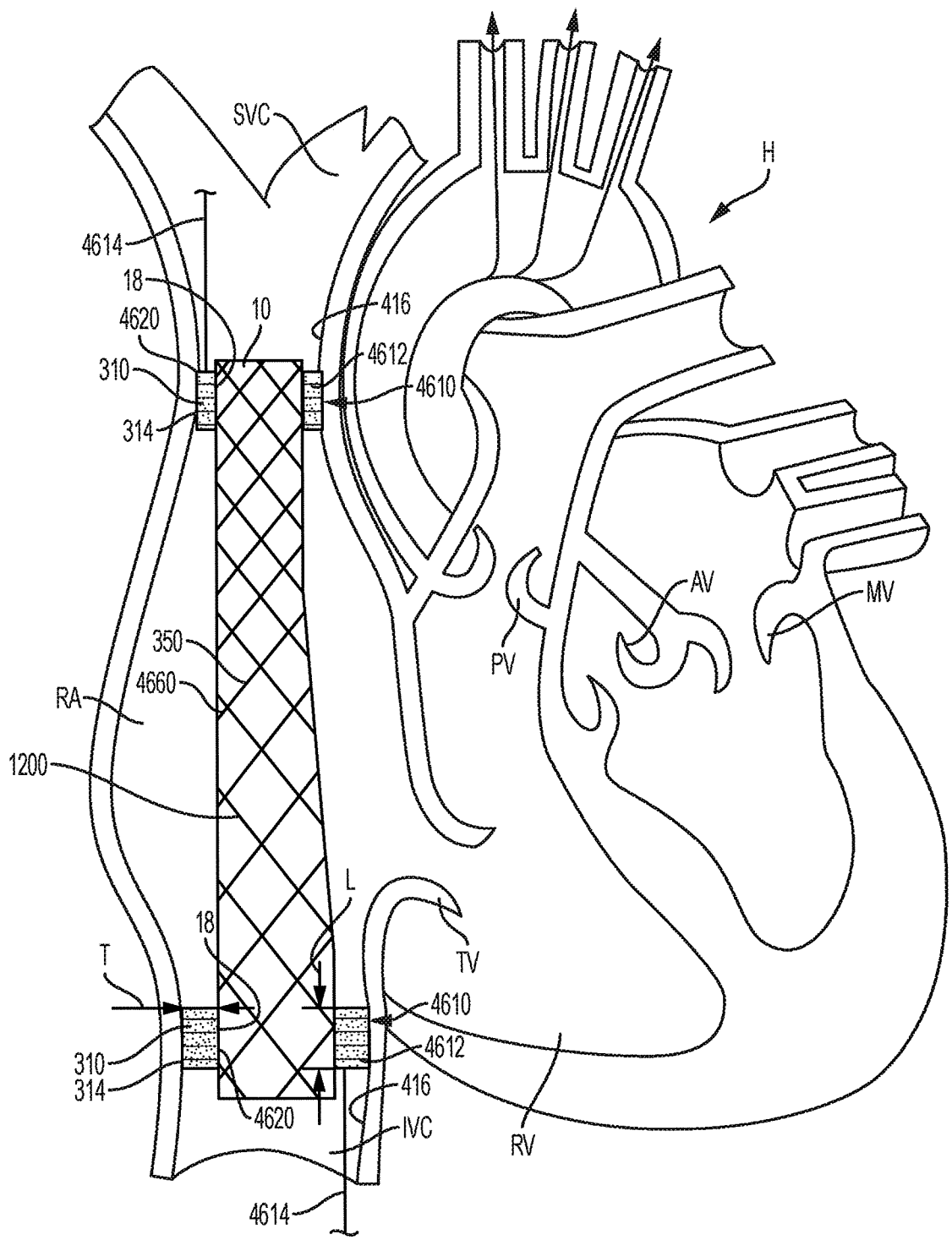
FIG. 47 is a view of the docking station of FIG. 46 with sealing portions deployed.

In one embodiment, a docking station 10 can include sealing portions 310 and/or retaining portions 314 or combined sealing and retaining portions that are radially expandable. The sealing portions 310 and/or retaining portions 314 can be configured to expand in a wide variety of different ways. In the example of FIGS. 46 and 47, combined radially expandable sealing and retaining portions 4610 comprise a material 4612, such as a fabric, cloth, foam, etc., and a line or chord 4614. In FIG. 47, the line or chord 4614 is attached to the material 4612 such that pulling on the line or cord 4614 causes the material 4612 to linearly retract, bunch or accordion, and thereby expand radially outward as shown. The lines or cords 4614 are shown taut in FIG. 47 to represent pulling the lines or cords (e.g., pulling down on the lower line/cord 4614 in the IVC and pulling up on the upper line/cord 4614 in the SVC, but other pulling directions/combinations are also possible) to axially contract and radially expand the material 4612. For example, a first end 4620 of the material 4612 can be attached to the frame 350. The line or cord 4614 can be attached to a second end 4630. The line or chord 4614 can be repeatedly threaded back and forth through the material 4612 as it extends from the first end 4620 to the second end 4630. As such, the material is cinched up, with the length L retracted and radial thickness T expanded.

Sealing portions 310 and/or retaining portions 314 or combined sealing and retaining portions that are radially expandable can be implemented on any docking station 10 disclosed herein. In the example of FIGS. 46 and 47, the combined radially expandable sealing and retaining portions 4610 are provided on a stent or frame 4660 to form a docking station. The radially expandable portions extend around the circumference of the stent or frame 4660. The stent or frame 4660 can take a wide variety of different forms. For example, the stent or frame can be any conventional stent or frame or any of the frames 350 disclosed herein. In FIG. 46, the stent or frame 4660 is configured to extend from the superior vena cava SVC to the inferior vena cava IVC. However, in some embodiments, the stent or frame 4660 can be configured to engage and seal with only one inner surface area. The stent or frame 4660 can be configured to engage and seal with one or more interior surface areas of the heart H. For example, a stent or frame 4660 with one or more radially expandable portions 4610 can be configured to be deployed and act as a valve seat 18 in the inferior vena cava IVC, the superior vena cava SVC, the aorta, the pulmonary artery, the aortic valve AV, the mitral valve MV, the pulmonary valve PV, or the tricuspid valve TV.

The stent or frame 4660 can take a wide variety of different forms. In the example of FIGS. 46 and 47, the stent or frame 4660 is disposed in the right atrium RA. In one embodiment, the stent or frame 4660 or the portion of the stent or frame 4660 in the right atrium has and open configuration to allow blood in the atrium to easily flow through the stent or frame 4660. For example, the stent or frame 4660 can take any of the forms illustrated by FIGS. 42-44.

Figure 48:
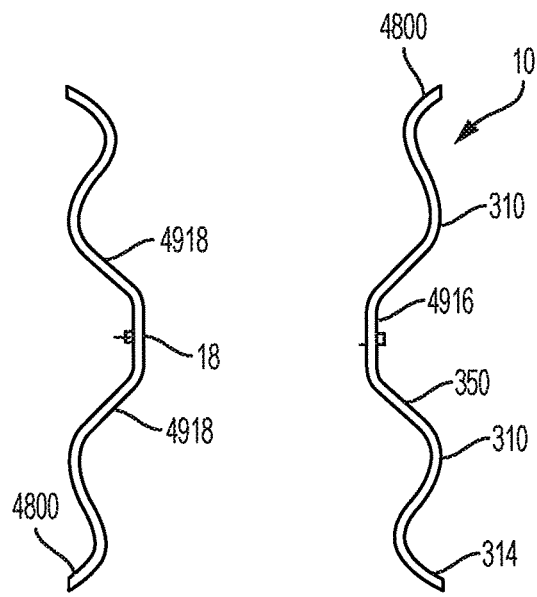
FIG. 48 illustrates an exemplary embodiment of a profile of a docking station.

The docking station profile illustrated by FIG. 48 is taken from U.S. patent application Ser. No. 15/422,354, titled "Docking Station for a Transcatheter Heart Valve," filed on Feb. 1, 2017 and published as US 2017/0231756, which claims priority to provisional application No. 62/292,142, filed on Feb. 5, 2016. These application are incorporated herein by reference in their entireties. Any concepts, aspects, features or other materials disclosed by these applications can be used in combination with any of the embodiments disclosed in this application, e.g., docking station 10 illustrated by FIG. 48 can be configured to be deployed in the aorta, IVC, and/or SVC.

Figure 49:
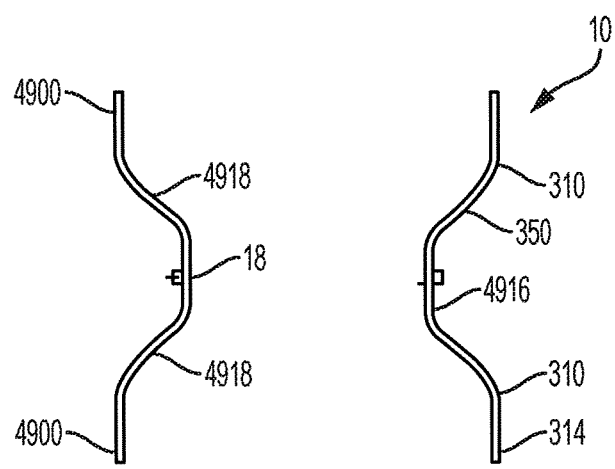
FIG. 49 illustrates an exemplary embodiment of a profile of a docking station.

FIG. 49 illustrates an exemplary embodiment of a docking station 10 that is similar to the docking station illustrated by FIG. 48, except the radially outwardly extending ends 4800 are replaced with ends 4900 that do not extend radially outward. For example, the ends 4900 can extend axially as illustrated or can extend radially inward.

Figure 50:
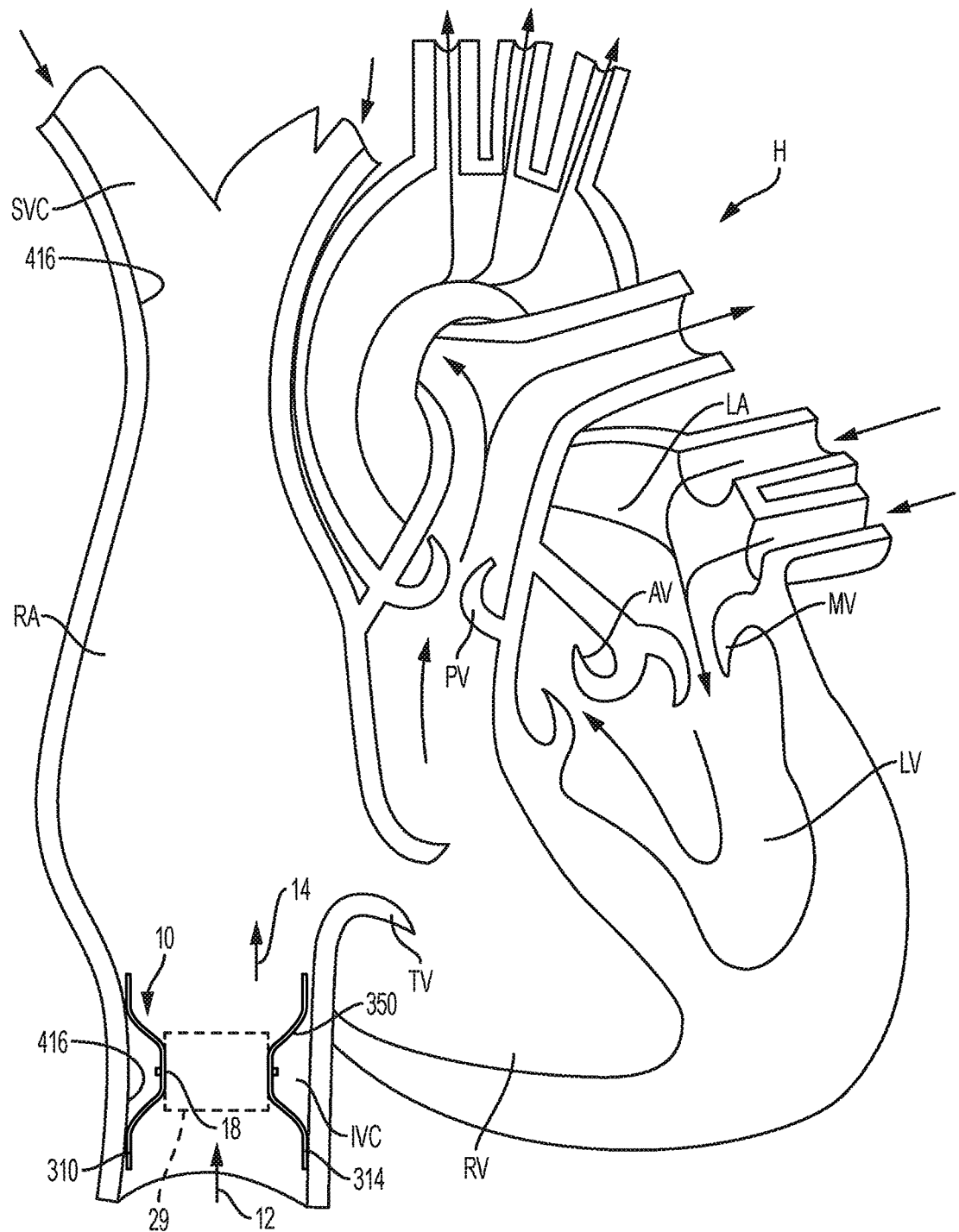
FIG. 50 is a cutaway view of the human heart with the docking station illustrated by FIG. 49 positioned in the inferior vena cava.

FIG. 50 illustrates an exemplary embodiment where the docking station 10 illustrated by FIG. 48 or 49 is deployed in the circulatory system, such as in the inferior vena cava IVC. In the example illustrated by FIG. 50, the entire docking station is held in place in the inferior vena cava IVC by the frame 350. The sealing portion 310 provides a seal between the docking station 10 and an interior surface 416 of the circulatory system, such as at the junction between the inferior vena cava IVC and the right atrium.

In the example of FIG. 50, the sealing portion(s) 310 are formed by providing a covering/material over the frame 350 or a portion thereof. Referring to FIGS. 48 and 49, the sealing portion(s) 310 can comprise the narrow portion 4916, one or both of the tapered portions 4918 and/or the retaining portion 314. In an exemplary embodiment, a covering/material (which can be the same as or similar to other coverings/materials described elsewhere herein) covers the narrow portion 4916, the tapered portion 4918, and a portion of the retaining portion 314. In one embodiment, the covering/material can be configured to encourage or enhance tissue ingrowth (e.g., covering/material can have a large surface area and/or be hydrophilic to enhance tissue ingrowth). This makes the docking station impermeable or substantially impermeable from the sealing portion 310 to the seal between the valve 29 and the docking station 10 at the valve seat 18. As such, blood flowing in the inflow direction 12 toward the outflow direction 14 is directed to the valve seat 18 (and valve 29 once installed or deployed in the valve seat).

As one non-limiting example, when the docking station 10 is placed in the inferior vena cava IVC, which is a large vessel, the significant volume of blood flowing through the vein is funneled into the valve 29 by a covering/material. The covering/material can be fluid impermeable or become fluid impermeable (e.g., via tissue ingrowth) so that blood cannot pass through. Again, a variety of other biocompatible covering materials can be used such as any materials described elsewhere herein, including, for example, foam or a fabric that is treated with a coating that is impermeable to blood, polyester, or a processed biological material, such as pericardium. More or all of the docking station frame 350 can be provided with the covering/material, forming a relatively large impermeable portion.

Figure 51:
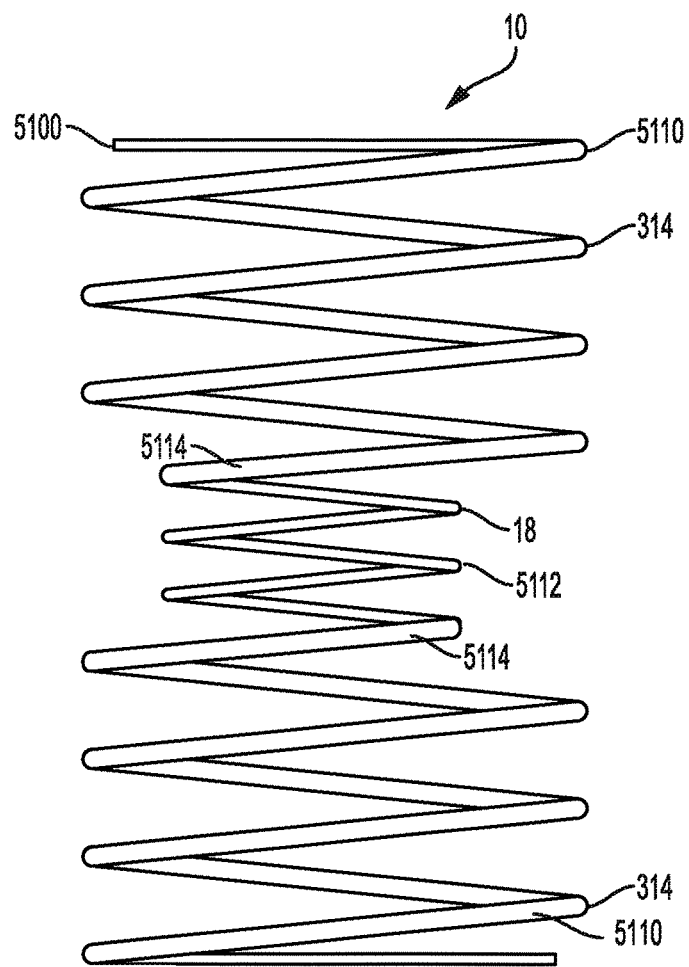
FIG. 51 is a side view of an exemplary embodiment of a docking station.

FIG. 51 illustrates an exemplary embodiment of a docking station frame 350 constructed from a coil 5100 of material. The coil 5100 can take a wide variety of different forms and FIG. 51 illustrates just one of the many possible configurations. In the example of FIG. 51, the retaining portion 314 comprises two relatively larger diameter coil segments 5110 and a smaller diameter segment 5112 that forms the valve seat 18. However, in other exemplary embodiments, only a single larger diameter coil segment 5110 may be included. Transition coil segments 5114 join the smaller diameter segment 5112 to the larger diameter segment 5112.

A covering/material (not shown), such as one of the coverings/materials described elsewhere herein, a cloth, fabric, or a protective foam can be provided inside or outside the coil to provide a sealing portion to the coil 5100 and create a sealing docking station. Such a covering/material can be connected to the coil or can be deployed separately from the coil 5100 (e.g., deployed either before or after deployment of the coil 5100) and/or with the transcatheter valve 29. The valve 29 expands and is implanted in the smaller diameter segment 5112, which forms the valve seat 18.

The docking station coil 5100 can be made from a very resilient or compliant material to accommodate large variations in the anatomy. For example, the docking station coil 5100 can be made from a highly flexible metal, metal alloy, or polymer. An example of a highly resilient metal is nitinol, but other metals and highly resilient or compliant non-metal materials can be used. The docking station 10 can be self-expandable, manually expandable (e.g., expandable via balloon), mechanically expandable, or a combination of these. A self-expandable docking station 10 can be made of a shape memory material such as, for example, nitinol.

Figure 52:
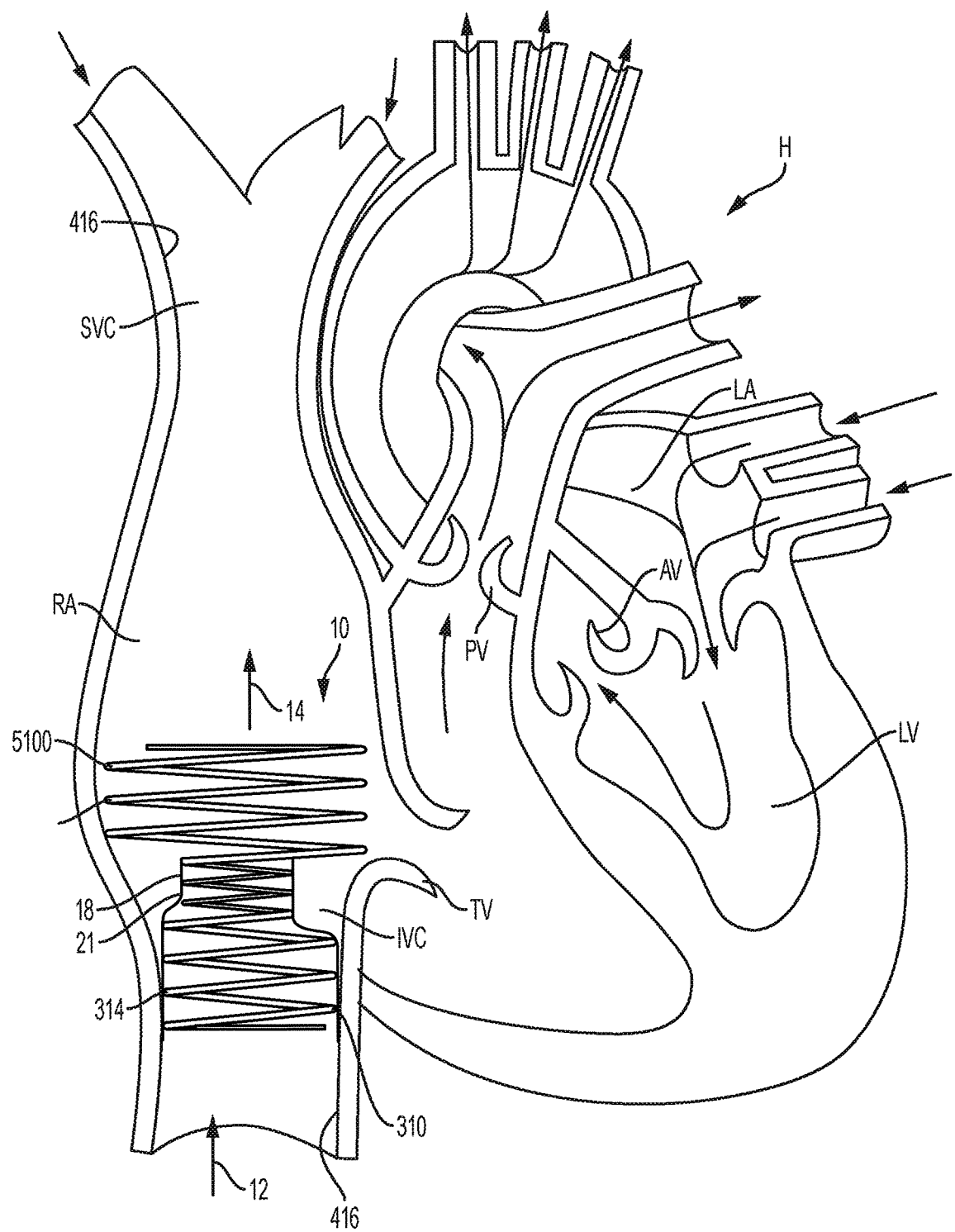
FIG. 52 is a cutaway view of the human heart with the docking station illustrated by FIG. 51 positioned in the inferior vena cava.

FIG. 52 illustrates the docking station coil 5100 of FIG. 51 implanted in the circulatory system, such as in the inferior vena cava IVC. In the example of FIG. 52, the coil is held in place in the inferior vena cava IVC by a lower larger diameter segment 5110. An upper larger diameter segment 5110 is disposed in the right atrium RA. The larger diameter segment 5110 can expand to a larger size in the right atrium as illustrated, the larger diameter segments can expand to the same size, or the larger diameter segment in the IVC can expand to a larger size than the larger diameter segment in the right atrium RA. Sealing portion(s) 310 can be formed by providing the covering/material 21 (which can be the same as or similar to other coverings/materials described herein) over or inside the frame 350 or a portion thereof. In an exemplary embodiment, covering/material 21 covers the smaller diameter segment 5112 and one or both of the larger diameter segments 5110. This can make a docking station 10 that includes the coil 5100 impermeable or substantially impermeable from the sealing portion 310 to the seal between the valve 29 and the docking station 10 at the valve seat 18. As such, blood flowing in the inflow direction 12 toward the outflow direction 14 is directed to the valve seat 18 (and valve 29 once installed or deployed in the valve seat).

As one non-limiting example, when the docking station 10 is placed in the inferior vena cava IVC, which is a large vessel, the significant volume of blood flowing through the vein is funneled into the valve 29 by a covering or inner layer. The covering can be fluid impermeable or substantially impermeable so that blood or most blood cannot pass through. Again, a variety of other biocompatible covering materials can be used such as any materials described elsewhere herein, including, for example, foam or a fabric that is treated with a coating that is impermeable to blood, polyester, or a processed biological material, such as pericardium. More or all of the docking station frame 350 can be provided with the covering/material (e.g., an impermeable covering/material), forming a relatively large impermeable portion.

Figure 53:
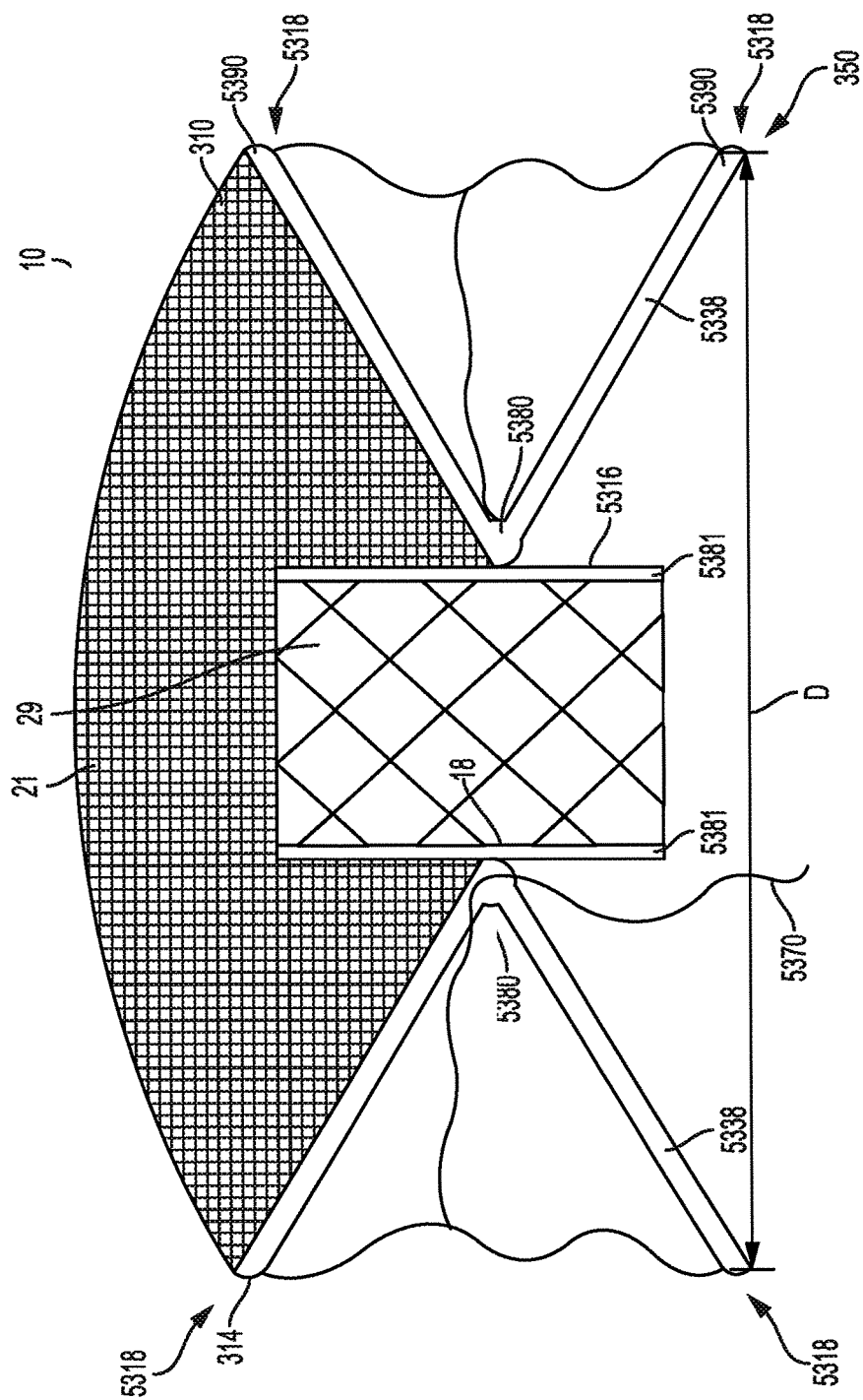
FIG. 53 is a schematic illustration of an exemplary embodiment of a docking station.

FIGS. 53 and 54 illustrate exemplary embodiments of a docking station 10. The frame 350 or body can take a wide variety of different forms and FIG. 53 illustrates just one of the many possible configurations. A relatively narrower/smaller diameter portion 5316 forms the seat 18. The relatively narrow portion 5316 can take a wide variety of different forms. For example, the narrow portion 5316 can be any of the valve seats 18 disclosed herein, a ring, any conventional stent or frame, etc. In one exemplary embodiment, the inner ends 5380 themselves act as the valve seat 18. In one exemplary embodiment, the narrow portion 5316 is replaced with a valve/THV 29, e.g., the valve is integrated with the docking station structure such that the entire assembly acts as a transcatheter valve and can be implanted as one in the same implantation step.

Referring to FIGS. 53 and 54, spaced apart radially outwardly extending arms 5318 disposed around a perimeter of the narrow portion 5316 form the retaining portion 314. In the example of FIG. 53, inner ends 5380 of the arms 5318 are connected to each other, are positioned adjacent to one another, or are spaced apart, but positioned close to one another. The example illustrated by FIG. 54 is substantially the same as the example of FIG. 53, except the inner ends 5380 of the arms 5318 are connected to ends 5381 of the narrow portion 5316. The docking station can include a variety of combinations and arrangements of arms 5318, and can include 2-32 arms (e.g., 2-16 arms) or more arms.

The radially outwardly extending arms 5318 can take a wide variety of different forms. In the illustrated example, the arms 5318 comprise upper arms 5328 and lower arms 5338. The docking station can comprise 1-16 upper arms 5328 (e.g., 1-8 upper arms) or more and can be radially spaced apart evenly or unevenly, and can comprise 1-10 lower arms 5338 (e.g., 1-8 lower arms) or more and can be radially spaced apart evenly or unevenly. In one exemplary the upper arms 5328 are coupled to the lower arms 5338 and/or the inner portion 5316 such that the upper and lower arms 5328, 5338 are moveable relatively toward and away from one another.

Figure 55A:
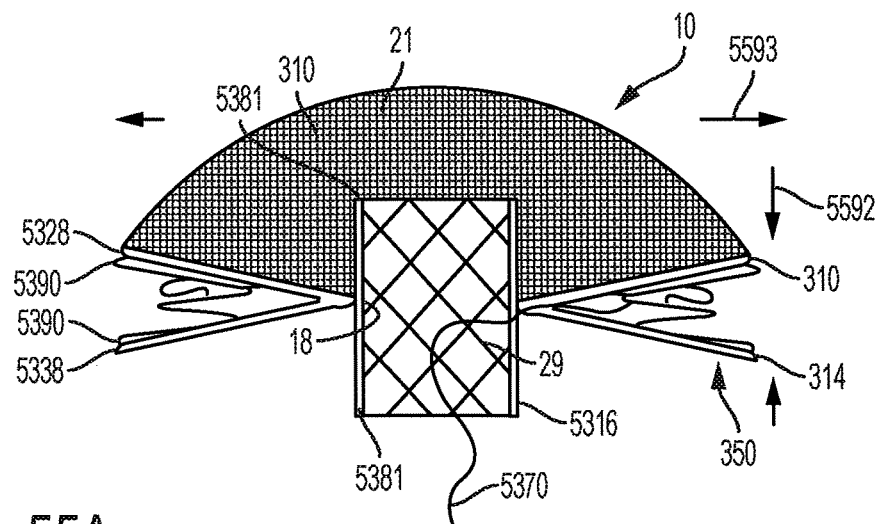
FIGS. 55A-55C illustrate three different positions of the docking station of FIG. 53.
Figure 55B:
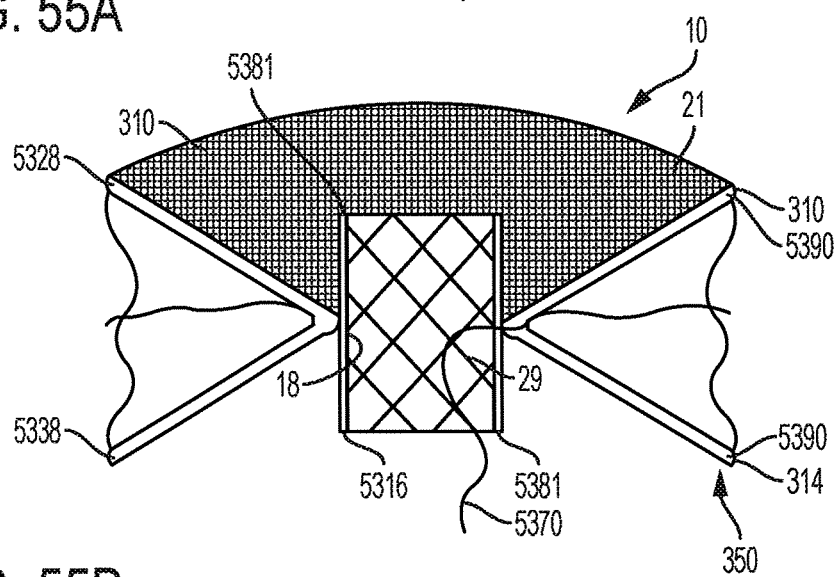
Figure 55C:
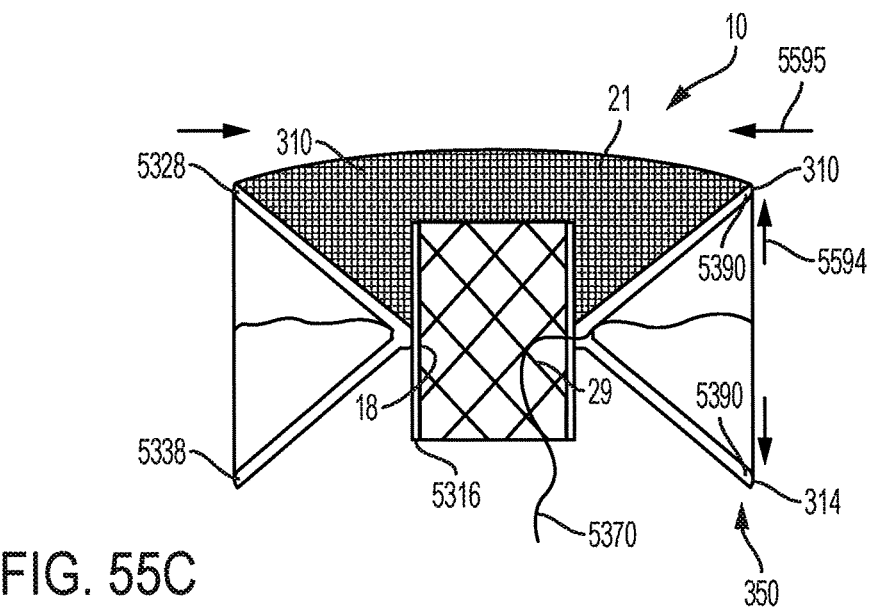

Referring to FIGS. 55A-55C, moving the upper arms 5328 and lower arms 5338 relatively toward and away from one another increases and decreases the diameter D or width of the docking station 10. For example, FIG. 55B can correspond to a nominal position, such as an average size of an implantation site (e.g., vessel, annulus, etc.) that the docking station will be deployed in. However, any size can be selected. FIG. 55A illustrates that moving 5592 the arms 5328, 5338 relatively toward one another increases 5593 the diameter D or width of the docking station. That is, the arms 5328 extend more in the radial direction 5593 and less in the axial direction 5592 (as compared to FIG. 55B) and the width or diameter D increases. FIG. 55C illustrates that moving 5594 the arms 5328, 5338 relatively away from one another decreases the diameter D (as compared to FIG. 55B) or width of the docking station 10. That is, the arms 5328, 5338 extend less in the radial direction 5595 and more in the axial direction 5594 and the width or diameter D of the docking station decreases.

The arms 5328, 5338 can be moved relatively toward and away from one another in a wide variety of different ways. For example, the arms 5328, 5338 can be made from a shape memory alloy with the shape set to the closest spacing between the arms 5328, 5338 (i.e. the largest diameter). Or, a spring can be provided between the arms 5328, 5338 to bias the arms to a desired spacing. When the arms 5328, 5338 are biased to the largest diameter, the docking station 10 will deploy until the arms engage an inside surface 416 (e.g., vessel walls, IVC walls, SVC walls, aorta walls, an annulus of a native heart valve, tissue surrounding an annulus of a native heart valve, leaflets, etc.) with enough force to stop expanding and to securely hold the docking station in place.

In one exemplary embodiment, the distance between the arms 5328 and thus the diameter D or width can be adjusted manually. The distance between the arms 5328 and thus the diameter D or width can be adjusted manually in a wide variety of different ways. For example, the arms 5328, 5338 can be biased to a first position and an adjustment cord, line or wire 5370 is coupled to the arms 5328, 5338 to move the arms from the first position. The arms 5328, 5338 can be biased to a first position in a wide variety of different ways. For example, the arms 5328, 5338 can be made from a shape memory alloy with a shape set or the arms can be coupled with a spring, etc. The shape set or spring, etc. can be set to make the spacing between the arms 5328 and the corresponding arms 5338 as great as possible, such as a 180 degree angle or approximately 180 degree angle (e.g., ±10 degrees, ±5 degrees) defined between (i.e. extending directly apart in the axial direction). When the arms 5328 and the arms 5338 are biased very far apart, the docking station 10 can be initially deployed in a very narrow configuration. In the narrow configuration, the docking station 10 can be moved to a selected final deployment site and proper positioning can be checked. Once properly positioned, the diameter D or width can be adjusted with the adjustment cord, line or wire 5370. For example, the cord, line or wire 5370 can be pulled to reduce the spacing between the arms 5328 and the arms 5338 and thereby increase the diameter D or width of the docking station 10 and the strength of engagement with inner surface 416 (e.g., vessel walls, IVC walls, SVC walls, aorta walls, an annulus of a native heart valve, tissue surrounding an annulus of a native heart valve, leaflets, etc.). Once the docking station 10 is properly, securely engaged with the inner surface 416, the position of the arms 5328, 5338 can be secured to secure the docking station in place. In some embodiments, the shape set or spring, etc. can be set to make the spacing between the arms 5328 and the corresponding arms 5338 as small as possible, such as touching each other or with 5, 10, 20, 30 degrees or less defined between (i.e. the arms all extending in the radial or generally radial direction).

In another exemplary embodiment, the distance between the arms 5328 and thus the diameter D or width can be adjusted manually to both increase the diameter D or width and decrease the diameter or width. For example, adjustment cords, lines or wires 5370 are coupled to the arms 5328, 5338 such that they can both move the arms toward each other and away from each other. The spacing between the arms 5328, 5338 can be as great as possible during initial deployment, such as a 180 degree angle or approximately 180 degree angle defined between (i.e. extending directly apart in the axial direction). In the narrow configuration, the docking station 10 can be moved to a selected final deployment site and proper positioning can be checked. Once properly positioned, the diameter D or width can be adjusted with the adjustment cord, line or wire 5370. For example, the cord, line or wire 5370 can be pulled to reduce the spacing between the arms 5328, 5338 and thereby increase the diameter D or width of the docking station 10 and the strength of engagement with inner surface 416 (e.g., vessel walls, IVC walls, SVC walls, aorta walls, an annulus of a native heart valve, tissue surrounding an annulus of a native heart valve, leaflets, etc.). Once the docking station 10 is properly, securely engaged with the inner surface 416, the position of the arms 5328, 5338 can be secured to secure the docking station in place.

In the example of FIGS. 53 and 54, the sealing portion 310 comprises a covering/material 21 (which can be the same as or similar to other coverings/materials described elsewhere herein), such as a cloth or fabric or a protective foam provided on the arms 5328, the arms 5338, or both sets of arms 5328, 5338. The covering/material (e.g., an impermeable material or semi-permeable material) can extend from the inner ends 5380 and valve seat 18 to outer ends 5390 of the arms 5328 and/or 5338 to form the sealing portion 310 of the docking station 10. The valve 29 can expand and be implanted in the narrow portion 5316, which forms the valve seat 18. It should be understood that the covering/material can extend three-dimensionally to create a sealing region circumferentially around the valve 29 when deployed in the circulatory system. For example, the covering/material can have a conical shape, frustoconical shape, funnel shape, other shape, etc. that can guide blood flow to the valve 29 and inhibit or prevent paravalvular leakage.

The docking stations 10 illustrated by FIGS. 53 and 54 can be made from a very resilient or compliant material to accommodate large variations in the anatomy. For example, the docking station can be made from a highly flexible metal, metal alloy, polymer, or an open cell foam. An example of a highly resilient metal is nitinol, but other metals and highly resilient or compliant non-metal materials can be used. The docking station 10 can be self-expandable, manually expandable, mechanically expandable, or a combination of these. A self-expandable docking station 10 can be made of a shape memory material such as, for example, nitinol.

Figure 56:
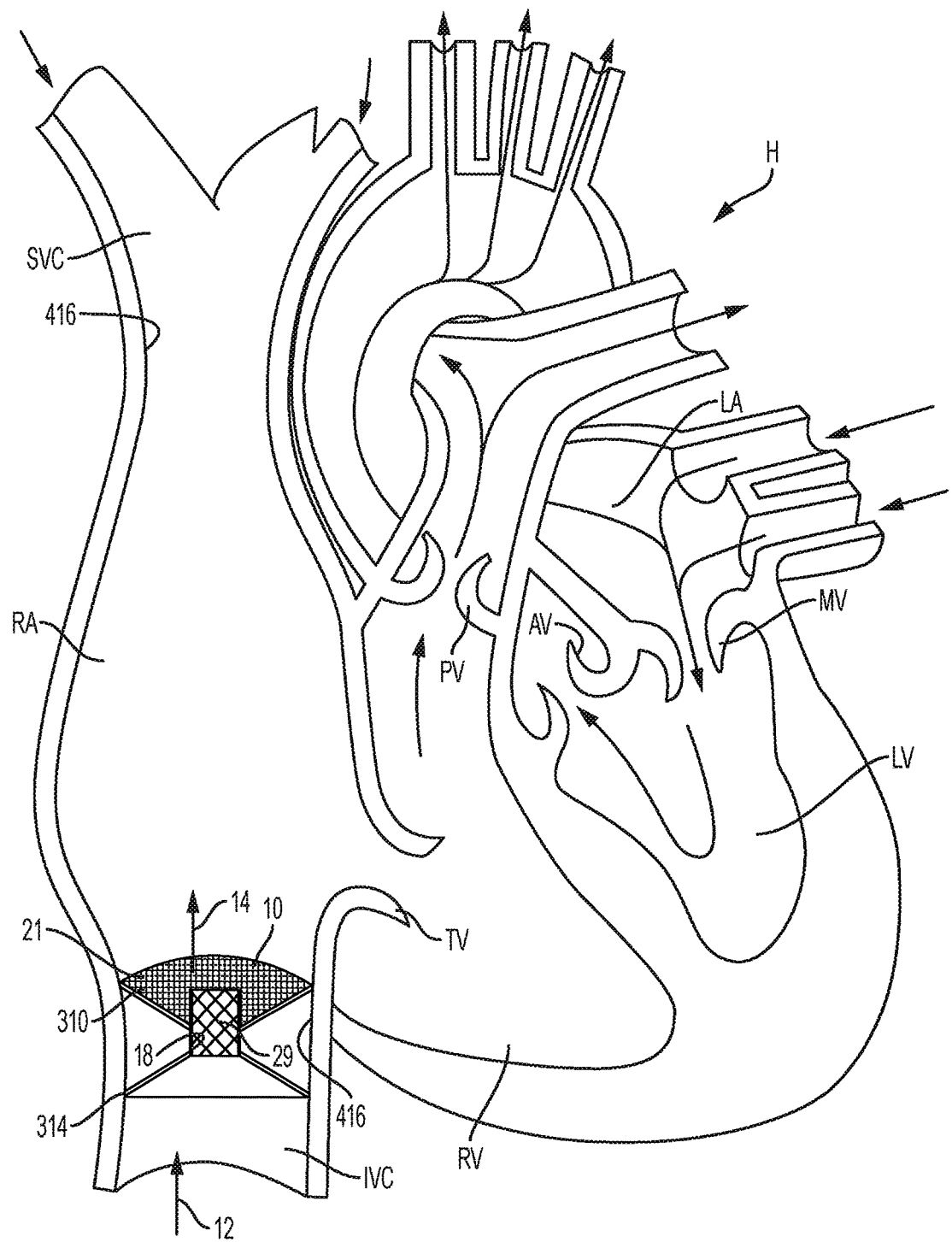
FIG. 56 is a cutaway view of the human heart with the docking station illustrated by FIG. 53 positioned in the inferior vena cava.

FIG. 56 illustrates the docking station 10 of FIG. 53 or 54 implanted in the circulatory system, such as in the inferior vena cava. In FIG. 56, the entire docking station is held in place in the inferior vena cava by the arms 5328, 5338. The covering/material 21 of the sealing portion 310 can make docking station 10 impermeable or substantially impermeable from the sealing portion 310 to the seal between the valve 29 and the docking station 10 at the valve seat 18. As such, blood flowing in the inflow direction 12 toward the outflow direction 14 flows through the valve seat 18 (and valve 29 once installed or deployed in the valve seat).

As one non-limiting example, when the docking station 10 is placed in the inferior vena cava IVC, which is a large vessel, the significant volume of blood flowing through the vein is funneled into the valve 29 by the covering or inner layer. The covering can be fluid impermeable or substantially impermeable so that blood cannot pass through. Again, a variety of other biocompatible covering materials can be used such as any materials described elsewhere herein, including, for example, foam or a fabric that is treated with a coating that is impermeable to blood, polyester, or a processed biological material, such as pericardium.

Figure 57:
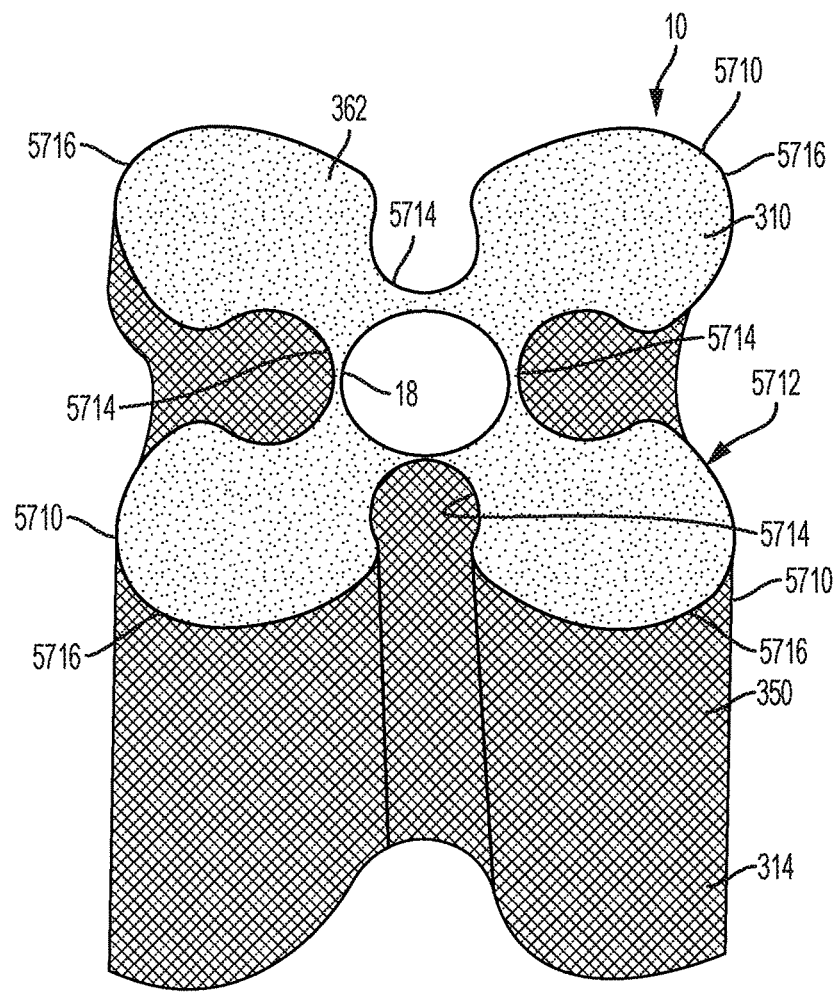
FIG. 57 is a perspective view of an exemplary embodiment of a docking station.

In some exemplary embodiments, the wall 368 of the frame 350 of the docking station can have a non-circular shape or non-circular radial cross-section. A wide variety of different non-circular shapes can be implemented. FIG. 57 illustrates one example of a docking station 10 having a frame 350 with a non-circular shape or non-circular radial cross-section. In this example, the expandable docking station 10 includes one or more sealing portions 310, a valve seat 18, and one or more retaining portions 314. In an alternate embodiment, the docking station 10 and the valve 29 can be integrally formed, such that the combination forms a transcatheter valve that can be implanted as one in the same implantation step.

In the example of FIG. 57, the non-circular shape of the frame 350 allows an axially extending frame with a constant shape or cross section along its length (prior to engagement by an inner surface 416) to both engage the interior surface 416 of the circulatory system and provide a seat 18 for the valve 29. The frame 350 with a constant axial shape can be configured to provide a valve seat 18 and an outer engagement surface 5710 in a wide variety of different ways. In the example of FIG. 57, the frame 350 has an undulating perimeter 5712 with alternating inner portions 5714 and outer portions 5716. The frame 350 can consist only of a wall 368 having the undulating configuration. However, the frame 350 can have additional structures, such as a band or other reinforcement for constraining the size of the valve seat 18.

The inner and outer portions 5714, 5716 can have a wide variety of different shapes and there can be any number of inner portions 5714 and outer portions 5716. For example, the inner and outer portions 5714, 5716 can be formed by any series of lines and/or curves. In the illustrated embodiment, the frame 350 has four outer portions 5714 and four inner portions 5716, but the frame can have any number of inner portions and outer portions. For example, the frame 350 can have any number of inner portions and outer portions 5714, 5716 in the range from 3 to 100.

In the example of FIG. 57, the inner portions 5714 comprise concave curves and the outer portions 5716 comprise convex curves. The concave curves and the convex curves are connected together to form a petal shape. However, the inner portions 5714 and the outer portions can form any shape. For example, increasing the number of inner portions 5714 and outer portions 5716 increases a number of points of contact between the frame 350 and inside surface 416 of the circulatory system and the number of points of contact between the frame 350 and the valve 29.

The expandable frame 350 can take a wide variety of different forms. In the illustrated example, the expandable frame 350 is an expandable lattice. The expandable lattice can be made from individual wires or can be cut from a sheet and then rolled or otherwise formed into the shape of the expandable frame. The frame 350 can be made from a highly flexible metal, metal alloy, or polymer. Examples of metals and metal alloys that can be used include, but are not limited to, nitinol and other shape memory alloys, elgiloy, and stainless steel, but other metals and highly resilient or compliant non-metal materials can be used to make the frame 350. These materials can allow the frame to be compressed to a small size, and then when the compression force is released, the frame will self-expand back to its pre-compressed diameter and/or the frame can be expanded by inflation of a device positioned inside the frame.

The sealing portions 310 of the docking station 10 illustrated by FIG. 57 can take a wide variety of different forms. A covering/material (which can be the same as or similar to other coverings/materials described elsewhere herein) can be attached to a portion of the frame 350 to form the sealing portion 310. For example, the covering/material can cover an end 3762 as illustrated. In one embodiment, the covering/material can cover (e.g., extend over or fill) the gaps or portions of the gaps between the inner portions 5714 and outer portions 5716. Optionally, the covering/material can extend along the frame wall 368. A portion of the frame wall 368 or the entire frame wall can be covered with the covering/material. However, the sealing portion 310 can also be formed in a wide variety of other ways.

In the example of FIG. 57, the retaining portion 314 comprises the wall 368 of the frame 350. A shape set of the wall 368 biases the outer portions 5716 radially outward and into contact with the interior surface 416 (See FIG. 2) of the circulatory system to retain the docking station 10 and the valve 29 at the implantation position. In the illustrated embodiment, the retaining portion 314 is elongated to allow a small force to be applied to a large area of the interior surface 416, which can allow the docking station to be securely held in place without exerting too much radial force on or damaging the interior surface 416. For example, the length of the retaining portion 314 can be twice, three times, four times, five times, or greater than five times the outside diameter of the transcatheter valve.

Figure 58:
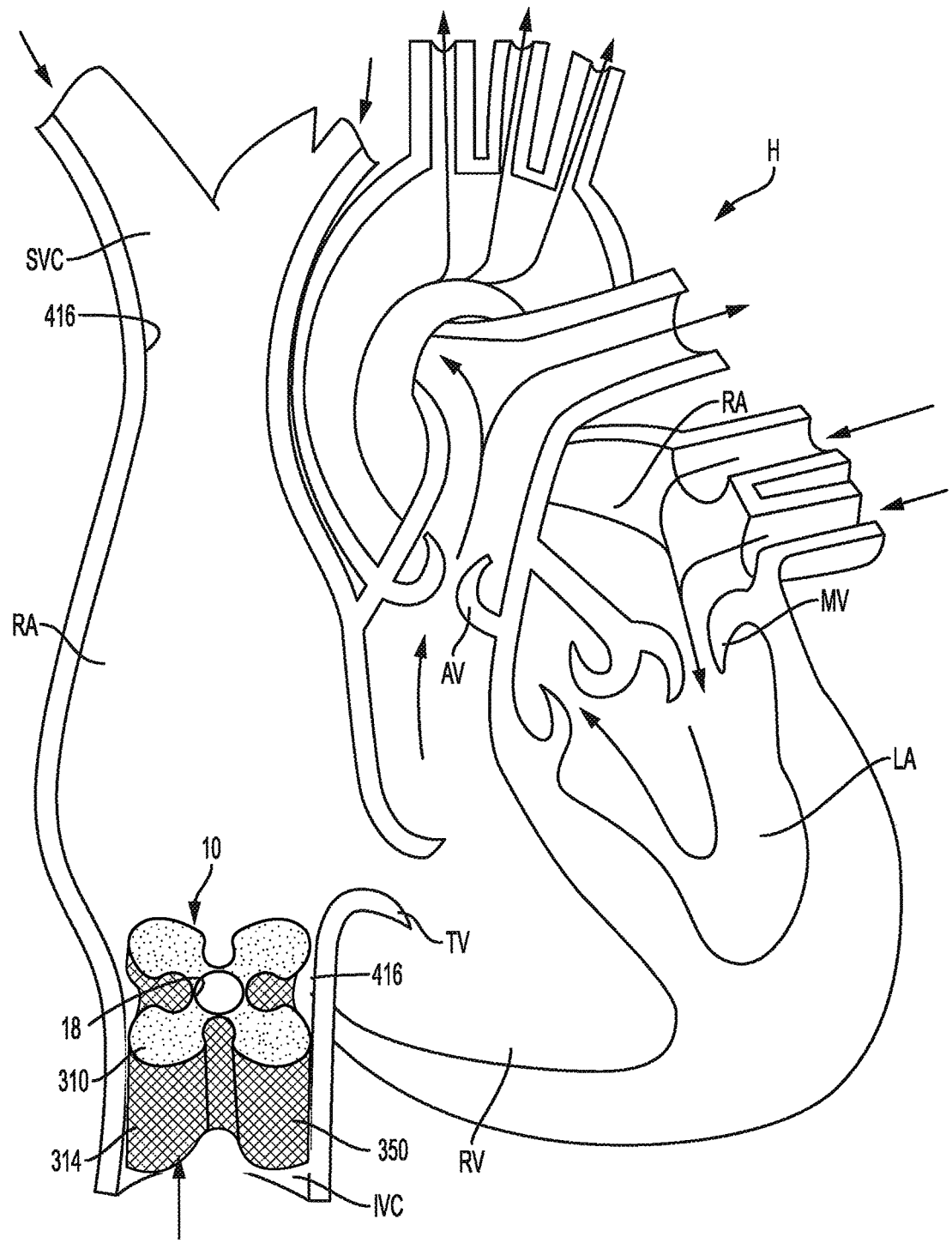
FIG. 58 is a cutaway view of a human heart with the docking station illustrated by FIG. 57 positioned in the inferior vena cava IVC.

FIG. 58 illustrates the docking station 10 of FIG. 58 implanted in the circulatory system, such as in the inferior vena cava IVC. In the example of FIG. 58, the entire docking station is positioned in the inferior vena cava IVC and held in place by the frame 350 pressing against the inner surface 416. As mentioned above, the docking station 10 can be adapted for use at a variety of different positions in the circulatory system.

Figure 59A:
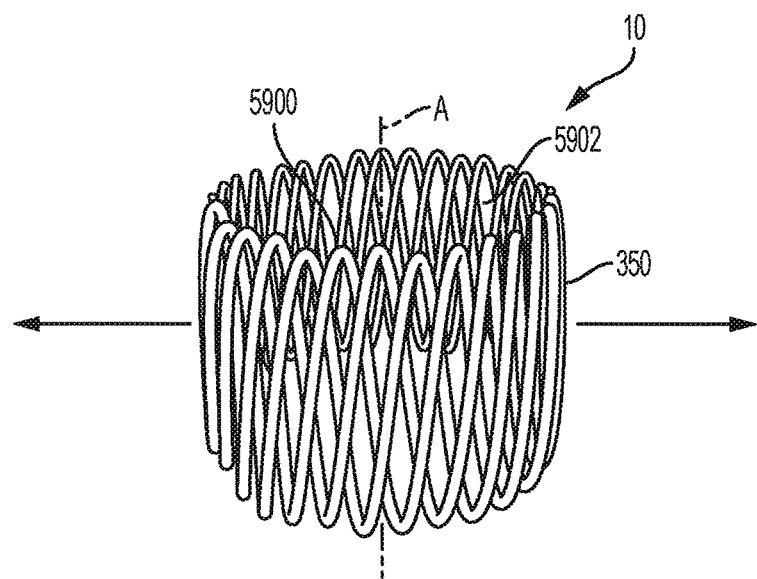
FIG. 59A is a perspective view of an exemplary embodiment of a docking station in a partially compressed state.
Figure 59B:
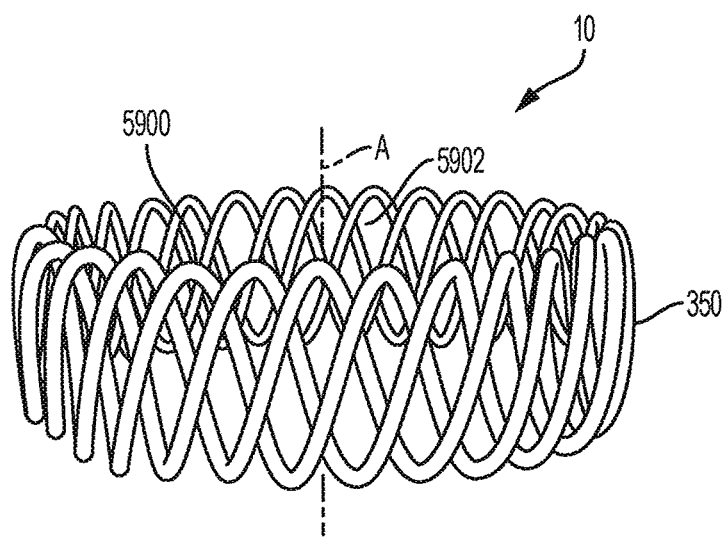
FIG. 59B illustrates the docking station of FIG. 59B in an expanded state.

FIGS. 59A and 59B illustrate an exemplary embodiment of a docking station frame 350 constructed from one or more coils 5900 of material that are formed into one or more rings 5902. The coil 5900 can take a wide variety of different forms and FIGS. 59A and 59B illustrates just one of the many possible configurations. In the example of FIGS. 59A and 59B, the coil 5900 is rotated 90 degrees compared to the coil 5100 illustrated by FIG. 51, and is formed into a ring shape, whereas the coil 5100 is not. The ring(s) 5902 can be formed by bending one or more wires into a coiled configuration and then wrapping or bending the coil around an axis A of the docking station frame 350. The docking station can transition between a collapsed configuration (e.g., for easier, lower-profile delivery to an implantation site) and an expanded configuration (e.g., for securing the docking station in the implantation site and allowing a transcatheter valve to be deployed therein). FIG. 59A shows the docking station transitioning from a collapsed configuration to an expanded configuration. FIG. 59B shows the docking station in an expanded configuration. The interior surface of the coil 5900 can act as the valve seat for receiving the transcatheter valve. The docking station and coil 5900 can be formed from any of the materials described as being used to form other frame bodies 350 elsewhere herein, including nitinol or another shape memory material.

Figure 59C:
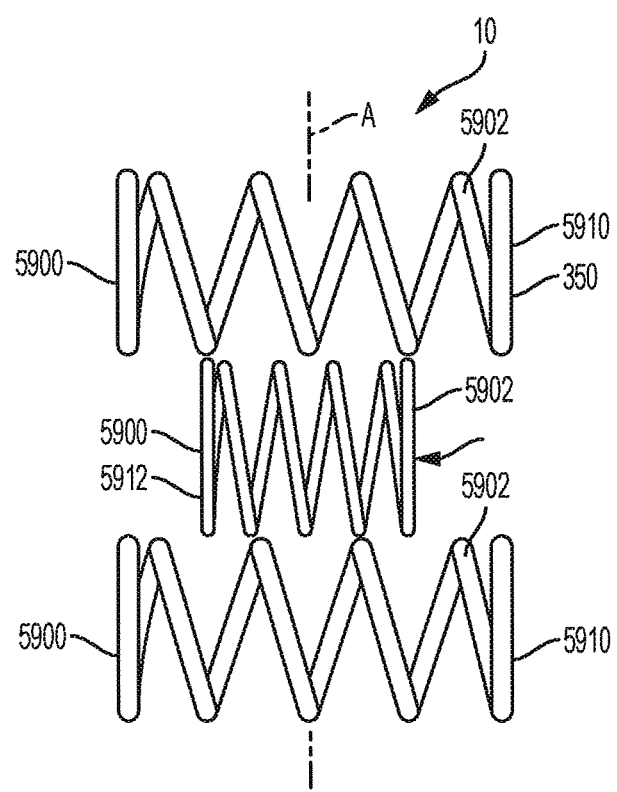
FIG. 59C illustrates an exemplary embodiment of a docking station.

The coil 5900 can be used to form a docking station 10 in a wide variety of different ways. A valve seat 18 can be formed inside or attached to coil 5900 illustrated by FIGS. 59A and 59B. Referring to FIG. 59C, in another exemplary embodiment, a docking station 10 is formed from three coils 5900 or coil portions. The coils 5900 can be integrally formed, for example, from a single wire or three separate coils 5900 can be connected or linked together to form a docking station 10. In the example of FIG. 59C, the docking station 10 comprises two relatively larger diameter coil rings 5910 and a smaller diameter coil ring 5912 that forms the valve seat 18. However, in some embodiments, only a single larger diameter coil ring 5910 is included.

A covering/material 21 (See e.g., FIG. 59D), such as a cloth or fabric or a protective foam can be provided inside and/or outside the coil(s) 5900 (e.g., the coil(s) shown in any of FIGS. 59A-59D) or a portion of the coil(s) to provide a sealing portion to the coil(s) 5900 and/or one or more coil rings 5902, 5910, 5912, and create a sealed docking station. Such a covering/material can be connected to one or more of the rings 5902, 5910, 5912 or can be deployed separately from the coil rings (e.g., deployed either before or after deployment of the coil(s) 5900) and/or with the valve/THV 29. The valve 29 (not shown in FIGS. 59A-59D) can expand in the center of coil 5900 of FIGS. 59A-59B or can expand in the smaller coil ring 5912 of FIGS. 59C-59D, which forms the valve seat 18.

The docking station coil(s) 5900 and coil ring(s) 5902, 5910, 5912 can be made from a very resilient or compliant material to accommodate large variations in the anatomy or any of the materials described elsewhere with respect to the various frame bodies 350 herein. For example, the docking station coil(s) 5900 and coil ring(s) 5902, 5910, 5912 can be made from a highly flexible metal, metal alloy, or polymer. An example of a highly resilient metal is nitinol, but other metals and highly resilient or compliant non-metal materials can be used. The docking station 10 can be self-expandable, manually expandable (e.g., expandable via balloon), mechanically expandable, or a combination of these.

Figure 59D:
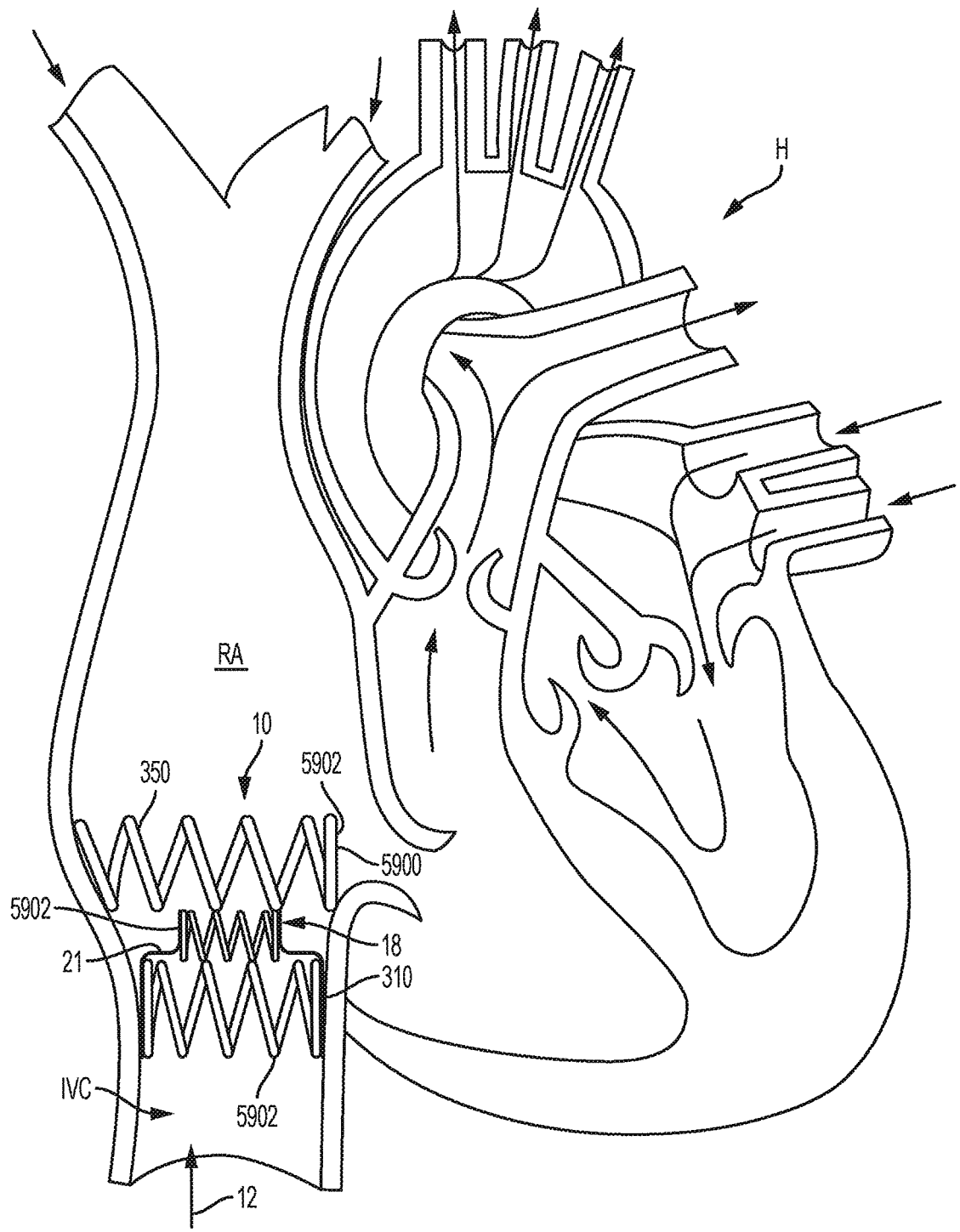
FIG. 59D is a cutaway view of the human heart with the docking station illustrated by FIG. 59C positioned in the inferior vena cava IVC.

FIG. 59D illustrates the docking station 10 of FIG. 59C implanted in the circulatory system, such as in the inferior vena cava IVC. In the example of FIG. 59D, the docking station 10 is held in place in the inferior vena cava IVC by a lower larger diameter ring 5910. An upper larger diameter segment 5910 is disposed in the right atrium RA. The larger diameter ring 5910 may expand to a larger size in the right atrium than the ring in the IVC as illustrated, the larger diameter ring in the atrium and IVC may expand to the same size, or the larger diameter ring in the IVC may expand to a larger size than the larger diameter ring in the right atrium RA. Sealing portion(s) 310 can be formed by providing the covering/material 21 over or inside one or more of the coil(s) 5900 and coil ring(s) 5902, 5910, 5912 or a portion thereof. In one embodiment, covering/material 21 covers the smaller diameter ring 5912 and one or both of the larger diameter rings 5110. This can make docking station 10 impermeable or substantially impermeable from the sealing portion 310 to the seal between the valve 29 and the docking station 10 at the valve seat 18. As such, blood flowing in the inflow direction 12 toward the outflow direction 14 is directed to the valve seat 18 (and valve 29 once installed or deployed in the valve seat).

FIGS. 60A-60J illustrate exemplary embodiments that are similar to the embodiment illustrated by FIGS. 3A-3C, except the free ends of the frame 350 are connected together and/or extend closer together. For example, an end 6000 of the valve seat 18 or inner ring is connected to an end 6002 of the frame 350/outer wall 368 and/or is extended to or toward the end 6002 of the frame 350/outer wall 368. The end 6000 of the valve seat 18 or inner ring can be connected and/or extended to or toward an end 6002 of the frame 350 in a wide variety of different ways. FIGS. 60A-60J illustrate a few of the possible ways that the end 6000 of the valve seat 18 or inner ring can be connected and/or extended to or toward an end 6002 of the frame 350.

Connecting the end 6000 of the valve seat 18 or inner ring to the end 6002 of the frame 350 or extending the end 6000 of the valve seat 18 or inner ring to the end 6002 of the frame 350 can provide a number of advantages. For example, the docking station 10 can be more easily loaded in the delivery catheter/sheath, and the docking station 10 can be more easily recaptured or pulled back into the catheter/sheath if initial placement of the docking station is incorrect, imperfect, or if the medical professional wants to abort or redo the procedure for any reason. Having the bottom/proximal end 6000 of the valve seat 18 coupled to the end 6002 of the frame can help urge the end 6000 of the valve seat 18 radially inwardly and into the catheter/sheath. As can be seen, for example, in FIGS. 21A-21H, the bottom/proximal end of the valve seat 18 (identified in these Figures as end 2122) tends to extend outwardly even after the outer wall 368 begins to be compressed radially inwardly. During recapture, the end 6002 and/or proximal portion of the frame can be first captured and/or retracted further into the delivery catheter/sheath and, by having the bottom/proximal of the valve seat 18 connected to the end 6002 of the frame, the retraction and compression of end 6002 and the connections and/or portions of the frame proximal to the valve seat 18 can help urge the bottom/proximal end of the valve seat 18 radially inwardly and into the delivery catheter/sheath. This can also beneficially result in more gradual compression of the valve seat 18. Even if the ends are not connected, but end 6000 merely extends to a location proximate end 6002 (e.g., such that the valve seat or inner ring or an extension therefrom has a similar length to the outer wall 368), this can help with loading, recapture, etc. For example, the longer end or extensions from the valve seat can remain in the catheter/sheath during partial deployment and allow for smoother recapture of the partially deployed docking station. Also, the longer end/extension could help the transition into the catheter/sheath to be more gradual and controlled.

Similarly, the valve seat 18 or ring of the docking station 10 can be more uniformly compressed during the crimping process. For example, the compression of the outer wall 368 before the outer wall 368 contacts the valve seat 18 can aid or cause compression of both the proximal and distal ends of the valve seat 18 or inner ring.

Another advantage of connecting the free ends of the frame 350 together or connecting end 6000 and end 6002 (and/or having the free ends extend closer together) is that it can improve deployment of the docking station and make deployment more controlled. If not connected (or where the unconnected ends are not similarly located/extended or of similar lengths), the docking station can tend to jump or move unpredictably out of the delivery catheter/sheath when the free end (e.g., end 2122 shown in FIGS. 21A-21H) of the valve seat is released from the delivery catheter/sheath. When no longer constrained by the delivery catheter/sheath, the free end (e.g., end 2122) can expand suddenly and cause the docking station to jump or move. By connecting the free ends of the docking station frame together or connecting end 6000 and end 6002 (and/or by extending the end of the valve seat closer to the end of the outer wall), the expansion of end 6000 can be more restrained and controlled as it is released from the delivery catheter/sheath such that the docking station deployment is more controlled and less likely to jump, move at all, or as much, i.e., it can prevent or inhibit/restrain jumping or uncontrolled movement of the docking station.

Figure 60A:
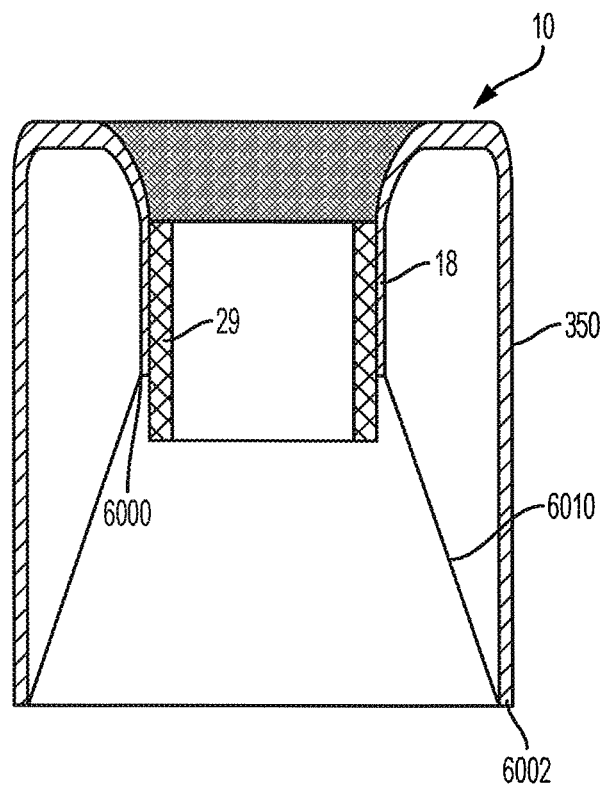
FIG. 60A is a sectional view an exemplary embodiment of a docking station with a transcatheter valve disposed inside the docking station.
Figure 60B:
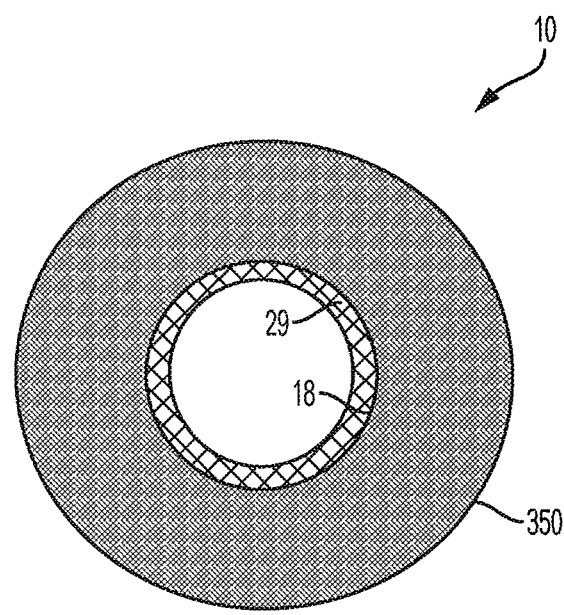
FIG. 60B is a top view of the docking station and transcatheter valve illustrated by FIG. 60A.

In the example of FIG. 60A (cross-sectional side view) and 60B (top end view), the end 6000 of the valve seat 18 or inner ring is connected to an end 6002 of the frame 350 by one or more lines 6010. The line(s) 6010 can take a wide variety of different forms. For example, the line(s) 6010 can be a suture(s), a wire(s), rod(s), arm(s), strut(s), or any other elongated member, and can be rigid, semi-rigid, or flexible. In one embodiment, instead of a line(s), a covering/material (e.g., similar to the coverings/materials 21 described elsewhere herein) extends from end 6000 to 6002 (e.g., in a conical or frustoconical shape).

Figure 60C:
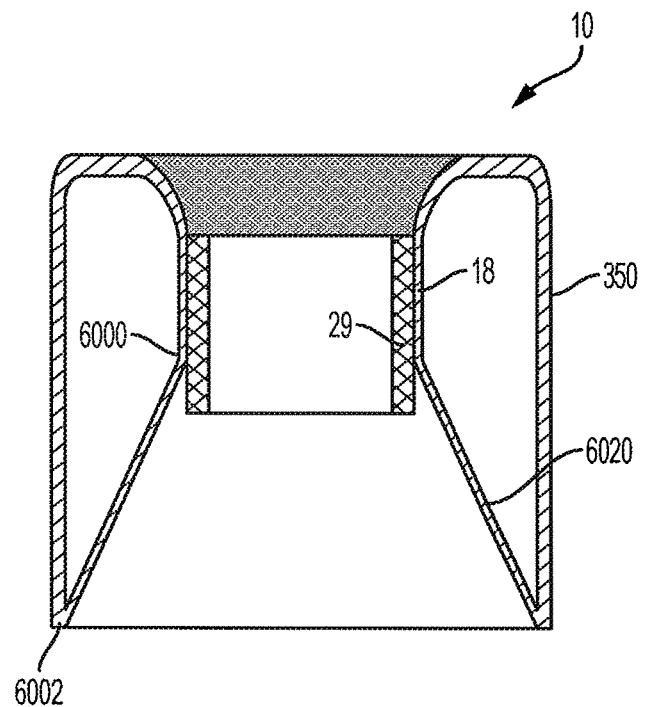
FIG. 60C is a sectional view an exemplary embodiment of a docking station with a transcatheter valve disposed inside the docking station.
Figure 60D:
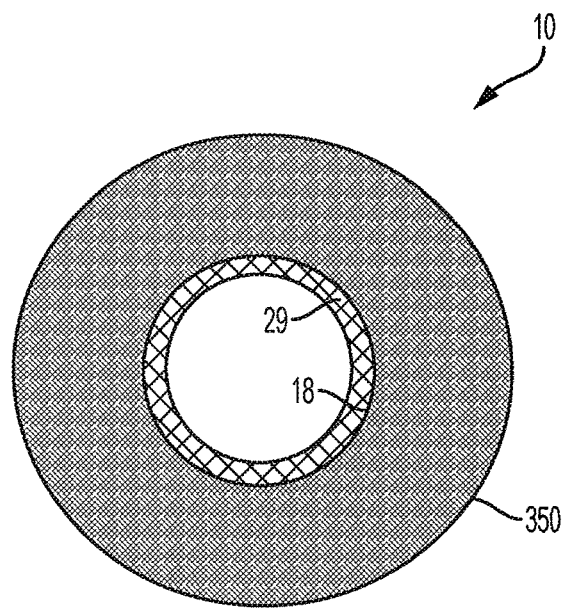
FIG. 60D is a top view of the docking station and transcatheter valve of FIG. 60C.

In the example of FIG. 60C (cross-sectional side view) and 60D (top end view), the end 6000 of the valve seat 18 or inner ring includes an integral extension 6020 that extends to the end 6002 of the frame 350. In the illustrated embodiment, the extension 6020 is connected to the end 6002 of the frame 350. In another exemplary embodiment, the extension 6020 is in substantially the same position as illustrated by FIG. 60C, but the extension 6020 is not connected to the frame. The extension can take a wide variety of different forms. In one exemplary embodiment, a bottom row of cells of the valve seat 18 or inner ring is elongated and extends (e.g., has apices that extend) to the end 6002 of the frame 350. In one exemplary embodiment, the lattice of struts and cells forming the frame body can continue to form the extension 6020.

Figure 60E:
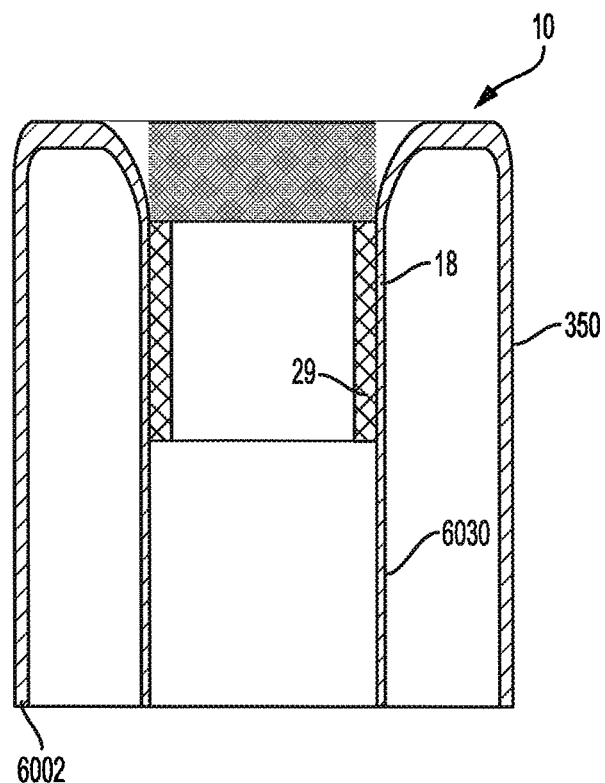
FIG. 60E is a sectional view an exemplary embodiment of a docking station with a transcatheter valve disposed inside the docking station.
Figure 60F:
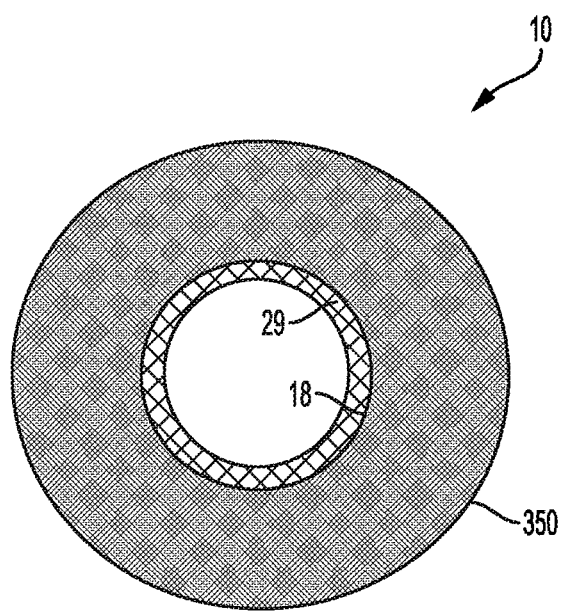
FIG. 60F is a top view of the docking station and transcatheter valve of FIG. 60E.
Figure 60G:
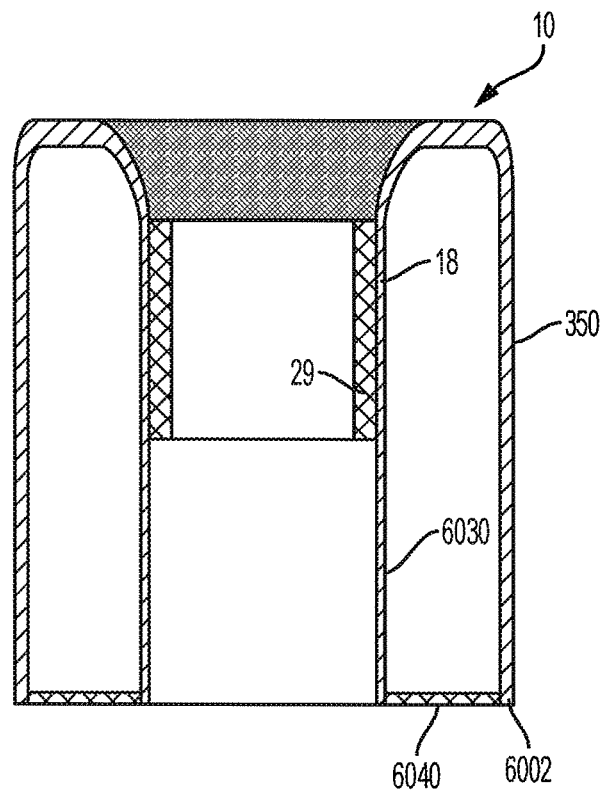
FIG. 60G is a sectional view an exemplary embodiment of a docking station with a transcatheter valve disposed inside the docking station.
Figure 60H:
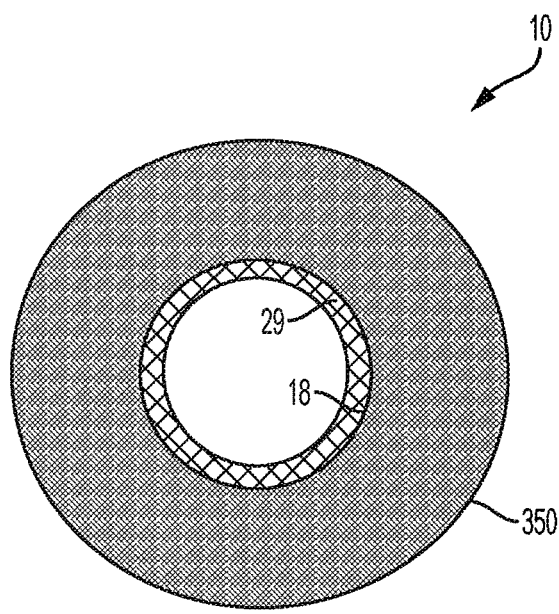
FIG. 60H is a top view of the docking station and transcatheter valve of FIG. 60G.

In the example of FIG. 60E (cross-sectional side view) and 60F (top end view), the end 6000 of the valve seat 18 or inner ring includes an integral extension 6030 that is substantially parallel to the outer wall 368 in cross-section when expanded and extends to a location/length similar to outer wall 368. In the example of FIGS. 60E and 60F, the extension 6030 is not connected to the end 6002 of the frame 350. In the example of FIG. 60G (cross-sectional side view) and 60H (top end view), the extension 6030 is in substantially the same position as of FIG. 60E, but the extension 6030 is connected to the frame by a connecting portion 6040. The extension 6030 can take a wide variety of different forms. In one exemplary embodiment, a bottom row of cells of the valve seat 18 or inner ring is elongated and extends (e.g., has apices that extend) as shown. The optional connecting portion 6040 can take a wide variety of different forms. For example, the connecting portion 6040 can comprise one or more line(s), such as a wire(s), suture(s), rod(s), arm(s), strut(s), and/or a covering/material 21.

Figure 60I:
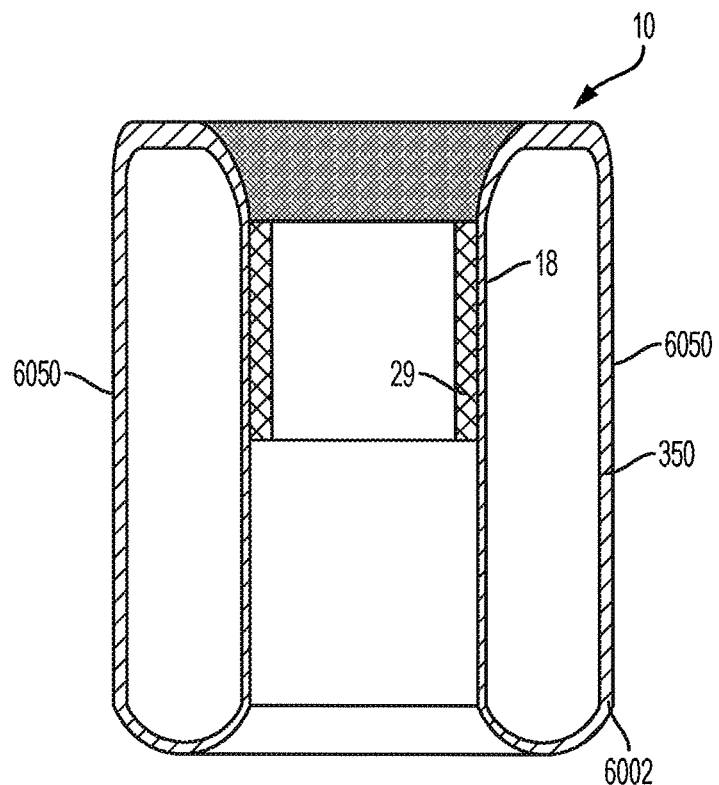
FIG. 60I is a sectional view an exemplary embodiment of a docking station with a transcatheter valve disposed inside the docking station.
Figure 60J:
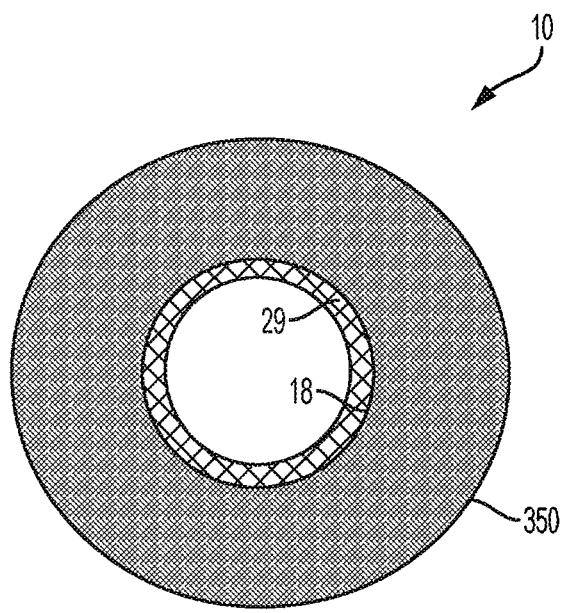
FIG. 60J is a top view of the docking station and transcatheter valve of FIG. 60I.

In the example of FIG. 60I (cross-sectional side view) and 60J (top end view), the frame 350 and seat 18 are integrally formed and can have a toroidal shape. Referring to FIG. 60I, in cross-section the frame 350 and valve seat 18 form a loop or loops 6050. In one exemplary embodiment, the loop 6050 is formed of a continuous lattice of struts and cells. However, the loop(s) can be formed in a wide variety of different ways.

Figure 61:
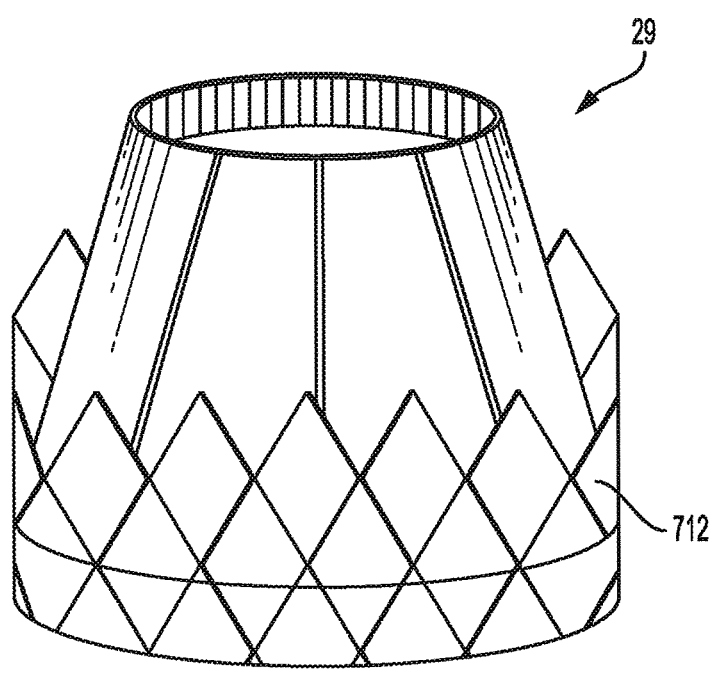
FIGS. 61-64, and 65A-65C illustrate some non-limiting examples of types of valves that can be deployed in a docking station, e.g., in any one of the docking stations herein.
Figure 62:
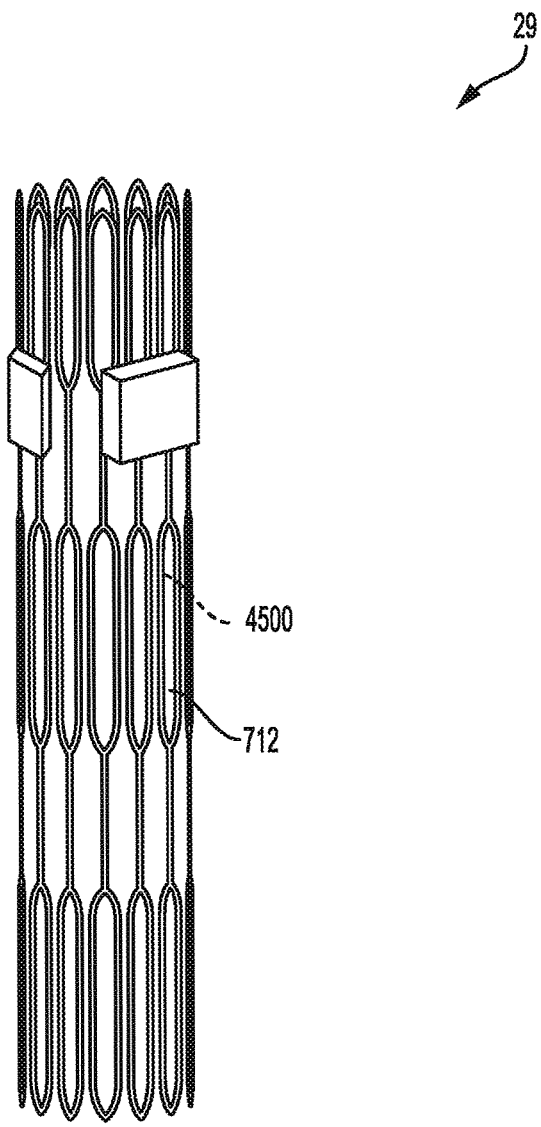
Figure 63:
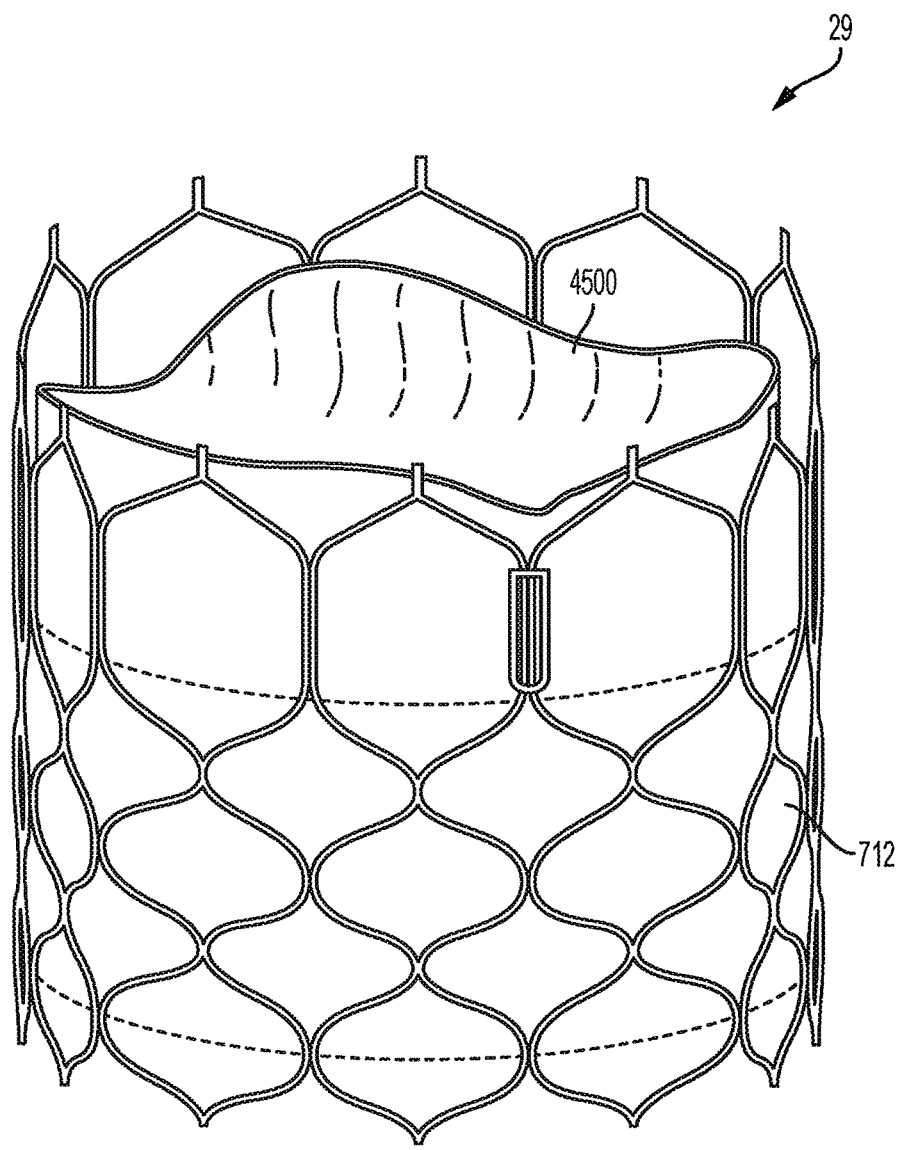
Figure 64:
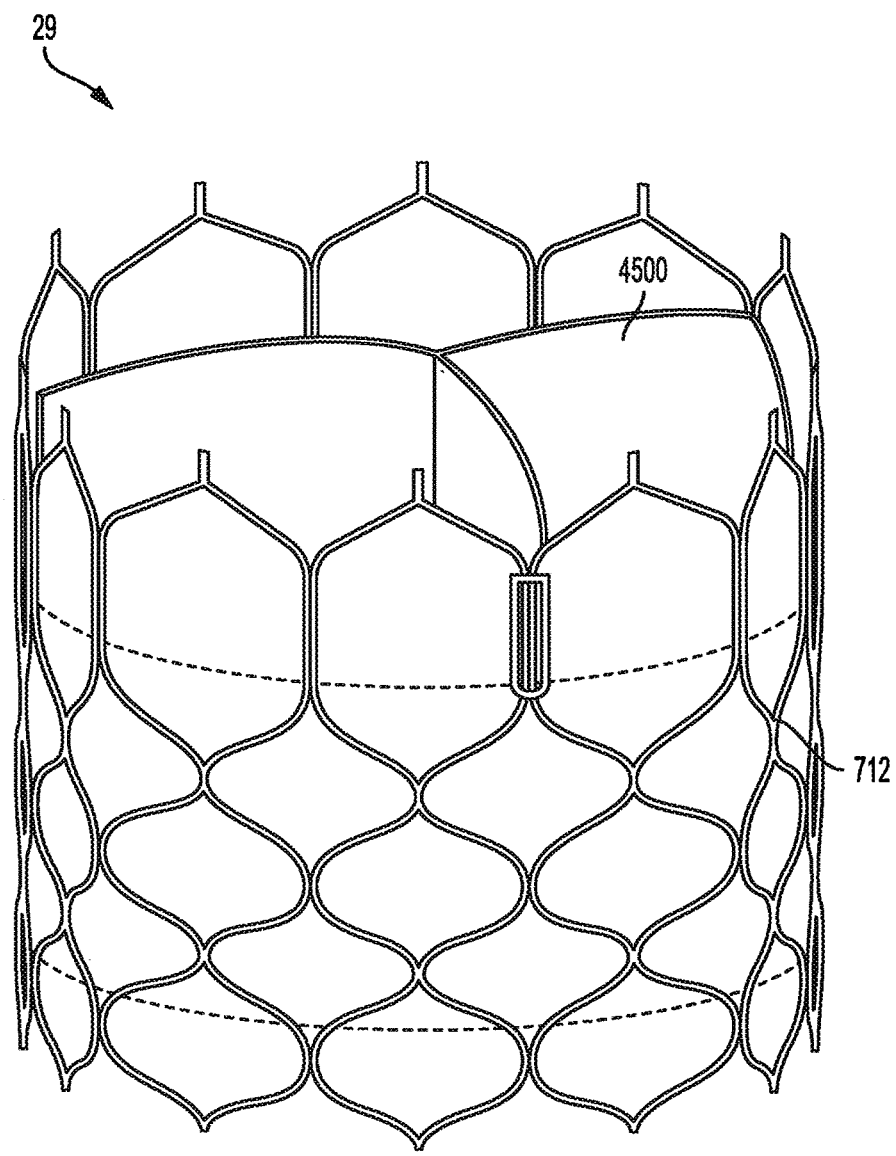
Figure 65A:
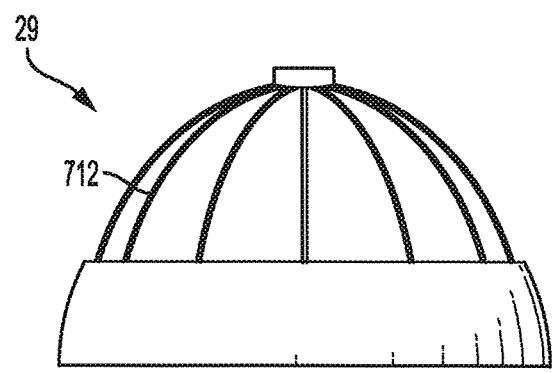
Figure 65B:
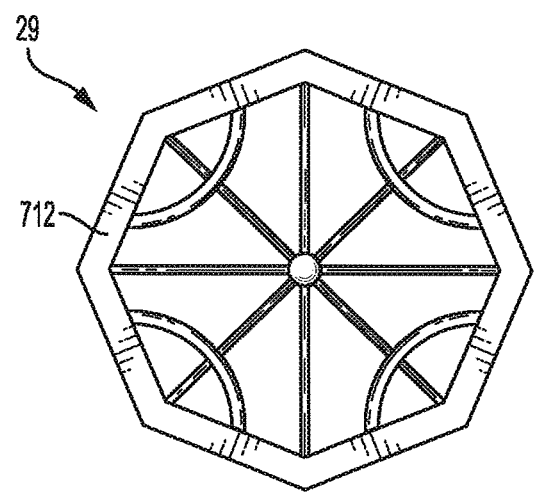
Figure 65C:
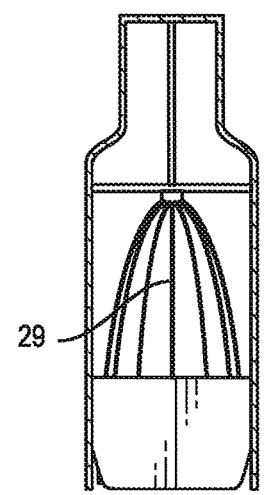

In various figures herein, a "V" or generic valve symbol is used to represent generically a variety of valves that can have different structures for closing/opening the valve and can operate in different ways. FIGS. 61-65 illustrate a few examples of the many valves or valve configurations that can be used. Any valve type can be used and some valves that are traditionally applied surgically can be modified for transcatheter implantation. A transcatheter valve can be expanded in a variety of ways, e.g., it can be self-expanding, expanded with a balloon, mechanically-expandable, and/or a combination of these. In one example, a mechanical opening mechanism, such as a hinged mechanism can be used to expand the transcatheter valve and/or a frame of the transcatheter valve can comprise a hinged mechanism. FIG. 61 illustrates an expandable valve 29 for transcatheter implantation that is shown and described in U.S. Pat. No. 8,002,825, which is incorporated herein by reference in its entirety. An example of a tri-leaflet valve is shown and described in Published Patent Cooperation Treaty Application No. WO 2000/42950, which is incorporated herein by reference in its entirety. Another example of a tri-leaflet valve is shown and described in U.S. Pat. No. 5,928,281, which is incorporated herein by reference in its entirety. Another example of a tri-leaflet valve is shown and described in U.S. Pat. No. 6,558,418, which is incorporated herein by reference in its entirety. FIGS. 62-64 illustrate an exemplary embodiment of an expandable tri-leaflet valve 29, such as the Edwards SAPIEN Transcatheter Heart Valve. The valve 29 can comprise a frame 712 that contains a tri-leaflet valve 4500 compressed inside the frame 712. FIG. 63 illustrates the frame 712 expanded and the valve 29 in an open condition. FIG. 64 illustrates the frame 712 expanded and the valve 29 in a closed condition. FIGS. 65A, 65B, and 65C illustrate an example of an expandable valve 29 that is shown and described in U.S. Pat. No. 6,540,782, which is incorporated herein by reference in its entirety. Another example of a valve is shown and described in U.S. Pat. No. 3,365,728, which is incorporated herein by reference in its entirety. Another example of a valve is shown and described in U.S. Pat. No. 3,824,629, which is incorporated herein by reference in its entirety. Another example of a valve is shown and described in U.S. Pat. No. 5,814,099, which is incorporated herein by reference in its entirety. Any of these, the valves described in the incorporated references, or other valves can be used as valve 29 in the various embodiments herein.

The docking stations described above can be used to form a docking station assembly, e.g., including a graft or other elements. For example, a docking station assembly can include a graft and a docking station. The graft can be shaped to conform to a portion of an interior shape of a first portion of a circulatory system (e.g., of a blood vessel, vasculature, native heart valve, etc.). The docking station and the graft can be coupled to each other. The various docking stations described herein can be used in the assembly and can include an expandable frame, at least one sealing portion, and a valve seat as discussed above. The expandable frame can be configured to conform to an interior shape of a second portion of the circulatory system (e.g., of a blood vessel, vasculature, native heart valve, etc.) when expanded inside the circulatory system. The sealing portion can be configured to contact an interior surface of the circulatory system. The valve seat can be connected to the expandable frame. The valve seat can be configured to support an expandable transcatheter valve. The docking station can be integrally formed with a valve, e.g., such that the docking station and valve combination is a prosthetic valve or transcatheter prosthetic valve that can be implanted in the same step. The frame can be formed and configured in any of the ways described in this disclosure, for example, the frame can be made of nitinol, elgiloy, or stainless steel. A portion of the docking station can engage an interior of the graft. The graft can be shaped or configured to fit an interior surface of the circulatory system.

Referring to FIGS. 66A through 72C, exemplary docking station deployment assemblies/systems 7000 for deploying a docking station/device are depicted. The various docking station deployment assemblies/systems 7000 herein can be used with any of the docking stations/devices described or depicted in this disclosure (e.g., those shown in FIGS. 2A-36, 42-60J, and), which can be modified as appropriate. The docking deployment assemblies/systems 7000 (e.g., docking station deployment assembly, docking station deployment system, docking device deployment assembly, etc.) can include a catheter 2200 defining a lumen or delivery passage 2202 with an inner surface 2203 and having a distal opening 2206 (optionally, a proximal opening 2204 as well), a docking station frame 350 capable of being radially compressed and expanded, and a pusher or other retention device 2300 having a distal end 2302 and an outer circumferential surface 2304. The docking deployment assemblies/systems can also include a handle connected to a proximal end of the catheter 2200. The handle can include controls (e.g., knobs, buttons, switches, etc.) for adjusting the assembly/system.

The docking deployment assemblies/systems herein can also (or as an alternative to the pusher) include an inner shaft or inner catheter. The inner shaft/catheter can extends inside the catheter 2200, the docking station, and/or the pusher. The inner shaft/catheter can include a nose cone (e.g., a flexible nose cone) to aid in navigation to the target deployment site in the body. The inner shaft/catheter can include a guide wire lumen so the docking deployment assembly/system can more easily be advanced to the target deployment site. The proximal end of the inner shaft/catheter can connect to the handle.

The pusher 2300 can be made of any semi-flexible or flexible material that can pass or wind through the catheter 2200 (e.g., when the catheter is positioned in the body and the catheter includes multiple turns in different directions along the anatomy) and exert a distal force at the distal end 2302 of the pusher 2300. The pusher 2300 can be hollow, a tube, a coil, and/or can be solid or have a solid cross-section. The pusher 2300 can have no lumen or have one or more lumens, etc. The frame 350 of the docking station 10 can be made from any combination of the materials disclosed herein. For example, the docking station 10 and its components can be made from a shape memory alloy frame, foam, fabric coverings, a combination of these, etc. The docking station frame 350 can also take any shape, form, or configuration disclosed herein. The docking station frame 350, when in a compressed state, and the pusher 2300 can be receivable in the lumen/delivery passage 2202 of the catheter 2200 with the docking station frame 350 near the distal opening 2206 of the catheter 2200 and the pusher 2300 proximal of the docking station or relatively closer to the proximal end. The distal end 2302 of the pusher 2300 can be disposed in abutting contact with or near a proximal end 315 of the docking station frame 350, and a distal end 317 of the docking station frame 350 can be disposed within the lumen/delivery passage 2202 of the catheter 2200. At least a portion of the pusher 2300 can be sized to have a diameter that is at least as large as an inner diameter of the docking station frame 350 when in the compressed state.

Turning to FIGS. 66A and 66B, the docking station frame 350 and pusher 2300 can be disposed in the catheter 2200 such that a distal movement of the pusher 2300 (i.e., movement toward the distal opening 2206 of the catheter 2200) will apply a distal force to the proximal end 315 of the docking station frame 350, moving the proximal end 315 of the frame 350 toward the distal opening 2206 of the catheter 2200. As shown in FIG. 66A, as the docking station frame 350 is moved distally through the lumen/delivery passage 2202 (or the catheter 2200 is retracted proximally over the frame 350), the distal end 317 of the frame 350 moves distally past the distal opening 2206 of the catheter 2200 and the distal portion of the frame 350 that is outside the catheter 2200 will begin to expand radially outwardly. The portion of the frame 350 outside the catheter 2200 will expand radially outwardly to a diameter greater than that of the catheter 2200 and the portion of the frame 350 within the catheter 2200 will remain in the compressed state. As shown in FIG. 66B, once the pusher 2300 distally pushes the frame 350 past the distal opening 2206 of the catheter 2200 (or the distal opening 2206 of the catheter 2200 is proximally retracted beyond the frame 350), the frame 350 will be distally past the distal opening 2206 of the catheter 2200 and will be fully radially expanded in the desired position.

Optionally, instead of having pusher 2300 be advanced/advanceable axially through the catheter 2200 to push the docking station/device out of the catheter 2200, the pusher 2300 can be configured as an inner shaft or inner catheter (or be replaced by an inner shaft or inner catheter) that remains stationary (e.g., relative to a handle). The inner shaft/catheter can include, or have attached thereto, a retention device to hold the docking station/device until a desired time (e.g., until full deployment). Instead of a pusher being advanced through the catheter 2200, the catheter 2200 (e.g., a retention sheath, delivery capsule, outer sheath, etc.) can be retracted to release and deploy the docking station/device. This type of deployment assembly/system can be otherwise similar to those discussed elsewhere herein and include features and/or components of other deployment assembly/systems herein (e.g., those shown in FIGS. 66A-72C).

Referring to FIGS. 12 and 67 through 72C, the pusher or retention device 2300 and/or docking station frame 350 of the docking deployment assembly/system 7000 can be sized, shaped, tethered, or otherwise designed such that the positioning of the frame 350 is maintained or otherwise controlled while deploying the frame 350 until the frame 350 is fully released from the catheter 2200. In one embodiment, the frame 350 is retained by or otherwise connected to the catheter 2200, the pusher 2300, inner shaft/catheter, and/or a retention device even after the frame 350 has completely radially expanded. The frame 350 can then be released from the catheter 2200, pusher 2300, inner shaft/catheter, and/or a retention device once the docking station frame 350 has completely radially expanded. The position of the frame 350 can be maintained in various ways.

Figure 68A:
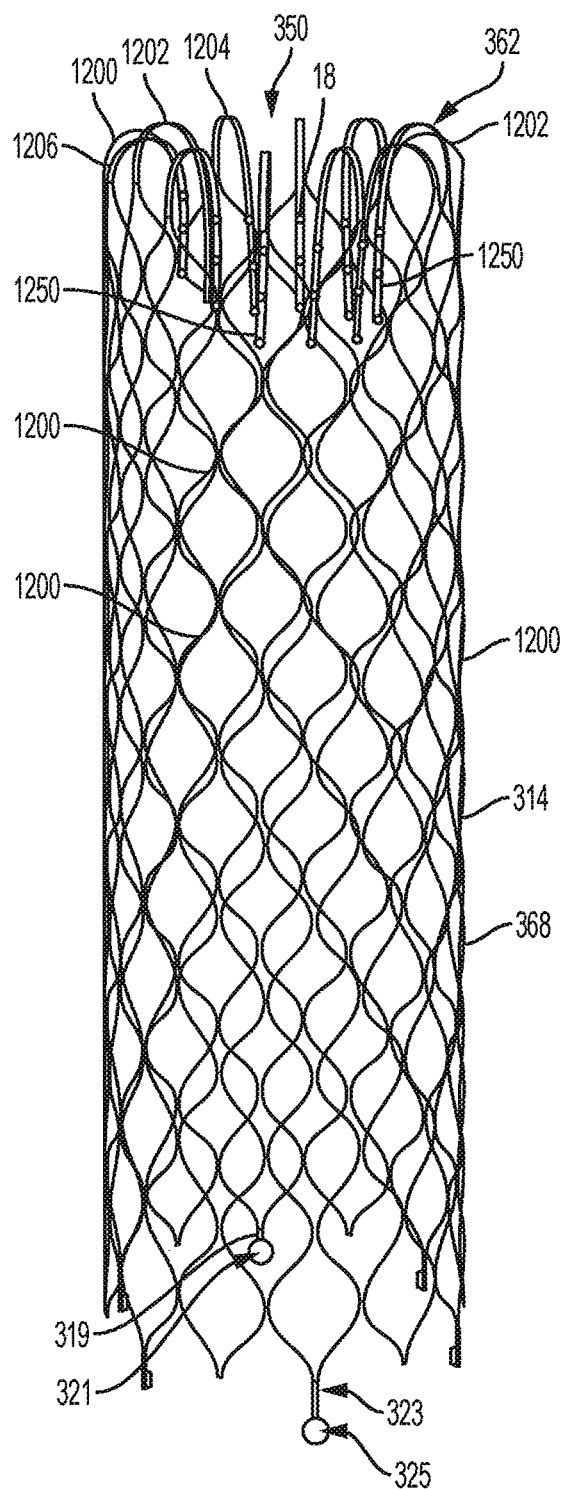
FIG. 68A is a perspective view of an exemplary embodiment of a docking station frame having an elongated leg.
Figure 68B:
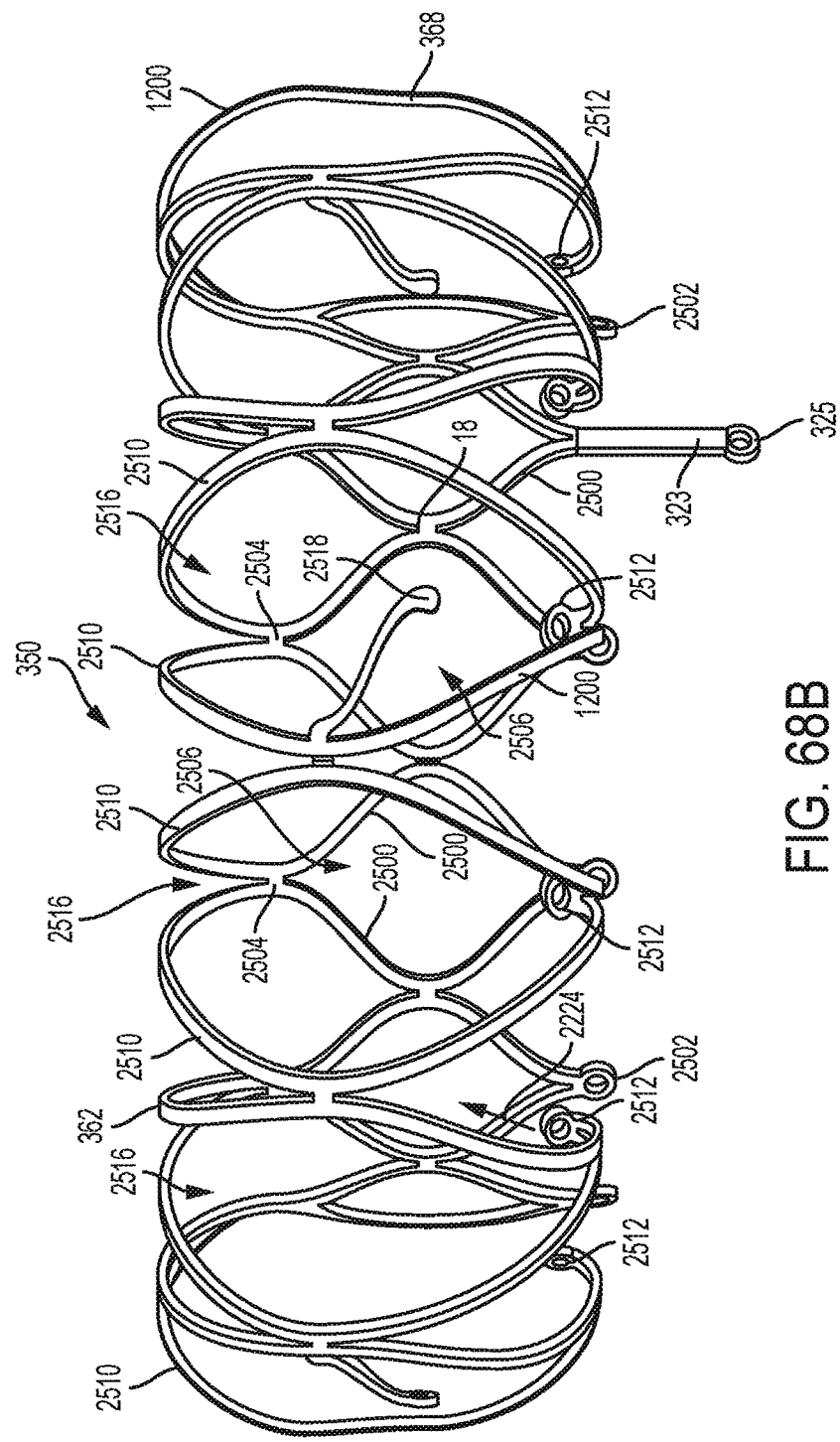
FIG. 68B is a side elevational view of an exemplary embodiment of a docking station frame having an elongated leg.
Figure 68C:
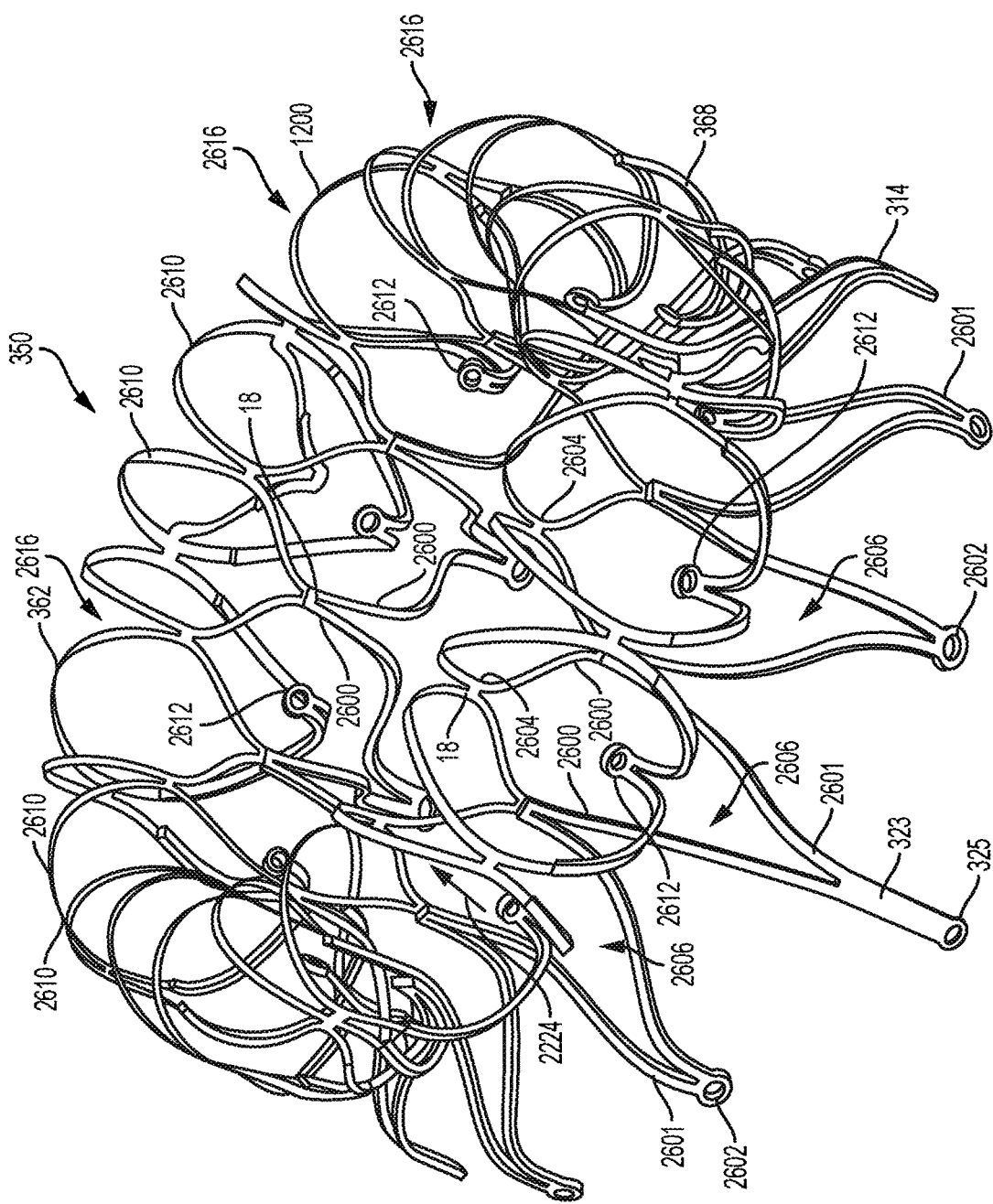
FIG. 68C is a perspective view of an exemplary embodiment of a docking station frame having an elongated leg.

Turning back to FIG. 12 and to FIG. 68A, the docking station frame 350 can include at least one leg or extension 319 or multiple legs/extensions 319. The legs/extensions 319 can be proximal legs/extensions that extend from a proximal end of the frame 350. Each proximal leg/extension 319 can be a singular rod which extends proximally (e.g., toward the pusher 2300 or retention device when the frame 350 is disposed in the catheter 2200) beyond other parts (e.g., beyond all other parts) of the docking station frame 350. In one embodiment, multiple proximal legs/extensions 319 are evenly spaced around the circumference of the frame 350 and extend proximally (e.g., longitudinally, axially, downward) from the proximal most struts 1200. Each proximal leg/extension 319 can include an end shape or foot 321 at an end (e.g., the proximal end) of the leg/extension 319. Each proximal shape/foot 321 can extend circumferentially, radially inwardly, and/or radially outwardly farther than the proximal leg/extension 319. In one embodiment, the proximal shape/foot 321 is substantially spherical or otherwise bulbous. However, it will be appreciated that the end shapes or feet 321 can be any shape or size receivable within a corresponding tab or slot in the pusher 2300 or other retention device, as described below. For example, the end shapes/feet 321 can be rectangular, elongated, pyramidal, triangular, slotted, grooved, hollow, ring-like, or any other design known in the art.

While the proximal legs/extensions 319 have been described as being a part of the frame 350 of FIG. 12, it will be appreciated that the proximal legs/extensions 319 can be incorporated into any of the docking station frames 350 disclosed herein. For example, proximal legs/extensions can be included at the proximal end of the docking station frames 350 of FIG. 25 or 26, or any other frame 350 described herein.

Turning to FIG. 67, an exemplary distal end 2302 of a pusher 2300 or other retention device (e.g., if no pusher is used) is depicted. The illustrated pusher 2300 (or retention device) includes a plurality of slots or tabs 2306 in the outer circumferential surface 2304 of the pusher 2300 (or retention device) and disposed around the distal end 2302 of the pusher 2300 (or retention device). Each of the slots 2306 can be sized, shaped, or otherwise designed to retain a proximal leg/extension 319 and/or end shape/foot 321 of the frame 350 when the frame 350 and pusher 2300 (or retention device) are disposed within the catheter 2200. In one embodiment, the number, size, and shape of the slots 2306 corresponds to the number, size, and shape of the proximal legs/extensions 319 and/or end shapes/feet 321 of the docking station frame 350.

Before deployment of the docking station and frame 350, the docking station and frame 350 can be inserted into the catheter 2200 with the ends/feet 321 and proximal legs/extensions 319 of the docking station or frame 350 being disposed within the slots 2306 of the pusher 2300 or retention device. In one embodiment, the outer circumferential surface 2304 of the pusher 2300 or other retention device, the slots 2306, the proximal legs/extensions 319, and the ends/feet 321 are sized such that the proximal ends/feet 321 can be retained within the slots 2306 and between the pusher 2300 or other retention device and the inner surface 2203 of the catheter 2200 when disposed within the catheter 2200. In some embodiments, pusher 2300 moves or can move distally out of the catheter 2200 to push the docking station and its frame 350 distally out of the distal opening 2206. In some embodiments, the catheter 2200 (e.g., an outer sheath, sleeve, delivery capsule, etc.) is retracted to uncover and release the docking station and its frame 350. For a self-expandable frame, as the docking station or frame 350 is uncovered (e.g., by retracting the catheter 2200 and/or pushing it out of the catheter 2200), the uncovered portions begin to radially expand.

While the slots 2306 are still within the catheter 2200, the position of the frame 350 can be maintained or otherwise controlled, as the proximal feet 321 will still be retained within the catheter 2200. As such, the frame 350 can substantially expand radially outward while a portion of the frame 350 can be maintained or otherwise controlled by the catheter 2200, pusher 2300, inner shaft/catheter, and/or retention device. Once a substantial portion of the slots 2306 have moved distally past the distal opening 2206 of the catheter 2200, the proximal feet 321 can be released from the slots 2306 and the positioning of the frame 350 can be set. Self-expansion of the frame 350 can cause the extensions/legs and ends/feet to move radially out of the slots when uncovered.

Optionally, the pusher or other retention device can comprise or be configured as a lock and release connector similar to that shown and described in PCT Patent App. No. PCT/US2018/040337, filed Jun. 29, 2018, and U.S. Provisional Patent App. No. 62/527,577, filed Jun. 30, 2017, each of which is incorporated by reference in their entirety herein. The lock and release connector can comprise a body and a door (or, optionally, multiple doors) engaged with the body, wherein the at least one door (or each of the multiple doors) is moveable from a first position to a second position. The door can be integral with the body or connected to the body. The door can be constructed in a variety of ways and can comprise a variety of different materials. The lock and release connector can further comprise one fastener or multiple fasteners connecting at least one portion or end of the door to the body.

The docking station/device and frame 350 can have one or more extensions/legs and can be disposed in the catheter 2200. If an inner shaft/catheter is used, the lock and release connector can be connected to the inner shaft/catheter. Slots 2306 can be formed between the body and the door. An extension/leg of the docking station and frame can be interposed between the body and the door (e.g., in a slot). Optionally, the lock and release connector can further comprise a second door, and a second extension/leg of the docking station and frame can be interposed between the body and the second door. The body can be hingedly connected to the door(s).

The catheter 2200 with the docking station therein can be positioned at a target delivery site. The catheter 2200 can be retracted or the frame pushed out of the catheter 2200 until a distal end of the docking station or frame is positioned outside the catheter 2200. The catheter 2200 can further be displaced (e.g., withdrawn, etc.) with respect to or relative to the docking station and the lock and release connector until the door(s) open and release the extension(s) from between the body and the door. The door(s) can be biased (e.g., include a spring, etc.) to cause the door(s) to open when the catheter 2200 no longer covers the door to help release the extension.

Referring to FIG. 68A through FIG. 72C, three exemplary docking deployment assemblies/systems 7000 are depicted which permit a user to maintain or otherwise control the position of frame 350 once frame 350 has been fully radially expanded outside the catheter 2200.

Turning to FIG. 68A through FIG. 70, an exemplary docking station deployment assembly 7000 is shown. The frame 350 includes at least one elongated leg/extension 323 disposed at the proximal end of the frame 350 and attached or otherwise secured to a proximal strut 1200. Each elongated leg/extension 323 can include a foot/end shape 325 at the proximal end of the elongated leg/extension 323. Each end/foot 325 can extend circumferentially, radially inwardly, and/or radially outwardly farther than the elongated leg/extension 323. In one embodiment, the end/foot 325 is substantially spherical or otherwise bulbous. However, the end/foot 325 can be any shape or size receivable within a corresponding tab or slot in the pusher 2300 or other retention device. For example, the end/foot 325 can be rectangular, elongated, slotted, grooved, hollow, ring-shaped, or any other design known in the art. The frame 350 can also include proximal legs/extensions 319 and end shapes/feet 321 as previously described. In one embodiment, the elongated leg/extension 323 is included on the frame 350 in place of one of the proximal legs/extensions 319 and the elongated leg/extension 323 extends longitudinally farther away from the remainder of the frame 350 than the proximal legs/extensions 319. While the illustrated embodiments depict the frame 350 as having only one elongated leg/extension 323, more than one elongated leg/extension 323 can be included.

The at least one elongated leg/extension 323 of the frame 350 can take a variety of forms. As shown in FIGS. 69A and 69B, the at least one elongated leg/extension 323 of the frame 350 can be flexible, like a flexible rod (FIG. 69A), or rigid, like a rigid rod (FIG. 69B). The inclusion of a flexible (e.g., spring-like, coiled, thinned, slotted, etc.) elongated leg/extension 323 can permit the frame 350 to extend smoothly out of the catheter 2200 as the frame 350 radially expands as it is distally moved out of the catheter 2200. For example, after the proximal legs/extensions 319 have been released from the slots 2306 but while the end/foot 325 is still retained in the elongated recess or slot 2308 within the catheter 2200, the flexible (e.g., spring-like, etc.) elongated leg/extension 323 can flex, expand, or otherwise adjust to correspond to (or such that a portion thereof corresponds to) the radial expansion of the frame 350. The inclusion of a rigid (e.g., rod-like, etc.) elongated leg/extension 323 can permit the frame 350 to be positioned or otherwise moved once the frame radially expands as it is distally moved out of the catheter. For example, after the proximal legs/extensions 319 have been released from the slots 2306 but while the end/foot 325 is still retained in the slot 2308, the rigid elongated leg/extension 323 can securely retain the frame 350 to the pusher 2300, retention device, inner shaft/catheter, and/or catheter 2200 such that the frame 350 can more easily be positioned or otherwise moved after expansion. However, it will be appreciated that the elongated leg/extension 323 can take other forms. For example, the elongated leg/extension 323 can be curved, twisted, bent, or otherwise shaped according to the desired deployment and/or control of the frame 350 out of the catheter 2200.

Figure 70:
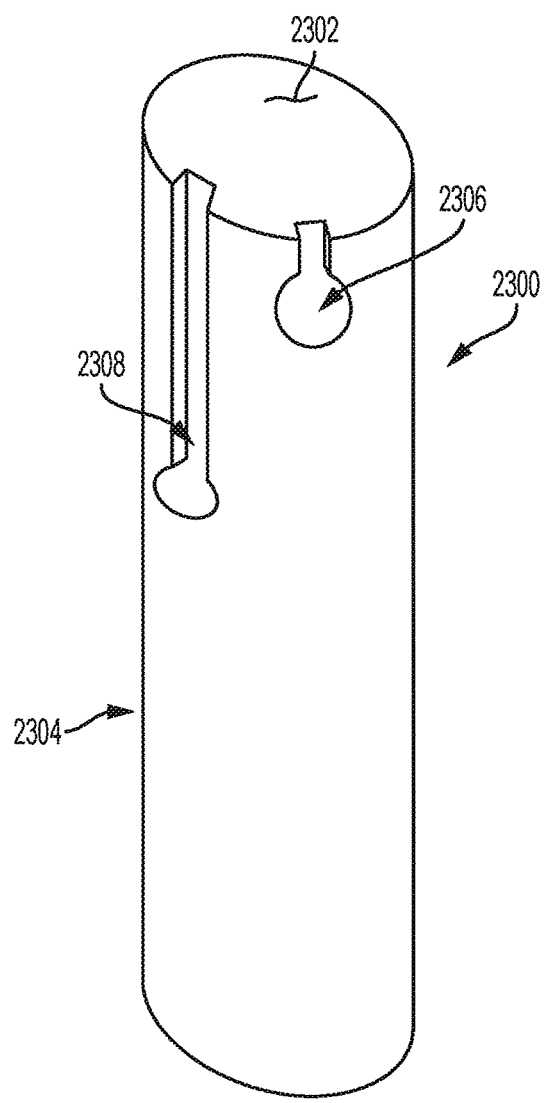
FIG. 70 is a perspective view of an exemplary distal end of an exemplary pusher or retention device.

As shown in FIG. 70, the distal end 2302 of the pusher 2300 or other retention device can include at least one elongated slot 2308 in the outer circumferential surface 2304 of the pusher 2300 or other retention device. The at least one elongated slot 2308 can be sized and shaped to correspond to the size and shape of the elongated leg/extension 323 (or a portion thereof) and/or end/foot 325 of the frame 350. The pusher 2300 or other retention device can optionally include one or more additional slots 2306 (e.g., in the outer circumferential surface 2304 of the pusher 2300 or other retention device, between a body and door(s)/latch(es), etc.). The optional one or more elongated slots 2308 and one or more shorter slots 2306 can extend from the distal end 2302 of the pusher 2300 or other retention device toward the proximal end of the pusher 2300 or other retention device (e.g., axially or parallel to a longitudinal axis). In one embodiment, the one or more slots 2308 extend proximally farther from the distal end 2302 of the pusher 2300 or other retention device than the one or more optional slots 2306.

Before deployment of the frame 350, the frame 350 (and, optionally, a pusher) can be inserted into the catheter 2200 with the proximal ends/feet 321 and proximal legs/extensions 319 of the frame 350 being directed proximally. The ends/feet 321 and/or proximal legs/extensions 319 (e.g., a portion thereof) of the frame 350 can be disposed within the slots 2306 of the pusher or retention device 2300. In one embodiment, the outer circumferential surface 2304 of the pusher or retention device 2300, the slots 2306, the slots 2308, the proximal legs/extensions 319, the proximal ends/feet 321, the elongated legs/extensions 323, and the ends/feet 325 are sized such that the ends/feet 321 can be retained within the slots 2306 (e.g., between the pusher or retention device 2300 and the inner surface 2203 of the catheter 2200 or between the body of the retention device and a door/latch) and the one or more ends/feet 325 of the one or more elongated legs/extensions 323 can be retained within the slots 2308 (e.g., between the pusher or retention device 2300 and the inner surface 2203 of the catheter 2200 or between the body of the retention device and a door/latch) when the pusher or retention device 2300 and one or more ends/feet are disposed within the catheter 2200.

As the docking station/device moves out of the catheter 2200, the frame 350 exits the distal opening 2206 and the frame 350 begins to expand. While at least one extension/leg (e.g., a portion thereof) and/or end/foot is still retained within the catheter 2200 (e.g., in a retention device), the position of the frame 350 can be maintained or otherwise controlled. As such, the frame 350 (e.g., progressively the distal end, then other distal portions of the frame, then the middle of the frame, then proximal portions, and substantially all of the frame) can be substantially expand radially outward while a portion of the frame 350 (e.g., one or more extensions/legs, a portion(s) thereof, and/or one or more feet/end(s) thereof) is maintained or otherwise controlled by the catheter 2200 and/or pusher or retention device 2300.

In one embodiment, where the retention device (e.g., pusher) includes at least one elongated slot 2308 and at least one shorter slot 2106, after all or most of the shorter slot(s) 2306 have moved distally past the distal opening 2206 of the catheter 2200 (e.g., is uncovered by retraction the catheter or advancing a shaft or pusher), one or more ends/feet 321 are released from the slot(s) 2306 and frame 350 is fully radially expanded (e.g., expanded until in contact with the circulatory system). Even after shorter slot(s) 2306 have moved distally past the distal opening 2206 of the catheter 2200, the at least one end/foot 325 of at least one elongated leg/extension can still be retained within the elongated slot 2308 (e.g., all or a portion thereof). As such, the frame 350 can completely radially expand and the position of the frame 350 can be maintained or otherwise controlled by the retention of the elongated leg/extension 323 and/or end/foot 325 within the catheter 2200. Once all or most of the at least one elongated slot 2308 is uncovered or moves distally past the distal opening 2206 of the catheter 2200 (e.g., is uncovered by retraction of the catheter or advancing a shaft or pusher), the at least one end/foot 325 can be released from the at least one elongated slot 2308 and the positioning of the frame 350 can be set. If a door/latch is used over any of the slot(s), the door opens to allow the end/foot thereunder to be released.

In one embodiment, where the retention device (e.g., pusher) includes only one elongated slot 2308, as the frame 350 moves distally past the distal opening 2206 of the catheter 2200 (e.g., is uncovered by retraction the catheter or advancing a shaft or pusher), the frame 350 is progressively expanded from distal to proximal until fully radially expanded (e.g., expanded until in contact with the circulatory system). Even after all but the end/foot 325 of frame 350 has moved distally past the distal opening 2206 of the catheter 2200, the end/foot 325 of the elongated leg/extension can still be retained within the elongated slot 2308 (e.g., all or a portion thereof). As such, the frame 350 can completely radially expand and the position of the frame 350 can be maintained or otherwise controlled by the retention of the elongated leg/extension 323 and/or end/foot 325 within the catheter 2200. Once all or most of the elongated slot 2308 moves distally past the distal opening 2206 of the catheter 2200 (e.g., is uncovered by retraction of the catheter or advancing a shaft or pusher), the at least one end/foot 325 can be released from the at least one elongated slot 2308 and the positioning of the frame 350 can be set. If a door/latch is used over the slot 2308, the door opens to allow the end/foot 325 thereunder to be released.

Having only one extension/leg or only one elongated extension/leg 323 on a self-expandable frame acts to help prevent the frame from jumping out of the distal end of the catheter and throwing off the placement. As the proximal end 315 of the frame 350 approaches the distal opening 2206 of the catheter, forces can build between the proximal end 315 and distal opening 2206 that can cause the frame to jump forward out of the catheter. Having multiple legs/extensions at the proximal-most end of the frame 350 can make jumping more likely, as the legs/extensions can act against each other and create opposing forces against the distal end of the catheter. By having the proximal end 315 of the frame 350 have only one elongated extension/leg 323 (e.g., with or without shorter extensions/legs 319) or only one extension/leg at all (e.g., 319 or 323), the frame 350 is allowed to fully expand while retained by only one extension/leg, then this one remaining extension/leg can release the frame 350 without causing jumping.

Figure 71A:
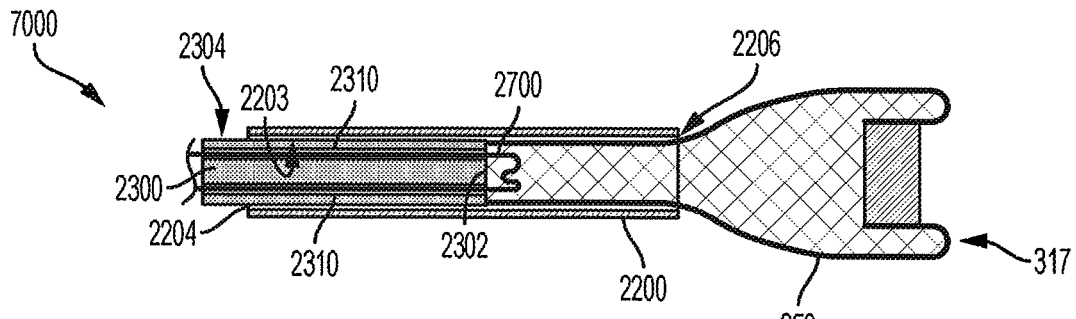
FIGS. 71A-71C illustrate an exemplary deployment of an exemplary docking station.
Figure 71B:
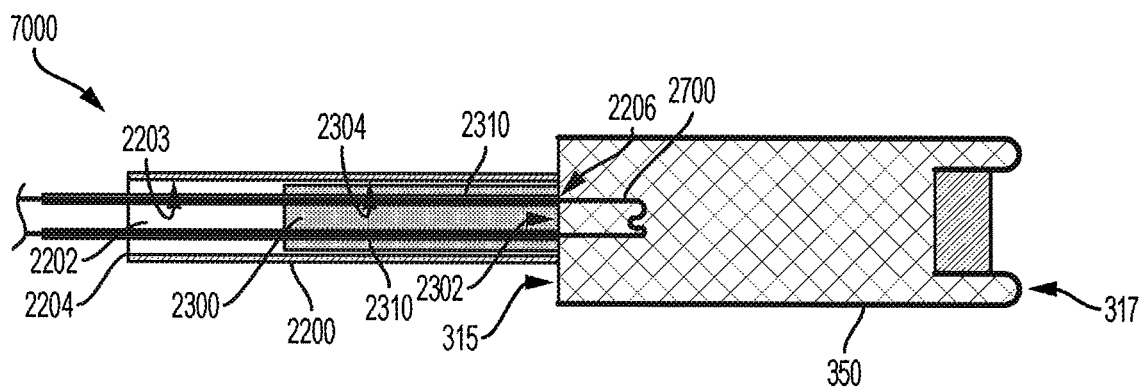
Figure 71C:
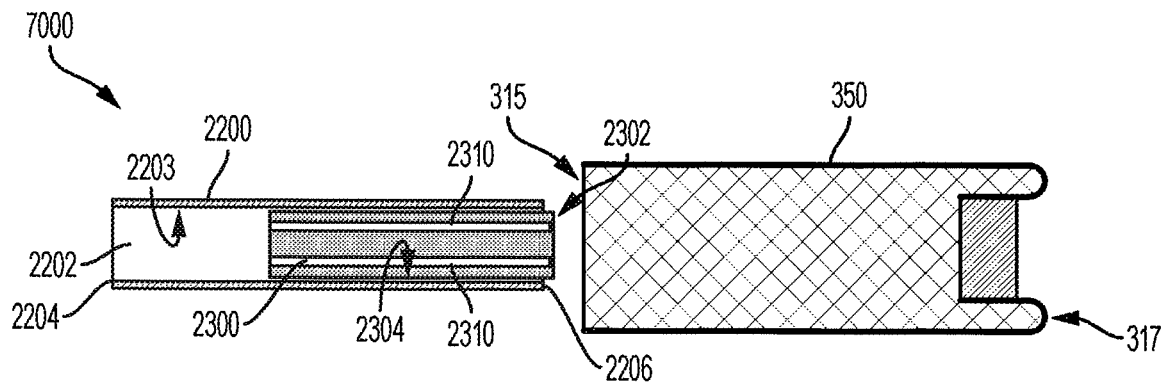

Turning to FIGS. 71A through 71C, an exemplary docking device deployment assembly 7000 is shown. The docking device deployment assembly 7000 can be similar to those described above and alternatively or additionally include a suture or retaining line 2700 which can be used to maintain the position of the frame 350 as the frame 350 is deployed from the catheter 2200 and fully radially expanded. The inner shaft, retention device, or pusher 2300 is shown as including two suture passages 2310 which extend longitudinally through the inner shaft, retention device, or pusher 2300 and which each can receive a portion or an end of the suture 2700; however, only a single passage can be used. In one embodiment, the suture 2700 is threaded through one of the suture passages 2310, around a portion of the frame 350, and back through the other suture passage 2700 such that both ends of the suture 2700 extend through the proximal portion of the catheter 2200. The suture 2700 can be secured around any portion of the frame 350. In one embodiment, the suture 2700 is looped around one or more struts 1200 or apexes of struts of the frame 350. In another embodiment, the frame (e.g., apexes of the frame) includes one or more loops, apertures, holes, etc. that the suture 2700 can be threaded through.

In one embodiment, the pusher 2300 is used to apply a distal force on the frame 350 to move the frame 350 distally through the distal opening 2206 of the catheter 2200 while the suture 2700 applies a proximal force on the frame 350 to keep the frame 350 in contact with and/or proximate the pusher 2300 (e.g., by holding the suture or pulling proximally on the suture). As shown in FIG. 71A, once the pusher 2300 pushes a portion of the frame 350 through the distal opening 2206 of the catheter 2200, the portion of the frame 350 extending beyond the distal opening 2206 will begin to expand radially outward, and the proximal force applied by the suture 2700 will keep the frame 350 (e.g., a proximal end of frame 350) in contact with and/or proximate the pusher 2300. In FIG. 71B, once the pusher 2300 has pushed the frame 350 completely through the distal opening 2206, the frame 350 can be fully radially expanded and the proximal force applied by the suture 2700 on the frame 350 will maintain the frame 350 proximate the distal end of the pusher 2300 and/or catheter 2200. In FIG. 71C, once the frame has been fully radially expanded in the desired position, the suture 2700 can be removed from the suture passage(s) 2310 and frame 350 such that the expanded frame 350 is deployed in the desired position.

In one embodiment, the suture 2700 applies a proximal force on the frame 350 to keep the frame 350 in contact with and/or proximate the inner shaft, retention device, or pusher 2300 (e.g., by holding the suture or pulling proximally on the suture) as the catheter 2200 (e.g., outer sheath, delivery capsule, sleeve, etc.) is withdrawn. As shown in FIG. 71A, once the catheter is retracted such that a portion of the frame 350 is exposed, the portion of the frame 350 extending beyond the distal opening 2206 expand radially outward, and the proximal force applied by the suture 2700 will keep the frame 350 (e.g., a proximal end of frame 350) in contact with and/or proximate the inner shaft, retention device, or pusher 2300. As shown in FIG. 71B, once the catheter has been completely retracted from over the frame 350, the frame 350 is fully radially expanded and the proximal force applied by the suture 2700 on the frame 350 can maintain the frame 350 proximate the distal end of the inner shaft, retention device, or pusher 2300 and/or catheter 2200. As shown in FIG. 71C, once the frame has been fully radially expanded in the desired position, the suture 2700 can be removed from the suture passage(s) 2310 and frame 350 such that the expanded frame 350 is deployed in the desired position.

While this exemplary docking station deployment assembly 7000 has been described and depicted as including only a suture 2700 (e.g., no extensions/legs are necessary) to maintain the position of the frame 350 after the frame 350 has been fully radially expanded, other features can also be included to maintain the position of the frame 350 after the frame 350 has been fully radially expanded. For example, the frame 350 can include proximal legs/extensions 319 and proximal ends/feet 321 and/or one or more elongated legs/extensions 323 and one or more ends/feet 325 and the pusher/inner shaft/retention device can include shorter slots 2306 and/or one or more elongated slots 2308 to maintain the position of the frame 350 after the frame 350 has been fully radially expanded, as described above.

Figure 72A:
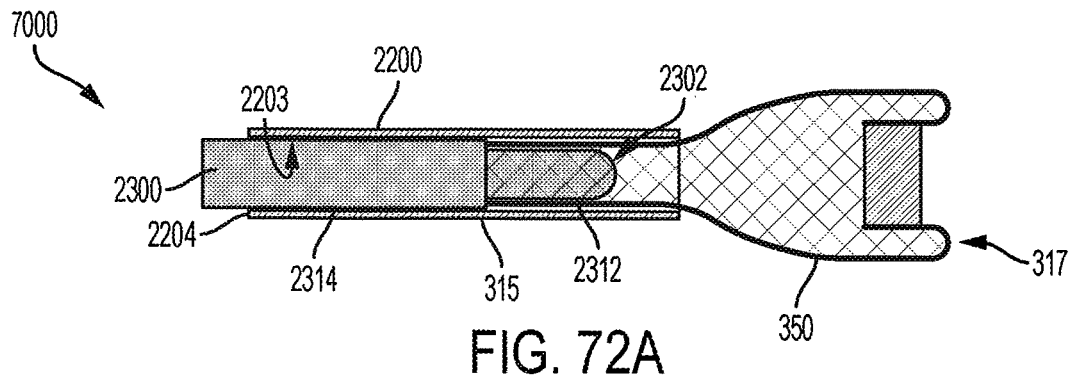
FIGS. 72A-72C illustrate an exemplary deployment of an exemplary docking station.
Figure 72B:
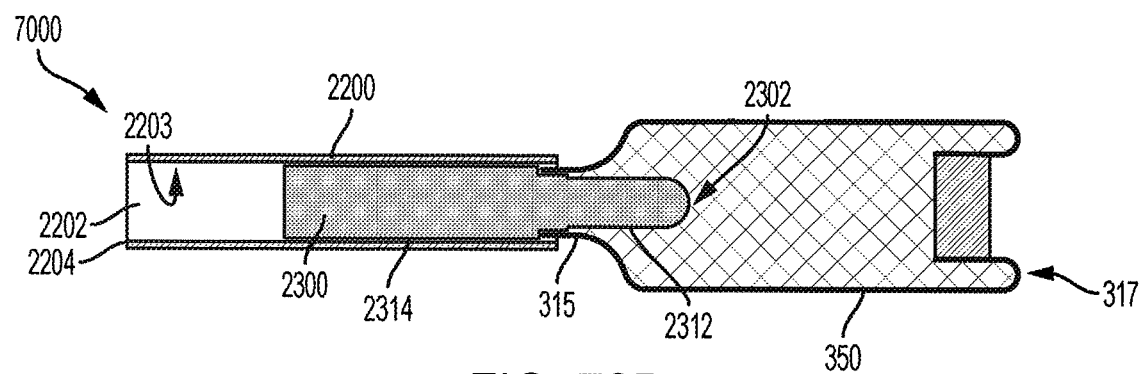
Figure 72C:
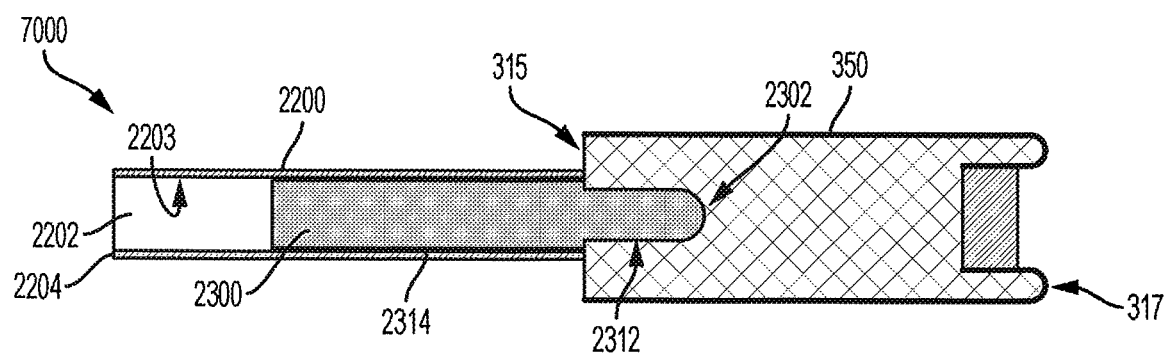
Figure 73A:
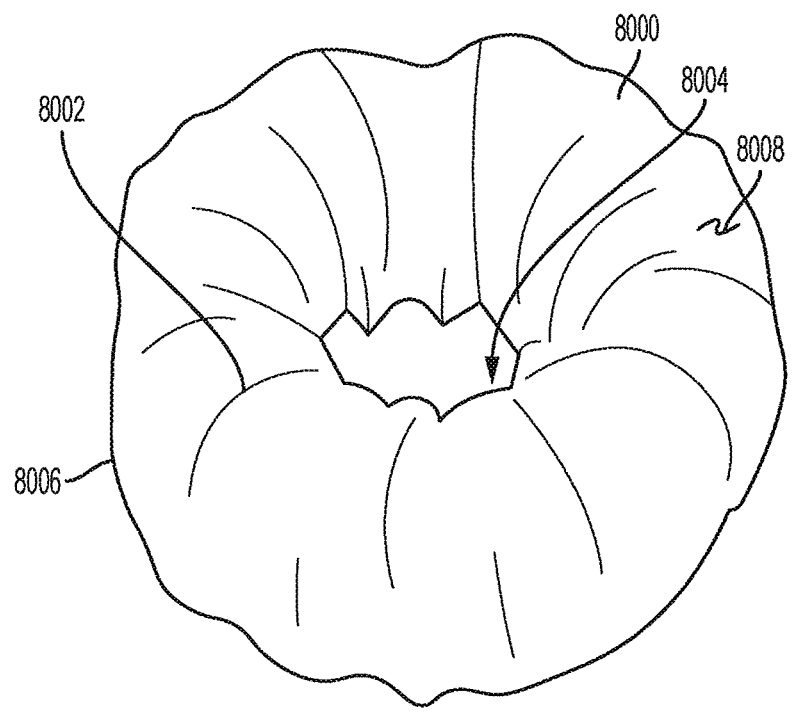
FIG. 73A is a perspective view of an exemplary cover for a docking station frame.
Figure 73B:
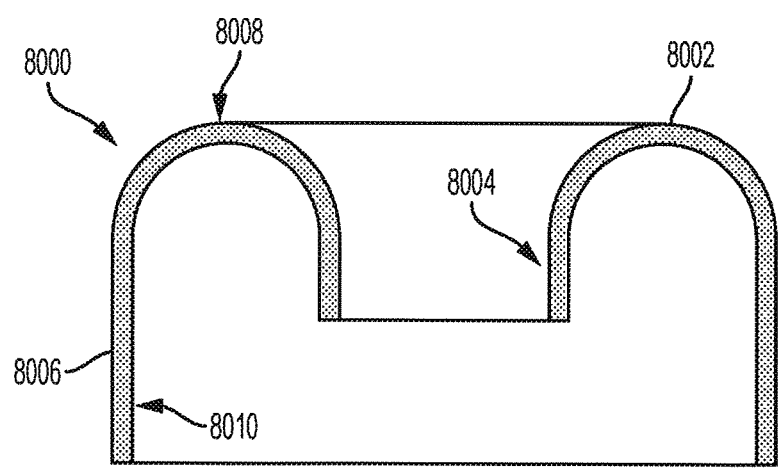
FIG. 73B is a sectional view of an exemplary cover for a docking station frame.

Turning to FIGS. 72A through 72C, an exemplary docking station deployment assembly 7000 is shown. In the illustrated embodiment, the pusher/inner shaft/retention system 2300 includes a distal portion having a first outer circumferential surface 2312 and a proximal portion having a second outer circumferential surface 2314. The distal portion and the proximal portion can be integrally formed or the distal portion 327 can be a separate component, such as a pin, that is attached to the proximal portion or extends through a lumen of the proximal portion. In one embodiment, a pin is used as surface 2312 without any larger diameter proximal portion. The pin and/or distal portion can include a lumen through which another portion of the system and/or a guidewire can pass. The distal end 2302 of the distal portion can optionally be tapered or otherwise rounded. The first outer circumferential surface 2312 of the pusher/retention system 2300 is narrower than or have a smaller diameter than the inside diameter of the frame 350 (or have the same or a similar diameter) when the frame 350 is in the compressed state within the catheter 2200 and the second outer circumferential surface 2314 of the pusher/retention system 2300 can be wider or have a larger diameter than the inside diameter of the frame 350 when the frame 350 is in the compressed state and be narrower or have a smaller diameter than the inner surface 2203 of the catheter 2200. For example, the frame 350 can be crimped around the outer circumferential surface 2312. In one embodiment, the first outer circumferential surface 2312 has a large enough diameter to retain a proximal portion of the frame 350 in abutting contact with the inner surface 2203 of the catheter 2200.

In use, when the pusher/inner shaft/retention system 2300 and frame 350 are disposed within the catheter 2200, the distal portion second outer circumferential surface 2314 of the pusher 2300 can abut the proximal end 315 of the frame 350 and the distal portion of the first circumferential surface 2312 (e.g., a narrowed portion, a pin, etc.) will be disposed within the inner diameter of the compressed frame 350. Within the catheter 2200, the first circumferential surface 2312 and the inside surface 2203 can trap or constrain a portion of the frame 350 that is within the catheter 2200 therebetween. A user can use the pusher/retention system 2300 to apply a distal force on the frame 350 to move the frame 350 distally through the distal opening 2206 of the catheter 2200 and/or can retract the catheter 2200 from over the frame 350.

In one embodiment, as shown in FIG. 72A, the pusher/inner shaft/retention system 2300 can be used to push a portion of the frame 350 through the distal opening 2206 of the catheter 2200, and the portion of the frame 350 extending beyond the distal opening 2206 begins to expand radially outward. In one embodiment, also represented by FIG. 72A, the catheter 2200 can be retracted proximally from over the frame 350, and the portion of the frame 350 extending beyond the distal opening 2206 expands radially outward. As shown in FIG. 72B, as long as any portion of the frame 350 remains in the catheter 2200, the first circumferential surface 2312 of the pusher/inner shaft/retention system 2300 and the inside surface 2203 can trap, constrain, or pinch a portion (e.g., at least a proximal portion) of the frame that is in the catheter. This can help prevent or inhibit the expansion force of the frame 350 from causing the frame 350 to jump and/or exit the catheter 2200 before the transition or step between the outer circumferential surface 2314 and the inner circumferential surface 2314 reaches the end of the catheter 2200. As such, the frame 350 will have been maintained in position throughout the deployment of the frame 350 from the catheter 2200. As shown in FIG. 72C, when the frame 350 is entirely outside the distal end of the catheter 2200, the frame 350 can fully radially expand and be deployed in the desired target position. The pusher/inner shaft/retention system 2300 can be retracted from the frame 350 and pulled back into or be re-covered by the catheter 2200.

In one embodiment, docking station deployment assembly 7000 includes only a pusher/inner shaft/retention system 2300 with first and second circumferential surfaces to maintain the position of the frame 350 after the frame 350 has been fully radially expanded. However, in some embodiments, other features are included to maintain the position of the frame 350 after the frame 350 has been fully radially expanded. For example, the frame 350 can include proximal legs/extensions 319 and proximal ends/feet 321 and/or one or more elongated legs/extensions 323 and one or more ends/feet 325 and the pusher/retention system 2300 can include shorter slots 2306 and or one or more elongated slots 2308, and/or the docking station deployment assembly 7000 can include a suture 2700 to maintain the position of the frame 350 after the frame 350 has been fully radially expanded, as described above. Especially where other retention features (e.g., extensions and slots, doors/latches, sutures, etc.) are used, the distal portion or pin (e.g., surface 2312) need trap the frame 350 and can have a smaller diameter than the inner surface of the frame.

The distal portion or pin with surface 2312 acts to help prevent a self-expandable frame from jumping out of the distal end of the catheter and throwing off the placement. As the proximal end 315 of the frame 350 approaches the distal opening 2206 of the catheter, forces can build between the proximal end 315 and distal opening 2206 that can cause the frame to jump forward out of the catheter. These forces make jumping more likely, and this is especially true when the proximal end 315 of the frame is angled radially inwardly relative to the inner surface of the catheter 2200. For example, as more of the frame 350 expands outside the catheter, the proximal end 315 remaining in the catheter tends to angle radially inwardly and can build up pressure against the distal opening 2206 and this can flip or spring the frame 350 out of the catheter as the proximal end tries to expand. By having the distal portion or pin with surface 2312 inside the proximal end 315 of the frame 350, the proximal end 315 is prevented from angling too much out of parallel (e.g., helps the proximal end 315 to remain parallel, nearly parallel, or more closely parallel) relative to the inner surface of the catheter 2200 as the frame expands, and this can help prevent or inhibit the frame 350 from jumping out of the distal end of the catheter 2200.

Referring now to FIGS. 73A through 75B, the frame 350 can include a sealing material or cover/covering 8000 disposed on the end 362 of the frame 350 to effectuate a seal between the valve 29 and interior surface 416 of the circulatory system when the valve 29 is disposed in the valve seat 18 of the frame 350 and the frame 350 is radially expanded and placed in the body. The cover 8000 can be a cylinder or substantially a cylinder rolled partially backward on itself and can have an end 8002 having an inside diameter 8004, an outside diameter 8006, a distal surface 8008, and a proximal surface 8010. The cover 8000 can comprise a single sheet of PET (Polyethylene terephthalate), PTFE, ePTFE, another polymer, or other biocompatible material which can provide an effective seal. In one embodiment, the cover 8000 can comprise a woven ribbon or fabric, such as a woven ribbon or fabric that comprises PET, PTFE, ePTFE, another polymer, or other biocompatible material.

Figures 74A, 74B:
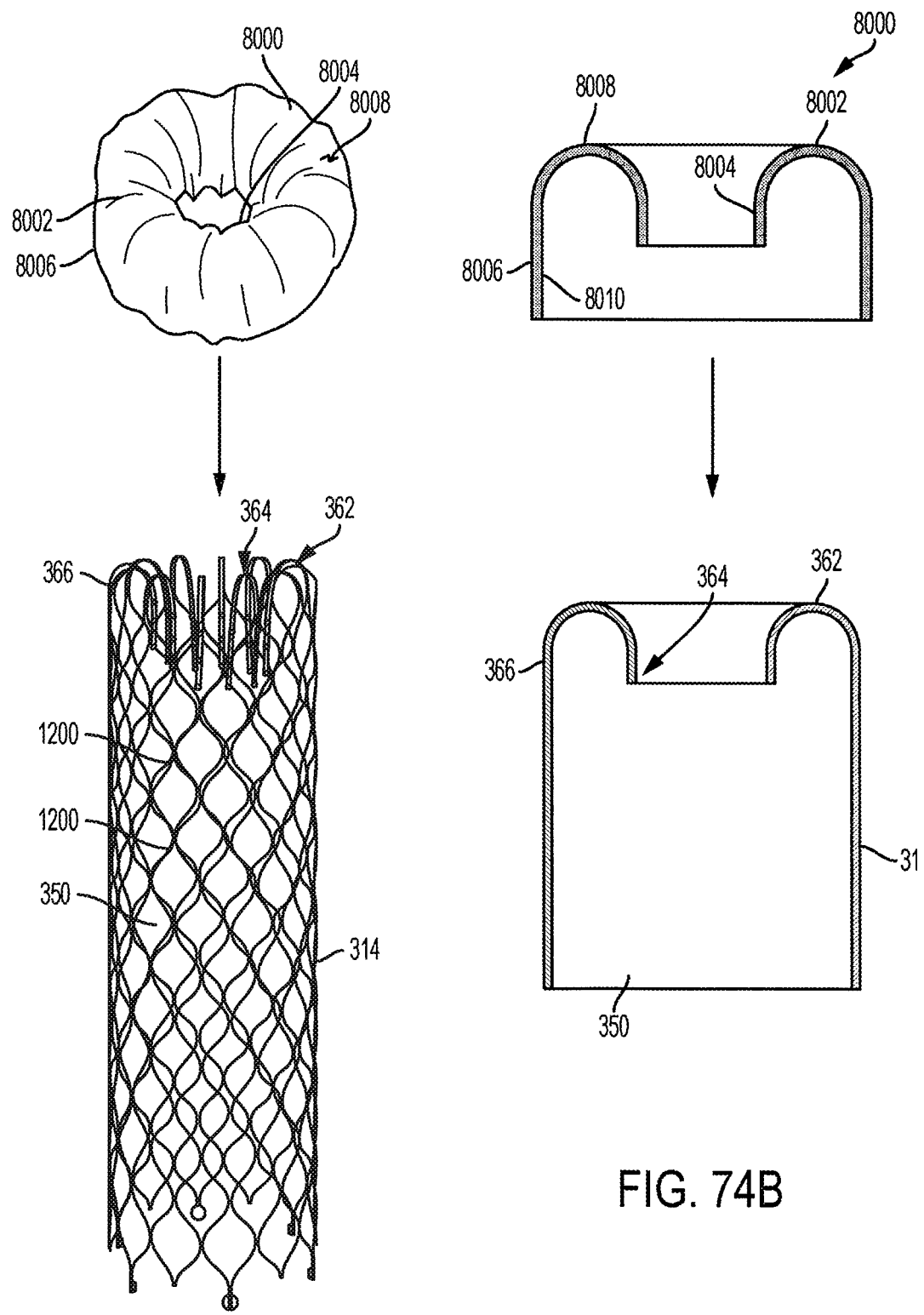
FIGS. 74A and 74B illustrate an exemplary installation of an exemplary cover on a docking station.

As shown in FIGS. 74A through 75B, the cover 8000 can be disposed over the end 362 of the frame 350. The cover 8000 can be secured to the frame 350 in a wide variety of different ways. For example, the cover 8000 can be attached to the frame with sutures, adhered, tied, fused, etc. Turning to FIGS. 74A and 74B, the cover 8000 can be placed onto the end 362 of the frame 350. In one embodiment, the end 8002 of the cover 8000 abuts the end 362 of the frame 350. The inside diameter 8004 of the cover 8000 is radially inward of and adjacent to the inside diameter 364 of the frame 350. The outside diameter 8006 the cover 8000 is radially outward of and adjacent to and adjacent to the outside diameter 366 of the frame 350. The proximal surface 8010 of the cover 8000 can extend around a portion of the retaining portions 314 of the frame 350. In one embodiment, the outside diameter 8006 of the cover provides a secure fit and/or seal between the frame 350 and the interior surface 416 of the circulatory system.

Figure 75A:
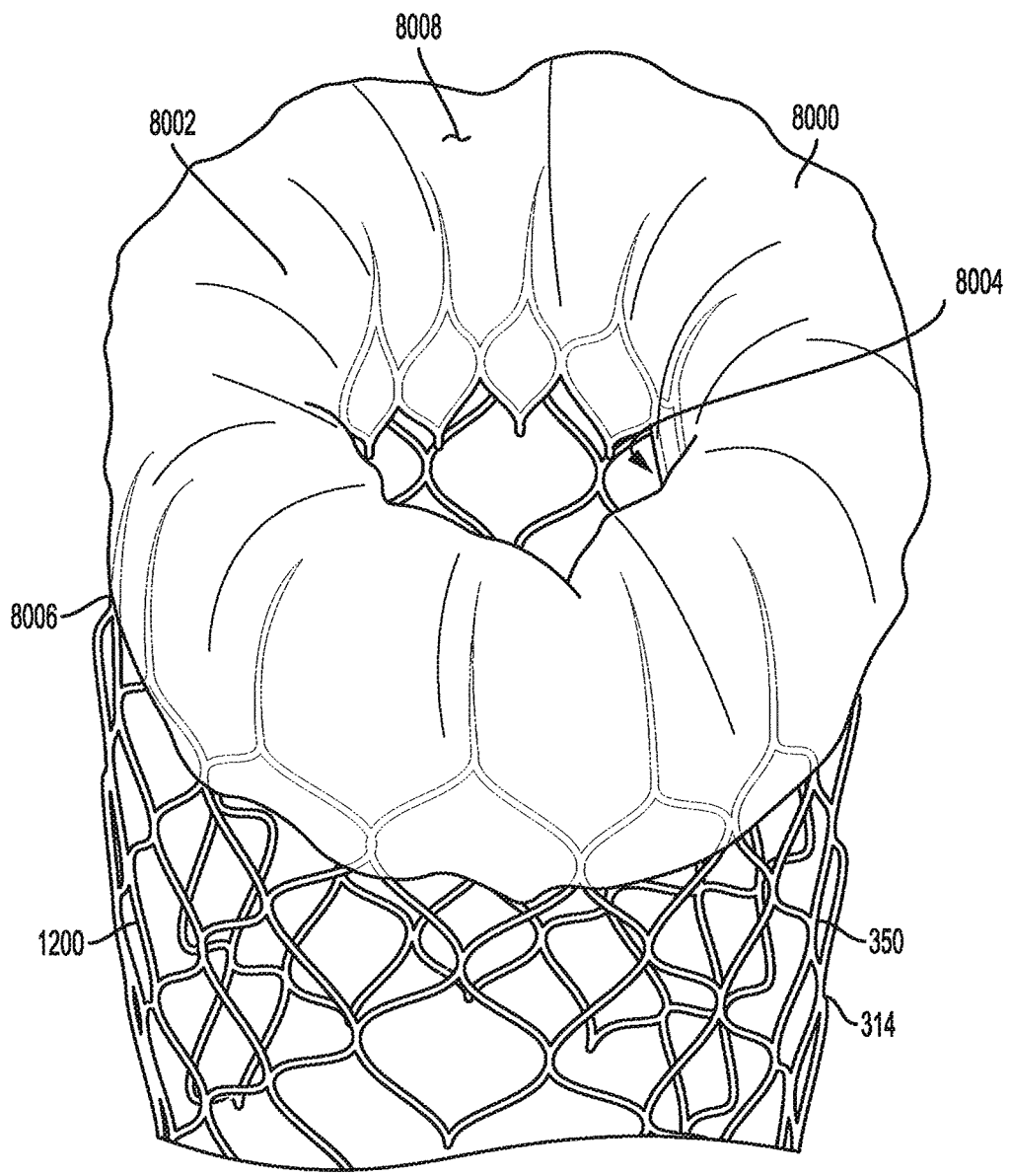
FIG. 75A is a perspective view of an exemplary cover disposed on a frame.
Figure 75B:
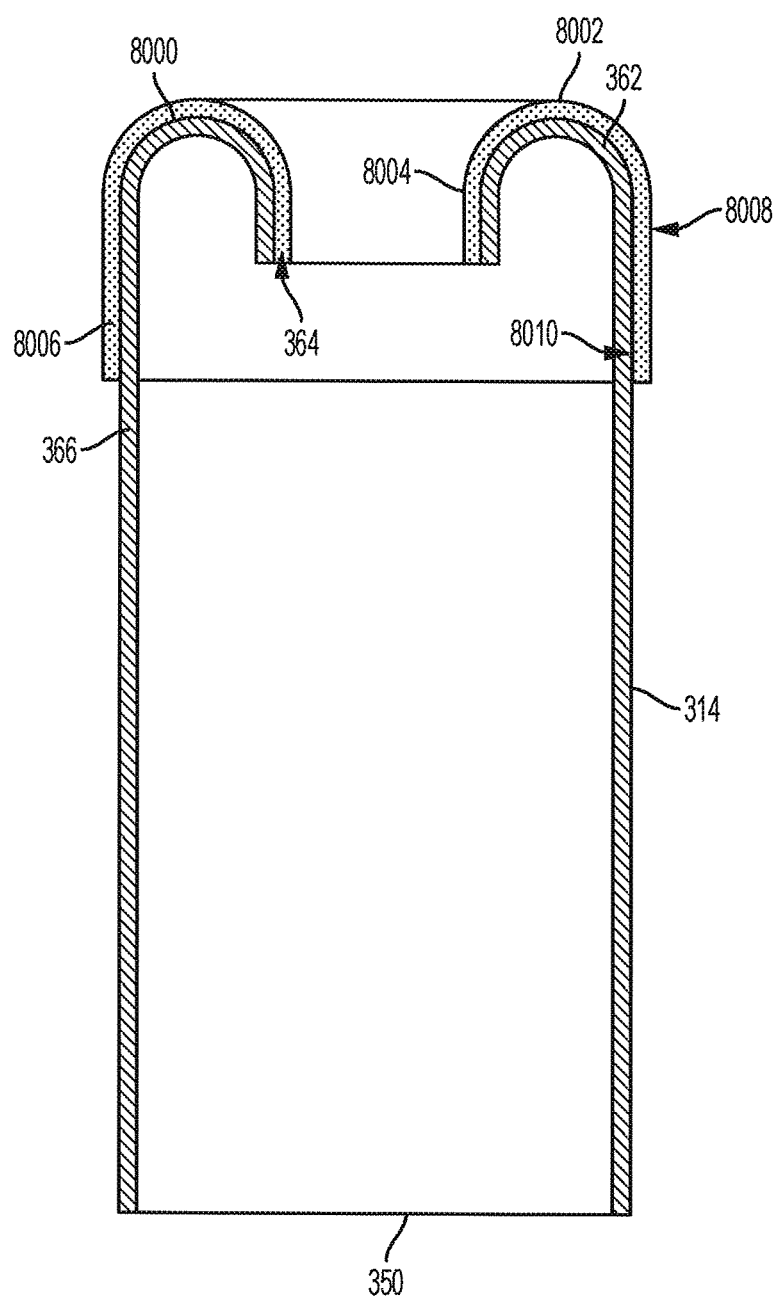
FIG. 75B is a sectional view of an exemplary cover disposed on a docking station frame.

Referring to FIGS. 75A and 75B, the cover 8000 can be draped or otherwise disposed entirely around the end 362 of the frame 350. The cover 8000 can have contours or otherwise undulate between the struts 1200 of the frame 350 (FIG. 75A) or the cover 8000 can be flush with the end 362 of the frame 3530 (FIG. 75B). A valve 29 (See e.g. FIG. 63) can be inserted into the valve seat 18 defined by the inside diameter 364 of the frame 350 and the inside diameter 8004 of the cover 8000. In such a configuration, the cover 8000 can effectuate a continuous seal between the outside diameter 366 of the frame 350 and the interior surface 416 of the circulatory system, around the end 362 of the frame 350, and between the inside diameter 364 of the frame 350 and the valve 29. For example, when the valve 29 is in the closed position, the valve 29 and the cover 8000 provide a seal against blood flow.

Figure 76:
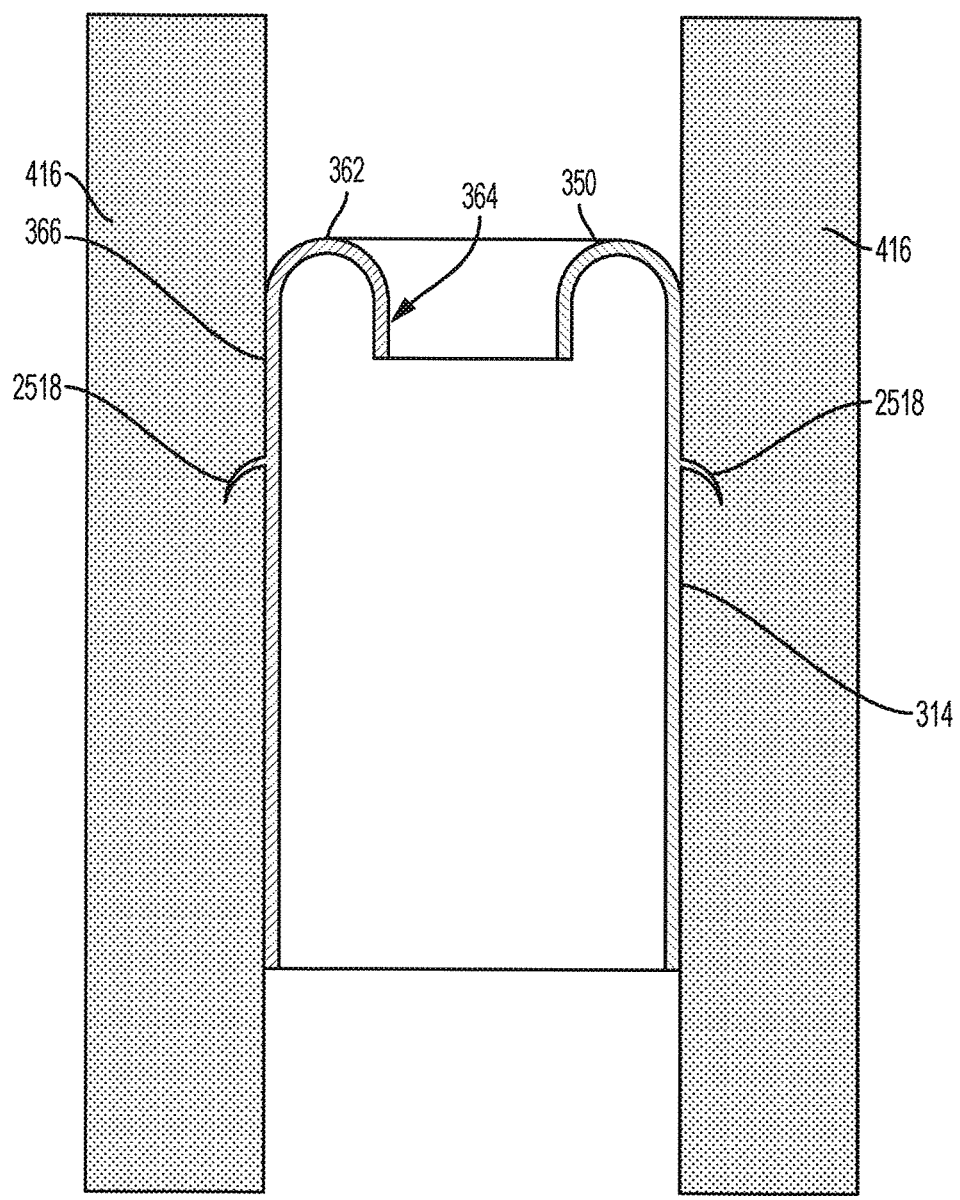
FIG. 76 illustrates an exemplary docking station deployed in a circulatory system.

Referring, for example, to FIGS. 25, 26, and 76, the frame 350 can also include one or more friction-enhancing features, such as barbs 2518 shown in FIG. 76 projecting radially outwardly from the retaining portion 314 of the frame 350. The barbs 2518 can be curved and/or otherwise oriented to prevent the frame 350 from moving from an installed position. In one embodiment, the barbs 2518 project radially outwardly from one or more struts 1200. As shown in FIG. 76, when the frame 350 is deployed and expands radially outwardly, the barbs 2518 can insert into the interior surface 416 of the circulatory system to secure or otherwise maintain the position of the frame 2518. The barbs 2518 can be oriented such that the frame 350 does not move due to the force of blood flowing through the heart or other portions of the body (e.g., angled or curved to point in the direction of blood flow). Any frame 350 described or depicted herein can include similar barbs 2518.

As mentioned above, the docking station 10 can be adapted for use at a variety of different positions in the circulatory system. FIGS. 77 and 78 illustrate exemplary embodiments where a docking station 10 is configured for use in the aorta 900. In FIG. 77, the docking station 10 is shown used alone in the aorta. In FIG. 78, the docking station 10 is shown used in conjunction with a graft 902. The docking station 10 used in the aorta 900 can take a wide variety of different forms. For example, the docking station 10 shown in FIGS. 77 and 78 can be any of the docking stations 10 disclosed herein.

Referring to FIGS. 77 and 78, the docking station can be placed in the aorta 900 and an extension 950 extends to stabilize the docking station 10. In FIG. 77, the docking station 10 is placed inside the annulus of the aortic valve AV and the extension 950 extends into the aorta, such as into the aortic arch. In FIG. 11, the docking station 10 is placed inside the annulus of the aortic valve AV and the extension 950 extends into the aorta, such as into the graft 902. However, the extension 950 and the graft 902 can take a wide variety of different forms. The graft can be a surgically installed graft or a graft that is installed through a catheter, without open heart surgery. In one exemplary embodiment, the extension acts as a graft.

The extension 950 can take a wide variety of different forms. In one exemplary embodiment, the extension 950 is constructed to allow blood to freely flow through the extension. For example, the extension 950 can be an open cell frame. The extension 950 can comprise spring elements 3700. The extension 950 can comprise wires. In one exemplary embodiment, the extension 950 comprises an open cell frame, spring elements 3700, and/or wires. In the illustrated embodiment, the extension 950 is configured to bend as it extends in the aorta. The extension 950 can be integrally formed with the docking station 10 or the extension can be made separately from the docking station 10 and attached to the docking station. Optionally, the extension 950 can be configured as a graft or stent-graft.

Referring to FIGS. 77 and 78, when the docking station 10 is placed in the aorta, a significant volume of blood flowing through the aorta can be directed into the valve 29 by a covering/material 21. The covering/material 21 can be the same as or similar to other coverings/materials described herein. The covering/material can be fluid impermeable or substantially impermeable so that blood cannot pass through. More or all the docking station frame 350 can be provided with the covering/material 21, forming a relatively large impermeable or substantially impermeable portion.

The foregoing primarily describes embodiments of docking stations that are self-expanding. But the docking stations shown and described herein can be modified for delivery of balloon-expandable, mechanically-expandable docking devices, and/or a combination of these, within the scope of the present disclosure. Delivering balloon-expandable and/ or mechanically-expandable docking stations, etc. to an implantation location can also be performed.

A variety of methods of implanting the docking stations and valves described herein can be used. Steps described herein can be used in various orders and the various steps can be combined or omitted. As one example, a method can include: inserting a docking station delivery catheter/sheath into vasculature (or a circulatory system) of a patient, the docking station holding a docking station in a compressed configuration; navigating the docking station delivery catheter/sheath through the vasculature (or circulatory system) to a desired implantation location/site; deploying/releasing the docking station such that it expands to an expanded configuration and engages an interior surface of the circulatory system, vasculature, heart, etc.; inserting a valve delivery catheter (e.g., a THV delivery catheter) into the vasculature (or circulatory system), the valve delivery catheter holding a transcatheter valve in a compressed configuration; navigating the valve delivery catheter through the vasculature (or circulatory system) to a desired implantation location/site or to the docking station (e.g., within the docking station or within a valve seat of the docking station); deploying/releasing the valve such that it expands to an expanded configuration and engages an interior surface of the docking station or of the valve seat of the docking station and is securely held thereby; (expanding can be done by allowing the transcatheter valve to self-expand out of the catheter/sheath, inflating a balloon to manually expand the valve, mechanically expanding the valve, or a combination of these).

The deploying/releasing the docking station such that it expands to an expanded configuration and engages an interior surface of the vasculature, IVC, SVC, aorta, aortic valve, heart, circulatory system, etc. can comprise a partial deployment/release of the docking station such that a portion of the docking station remains in the catheter/sheath. A step of retrieving or recapturing the docking station (whether fully deployed or partially deployed) can be used and can involve retracting the docking station into the sheath/catheter or advancing the sheath/catheter over the docking station. If retrieved or recaptured, a step of repositioning the docking station catheter/sheath and the docking station to a second or different/modified location can be used, then the docking station can be fully deployed/released such that it expands to the expanded configuration and engages an interior surface of the vasculature, IVC, SVC, aorta, aortic valve, heart, circulatory system, etc.

In view of the many possible embodiments to which the principles of the disclosed invention may be applied, the illustrated embodiments are only examples of the invention and should not be taken as limiting the scope of the invention. All combinations or subcombinations of features/components of the foregoing exemplary embodiments are contemplated by this application, e.g., features/components of one embodiment can be incorporated into other embodiments and the steps of various methods can be combined in different ways and orders. We therefore claim as our invention all that comes within the scope and spirit of the following claims.

The invention claimed is:

1. An expandable docking station frame comprising:
an annular valve seat having an end;
an annular outer wall comprising struts disposed around the valve seat; and
links that connect the end of the annular valve seat to the annular outer wall;
wherein each of the links extends from the struts of the annular outer wall directly toward a longitudinal axis that runs longitudinally through a center of the docking station, and to a corresponding one of a plurality of circumferentially spaced axially extending legs at least partially defining the annular valve seat; and
wherein the outer wall is configured to conform to an interior shape of a blood vessel, when expanded inside the blood vessel, such that the outer wall can expand in multiple locations to conform to multiple bulges of the blood vessel and can contract in multiple locations to conform to multiple narrowed regions of the blood vessel;
wherein an apex of the links is bent such that portions of the links on opposite sides of the apex extend away from each other at an acute angle.

2. The expandable docking station frame of claim 1, wherein the links and the struts are integrally formed.

3. The expandable docking station frame of claim 1, wherein the links are curved.

4. The expandable docking station frame of claim 1, wherein a thickness of the links at the apex of the links is the same as a thickness of the struts at a junction between the links and the annular outer wall.

5. An expandable docking station frame comprising a plurality of struts defining:
a proximal lattice portion including cells forming an axially extending annular outer wall defining a retaining portion; and
a distal end portion including links extending radially inward from endmost junctions of a distal row of the lattice portion cells, and legs extending axially inward from inner radial ends of corresponding links to define an inner annular valve seat;
wherein an apex of the links is bent such that portions of the links on opposite sides of the apex extend away from each other at an acute angle, wherein a thickness of the links at the apex of the links is the same as a thickness of the struts at a junction between the links and the annular outer wall.

6. The expandable docking station frame of claim 5, wherein the lattice portion, the links, and the legs are integrally formed.

7. The expandable docking station frame of claim 5, wherein the links are curved.

8. A docking station comprising:
an expandable frame configured to conform to an interior shape of a blood vessel when expanded inside the blood vessel, the expandable frame including an annular outer wall extending from a proximal end to a distal end portion and an annular inner wall radially spaced from the annular outer wall at the distal end portion and having a proximal end that terminates in the distal end portion of the annular outer wall such that the annular inner wall is limited to the distal end portion of the annular outer wall;
a cover disposed over and limited to a distal end portion of the expandable frame, such that a proximal end portion of the expandable frame is uncovered, the cover including an outer diameter portion covering the distal end portion of the annular outer wall and defining a sealing portion configured to provide a seal between the docking station and an interior surface of the blood vessel, and an inner diameter portion covering the annular inner wall to define, with the annular inner wall, a valve seat configured to support an expandable transcatheter valve at the distal end portion of the expandable frame.

9. The docking station of claim 8, wherein links connect the annular outer wall of the expandable frame to the annular inner wall of the expandable frame.

10. The docking station of claim 9, wherein the links are curved in a semi-circular shape.

11. The docking station of claim 9, wherein the outer wall of the expandable frame comprises a plurality of struts, and wherein a thickness of the links is less than a thickness of the struts.

12. The docking station of claim 9, wherein an apex of the links is bent such that portions of the links on opposite sides of the apex extend away from each other at an acute angle.

13. The docking station of claim 8, wherein the valve seat is entirely located radially inside and radially overlapping an outer wall of the frame.

14. The docking station of claim 8, wherein the expandable frame includes a first leg that extends proximally beyond the proximal end of the annular outer wall and an elongated second leg that extends proximally further beyond the proximal end of the annular outer wall, beyond a proximal end of the first leg.

15. The docking station of claim 8, wherein the expandable frame is configured to conform to the interior shape of the blood vessel, when expanded inside the blood vessel, such that the expandable frame can expand in multiple locations to conform to multiple bulges of the blood vessel and can contract in multiple locations to conform to multiple narrowed regions of the blood vessel.

16. The docking station of claim 15, wherein the blood vessel is an aorta, and wherein the expandable frame is configured to conform to an interior shape of the aorta when expanded inside the aorta.

17. The docking station of claim 8, further comprising a tubular graft coupled to the expandable frame that extends axially beyond an end of the expandable frame.

* * * * *